US012760453B2

(12) United States Patent
Naranjo-Briceño et al.

(10) Patent No.: US 12,760,453 B2
(45) Date of Patent: Oct. 13, 2026

(54) SIDEREAL MYCELIUM FABRICS

(71) Applicant: Spora Cayman Holdings Limited, Vitacura (CL)

(72) Inventors: Leopoldo Naranjo-Briceño, Vitacura (CL); Keyla M. Fuentes, Vitacura (CL); Melissa Gómez, Vitacura (CL); Carlos Gil-Durán, Vitacura (CL); Vicente Oliva, Vitacura (CL); Maximiliano Venegas, Vitacura (CL); Hernán Rebolledo De Lima, Vitacura (CL); José Miguel Figueroa, Vitacura (CL); Pablo Zamora, O'Higgins Region (CL)

(73) Assignee: Spora Cayman Holdings Limited, Vitacura (CL)

( * ) Notice: Subject to any disclaimer, the term of this patent is extended or adjusted under 35 U.S.C. 154(b) by 0 days.

(21) Appl. No.: 19/197,960

(22) Filed: May 2, 2025

(65) Prior Publication Data

US 2025/0382734 A1 Dec. 18, 2025

Related U.S. Application Data

(60) Provisional application No. 63/642,640, filed on May 3, 2024.

(51) Int. Cl.
*D04H 1/4266* (2012.01)
*A01G 18/20* (2018.01)
(Continued)

(52) U.S. Cl.
CPC ........... *D04H 1/4266* (2013.01); *A01G 18/20* (2018.02); *C12N 1/14* (2013.01); *D04H 1/413* (2013.01);
(Continued)

(58) Field of Classification Search
CPC .................................... D01F 9/00; C12N 1/14
See application file for complete search history.

(56) References Cited

U.S. PATENT DOCUMENTS

| | | |
|---|---|---|
| 4,125,708 A | 11/1978 | Masri et al. |
| 5,486,474 A | 1/1996 | Bradley et al. |

(Continued)

FOREIGN PATENT DOCUMENTS

| | | |
|---|---|---|
| AU | 2123999 A | 5/1999 |
| AU | 2013251269 B2 | 10/2015 |

(Continued)

OTHER PUBLICATIONS

Subashini, G., Bhuvaneswari, S. (2018). Nanoparticles from Fungi (Myconanoparticles). In: Gehlot, P., Singh, J. (eds) Fungi and their Role in Sustainable Development: Current Perspectives. Springer, Singapore. https://doi.org/10.1007/978-981-13-0393-7_39 ( Year: 2018).*

(Continued)

*Primary Examiner* — Larissa Rowe Emrich
(74) *Attorney, Agent, or Firm* — Shay Glenn LLP

(57) ABSTRACT

Methods and compositions (e.g., textiles, as well as components for forming, processing and using such textiles) of mycelium-based materials having superior durability, tensile strength and wear. In some cases, the methods, compositions and apparatuses described herein may include the use of primarily or exclusively dikaryotic fungal strains. These mycelium-based textiles, and methods of making them, may include nanoparticles formed in vivo during growth of the mycelium and/or nanoparticles synthesized in vitro by biogenic synthesis and added to the mycelium mat.

13 Claims, 58 Drawing Sheets

Specification includes a Sequence Listing.

(51) Int. Cl.

| | |
|---|---|
| ***C12N 1/14*** | (2026.01) |
| ***D04H 1/413*** | (2012.01) |
| ***D06M 10/00*** | (2006.01) |
| ***D06M 10/06*** | (2006.01) |
| ***D06M 15/15*** | (2006.01) |
| *D06M 101/04* | (2006.01) |

(52) U.S. Cl.

CPC .......... *D06M 10/001* (2013.01); *D06M 10/06* (2013.01); *D06M 15/15* (2013.01); *D06M 2101/04* (2013.01); *D10B 2401/063* (2013.01); *D10B 2401/13* (2013.01)

(56) References Cited

U.S. PATENT DOCUMENTS 5,583,041 A 12/1996 Bradley et al.
5,705,083 A 1/1998 Wyss et al.
5,939,065 A 8/1999 Bradley et al.
8,227,224 B2 7/2012 Kalisz et al.
8,227,225 B2 7/2012 Rocco et al.
8,227,233 B2 7/2012 Kalisz et al.
8,283,153 B2 10/2012 Rocco et al.
8,298,809 B2 10/2012 Kalisz et al.
8,298,810 B2 10/2012 Rocco et al.
9,447,477 B2 9/2016 Gamarino et al.
9,485,917 B2 11/2016 Bayer et al.
9,555,395 B2 1/2017 Araldi et al.
9,714,180 B2 7/2017 McIntyre et al.
10,537,070 B2 1/2020 Betts et al.
10,561,587 B2 2/2020 Koide et al.
10,687,482 B2 6/2020 Ross et al.
11,015,059 B2 5/2021 Smith et al.
11,135,287 B2 10/2021 Brito et al.
11,331,305 B2 5/2022 Dreher
11,576,311 B2 2/2023 Ross
11,993,068 B2 5/2024 Naranjo-Briceno et al.
2002/0006650 A1* 1/2002 Bradley .................. C12N 1/14 435/395
2009/0307969 A1 12/2009 Bayer et al.
2010/0162490 A1 7/2010 Brym
2010/0218878 A1 9/2010 Wang et al.
2011/0268955 A1* 11/2011 Rocco ...................... B32B 5/18 264/122
2011/0306107 A1 12/2011 Kalisz et al.
2012/0124839 A1 5/2012 Kalisz et al.
2012/0135504 A1 5/2012 Ross
2012/0227899 A1 9/2012 McIntyre et al.
2013/0263500 A1 10/2013 McIntyre et al.
2014/0097008 A1 4/2014 Bayer et al.
2014/0120602 A1 5/2014 Winiski et al.
2015/0247115 A1 9/2015 Bayer et al.
2015/0293076 A1 10/2015 Widmaier et al.
2015/0376565 A1 12/2015 Schaak et al.
2016/0002589 A1 1/2016 Winiski
2016/0264926 A1 9/2016 Winiski et al.
2016/0302364 A1 10/2016 Lucht et al.
2017/0253852 A1 9/2017 Bayer et al.
2018/0216260 A1 8/2018 Breslauer et al.
2018/0282381 A1 10/2018 Kittleson et al.
2018/0282937 A1 10/2018 Bainbridge et al.
2019/0169242 A1 6/2019 Boulet-Audet et al.
2019/0338240 A1 11/2019 Carlton et al.
2019/0359931 A1 11/2019 Mueller et al.
2019/0389916 A1 12/2019 Rice et al.
2019/0390156 A1 12/2019 Bayer et al.
2020/0022451 A1 1/2020 Smith et al.
2020/0024577 A1 1/2020 Carlton et al.
2020/0025672 A1 1/2020 Scullin et al.
2020/0032434 A1 1/2020 Resneck et al.
2020/0102429 A1 4/2020 Smith et al.
2020/0131694 A1 4/2020 Scullin et al.
2020/0196541 A1 6/2020 Ross et al.
2020/0239830 A1 7/2020 O'Brien et al.
2020/0268031 A1 8/2020 Macur et al.
2020/0283750 A1 9/2020 Gamboa et al.
2020/0330378 A1 10/2020 Friedman
2020/0362295 A1 11/2020 Kozubal et al.
2020/0399328 A1 12/2020 Breslauer et al.
2020/0399824 A1 12/2020 Stewart et al.
2021/0059287 A1 3/2021 Kozubal et al.
2021/0155893 A1 5/2021 Kozubal et al.
2021/0171896 A1 6/2021 Harney et al.
2021/0177754 A1 6/2021 Keller et al.
2021/0317433 A9 10/2021 Schaak
2021/0388558 A1 12/2021 Stewart et al.
2022/0025318 A1 1/2022 Gandia et al.
2022/0073865 A1 3/2022 Attias et al.
2022/0090003 A1* 3/2022 Kozubal .................. C12N 1/14
2023/0014203 A1 1/2023 Kozubal et al.
2023/0265606 A1 8/2023 Picaut
2024/0269962 A1 8/2024 Naranjo-Briceño et al.
2025/0066991 A1 2/2025 Naranjo-Briceno et al.
2025/0122653 A1 4/2025 Naranjo-Briceno et al.

FOREIGN PATENT DOCUMENTS

AU 2019201553 A1 3/2019
AU 2019219768 A1 9/2019
AU 2020201013 A1 9/2020
BR 102013028238 B1 3/2021
CN 103171823 A 6/2013
CN 108503858 A 9/2018
IN 201921004709 A 5/2019
JP 2006124267 A 5/2006
JP 5131676 B2 1/2013
KR 20150014560 A 2/2015
WO WO92/13960 A1 8/1992
WO WO93/00793 A1 1/1993
WO WO95/010597 A1 4/1995
WO WO97/023416 A1 7/1997
WO WO2008/118543 A2 10/2008
WO WO2010/005476 A1 1/2010
WO WO2012/148995 A1 11/2012
WO WO2014/031810 A2 2/2014
WO WO2015/042164 A2 3/2015
WO WO2016/073453 A1 5/2016
WO WO2016/168563 A1 10/2016
WO WO2017093759 A1 6/2017
WO WO2018/014004 A1 1/2018
WO WO2018/037072 A1 3/2018
WO WO2018/053204 A1 3/2018
WO WO2018/132821 A2 7/2018
WO WO2018/183735 A1 10/2018
WO WO2019/046480 A1 3/2019
WO WO2019/060921 A1 3/2019
WO WO2019/099474 A1 5/2019
WO WO2019/178406 A1 9/2019
WO WO2019/222633 A1 11/2019
WO WO2019/226823 A1 11/2019
WO WO2020/006133 A1 1/2020
WO WO2020/033970 A2 2/2020
WO WO2020/072140 A1 4/2020
WO WO2020/086907 A1 4/2020
WO WO2020/087033 A1 4/2020
WO WO2020/102552 A1 5/2020
WO WO2020/106743 A1 5/2020
WO WO2020/112742 A1 6/2020
WO WO2020/115690 A1 6/2020
WO WO2020/176758 A1 9/2020
WO WO2020/186068 A1 9/2020
WO WO2020/237201 A1 11/2020
WO WO2020/243431 A1 12/2020
WO WO2021/011431 A1 1/2021
WO WO2021/035184 A1 2/2021
WO WO2021/055440 A1 3/2021
WO WO2021/092051 A1 5/2021
WO WO2021/124164 A1 6/2021
WO WO2021/136883 A1 7/2021

(56) References Cited

FOREIGN PATENT DOCUMENTS

| | | | |
|---|---|---|---|
| WO | WO2023/172999 | A2 | 9/2023 |
| WO | WO2023/199285 | A2 | 10/2023 |

OTHER PUBLICATIONS

Deeg et al.; Greener Solutions: Improving performance of mycelium-based leather; Final Report to MycoWorks; pp. 1-54; 2017. (Year: 2017).*

Jones, M., Gandia, A., John, S. et al. Leather-like material biofabrication using fungi. Nat Sustain 4, 9-16 (2021). https://doi.org/10.1038/s41893-020-00606-1 (Year: 2021).*

Mukherjee et al.; Fungus-mediated synthesis of silver nanoparticles and their immobilization in the mycelial matrix: a novel biological approach to nanoparticle synthesis; Nano letters; 1(10); pp. 515-519; Oct. 10, 2001.

Cruz-Luna et al.; Engineered metal oxide nanoparticles as fungicides for plant disease control; Plants; 12(13); 2461; 16 pages; doi.org/10.3390/plants12132461; Jun. 27, 2023.

Deeg et al.; Greener Solutions: Improving performance of mycelium-based leather; Final Report to MycoWorks; pp. 1-54; 2017.

Elsacker et al.; Recent technological innovations in mycelium materials as leather substitutes: a patent review, Frontiers in Bioengineering and Biotechnology; 11:1204861; 12 pages; Aug. 7, 2023.

Genbank JN164989.1; Trametes cubensis voucher CRM90 18S ribosomal RNA gene, partial sequence; internal transcribed spacer 1, 5.8S ribosomal RNA gene, and internal transcribed spacer 2, complete sequence; and 28S ribosomal RNA gene, partial sequence; 1 page; retrived from the internet (https://www.ncbi.nim.nih.gov/nuccore/JN164989.1) on May 22, 2023.

Genbank JX416577.1; *Basidiomycota* sp. FPF38a internal trnascribed spacer 1, partial sequence; 5.8S ribosomal RNA gene, complete sequence; and internal transcribed spacer 2, partial sequence; 2 pages; retrieved from the internet (https://www.ncbi.nlm.nih.gov/nuccore/JX416577.1) on May 22, 2023.

Genbank KX515895.1; Uncultured fungus clone ZMTDH201308-27 small subunit ribosomal RNA gene, partial sequence; internal transcribed spacer 1, 5.8S ribosomal RNA gene, and internal transcribed spacer 2, complete sequence; and large subunit ribosomal RNA gene, partial sequence; 1 page; retrieved from the internet (https://www.nobi.nlm.nih.gov/nuccore/1121643866) on May 22, 2023.

Nam et al.; Role of phosphate-modified mesoporous silica nanoparticles for altering biomimetic metal-induced aggregation process of pluronic F127 block copolymer. Materials Letters; vol. 110, pp. 176-179, Aug. 13, 2013.

Sojka-Ledakowicz et al.; Functionalization of textile materials by alkoxysilane-grafted titanium dioxide; Journal of materials science; vol. 44, pp. 3852-3860; May 15, 2009.

Wijayarathna et al.; Fungal textile alternatives from bread waste with leather-like properties; Resources, Conservation and Recycling; 179:106041; Apr. 1, 2022.

Islam et al.; Morphology and mechanics of fungal mycelium. Scientific reports; 7(1); 13070; pp. 1-12; Oct. 12, 2017.

McEvoy; Characterizing carbonyls with Infrared spectroscopy: an introductory chemistry experiment in a molecular bioscience program; Journal of Chemical Education; 91(5); pp. 726-729; May 13, 2014.

Vetter; Chitin content of cultivated mushrooms Agaricus bisporus, Pleurotus ostreatus and Lentinula edodes. Food Chemistry; 102(1); pp. 6-9; Jan. 1, 2007.

* cited by examiner

FIG. 13A
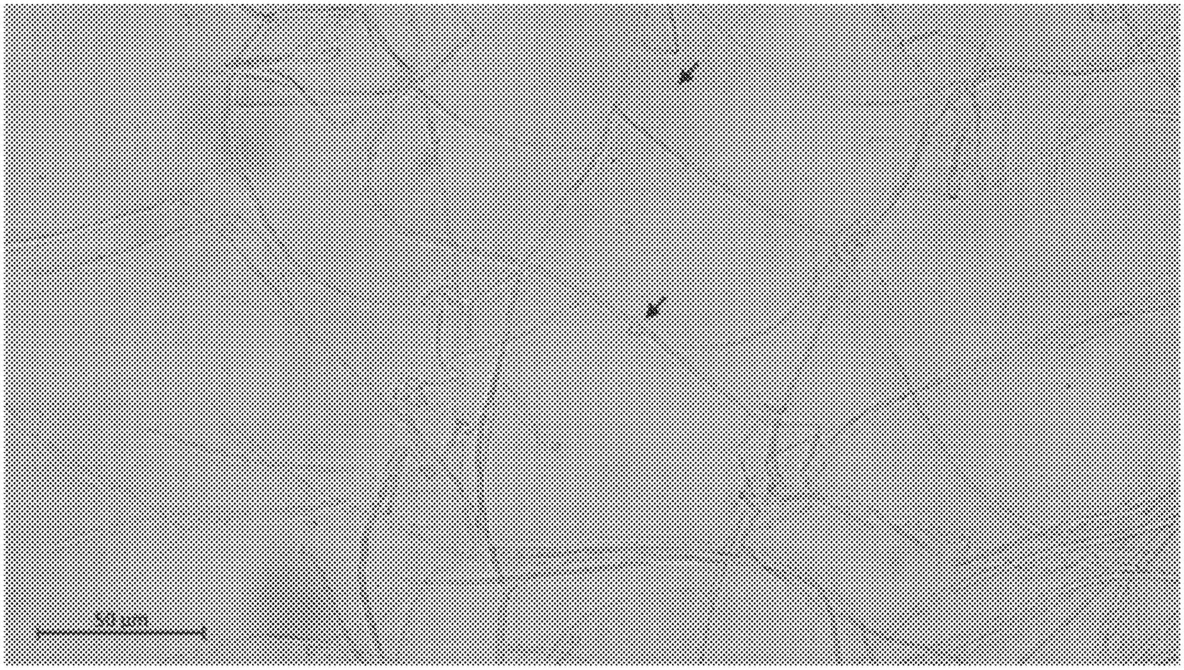
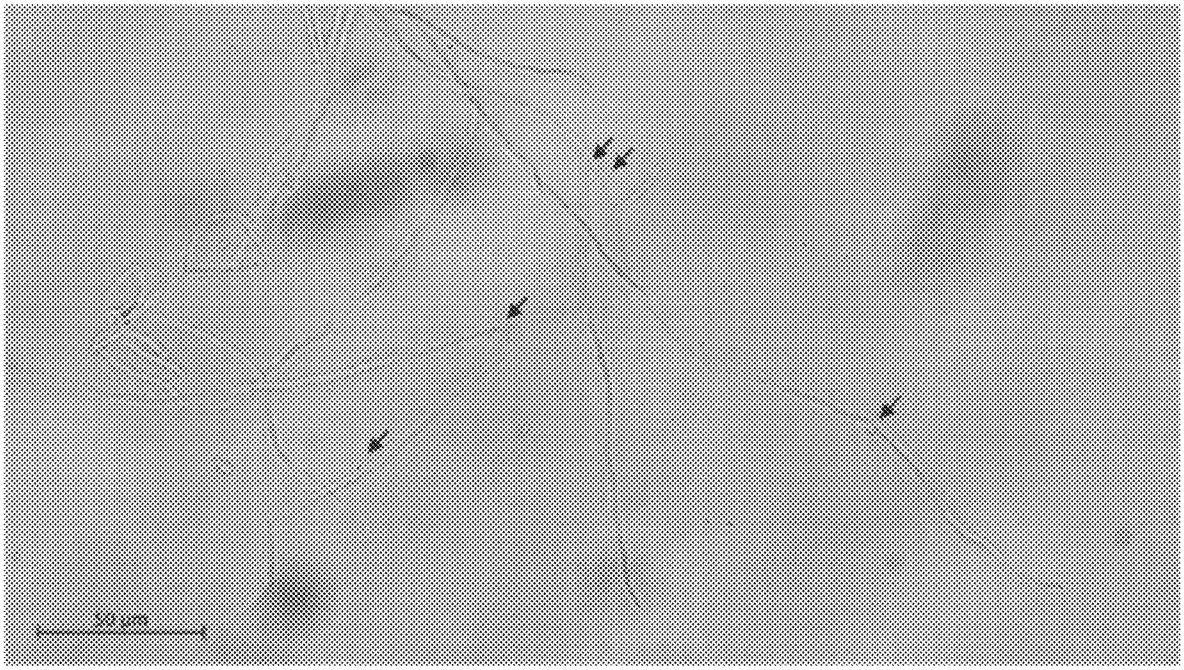
FIG. 13B

FIG. 14A
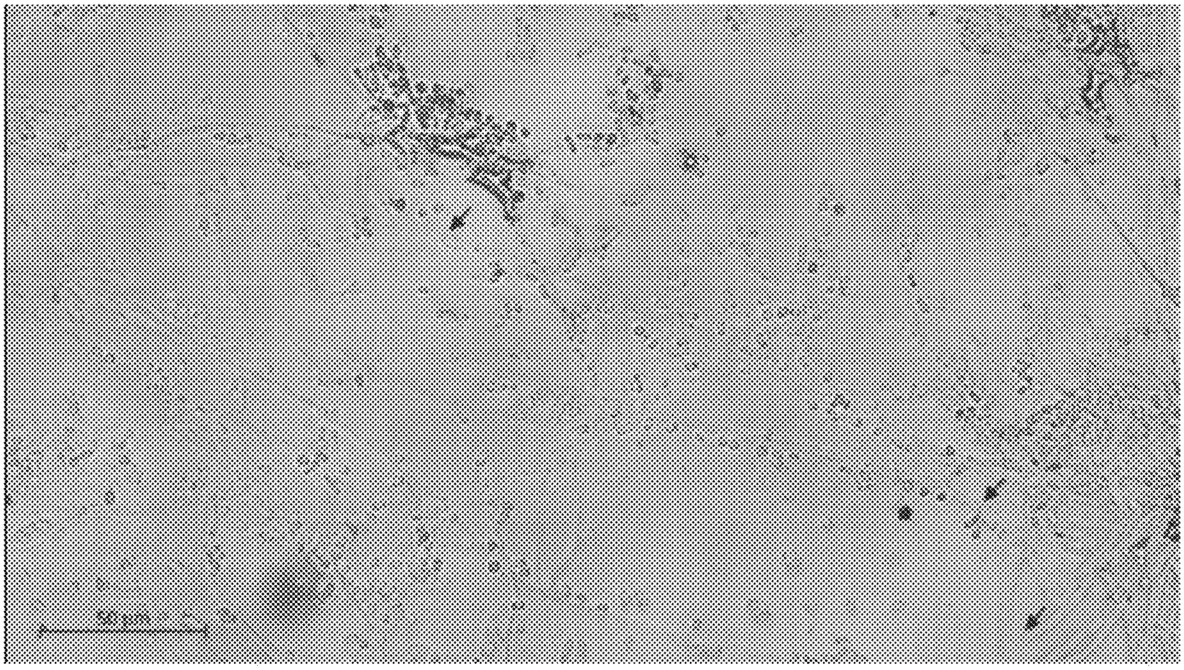
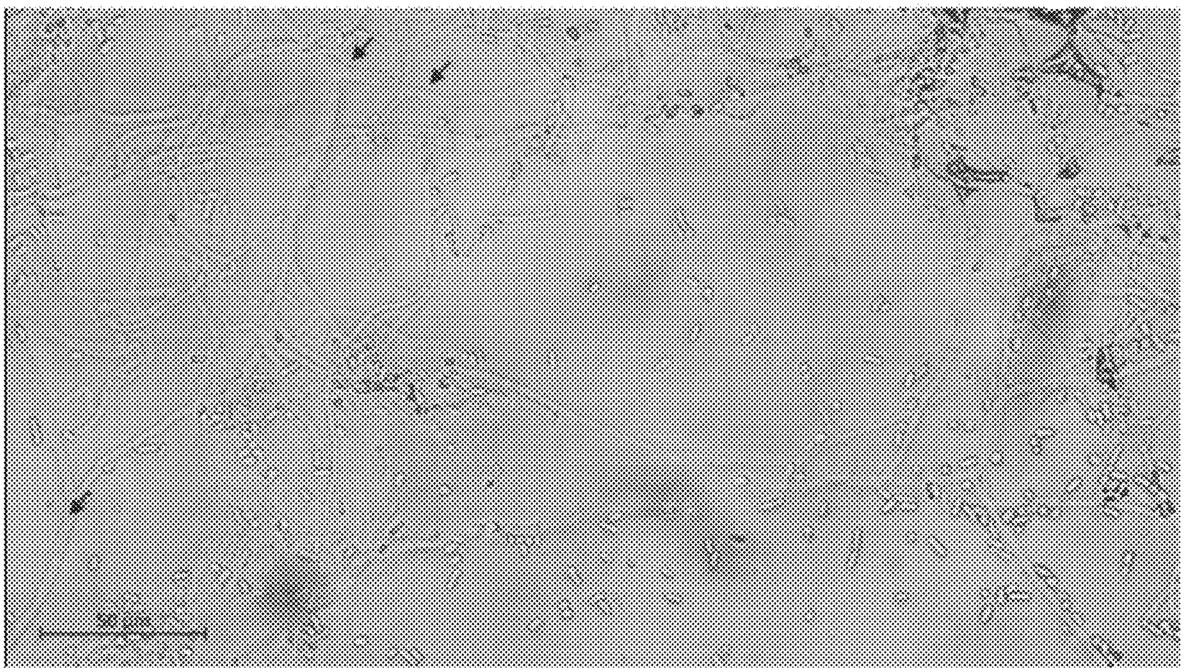
FIG. 14B

FIG. 15A
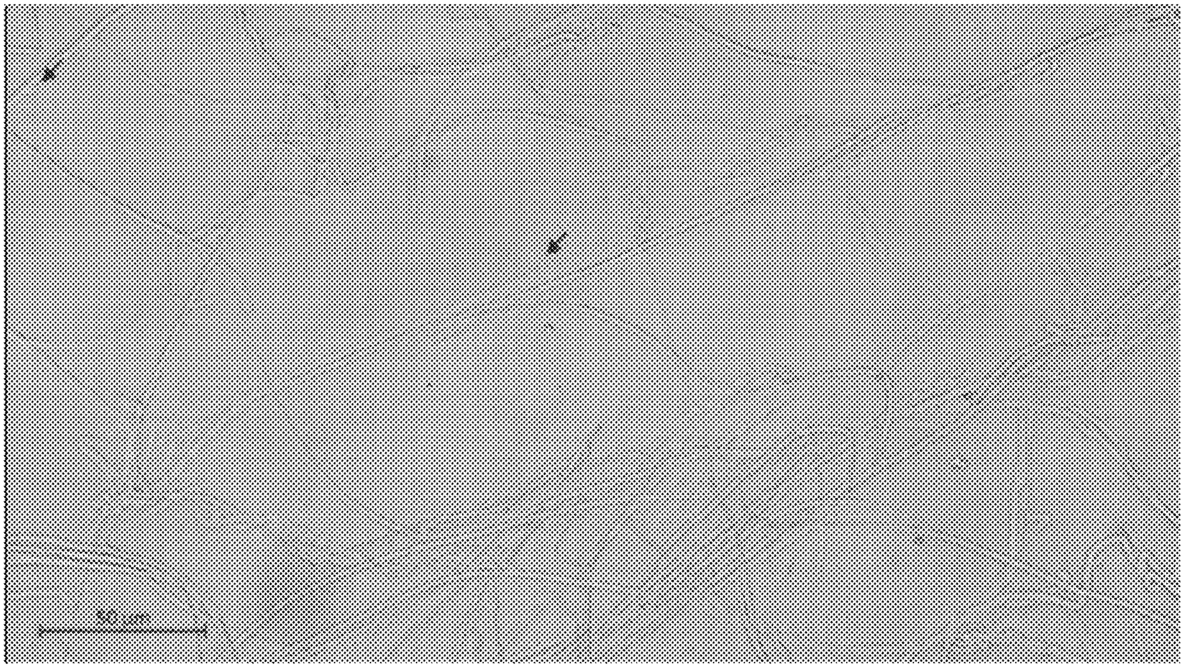
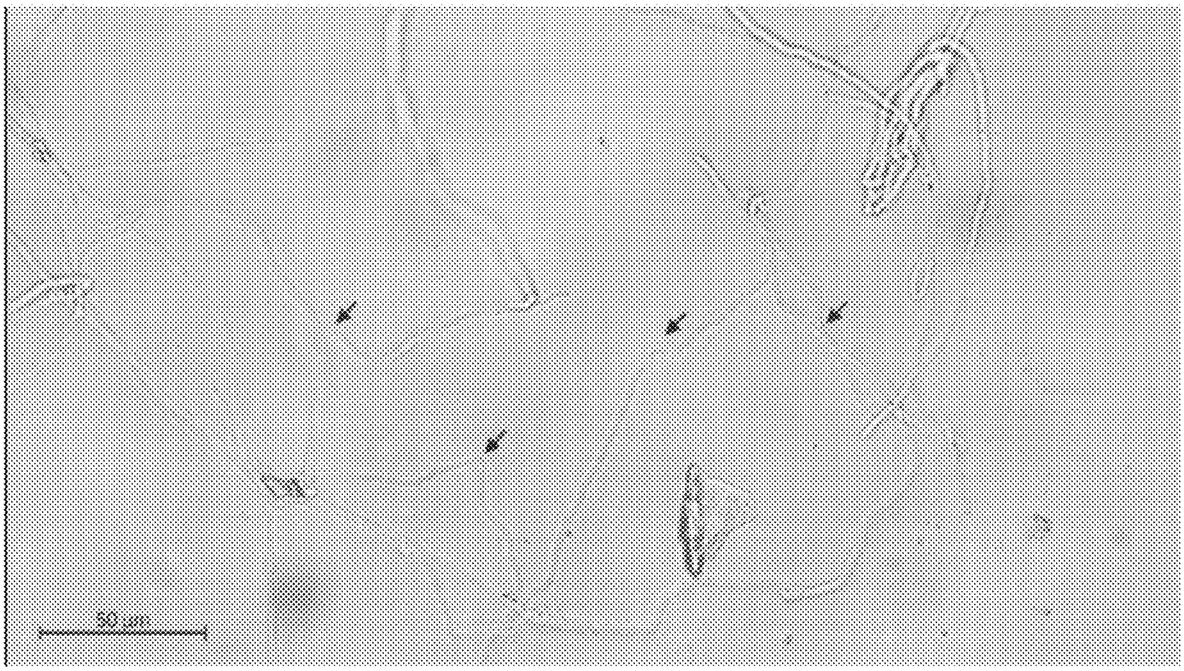
FIG. 15B

FIG. 16A
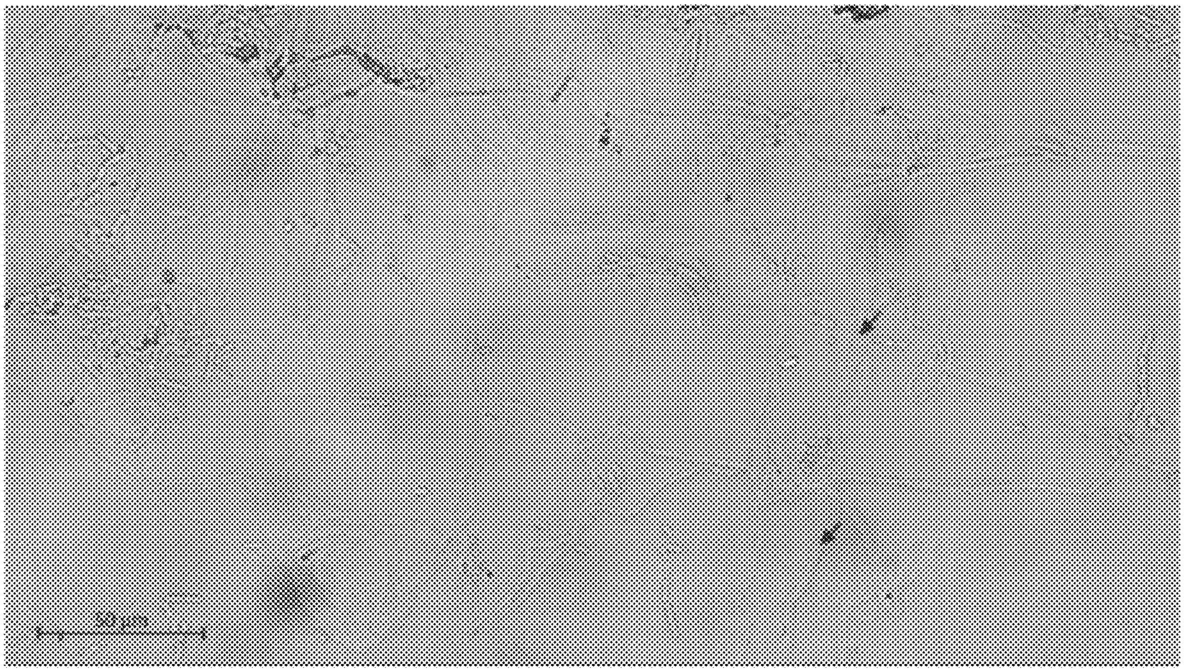
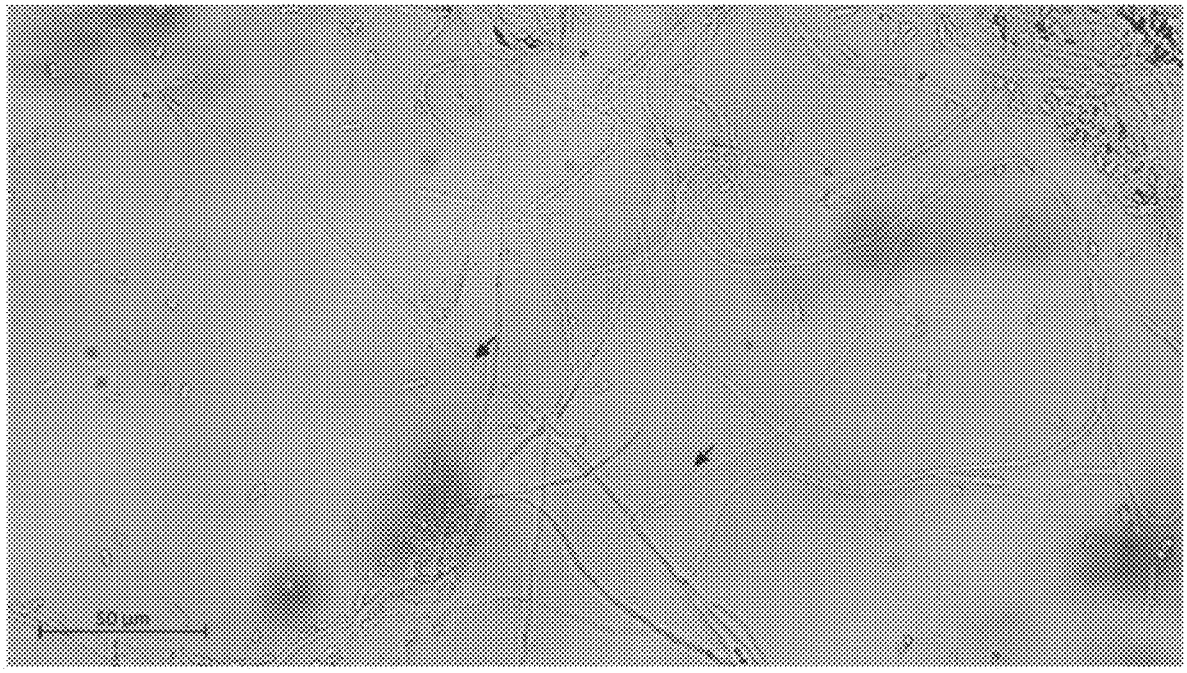
FIG. 16B

SCC-0006/3.1
(Monokaryon)

SCC-0006/3.6
(Dikaryon)

SCC-0006/3.9
(Monokaryon)

5 mM $AgNO_3$
(Overnight at 50°C)

5 mM $AgNO_3$
(Overnight at 60°C)

5 mM $AgNO_3$
(Overnight at 70°C)

Ag mapping

SCC-0006

SCC-0006/3.6

SCC-0013

SCC-0002

Au mapping

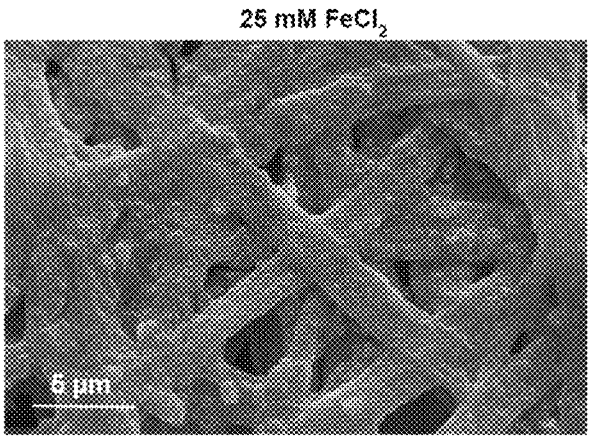
FIG. 41A
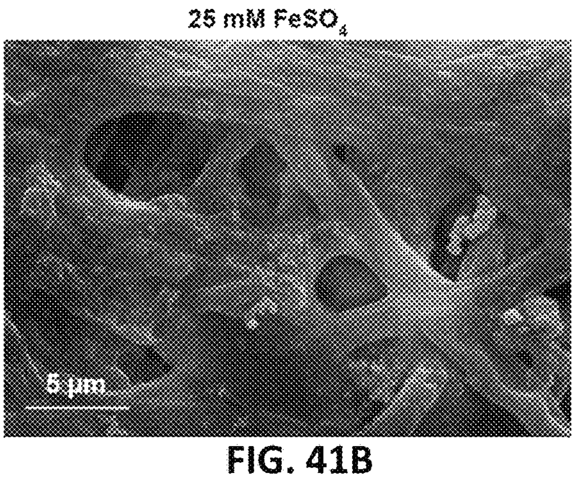
FIG. 41B
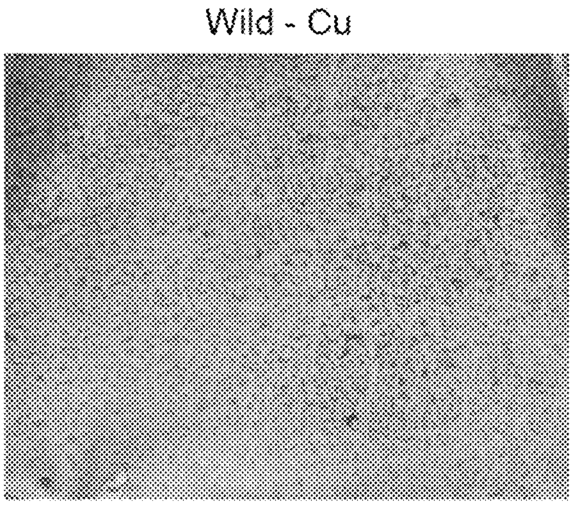
FIG. 42A1
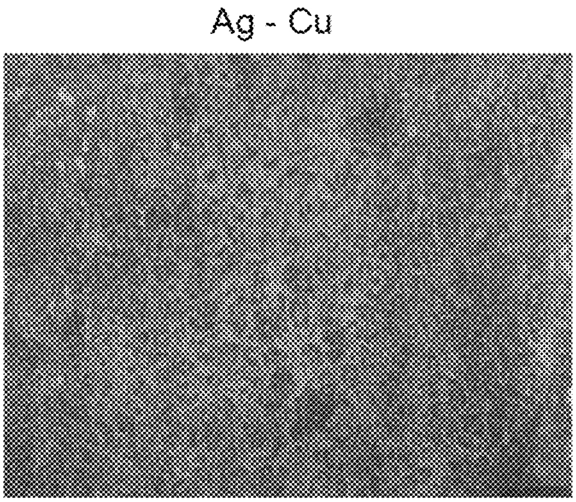
FIG. 42A2

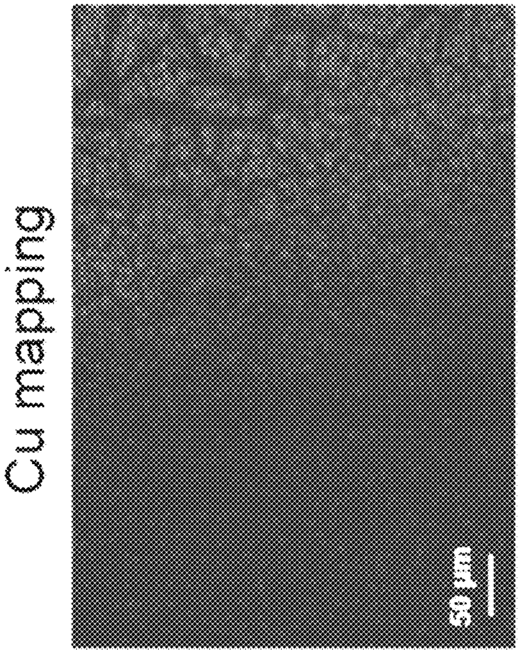
FIG. 42B2
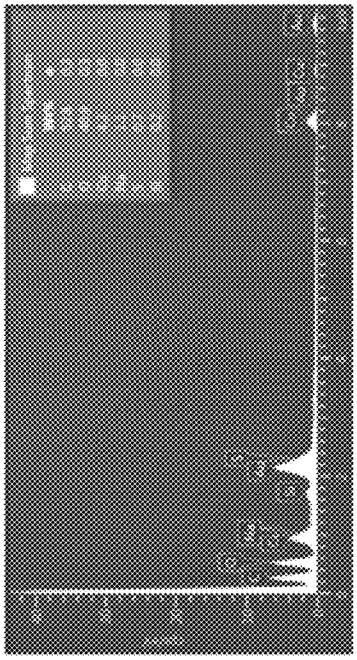
FIG. 42B3
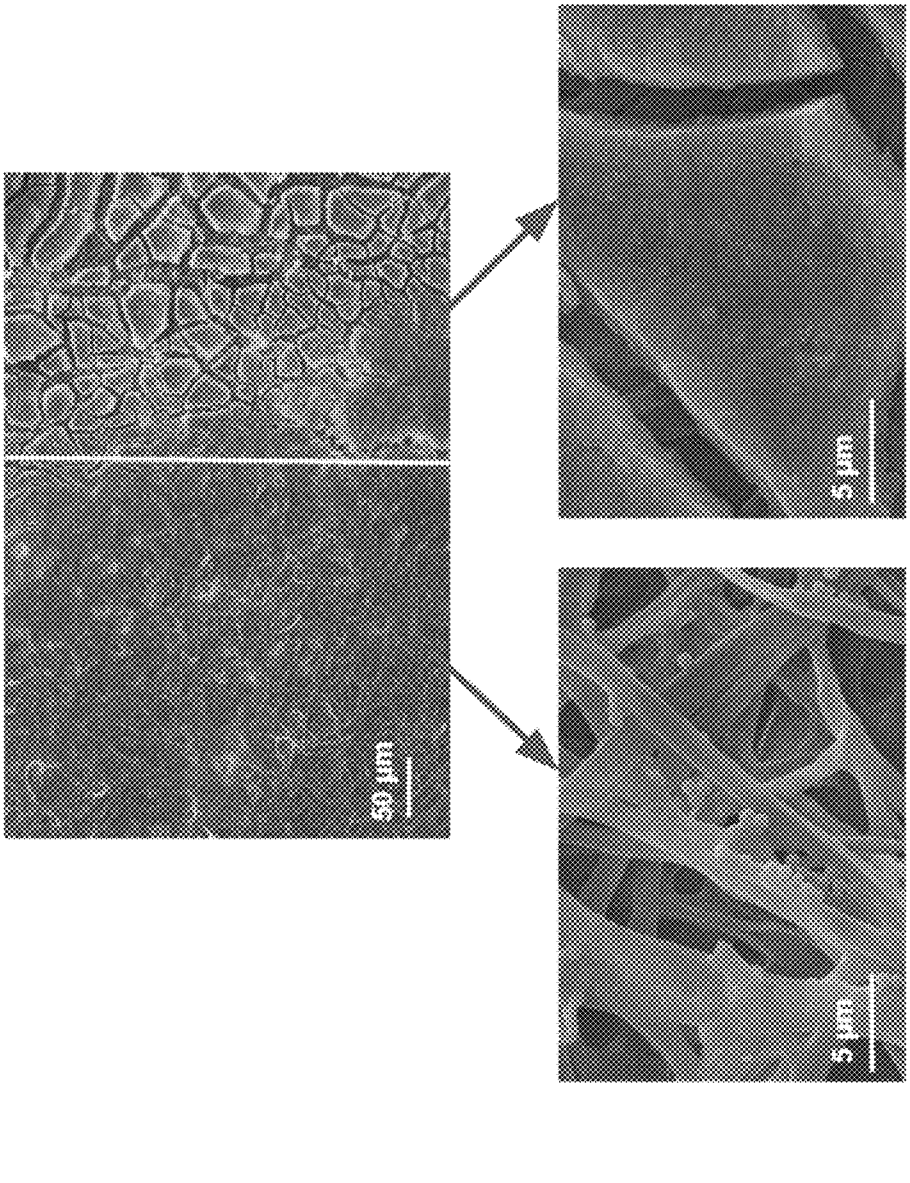
FIG. 42B1

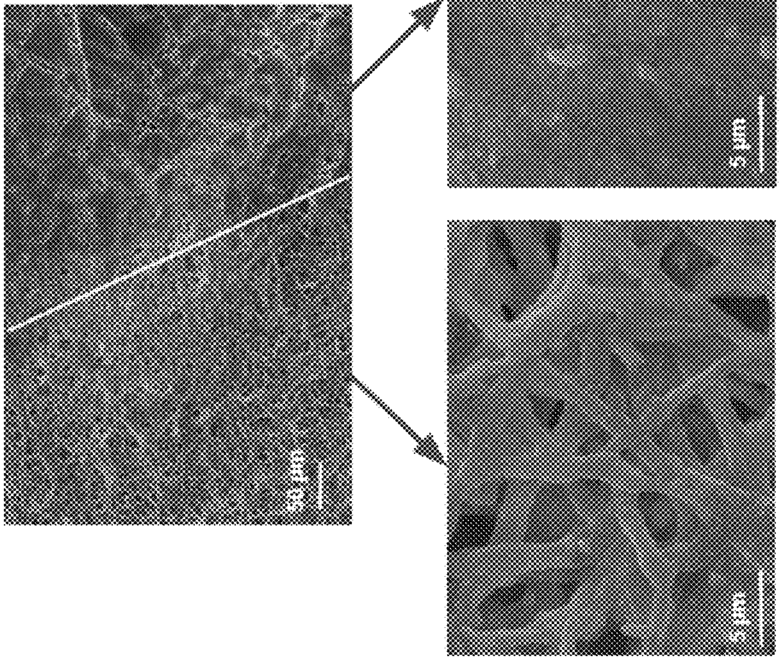
FIG. 42C1
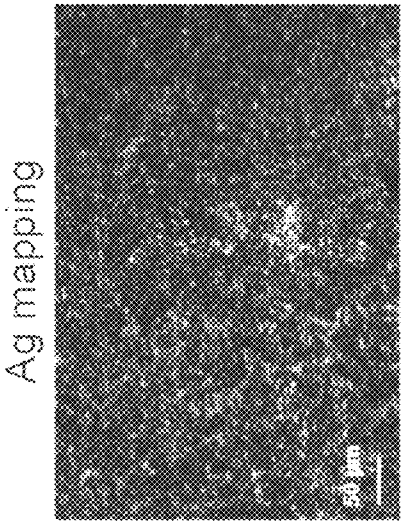
FIG. 42C2
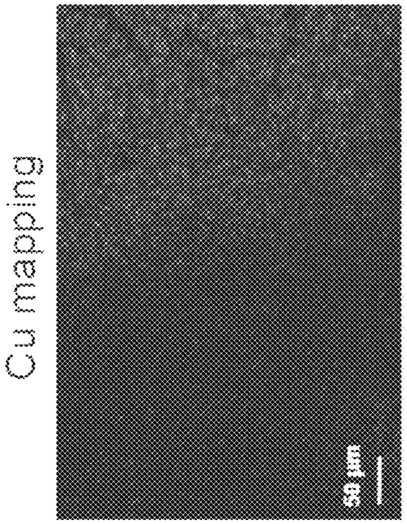
FIG. 42C3
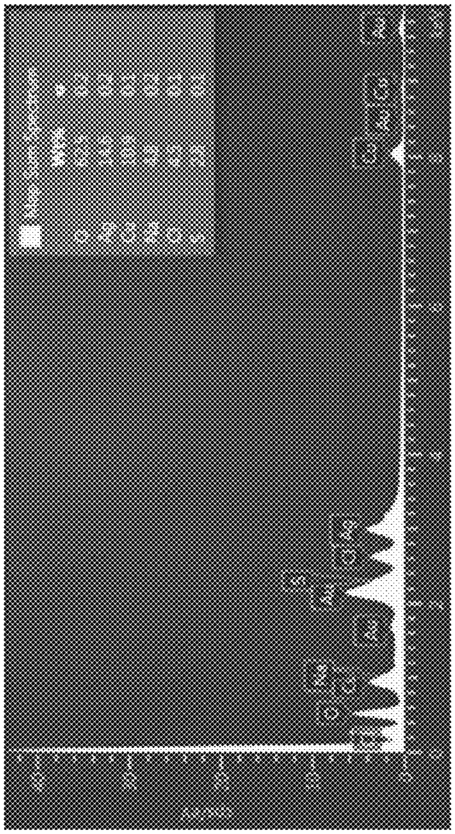
FIG. 42C4

Aqueous suspension of the stabilized magnetic-IO
FIG. 43A
Magnetic IO
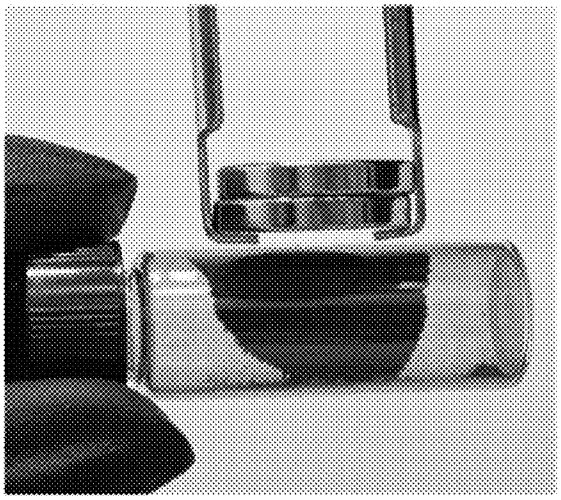
FIG. 43B
Wild - magnetic IO
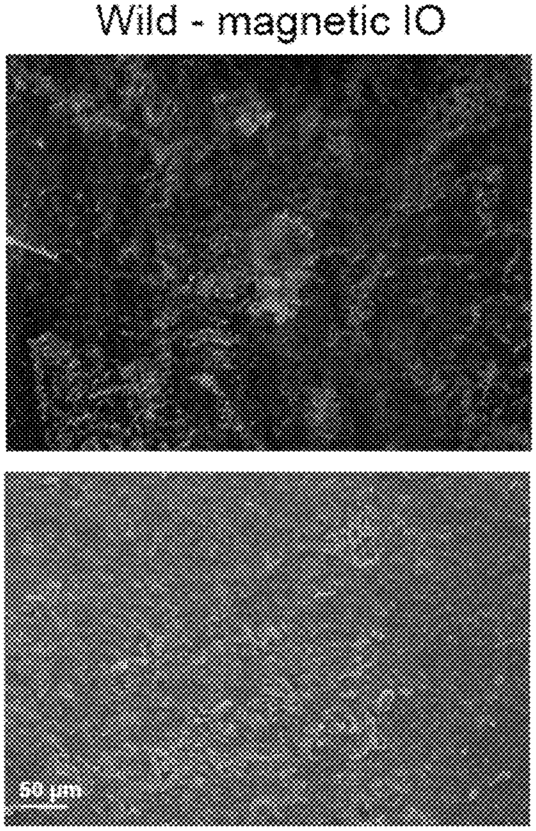
FIG. 44A1
Ag - magnetic IO
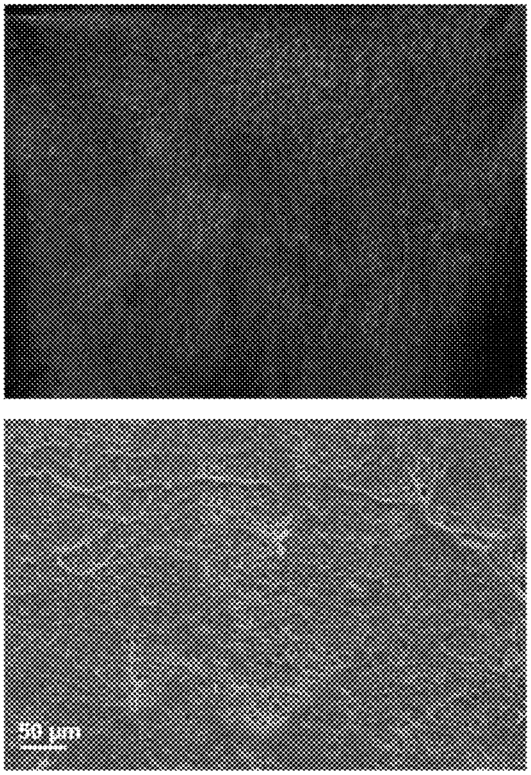
FIG. 44A2

Fe mapping
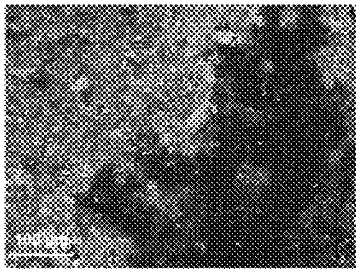
FIG. 44B1
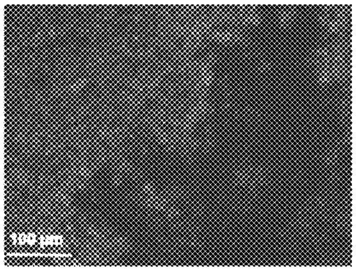
FIG. 44B2
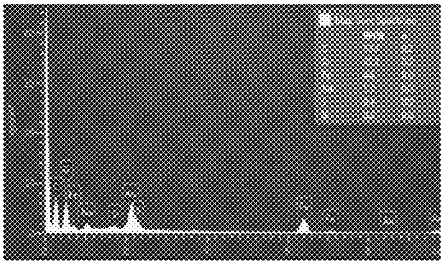
FIG. 44B3
Fe mapping
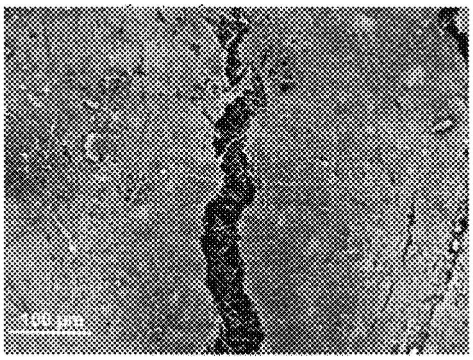
FIG. 44C1
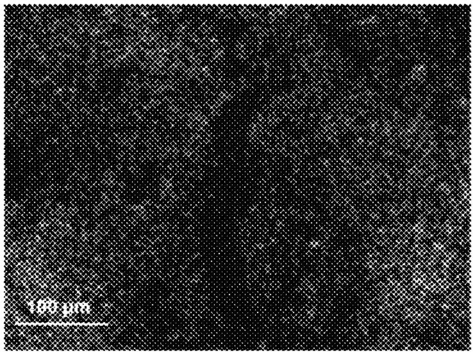
FIG. 44C2
Ag mapping
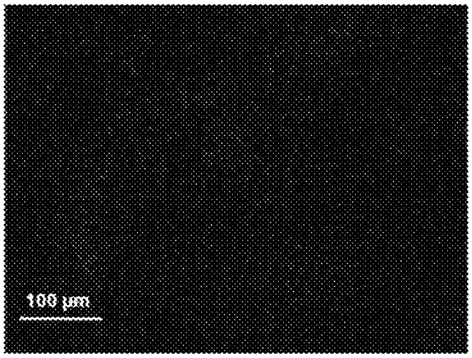
FIG. 44C3
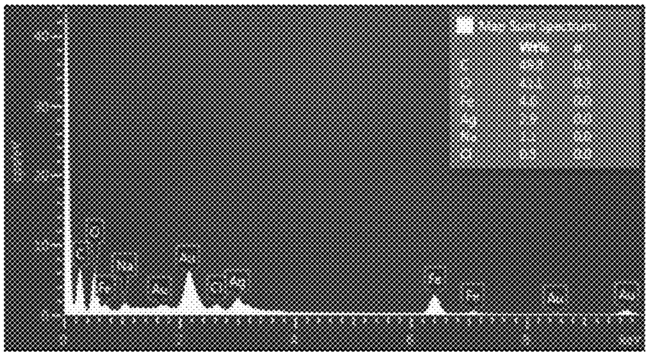
FIG. 44C4

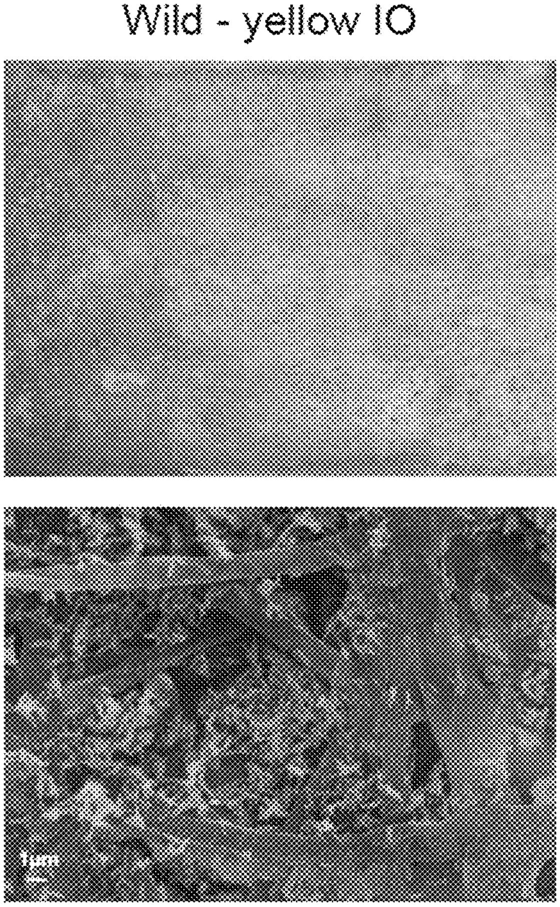
FIG. 45A1
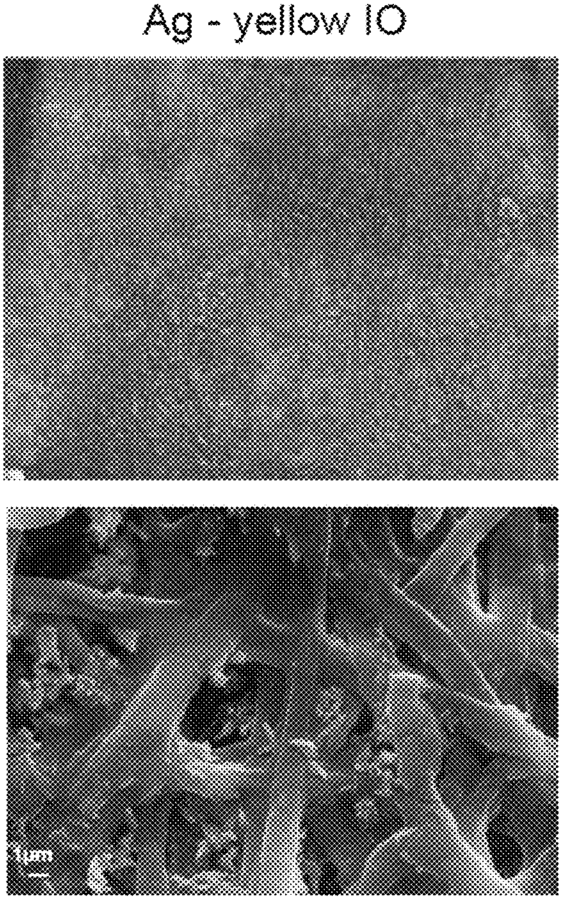
FIG. 45A2
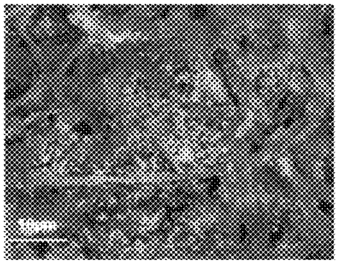
FIG. 45B1
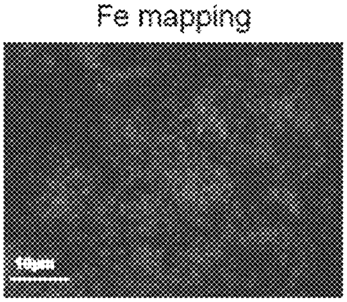
FIG. 45B2
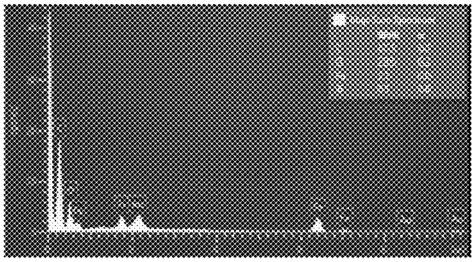
FIG. 45B3

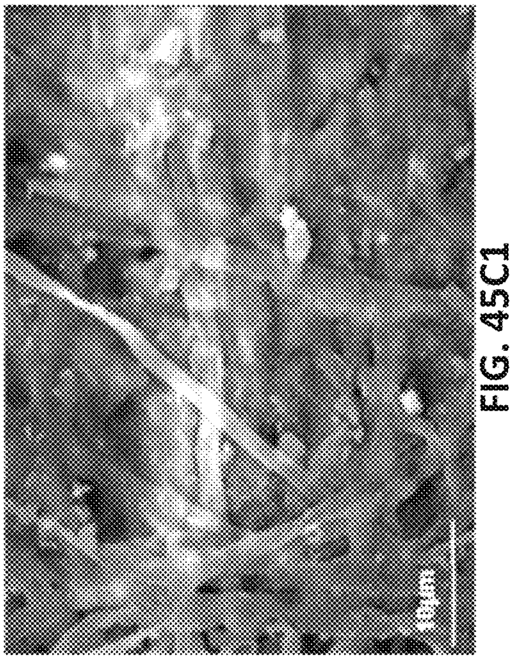
FIG. 45C1
Fe mapping
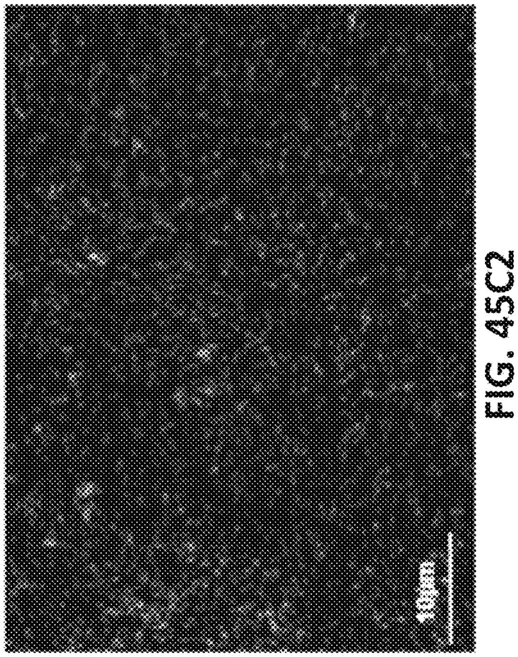
FIG. 45C2
Ag mapping
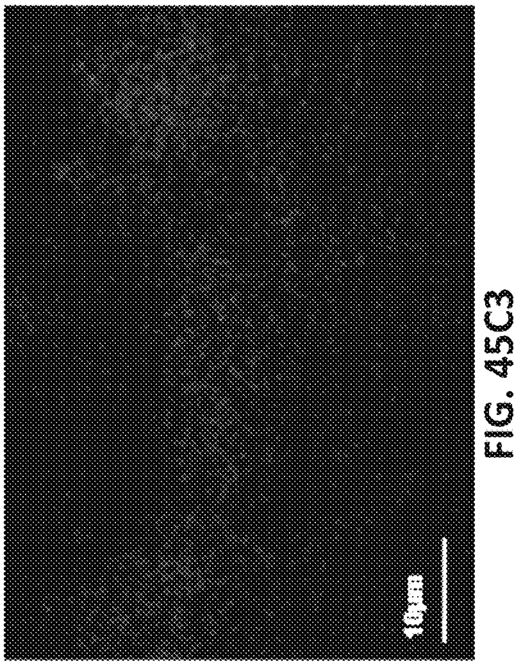
FIG. 45C3
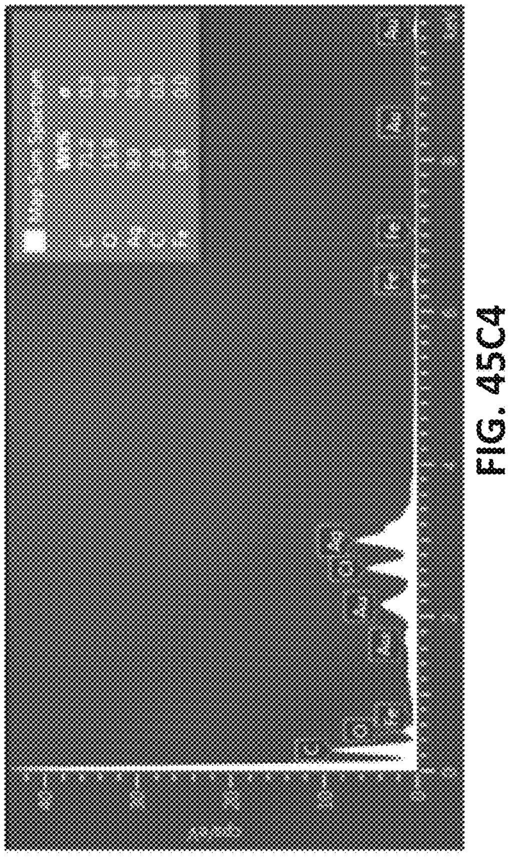
FIG. 45C4

Wild - red IO
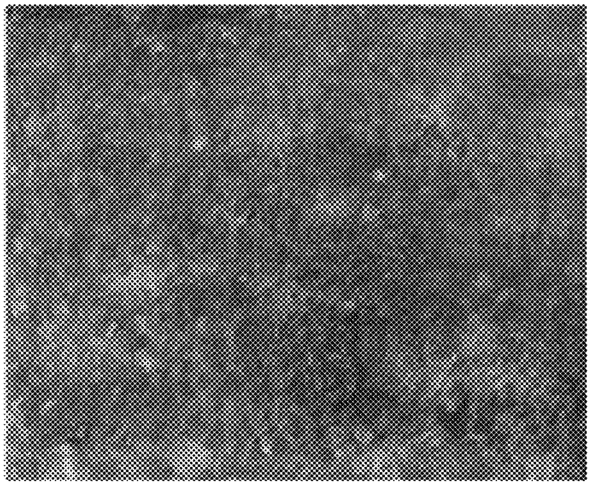
FIG. 46A1
Ag - red IO
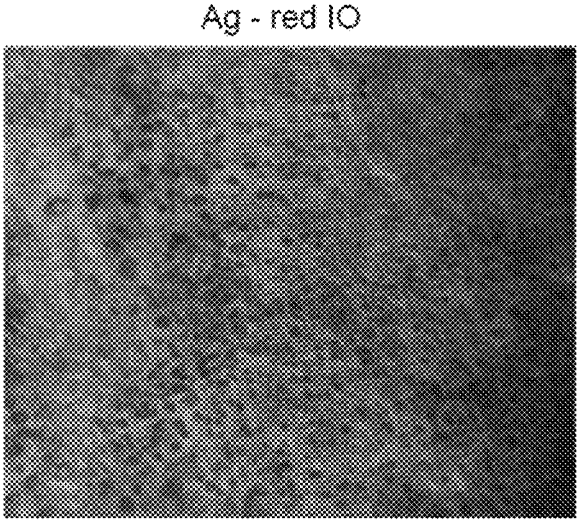
FIG. 46A2
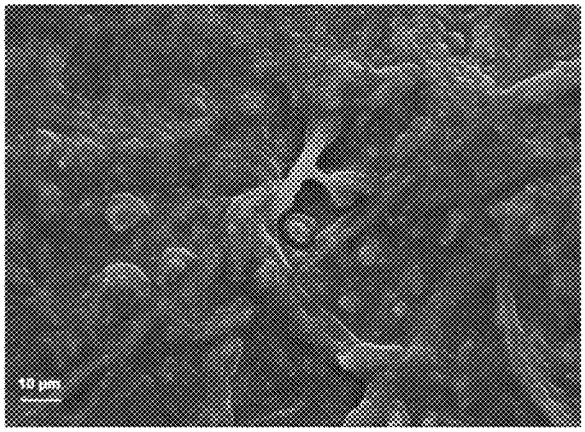
FIG. 46B1
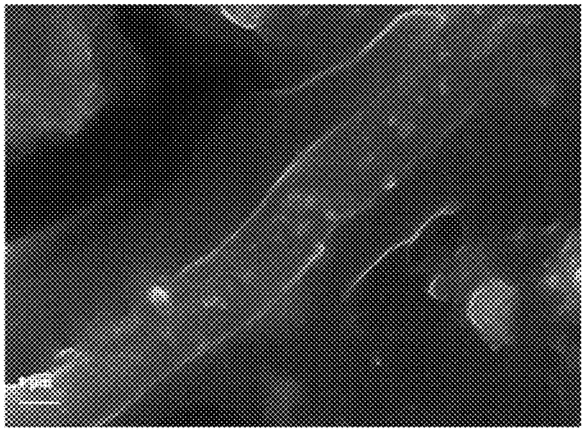
FIG. 46B2

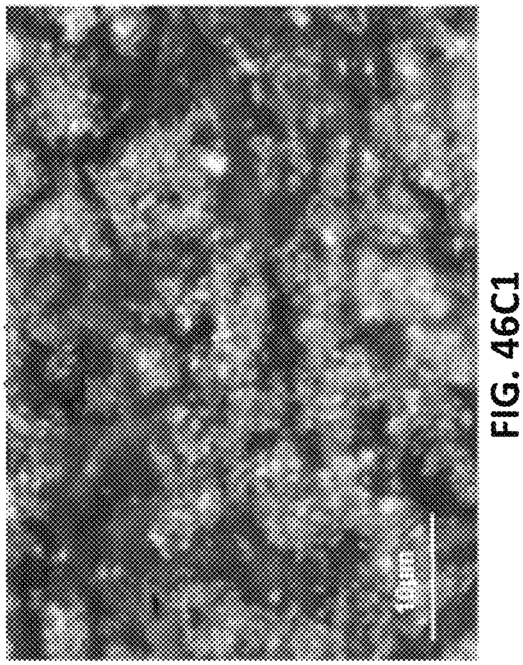
FIG. 46C1
Fe mapping
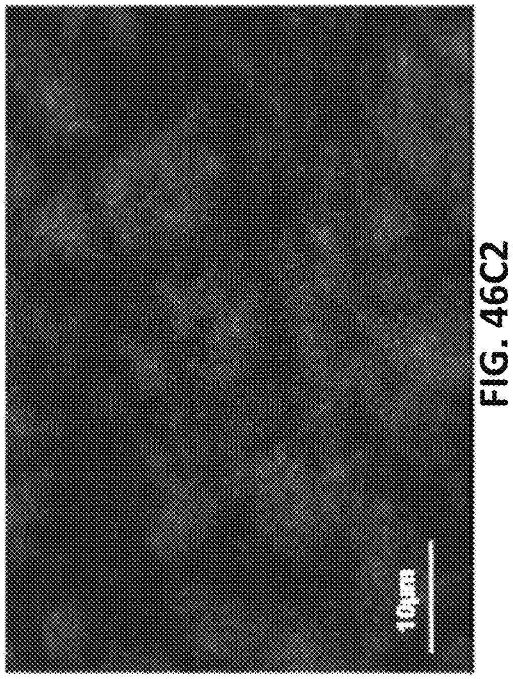
FIG. 46C2
Ag mapping
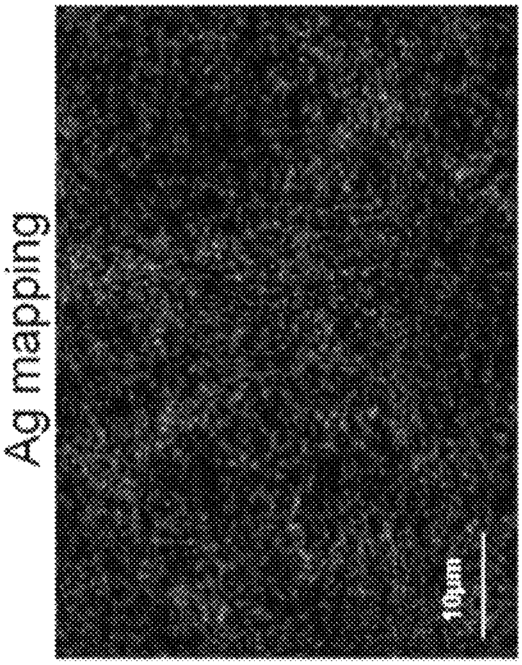
FIG. 46C3
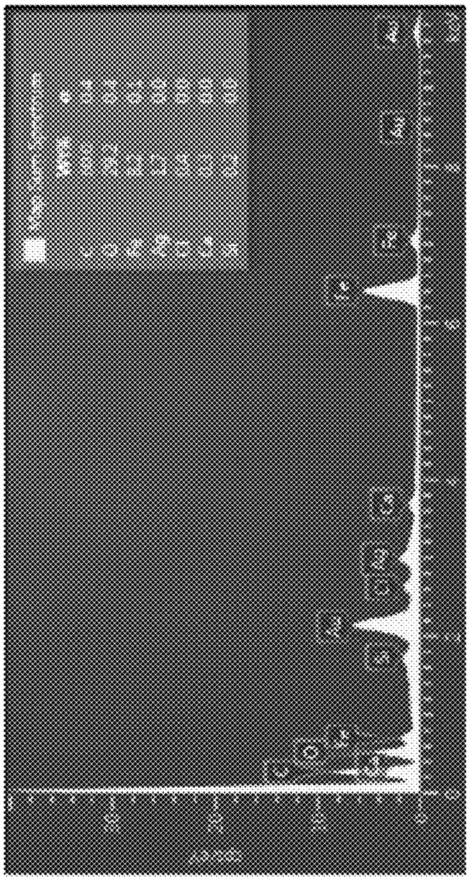
FIG. 46C4

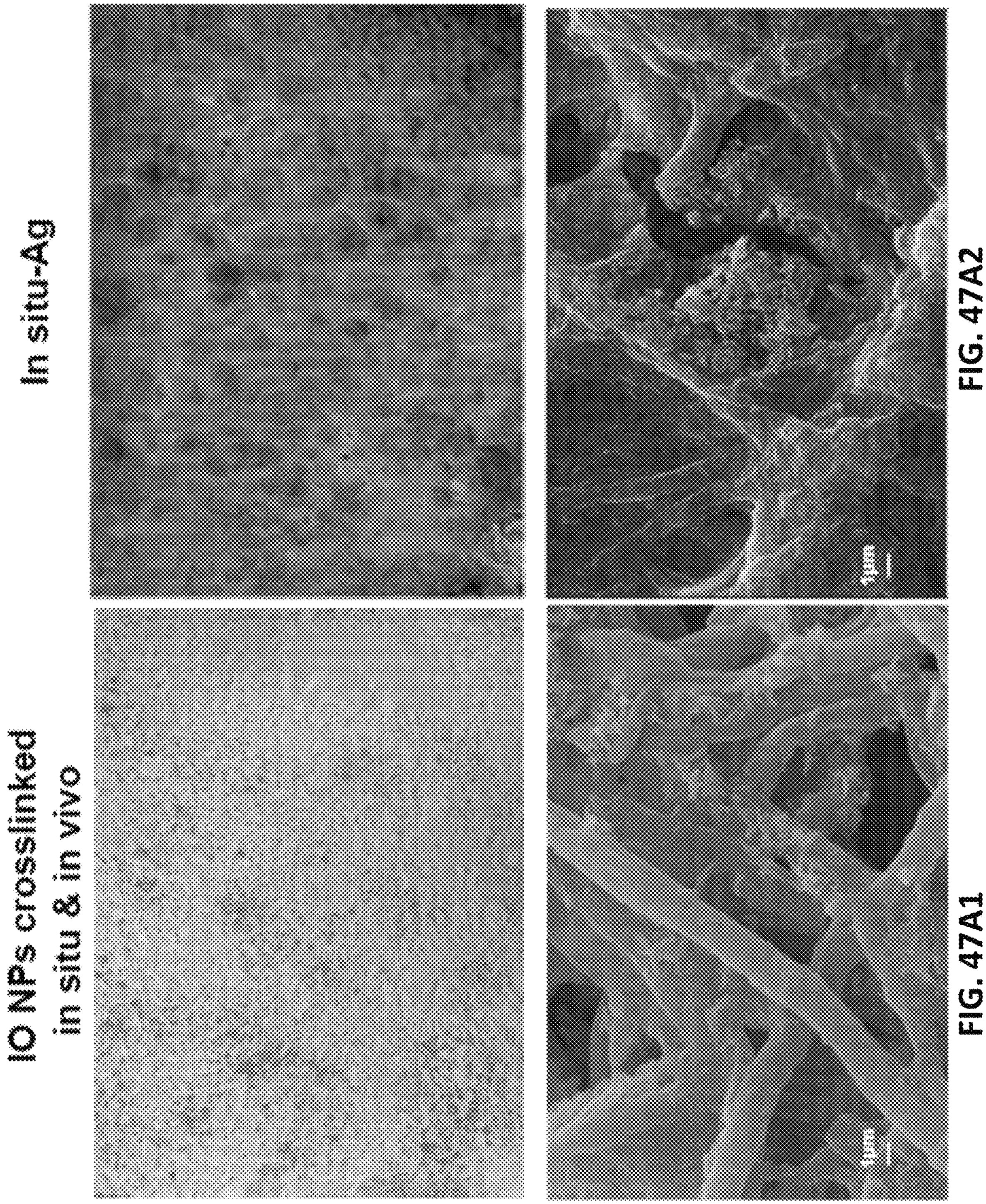
FIG. 47A1
FIG. 47A2

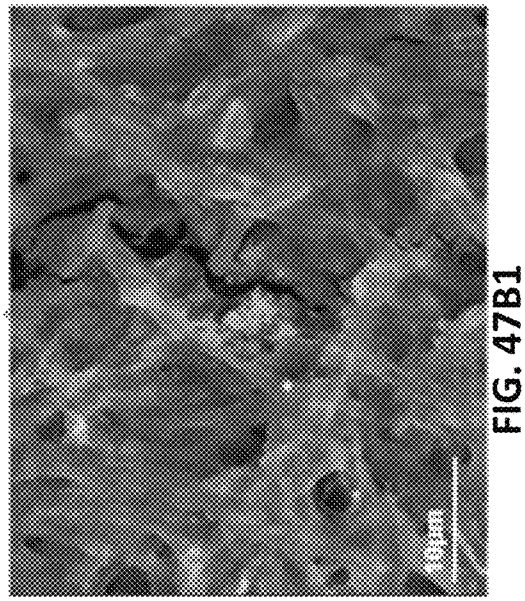
FIG. 47B1
Ag mapping
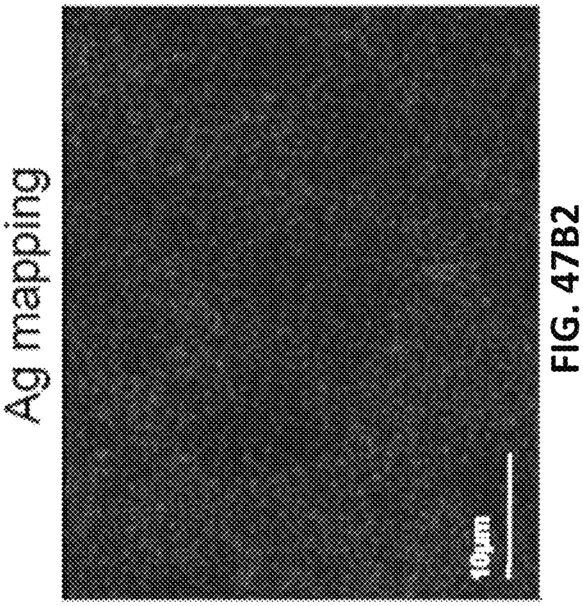
FIG. 47B2
Fe mapping
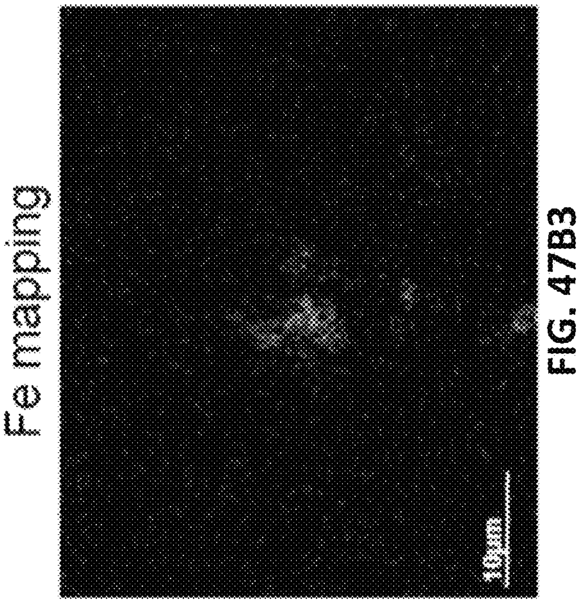
FIG. 47B3
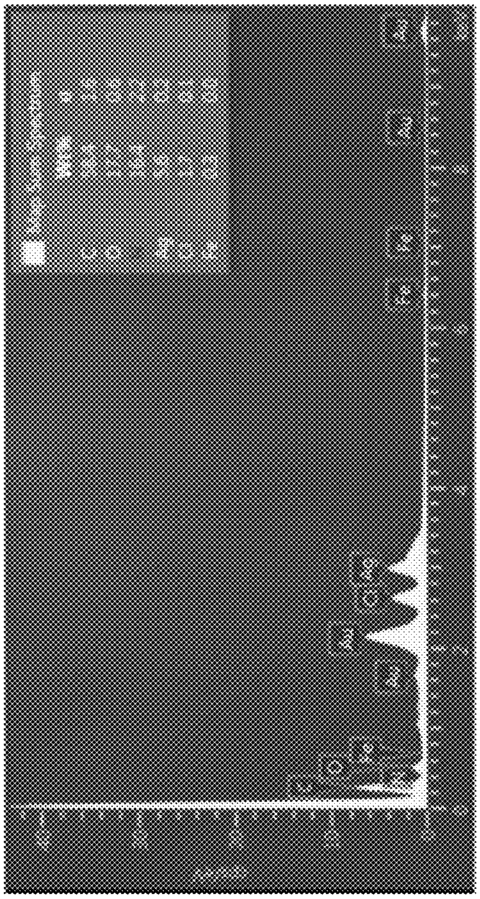
FIG. 47B4

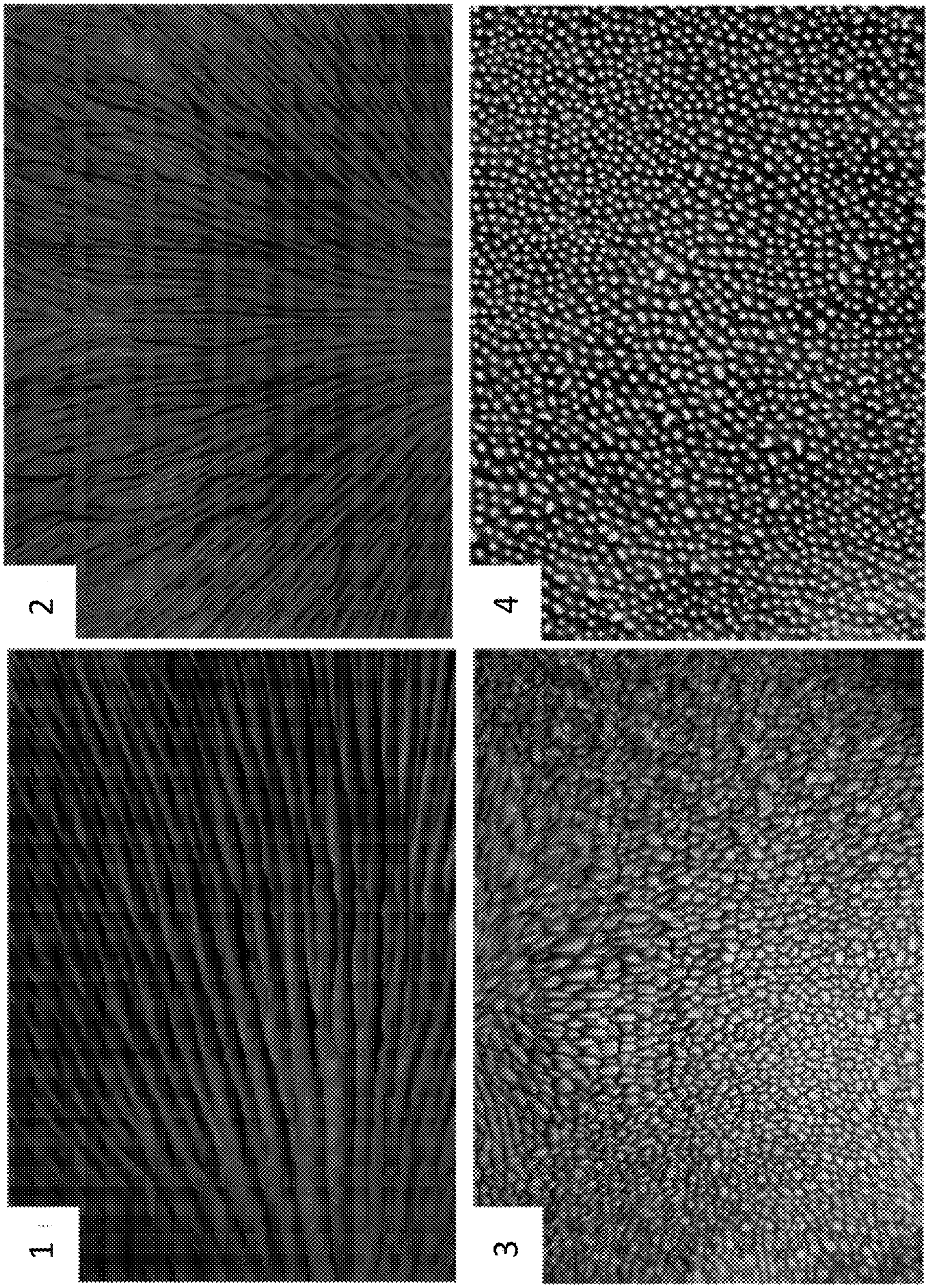
FIG. 48A1-48A4

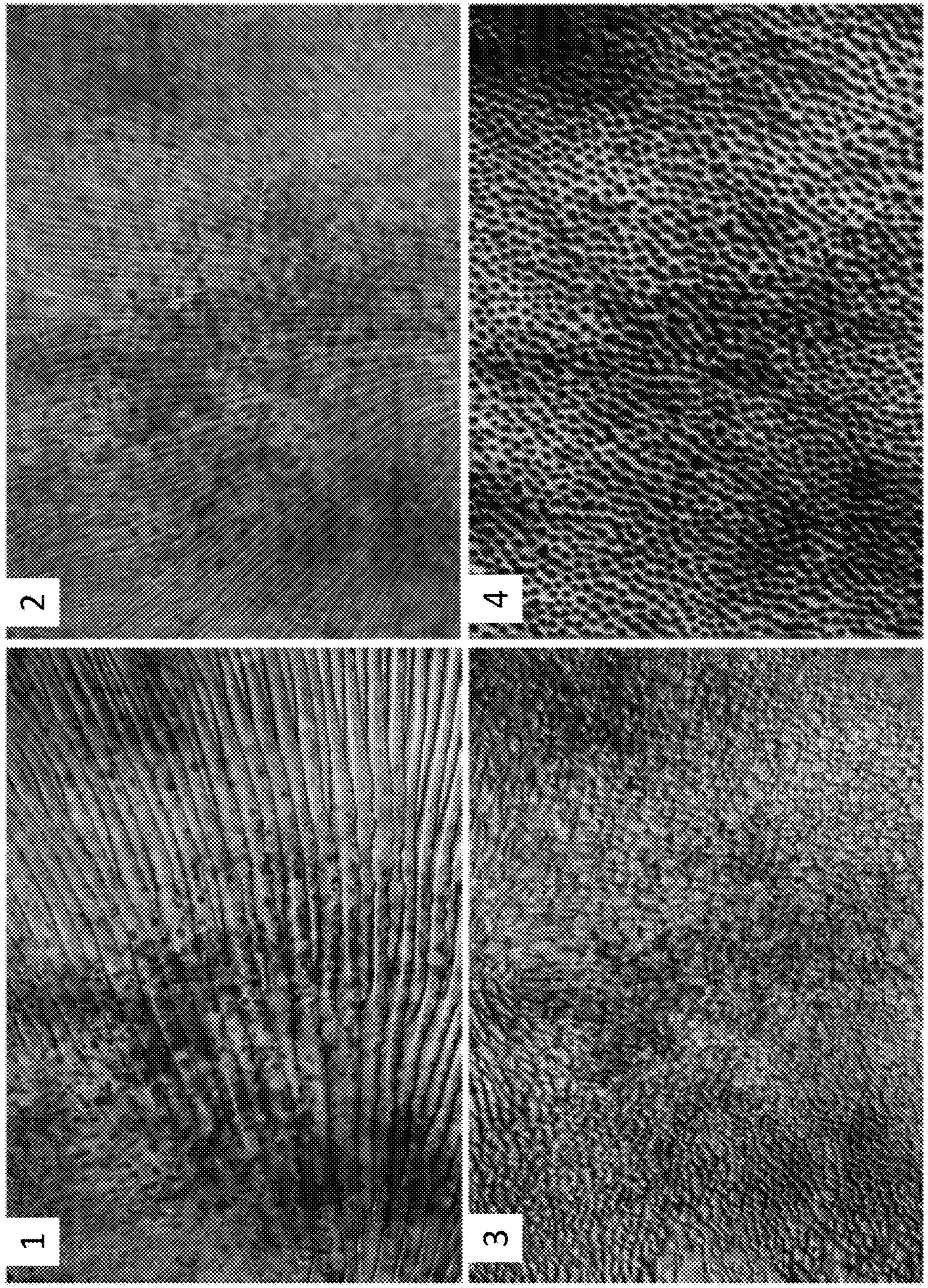
FIG. 48B1-48B4

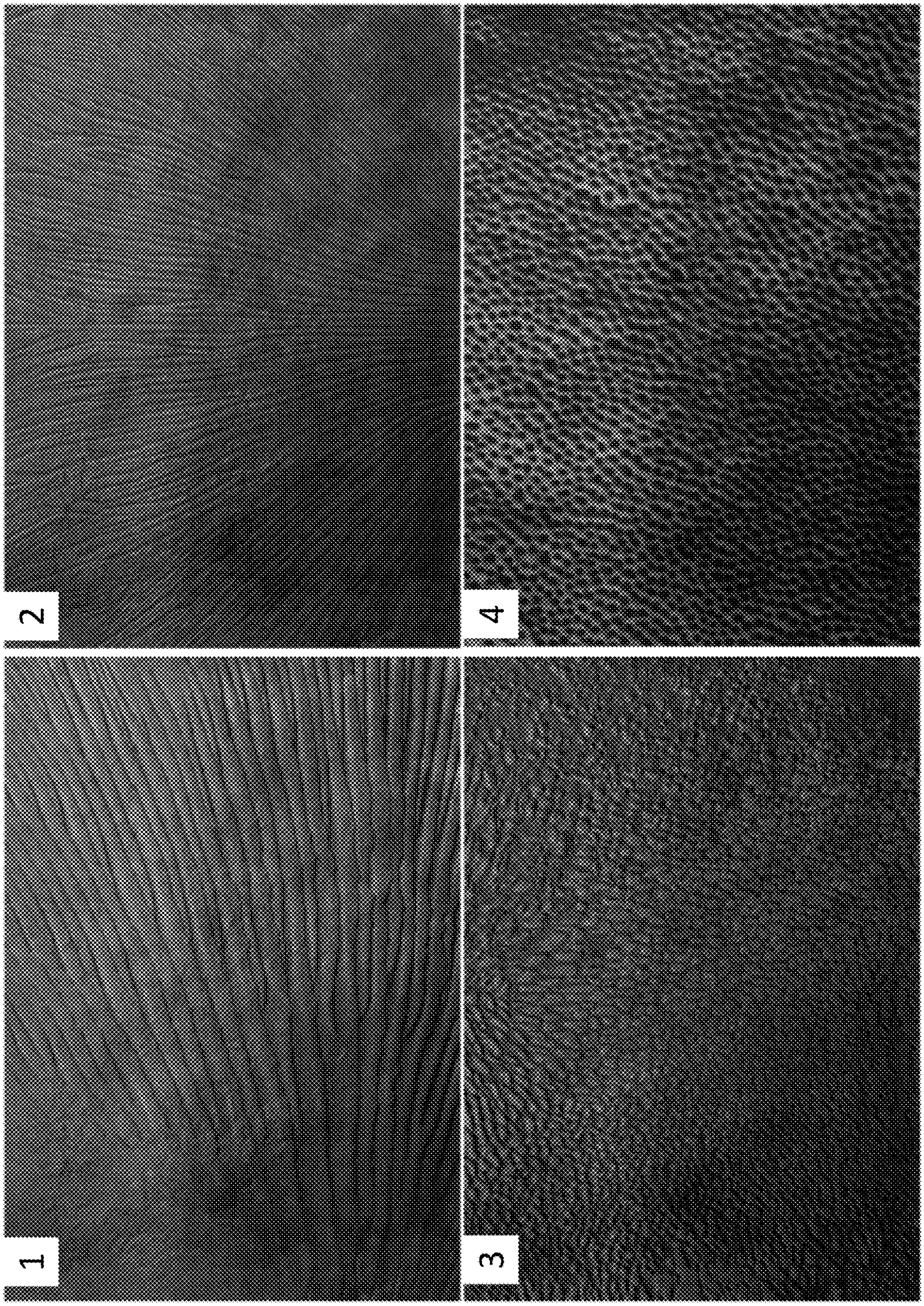
FIG. 48C1-48C4

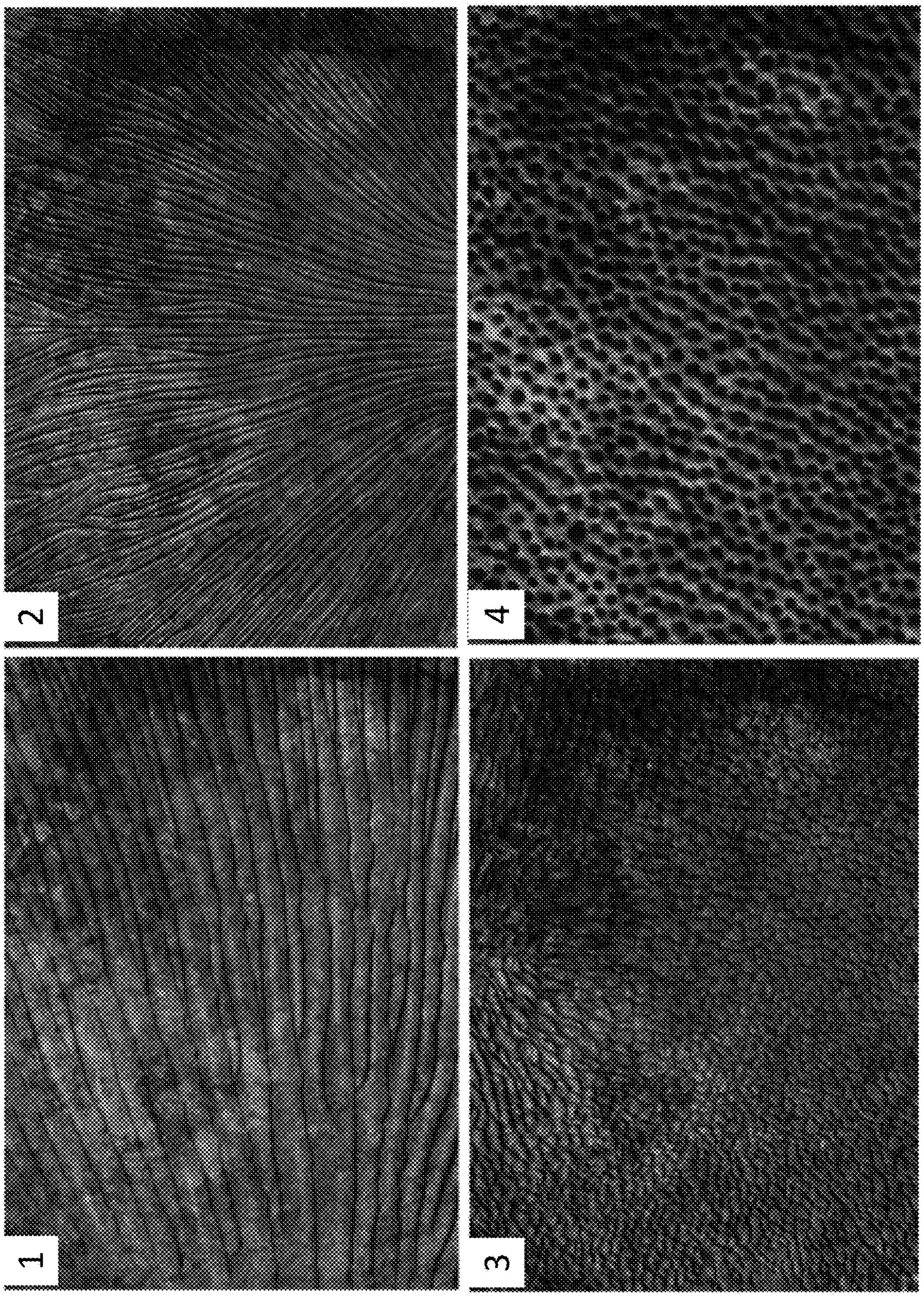
FIG. 48D1-48D4

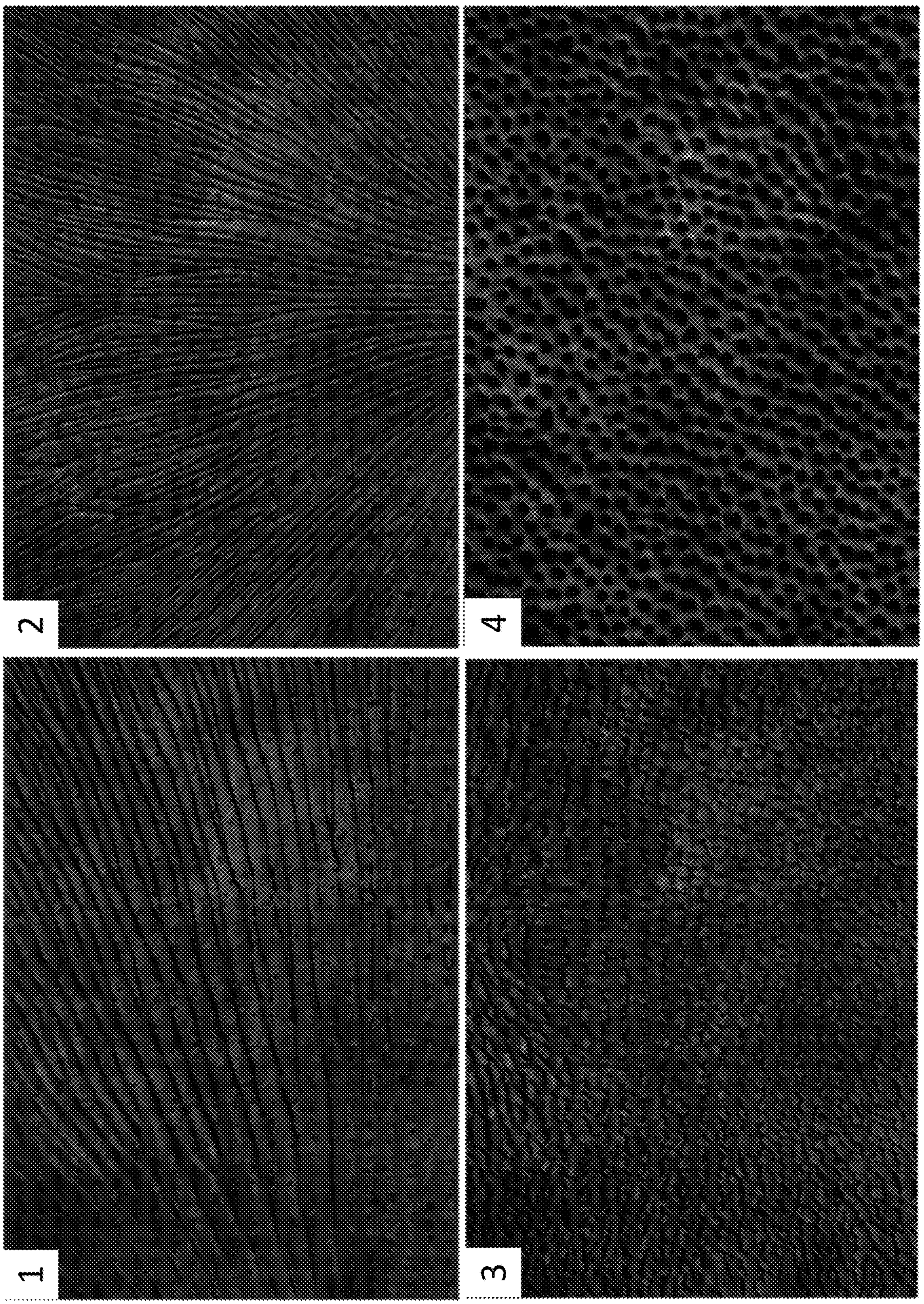
FIG. 48E1-48E4

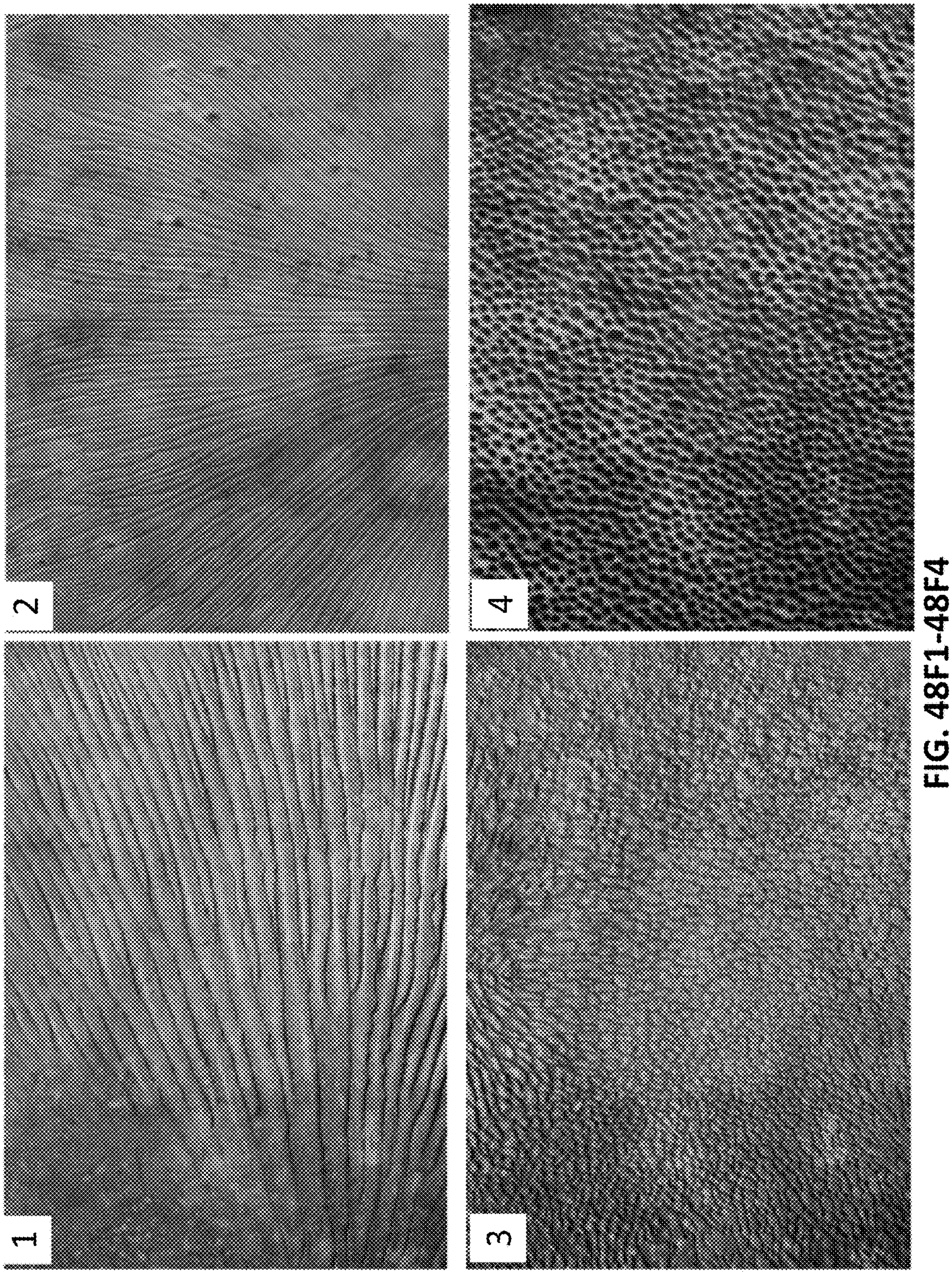
FIG. 48F1-48F4

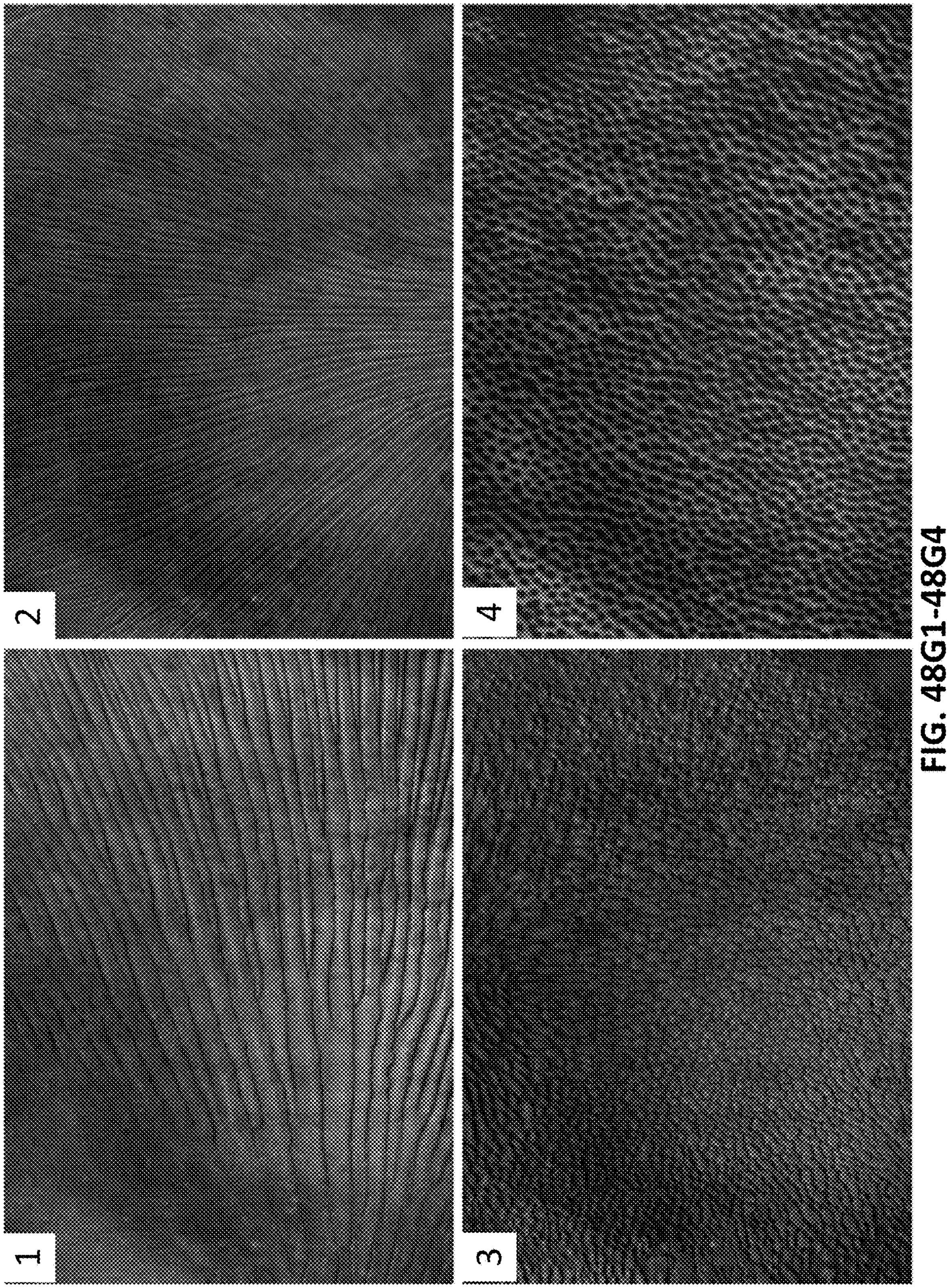
FIG. 48G1-48G4

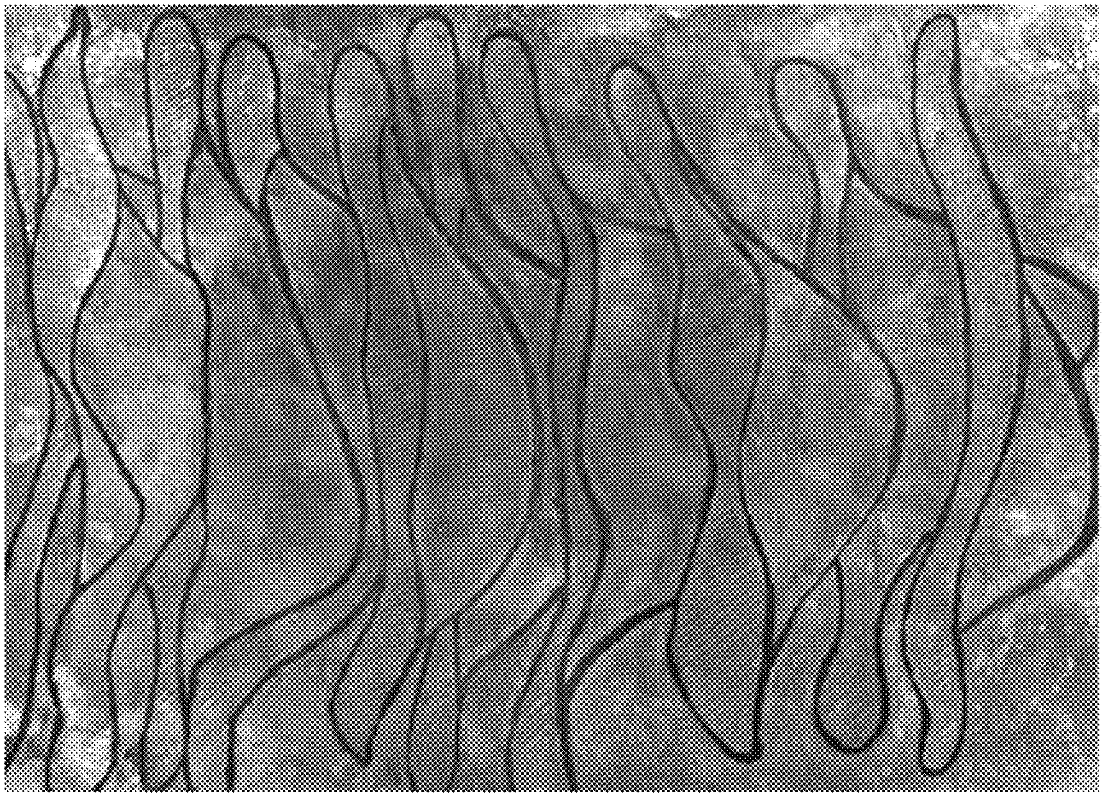
FIG. 49B2
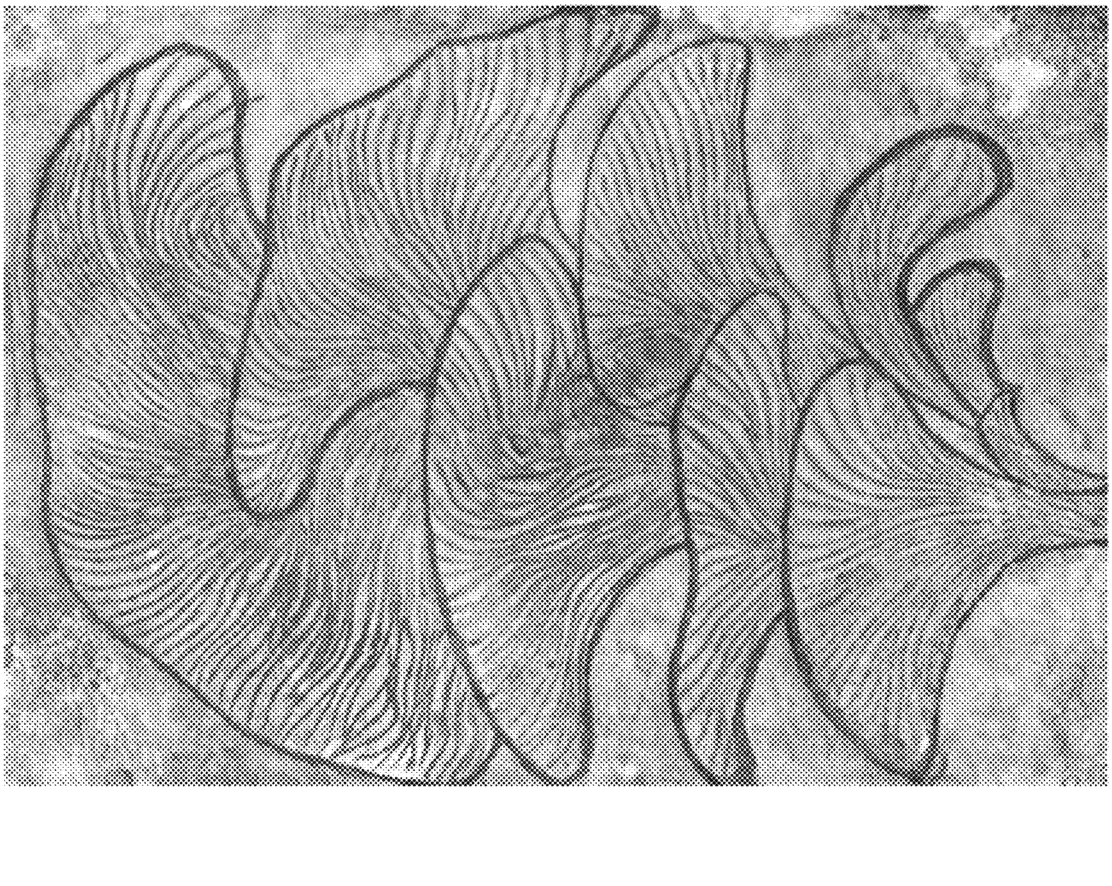
FIG. 49B1

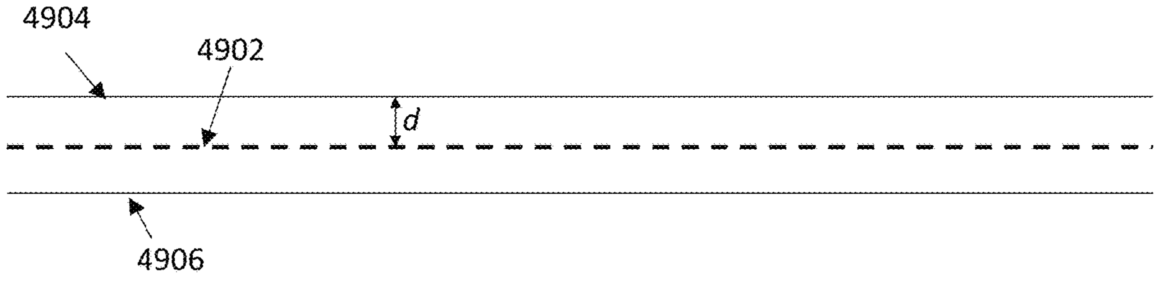
FIG. 49C1
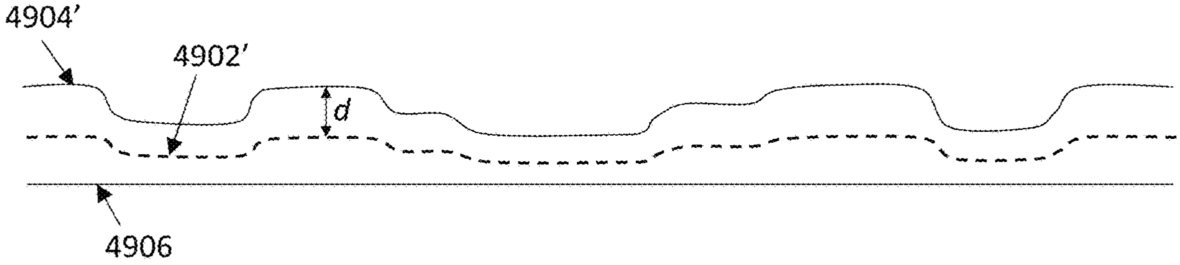
FIG. 49C2
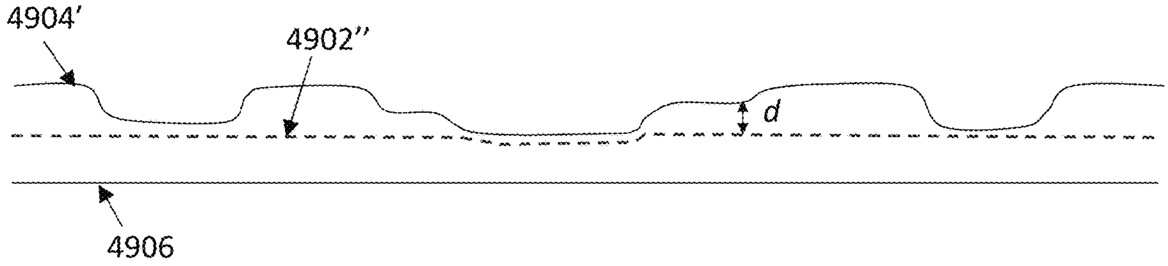
FIG. 49C3

Wild-magnetic IO

Ag-magnetic IO

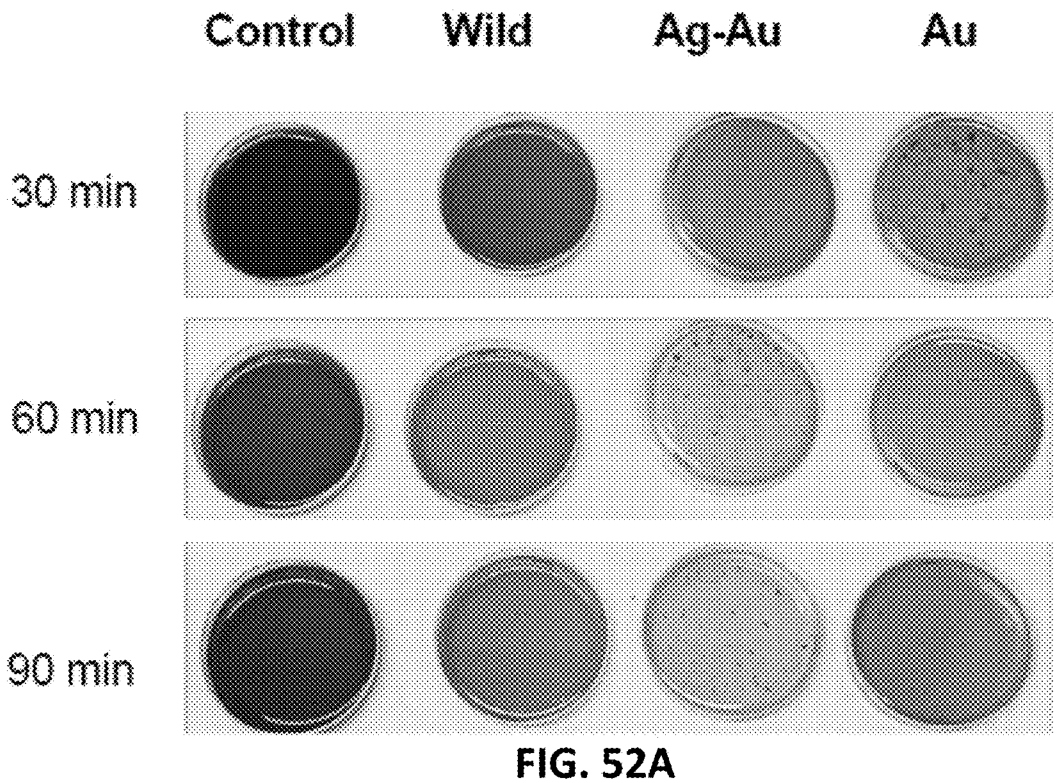
FIG. 52A
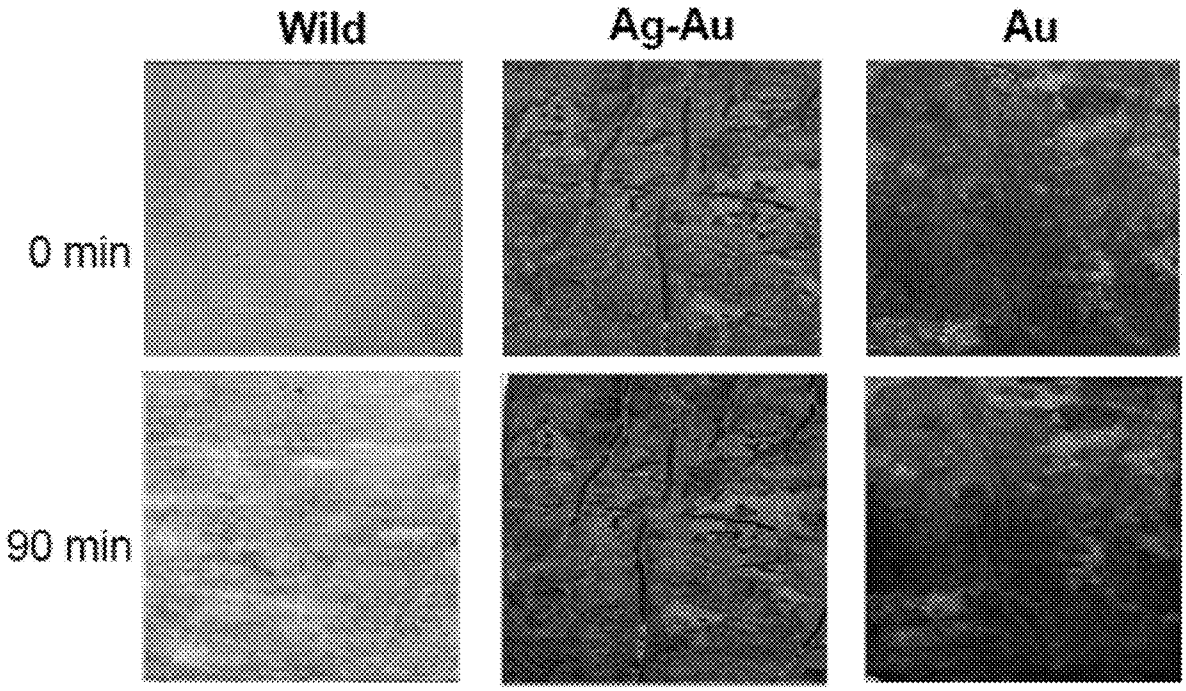
FIG. 52B1 FIG. 52B2 FIG. 52B3

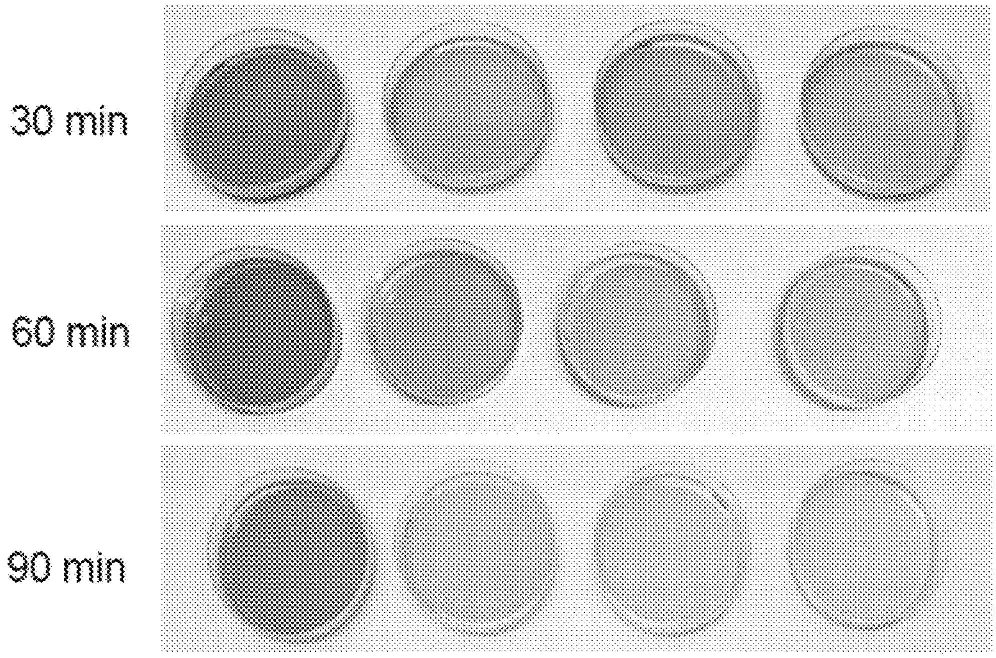
FIG. 53A
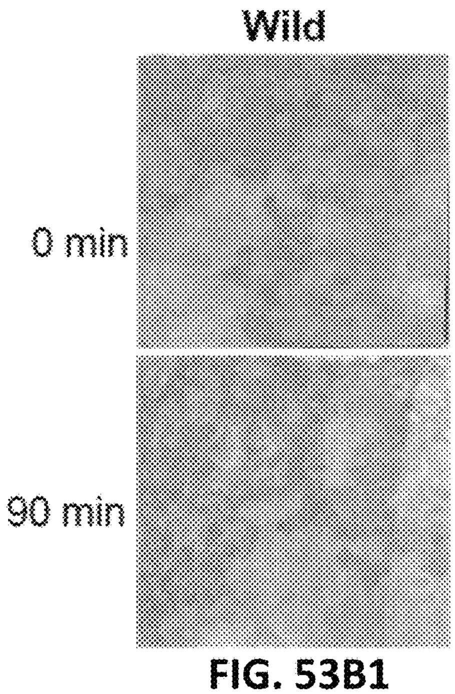
FIG. 53B1
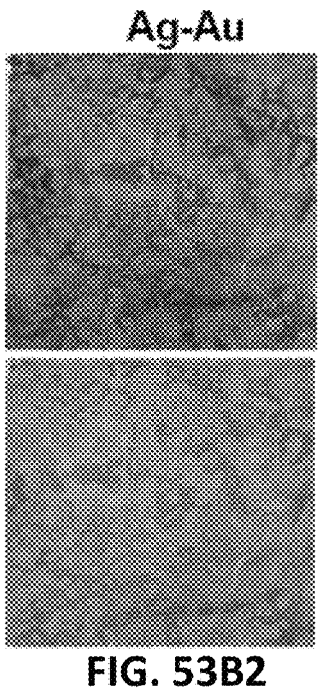
FIG. 53B2
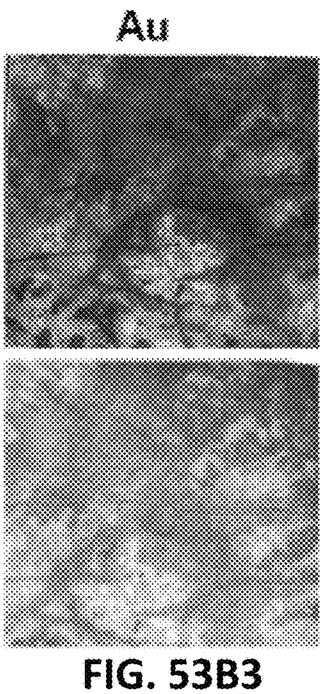
FIG. 53B3

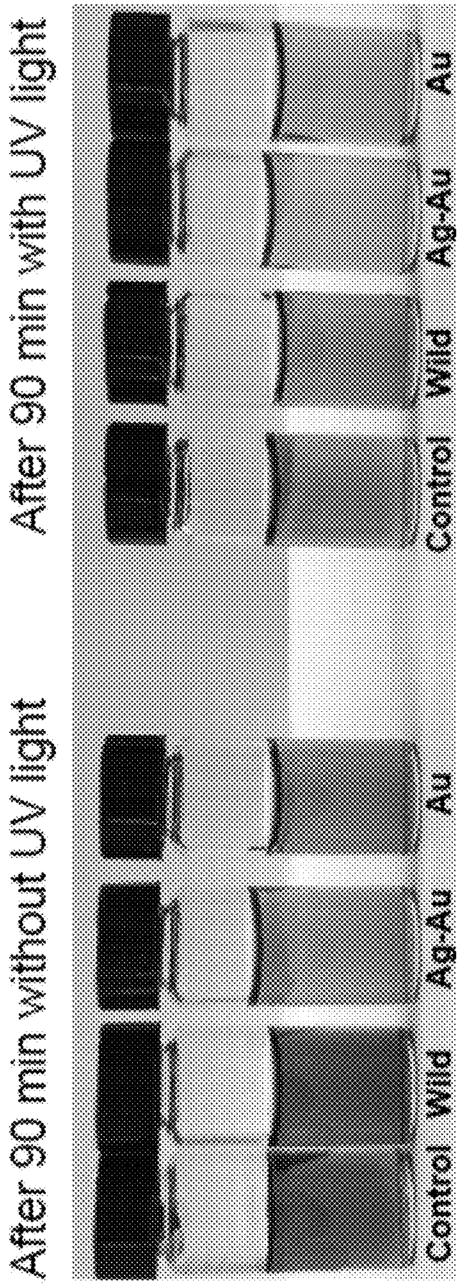
FIG. 54A
FIG. 54B
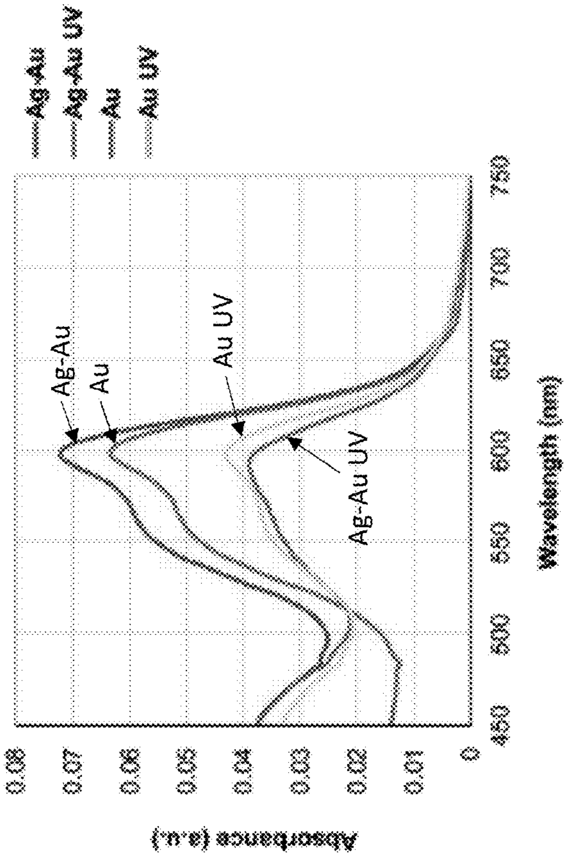
FIG. 54C

SEQUENCE LISTING

```
Sequence total quantity: 39
SEQ ID NO: 1            moltype = DNA  length = 20
FEATURE                 Location/Qualifiers
source                  1..20
                        mol_type = other DNA
                        organism = synthetic construct
SEQUENCE: 1
cgcaagtgat gtgtggtgtt                                                 20

SEQ ID NO: 2            moltype = DNA  length = 18
FEATURE                 Location/Qualifiers
source                  1..18
                        mol_type = other DNA
                        organism = synthetic construct
SEQUENCE: 2
gttccgcctc ttgtgacg                                                   18

SEQ ID NO: 3            moltype = DNA  length = 19
FEATURE                 Location/Qualifiers
source                  1..19
                        mol_type = other DNA
                        organism = synthetic construct
SEQUENCE: 3
ccttcccaac gacaagcag                                                  19

SEQ ID NO: 4            moltype = DNA  length = 20
FEATURE                 Location/Qualifiers
source                  1..20
                        mol_type = other DNA
                        organism = synthetic construct
SEQUENCE: 4
gaagttgggg gagatcttgg                                                 20

SEQ ID NO: 5            moltype = DNA  length = 20
FEATURE                 Location/Qualifiers
source                  1..20
                        mol_type = other DNA
                        organism = synthetic construct
SEQUENCE: 5
caagttcgcg gactacttcc                                                 20

SEQ ID NO: 6            moltype = DNA  length = 19
FEATURE                 Location/Qualifiers
source                  1..19
                        mol_type = other DNA
                        organism = synthetic construct
SEQUENCE: 6
atcaacgagc cgagcgtag                                                  19

SEQ ID NO: 7            moltype = DNA  length = 20
FEATURE                 Location/Qualifiers
source                  1..20
                        mol_type = other DNA
                        organism = synthetic construct
SEQUENCE: 7
ggaaggaaag aaggtcaagg                                                 20
```

```
SEQ ID NO: 8           moltype = DNA  length = 20
FEATURE                Location/Qualifiers
source                 1..20
                       mol_type = other DNA
                       organism = synthetic construct
SEQUENCE: 8
ccacggggaa cacaatcttg                                        20

SEQ ID NO: 9           moltype = DNA  length = 18
FEATURE                Location/Qualifiers
source                 1..18
                       mol_type = other DNA
                       organism = synthetic construct
SEQUENCE: 9
ctccgcaagg aagtccag                                          18

SEQ ID NO: 10          moltype = DNA  length = 19
FEATURE                Location/Qualifiers
source                 1..19
                       mol_type = other DNA
                       organism = synthetic construct
SEQUENCE: 10
ggtaaccgag ccaccatag                                         19

SEQ ID NO: 11          moltype = DNA  length = 17
FEATURE                Location/Qualifiers
source                 1..17
                       mol_type = other DNA
                       organism = synthetic construct
SEQUENCE: 11
acttaccggt cccaagg                                           17

SEQ ID NO: 12          moltype = DNA  length = 17
FEATURE                Location/Qualifiers
source                 1..17
                       mol_type = other DNA
                       organism = synthetic construct
SEQUENCE: 12
agcagtagag cagcgac                                           17

SEQ ID NO: 13          moltype = DNA  length = 22
FEATURE                Location/Qualifiers
source                 1..22
                       mol_type = other DNA
                       organism = synthetic construct
SEQUENCE: 13
gaattgggta cctgagttga at                                     22

SEQ ID NO: 14          moltype = DNA  length = 24
FEATURE                Location/Qualifiers
source                 1..24
                       mol_type = other DNA
                       organism = synthetic construct
SEQUENCE: 14
aagcttggtt gagaggatgg gatg                                   24

SEQ ID NO: 15          moltype = DNA  length = 1589
FEATURE                Location/Qualifiers
source                 1..1589
                       mol_type = other DNA
                       organism = synthetic construct
SEQUENCE: 15
cgccagaaaa catcgatatc gggcccgaat gaaccgcgac atgctcccaa gtgactggct  60
ggaaggtggc tccaccgcta ttctgtcaat gtcacttcca aggagccggc agatctatgc  120
acaagtattt gtgactggat tgtgagccgt aaatgtggat agcaccaaaa tgcgaggcca  180
ctatgtaaga aaacctttcg gtgggacctg ttgagagaat cggcgcttcc actcacgcct  240
cccttctgcc ggaacgacag taacaccaac ttagcacatt cacagctgag atttggagat  300
agaaggtcgc aaagatgtgc gaatcactgt gagggtggcc ggcttcatga gcttcagaag  360
tagtctccgc agcgcgggga gctagcttcg ttgcataacg gttgtgcgac atcccgcgga  420
ggatctacgt tgcgcaagat ggccccaacg ttggccgagg acggcacaag gcagcagtct  480
gcacataacg tacgttgtac gttgtacata tgccattggg cactcgcaag cgttccccac  540
aaacatacgg cttcgagacc ggggtaatgt ggtggcactt cgcatgcctc cgtgcacaga  600
tgcacacgtt cgactctaga gcagcccctt caaacgttca ccgcgaacaa ctaacgctgc  660
agctgactgg gcacgccgct ccttacgcac gctcggtagg gtcggtacga gagccgatga  720
aggggcggac attggggccg tcgggcgtgg tgggcaggtg acgcggagga agagacgttt  780
tgggtgtttg gcgagcacgc acctgcgtcg cgagcgtctg ggtaattgcg accgtcacca  840
agcatttctc gggggtacac atccgcctgg agaggctgtg gcatgggacg acatcgggca  900
gcttggtatt tgtcgcggcc agggcagcgg cgggggcgcc ctggagagat cgtggtccga  960
ccggcggctg aggcggggtc acaagacgga tggagagagg gagggcatgg accggccgag  1020
```

```
ggagagacac gtatgtcggg gaggggacat cggatcttct gaccctctca ccgcggaaag  1080
caatgatcgc gagggtattc ttgggtgggc caatccatcg cggaggaatg caagaaattg  1140
ttgggggcca aacgcaagac ccggacaggc gcacgcgagc ggcgtgcacg ggactcgtga  1200
gcgcgcgcac gggagtatgg caacacgaaa ggcggtgaga acagggccgt gctcgctgtg  1260
ctgcgtggtg agaaacgcgc tggttgcgac gtcctcggcc gacggagaat ggcatcggac  1320
gggtacgaag acgaggatgg gatgcaaacg ggaggaagga ttatcactcc gcccaggcaa  1380
ggacgggcgt ctgtgcgatt gtctagatct ggaccataac ccaaacgtta atgcagtctc  1440
ctccgcttga cgtatataaa atgccagggc ctccccattc cattcacttc tccctcttcc  1500
atctccccca tatcttcctc gcgcctctcc acactcacct cacctccgca tagcacacaa  1560
cgagcgcggt cacatccccc gacgcgacc                                   1589

SEQ ID NO: 16          moltype = DNA  length = 1023
FEATURE                Location/Qualifiers
source                 1..1023
                       mol_type = other DNA
                       organism = synthetic construct
SEQUENCE: 16
atgaagaagc ccgagctcac ggcgacgtcg gtcgagaagt tcctcatcga gaagttcgac  60
tcggtctcgg acctcatgca gctctcggag ggcgaggagt cgcgcgcgtt ctcgttcgac  120
gtcggcggcc gcggctacgt cctccgcgtc aactcgtgcg cggacggctt ctacaaggac  180
cgctacgtct accgccactt cgcgtcggcg gcgctcccca tccccgaggt cctcgacatc  240
ggcgagttct cggagtcgct cacgtactgc atctcgcgcc gcgcgcaggg cgtcacgctc  300
caggacctcc ccgagacgga gctccccgcg gtcctccagc ccgtcgcgga ggcgatggac  360
gcgatcgcgg cggcggacct ctcgcagacg tcgggcttcg gccccttcgg cccccagggc  420
atcggccagt acacgacgtg gcgcgacttc atctgcgcga tcgcggaccc ccacgtctac  480
cactggcaga cggtcatgga cgacacggtc tcggcgtcgg tcgcgcaggc gctcgacgag  540
ctcatgctct gggcggagga ctgccccgag gtccgccacc tcgtccacgc ggacttcggc  600
tcgaacaacg tcctcacgga caacggccgc atcacggcgg tcatcgactg gtcggaggcg  660
atgttcggcg actcgcagta cgaggtcgcg aacatcttct tctggcgccc ctggctcgcg  720
tgcatggagc agcagacgcg ctacttcgag cgccgccacc ccgagctcgc gggctcgccc  780
cgcctccgcg cgtacatgct ccgcatcggc ctcgaccagc tctaccagtc gctcgtcgac  840
ggcaacttcg acgacgcggc gtgggcgcag ggccgctgcg acgcgatcgt ccgctcgggc  900
gcgggcacgg tcggccgcac gcagatcgcg cgccgctcgg cggcggtctg gacggacggc  960
tgcgtcgagg tcctcgcgga ctcgggcaac cgccgcccct cgacgcgccc ccgcgcgaag  1020
aag                                                               1023

SEQ ID NO: 17          moltype = DNA  length = 723
FEATURE                Location/Qualifiers
source                 1..723
                       mol_type = other DNA
                       organism = synthetic construct
SEQUENCE: 17
atggtctcgt cgggcgagga catcttctcg ggcctcgtcc ccatcctcat cgagctcgag  60
ggcgacgtca acggccaccg cttctcggtc cgcggcgagg gctacggcga cgcgtcgaac  120
ggcaagctcg agatcaagtt catctgcacg acgggccgcc tccccgtccc ctggcccacg  180
ctcgtcacga cgctctcgta cggcgtccag tgcttcgcga agtaccccga gcacatgcgc  240
cagaacgact tcttcaagtc ggcgatgccc gacggctacg tccaggagcg cacgatctcg  300
ttcaaggagg acggcacgta caagacgcgc gcggaggtca agttcgaggg cgaggcgctc  360
gtcaaccgca tcgacctcaa gggcctcgag ttcaaggagg acggcaacat cctcggccac  420
aagctcgagt actcgttcaa ctcgcactac gtctacatca cggcggacaa gaaccgcaac  480
ggcctcgagg cgcagttccg catccgccac aacgtcgacg acggctcggt ccagctcgcg  540
gaccactacc agcagaacac gcccatcggc gagggccccg tcctcctccc cgagcagcac  600
tacctcacga cgaactcggt cctctcgaag gacccccagg agcgccgcga ccacatggtc  660
ctcgtcgagt tcgtcacggc ggcgggcctc tcgctcggca tggacgagct ctacaagtcg  720
tga                                                               723

SEQ ID NO: 18          moltype = DNA  length = 326
FEATURE                Location/Qualifiers
source                 1..326
                       mol_type = other DNA
                       organism = synthetic construct
SEQUENCE: 18
ggcgcagacg cacccgtcgg ccctcacgcg tcatagtcac acaaaagcta tcgggagact  60
cgtcgaattg aatacagtgt ggtaaaaggc aagaatcagc agtaaaccta atacggagcc  120
agccgctgct ccgctgtgta ccaagctccc atgtagaaga attgtatgat aatataaata  180
gtagattttc gtcatcgaga ttcattcgtt agattgtcag tgaggatgtc cgacatacaa  240
acgatcgaca ttgtatgtgc cgagggtcca acgttgtgca tatattgtgc tcactgctcg  300
tgcgctgaat ggaatcgaag ttcaca                                      326

SEQ ID NO: 19          moltype = DNA  length = 3703
FEATURE                Location/Qualifiers
source                 1..3703
                       mol_type = other DNA
                       organism = synthetic construct
SEQUENCE: 19
cgccagaaaa catcgatatc gggcccgaat gaaccgcgac atgctcccaa gtgactggct  60
ggaaggtggc tccaccgcta ttctgtcaat gtcacttcca aggagccggc agatctatgc  120
acaagtattt gtgactggat tgtgagccgt aaatgtggat agcaccaaaa tgcgaggcca  180
ctatgtaaga aaacctttcg gtgggacctg ttgagagaat cggcgcttcc actcacgcct  240
```

-continued

```
ccccttctgcc ggaacgacag taacaccaac ttagcacatt cacagctgag atttggagat  300
agaaggtcgc aaagatgtgc gaatcactgt gagggtggcc ggcttcatga gcttcagaag  360
tagtctccgc agcgcgggga gctagcttcg ttgcataacg gttgtgcgac atcccgcgga  420
ggatctacgt tgcgcaagat ggccccaacg ttggccgagg acggcacaag gcagcagtct  480
gcacataacg tacgttgtac gttgtacata tgccattggg cactcgcaag cgttccccac  540
aaacatacgg cttcgagacc ggggtaatgt ggtggcactt cgcatgcctc cgtgcacaga  600
tgcacacgtt cgactctaga gcagcccctt caaacgttca ccgcgaacaa ctaacgctgc  660
agctgactgg gcacgccgct ccttacgcac gctcggtagg gtcggtacga gagccgatga  720
aggggcggac attggggccg tcgggcgtgg tgggcaggtg acgcggagga agagacgttt  780
tgggtgtttg gcgagcacgc acctgcgtcg cgagcgtctg ggtaattgcg accgtcacca  840
agcatttctc gggggtacac atccgcctgg agaggctgtg gcatgggacg acatcgggca  900
gcttggtatt tgtcgcggcc agggcagcgg cgggggcgcc ctggagagat cgtggtccga  960
ccggcggctg aggcggggtc acaagacgga tggagagagg gagggcatgg accggccgag  1020
ggagagacac gtatgtcggg gaggggacat cggatcttct gaccctctca ccgcggaaag  1080
caatgatcgc gagggtattc ttgggtgggc caatccatcg cggaggaatg caagaaattg  1140
ttgggggcca aacgcaagac ccggacaggc gcacgcgagc ggcgtgcacg ggactcgtga  1200
gcgcgcgcac gggagtatgg caacacgaaa ggcggtgaga acagggccgt gctcgctgtg  1260
ctgcgtggtg agaaacgcgc tggttgcgac gtcctcggcc gacggagaat ggcatcggac  1320
gggtacgaag acgaggatgg gatgcaaacg ggaggaagga ttatcactcc gcccaggcaa  1380
ggacgggcgt ctgtgcgatt gtctagatct ggaccataac ccaaacgtta atgcagtctc  1440
ctccgcttga cgtatataaa atgccagggc ctccccattc cattcacttc tccctcttcc  1500
atctccccca tatcttcctc gcgcctctcc acactcacct cacctccgca tagcacacaa  1560
cgagcgcggt cacatccccc gacgcgacca ctagtatgaa gaagcccgag ctcacggcga  1620
cgtcggtcga gaagttcctc atcgagaagt tcgactcggt ctcggacctc atgcagctct  1680
cggagggcga ggagtcgcgc gcgttctcgt tcgacgtcgg cggccgcggc tacgtcctcc  1740
gcgtcaactc gtgcgcggac ggcttctaca aggaccgcta cgtctaccgc cacttcgcgt  1800
cggcggcgct ccccatcccc gaggtcctcg acatcggcga gttctcggag tcgctcacgt  1860
actgcatctc gcgccgcgcg cagggcgtca cgctccagga cctccccgag acggagctcc  1920
ccgcggtcct ccagcccgtc gcggaggcga tggacgcgat cgcggcggcg gacctctcgc  1980
agacgtcggg cttcggcccc ttcggccccc agggcatcgg ccagtacacg acgtggcgcg  2040
acttcatctg cgcgatcgcg gacccccacg tctaccactg gcagacggtc atggacgaca  2100
cggtctcggc gtcggtcgcg caggcgctcg acgagctcat gctctgggcg gaggactgcc  2160
ccgaggtccg ccacctcgtc cacgcggact tcggctcgaa caacgtcctc acggacaacg  2220
gccgcatcac ggcggtcatc gactggtcgg aggcgatgtt cggcgactcg cagtacgagg  2280
tcgcgaacat cttcttctgg cgcccctggc tcgcgtgcat ggagcagcag acgcgctact  2340
tcgagcgccg ccaccccgag ctcgcgggct cgccccgcct ccgcgcgtac atgctccgca  2400
tcggcctcga ccagctctac cagtcgctcg tcgacggcaa cttcgacgac gcggcgtggg  2460
cgcagggccg ctgcgacgcg atcgtccgct cgggcgcggg cacggtcggc cgcacgcaga  2520
tcgcgcgccg ctcggcggcg gtctggacgg acggctgcgt cgaggtcctc gcggactcgg  2580
gcaaccgccg cccctcgacg cgcccccgcg cgaagaagga attcggcggt ggcggtggcg  2640
gtggcggtat ggtctcgtcg ggcgaggaca tcttctcggg cctcgtcccc atcctcatcg  2700
agctcgaggg cgacgtcaac ggccaccgct tctcggtccg cggcgagggc tacggcgacg  2760
cgtcgaacgg caagctcgag atcaagttca tctgcacgac gggccgcctc cccgtcccct  2820
ggcccacgct cgtcacgacg ctctcgtacg gcgtccagtg cttcgcgaag taccccgagc  2880
acatgcgcca gaacgacttc ttcaagtcgg cgatgcccga cggctacgtc caggagcgca  2940
cgatctcgtt caaggaggac ggcacgtaca agacgcgcgc ggaggtcaag ttcgagggcg  3000
aggcgctcgt caaccgcatc gacctcaagg gcctcgagtt caaggaggac ggcaacatcc  3060
tcggccacaa gctcgagtac tcgttcaact cgcactacgt ctacatcacg gcggacaaga  3120
accgcaacgg cctcgaggcg cagttccgca tccgccacaa cgtcgacgac ggctcggtcc  3180
agctcgcgga ccactaccag cagaacacgc ccatcggcga gggccccgtc ctcctccccg  3240
agcagcacta cctcacgacg aactcggtcc tctcgaagga cccccaggag cgccgcgacc  3300
acatggtcct cgtcgagttc gtcacggcgg cgggcctctc gctcggcatg gacgagctct  3360
acaagtcgtg aggatccggc gcagacgcac ccgtcggccc tcacgcgtca tagtcacaca  3420
aaagctatcg ggagactcgt cgaattgaat acagtgtggt aaaaggcaag aatcagcagt  3480
aaacctaata cggagccagc cgctgctccg ctgtgtacca agctcccatg tagaagaatt  3540
gtatgataat ataaatagta gattttcgtc atcgagattc attcgttaga ttgtcagtga  3600
ggatgtccga catacaaacg atcgacattg tatgtgccga gggtccaacg ttgtgcatat  3660
attgtgctca ctgctcgtgc gctgaatgga atcgaagttc aca                    3703
```

```
SEQ ID NO: 20          moltype = AA  length = 591
FEATURE                Location/Qualifiers
source                 1..591
                       mol_type = protein
                       organism = synthetic construct
SEQUENCE: 20
MKKPELTATS VEKFLIEKFD SVSDLMQLSE GEESRAFSFD VGGRGYVLRV NSCADGFYKD  60
RYVYRHFASA ALPIPEVLDI GEFSESLTYC ISRRAQGVTL QDLPETELPA VLQPVAEAMD  120
AIAAADLSQT SGFGPFGPQG IGQYTTWRDF ICAIADPHVY HWQTVMDDTV SASVAQALDE  180
LMLWAEDCPE VRHLVHADFG SNNVLTDNGR ITAVIDWSEA MFGDSQYEVA NIFFWRPWLA  240
CMEQQTRYFE RRHPELAGSP RLRAYMLRIG LDQLYQSLVD GNFDDAAWAQ GRCDAIVRSG  300
AGTVGRTQIA RRSAAVWTDG CVEVLADSGN RRPSTRPRAK KEFGGGGGGG GMVSSGEDIF  360
SGLVPILIEL EGDVNGHRFS VRGEGYGDAS NGKLEIKFIC TTGRLPVPWP TLVTTLSYGV  420
QCFAKYPEHM RQNDFFKSAM PDGYVQERTI SFKEDGTYKT RAEVKFEGEA LVNRIDLKGL  480
EFKEDGNILG HKLEYSFNSH YVYITADKNR NGLEAQFRIR HNVDDGSVQL ADHYQQNTPI  540
GEGPVLLPEQ HYLTTNSVLS KDPQERRDHM VLVEFVTAAG LSLGMDELYK S           591
```

```
SEQ ID NO: 21          moltype = DNA  length = 1329
FEATURE                Location/Qualifiers
source                 1..1329
```

```
                         mol_type = other DNA
                         organism = synthetic construct
SEQUENCE: 21
tgagttgaat ggtattatgg ttgcgcatat tatgttgggt ttatccgtcg atacttcgaa  60
gatatatgtg aacgcttgga atggagagca ctgaggatgc aatttcgatg ctacggcatc  120
acaacgatat gcggacgcaa ctgctatagg ggagacacat tccctagaca gtcaacacat  180
cagcggtgcc ataagtagtc aagcaacata tgcgatttca tgacgtacgg tcgttgaaag  240
tgattcacgg ataccaatgt gcatgtgaag gttcagggcc tgggagagtt agtagtctag  300
tctgtctgaa gagctgacct ggcctacaaa tggctgtcat gattgacgta ggaggaggct  360
agtacctaca gtgaacgagg caccggaaga gcagagctat aagtgggata tgacggatgg  420
aaggaattat actgggccac tcacgctcga cgcatccaag ccgtgtattt cgagaggccg  480
tctccgtctc cagcggcagc ggacacaagc acacgaacgg cgtctgattg gtggagtggg  540
attagacgct cgtatgacgt cgtgggattg gagagcagac acggagaacg gatcttgctc  600
tcagcattcg agtcagaaaa aacatgggga gcatatgtcg cgatatgtac gaacagcgac  660
ctgtgcattg ctgacgagga cgagacaagt cgctgacaga gagggcgcgt acggatctac  720
tgtgtcctat tagcagtaca cttgctagaa ggtgccgtcg agacgcgcga acggaataag  780
gcgattggga gggcgcgtcg cgtccgagtc gcgtccagac cagacccccg tcaattcgga  840
gaacgggcct tcggcagcct tgcgcgtaca ttctctctgg taatacaccc cttgcagccc  900
ttcgcgccgt tcgtcctatc gattgatggc cgttggcgag agagagagag gcagtgtgtg  960
ccccaaaggg cgtcgcgact ggtggggaga cgcgtcgtac gctcctcctc aaagcaacca  1020
atcccgggcg ggtaaattct ggatcggtcg atggctgcgt atcgcccgca cgttcatccc  1080
tttcgcccga cggtcaccgc attccgtaca gcgcgctgtg ccctccgtat ggatttgtaa  1140
cgtgttcggt ctcattatga acgtctcgcc gtgggcaaat acgccgaaga atgtggagag  1200
agggaggaga gtaggagagg aaagaggcgc caggagagga cgaggacgag acgacgcggc  1260
gatcgaacat ctgagatgag ataacaatca tccgcccctt ataaaccctc ctcctctccc  1320
tcctccttc                                                          1329

SEQ ID NO: 22            moltype = DNA  length = 1026
FEATURE                  Location/Qualifiers
source                   1..1026
                         mol_type = other DNA
                         organism = synthetic construct
SEQUENCE: 22
atgaagaagc ccgagctcac ggcgacgtcg gtcgagaagt tcctcatcga gaagttcgac  60
tcggtctcgg acctcatgca gctctcggag ggcgaggagt cgcgcgcgtt ctcgttcgac  120
gtcggcggcc gcggctacgt cctccgcgtc aactcgtgcg cggacggctt ctacaaggac  180
cgctacgtct accgccactt cgcgtcggcg gcgctcccca tccccgaggt cctcgacatc  240
ggcgagttct cggagtcgct cacgtactgc atctcgcgcc gcgcgcaggg cgtcacgctc  300
caggacctcc ccgagacgga gctccccgcg gtcctccagc ccgtcgcgga ggcgatggac  360
gcgatcgcgg cggcggacct ctcgcagacg tcgggcttcg gccccttcgg cccccagggc  420
atcggccagt acacgacgtg gcgcgacttc atctgcgcga tcgcggaccc ccacgtctac  480
cactggcaga cggtcatgga cgacacggtc tcggcgtcgg tcgcgcaggc gctcgacgag  540
ctcatgctct gggcggagga ctgccccgag gtccgccacc tcgtccacgc ggacttcggc  600
tcgaacaacg tcctcacgga caacggccgc atcacggcgg tcatcgactg gtcggaggcg  660
atgttcggcg actcgcagta cgaggtcgcg aacatcttct tctggcgccc ctggctcgcg  720
tgcatggagc agcagacgcg ctacttcgag cgccgccacc ccgagctcgc gggctcgccc  780
cgcctccgcg cgtacatgct ccgcatcggc ctcgaccagc tctaccagtc gctcgtcgac  840
ggcaacttcg acgacgcggc gtgggcgcag ggccgctgcg acgcgatcgt ccgctcgggc  900
gcgggcacgg tcggccgcac gcagatcgcg cgccgctcgg cggcggtctg gacggacggc  960
tgcgtcgagg tcctcgcgga ctcgggcaac cgccgcccct cgacgcgccc ccgcgcgaag  1020
aagtga                                                             1026

SEQ ID NO: 23            moltype = DNA  length = 230
FEATURE                  Location/Qualifiers
source                   1..230
                         mol_type = other DNA
                         organism = synthetic construct
SEQUENCE: 23
gccaacgacg atggacttgt gtggtctgta cccgatgatc agtaggaacg gaagaagtat  60
ctcgtgtgta tgacgcctgt gtggaaacgt gtacatgtac ttgtactctg ctgcgtgcgt  120
cgtgtagcga gacgattgta atcataaaat gccatagacg tgcctcgtat ctgtccctcg  180
tgtgcgatgc gagactttcg agtacaagac aagcatggtg ccagtggagg             230

SEQ ID NO: 24            moltype = DNA  length = 2717
FEATURE                  Location/Qualifiers
source                   1..2717
                         mol_type = other DNA
                         organism = synthetic construct
SEQUENCE: 24
tgagttgaat ggtattatgg ttgcgcatat tatgttgggt ttatccgtcg atacttcgaa  60
gatatatgtg aacgcttgga atggagagca ctgaggatgc aatttcgatg ctacggcatc  120
acaacgatat gcggacgcaa ctgctatagg ggagacacat tccctagaca gtcaacacat  180
cagcggtgcc ataagtagtc aagcaacata tgcgatttca tgacgtacgg tcgttgaaag  240
tgattcacgg ataccaatgt gcatgtgaag gttcagggcc tgggagagtt agtagtctag  300
tctgtctgaa gagctgacct ggcctacaaa tggctgtcat gattgacgta ggaggaggct  360
agtacctaca gtgaacgagg caccggaaga gcagagctat aagtgggata tgacggatgg  420
aaggaattat actgggccac tcacgctcga cgcatccaag ccgtgtattt cgagaggccg  480
tctccgtctc cagcggcagc ggacacaagc acacgaacgg cgtctgattg gtggagtggg  540
attagacgct cgtatgacgt cgtgggattg gagagcagac acggagaacg gatcttgctc  600
```

```
tcagcattcg agtcagaaaa aacatgggga gcatatgtcg cgatatgtac gaacagcgac  660
ctgtgcattg ctgacgagga cgagacaagt cgctgacaga gagggcgcgt acggatctac  720
tgtgtcctat tagcagtaca cttgctagaa ggtgccgtcg agacgcgcga acggaataag  780
gcgattggga gggcgcgtcg cgtccgagtc gcgtccagac cagacccccg tcaattcgga  840
gaacgggcct tcggcagcct tgcgcgtaca ttctctctgg taatacaccc cttgcagccc  900
ttcgcgccgt tcgtcctatc gattgatggc cgttggcgag agagagagag gcagtgtgtg  960
ccccaaaggg cgtcgcgact ggtggggaga cgcgtcgtac gctcctcctc aaagcaacca  1020
atcccgggcg ggtaaattct ggatcggtcg atggctgcgt atcgcccgca cgttcatccc  1080
tttcgcccga cggtcaccgc attccgtaca gcgcgctgtg ccctccgtat ggatttgtaa  1140
cgtgttcggt ctcattatga acgtctcgcc gtgggcaaat acgccgaaga atgtggagag  1200
agggaggaga gtaggagagg aaagaggcgc caggagagga cgaggacgag acgacgcggc  1260
gatcgaacat ctgagatgag ataacaatca tccgcccctt ataaaccctc ctcctctccc  1320
tcctccttcc gcatctcctc ctctctccat cccatcctct caaccatgtc tgtgcgtacc  1380
atccataccc gtctcctttc cgtgtcgcat gctgatcgcc ctccacatgc agcaagtcaa  1440
ggtcggaagc ttcggatgaa gaagcccgag ctcacggcga cgtcggtcga gaagttcctc  1500
atcgagaagt tcgactcggt ctcggacctc atgcagctct cggagggcga ggagtcgcgc  1560
gcgttctcgt tcgacgtcgg cggccgcggc tacgtcctcc gcgtcaactc gtgcgcggac  1620
ggcttctaca aggaccgcta cgtctaccgc cacttcgcgt cggcggcgct ccccatcccc  1680
gaggtcctcg acatcggcga gttctcggag tcgctcacgt actgcatctc gcgccgcgcg  1740
cagggcgtca cgctccagga cctccccgag acggagctcc ccgcggtcct ccagcccgtc  1800
gcggaggcga tggacgcgat cgcggcggcg gacctctcgc agacgtcggg cttcggcccc  1860
ttcggccccc agggcatcgg ccagtacacg acgtggcgcg acttcatctg cgcgatcgcg  1920
gacccccacg tctaccactg gcagacggtc atggacgaca cggtctcggc gtcggtcgcg  1980
caggcgctcg acgagctcat gctctgggcg gaggactgcc ccgaggtccg ccacctcgtc  2040
cacgcggact tcggctcgaa caacgtcctc acggacaacg gccgcatcac ggcggtcatc  2100
gactggtcgg aggcgatgtt cggcgactcg cagtacgagg tcgcgaacat cttcttctgg  2160
cgcccctggc tcgcgtgcat ggagcagcag acgcgctact tcgagcgccg ccaccccgag  2220
ctcgcgggct cgcccgcct ccgcgcgtac atgctccgca tcggcctcga ccagctctac  2280
cagtcgctcg tcgacggcaa cttcgacgac gcggcgtggg cgcagggccg ctgcgacgcg  2340
atcgtccgct cgggcgcggg cacggtcggc cgcacgcaga tcgcgcgccg ctcggcggcg  2400
gtctggacgg acggctgcgt cgaggtcctc gcggactcgg gcaaccgccg cccctcgacg  2460
cgcccccgcg cgaagaagtg aggatccgcc aacgacgatg gacttgtgtg gtctgtaccc  2520
gatgatcagt aggaacggaa gaagtatctc gtgtgtatga cgcctgtgtg gaaacgtgta  2580
catgtacttg tactctgctg cgtgcgtcgt gtagcgagac gattgtaatc ataaaatgcc  2640
atagacgtgc ctcgtatctg tccctcgtgt gcgatgcgag actttcgagt acaagacaag  2700
catggtgcca gtggagg                                                 2717

SEQ ID NO: 25          moltype = AA  length = 341
FEATURE                Location/Qualifiers
source                 1..341
                       mol_type = protein
                       organism = synthetic construct
SEQUENCE: 25
MKKPELTATS VEKFLIEKFD SVSDLMQLSE GEESRAFSFD VGGRGYVLRV NSCADGFYKD  60
RYVYRHFASA ALPIPEVLDI GEFSESLTYC ISRRAQGVTL QDLPETELPA VLQPVAEAMD  120
AIAAADLSQT SGFGPFGPQG IGQYTTWRDF ICAIADPHVY HWQTVMDDTV SASVAQALDE  180
LMLWAEDCPE VRHLVHADFG SNNVLTDNGR ITAVIDWSEA MFGDSQYEVA NIFFWRPWLA  240
CMEQQTRYFE RRHPELAGSP RLRAYMLRIG LDQLYQSLVD GNFDDAAWAQ GRCDAIVRSG  300
AGTVGRTQIA RRSAAVWTDG CVEVLADSGN RRPSTRPRAK K                      341

SEQ ID NO: 26          moltype = DNA  length = 19
FEATURE                Location/Qualifiers
source                 1..19
                       mol_type = other DNA
                       organism = synthetic construct
SEQUENCE: 26
tggtcggagc gcgatgttc                                               19

SEQ ID NO: 27          moltype = DNA  length = 21
FEATURE                Location/Qualifiers
source                 1..21
                       mol_type = other DNA
                       organism = synthetic construct
SEQUENCE: 27
cgtgttctgc tggtagtggt c                                            21

SEQ ID NO: 28          moltype = DNA  length = 20
FEATURE                Location/Qualifiers
source                 1..20
                       mol_type = other DNA
                       organism = synthetic construct
SEQUENCE: 28
atggcgtcga tccttaagca                                              20

SEQ ID NO: 29          moltype = DNA  length = 20
FEATURE                Location/Qualifiers
source                 1..20
                       mol_type = other DNA
                       organism = synthetic construct
```

```
SEQUENCE: 29
ctatgcgctc gagccaatgc                                              20

SEQ ID NO: 30           moltype = DNA  length = 664
FEATURE                 Location/Qualifiers
source                  1..664
                        mol_type = other DNA
                        organism = synthetic construct
SEQUENCE: 30
ttagaggaag taaaagtcgt aacaaggttt ccgtaggtga acctgcggaa ggatcattaa  60
cgagttctga catgggttgt agctggcctc acgaggcatg tgcacgccct gctcatccac  120
tctacacctg tgcacttact gtaggtttgg cgtgggcttc gagggccttc acgggctttt  180
gaggcattct gcctgcctat gtatcactac aaacactata aagtaacaga atgtaatcgc  240
gtctaacgca tcttaataca actttcagca acggatctct tggctctcgc atcgatgaag  300
aacgcagcga aatgcgataa gtaatgtgaa ttgcagaatt cagtgaatca tcgaatcttt  360
gaacgcacct tgcgctcctt ggtattccga ggagcatgcc tgtttgagtg tcatggtatt  420
ctcaacccac acatccttgt gatgcttgtg aggcttggac ttggaggctt gctggcccgt  480
cgcggtcggc tcctcttgaa tgcattagct tggttccttg cggatcggct ctcagtgtga  540
taattgtcta cgctgtgacc gtgaagcgtt tggcgagctt ctaaccgtcc tgctagggac  600
aacttacttg acatctgacc tcaaatcagg taggactacc cgctgaactt aagcatatca  660
ataa                                                               664

SEQ ID NO: 31           moltype = DNA  length = 17
FEATURE                 Location/Qualifiers
source                  1..17
                        mol_type = other DNA
                        organism = synthetic construct
SEQUENCE: 31
gtaaaacgac ggccagt                                                 17

SEQ ID NO: 32           moltype = DNA  length = 17
FEATURE                 Location/Qualifiers
source                  1..17
                        mol_type = other DNA
                        organism = synthetic construct
SEQUENCE: 32
caggaaacag ctatgac                                                 17

SEQ ID NO: 33           moltype = DNA  length = 20
FEATURE                 Location/Qualifiers
source                  1..20
                        mol_type = other DNA
                        organism = synthetic construct
SEQUENCE: 33
ggaccactac cagcagaaca                                              20

SEQ ID NO: 34           moltype = DNA  length = 19
FEATURE                 Location/Qualifiers
source                  1..19
                        mol_type = other DNA
                        organism = synthetic construct
SEQUENCE: 34
cgtagcggtc cttgtagaa                                               19

SEQ ID NO: 35           moltype = DNA  length = 19
FEATURE                 Location/Qualifiers
source                  1..19
                        mol_type = other DNA
                        organism = synthetic construct
SEQUENCE: 35
tccgtaggtg aacctgcgg                                               19

SEQ ID NO: 36           moltype = DNA  length = 20
FEATURE                 Location/Qualifiers
source                  1..20
                        mol_type = other DNA
                        organism = synthetic construct
SEQUENCE: 36
tcctccgctt attgatatgc                                              20

SEQ ID NO: 37           moltype = DNA  length = 2036
FEATURE                 Location/Qualifiers
source                  1..2036
                        mol_type = other DNA
                        organism = synthetic construct
SEQUENCE: 37
atgctaccca ccactcacga tccttcctcc tccgcactca accaccagcc ctccctctac  60
cccgtcgtcc cccaccactc cctcccacag aaccccgttc accaccatcc ttatcctatt  120
ccccctcaga accctccctt tgatcaccac cagcaactcc agcagctgca ccccgccctc  180
```

-continued

```
tcccatcctc acaaccacca cccacacatc caccacctcc agcagaacca gacttgcgta  240
cccgctctca tcccaccagg catggaccct tcccaggtcg acatccgcac cttctatccc  300
tacaccccaa acgaagtaaa gcacagaaag cgcaccaccc gcgctcagct caaggtcctc  360
gagggtgtct acaaatatga cacaaagccc aacgcctccc ttcgcaagaa actcgcggca  420
gagctcgaca tgactccccg cggtgtccag gtacttgcct tcctcgattg caacccgttc  480
ccttctatct cctctccctc tgtcattgtc ccgtgcttat ctggtccttc cttcctctct  540
tcctccaggt ctggttccag aatcgccgtg ccaaaacaaa acagcaagcc aagaaggcgg  600
aggccgccaa cgccgccaag ggctccccgt ctgacccctc atcrtcggcg acggcagcag  660
cagccgcctc caaccccccg atagcacctc gtcctaccga agacgcggca gacgacgacg  720
acaacgacaa cgacgatcca gacgagccat gtgcattggc gcctccgtct cccaagcaat  780
cggaggacgc aacaccggaa aacgctgcaa cagctgacgg caccgttccc gcttcctcaa  840
acgcaaaccc gaacgccagt gcacagcagg acaacgaaca ggcccaccta acgcctgata  900
gccgccgctc ctccatggcc cctccccttc ctcggtcccc cgcttggtca tcgtcttctc  960
cctcggtctc cacggcgcct gccccctctt caaccgctcc ctcgtccgca ctcagcagtc  1020
ccaatcccgc gaatcatgcg aacagttccc acgttcgtct ctccactcac ccgccctccg  1080
ccacctcttc ctactcgcac aaccacctcg cgcccaccga catttactcg cagcgacgca  1140
cctctctccc gccttccctt tcctccacat ctggtcatgc ccccggcatg ctgagtaccc  1200
tccgtcgacg cggctatgac gacacccgcc gacgctcgac agacatgggc ggtcaccgca  1260
tcgtcgccca tccgtacatc tctgtcgccc agagcgccaa cggcccgcat aatatatacg  1320
gcgatggtga cgacgctccg cctgccaggc gtcccatgct catgcagcgt atgaccgcac  1380
cctacgcttc gaaccaccac tcgcaaggga cgcaagcgat gcactctccg caggcgcatt  1440
ctcaacatgc ccactcccag tcgatcttgc cctcccaggc gcagcaacag cgagcgcagc  1500
acctgggaca gcagcgccag cactacgaca tctcgcccat tcaggtgtcc atctcccatt  1560
cgcagggcta caaccagccg ccaaaccacc cgggcagtca cggctacgat ctgttcgcgc  1620
cccgacattc gatcgacggc agcgcgctcg gcctgaccca agcgcacgca cagatgagca  1680
tgggcctgtc tcccttgcac cctgcgcctg gcacaggaat ggacaacgac gcgtttagca  1740
tgggtctcgg gatgagcagc cactacgctg tgtcgcagcg tccactaccc cctaccatac  1800
ctggaccgct tccctctccc aactatcagt tcgggaaccc gttcgtacct gccccgaacg  1860
actcgtcttc tagctcttcc atgagcaact ctgcgtcggg cacgcctccc aatggcgctt  1920
cgccgccatt gctcagcctg cggcgtacaa gcgagagcgc attgtcagat ggagacacgg  1980
aggagagcag cggcgcgcct ctgtccagat ttggcagtat tgcgagtatc aacggc      2036

SEQ ID NO: 38          moltype = AA  length = 945
FEATURE                Location/Qualifiers
source                 1..945
                       mol_type = protein
                       organism = synthetic construct
SEQUENCE: 38
MLPTTHDPSS SALNHQPSLY PVVPHHSLPQ NPVHHHPYPI PPQNPPFDHH QQLQQLHPAL  60
SHPHNHHPHI HHLQQNQTCV PALIPPGMDP SQVDIRTFYP YTPNEVKHRK RTTRAQLKVL  120
EGVYKYDTKP NASLRKKLAA ELDMTPRGVQ VWFQNRRAKT KQQAKKAEAA NAAKGSPSDP  180
SSSATAAAAA SNPPIAPRPT EDAADDDDND NDDPDEPCAL APPSPKQSED ATPENAATAD  240
GTVPASSNAN PNASAQQDNE QAHLTPDSRR SSMAPPLPRS PAWSSSSPSV STAPAPSSTA  300
PSSALSSPNP ANHANSSHVR LSTHPPSATS SYSHNHLAPT DIYSQRRTSL PPSLSSTSGH  360
APGMLSTLRR RGYDDTRRRS TDMGGHRIVA HPYISVAQSA NGPHNIYGDG DDAPPARRPM  420
LMQRMTAPYA SNHHSQGTQA MHSPQAHSQH AHSQSILPSQ AQQQRAQHLG QQRQHYDISP  480
IQVSISHSQG YNQPPNHPGS HGYDLFAPRH SIDGSALGLT QAHAQMSMGL SPLHPAPGTG  540
MDNDAFSMGL GMSSHYAVSQ RPLPPTIPGP LPSPNYQFGN PFVPAPNDSS SSSSMSNSAS  600
GTPPNGASPP LLSLRRTSES ALSDGDTEES SGAPLSRFGS IASINGSEAS WTSAYVSDSA  660
AEGEEGDGSA SRKMSCASEF LGMFSGLDVG SNGGTPAPHG LQESHPLRQS RSSSHLSPNA  720
FVPHHMQAPA PTPPDSMGAD QQQQQHIHMQ APSDADGYPS PSSASTVSAG SNHGNGGSHT  780
HTLSHDTTPS HTTVGNGNGG HLQQQGANSM RNHSSSELAY ALQGEPEPPR GYQQHPPAGA  840
KEELQYPMYV SQEASETDAG DAAAYGYAQE QGHHDAREYA KAQMGHFPTL YEGYVYPHGN  900
VNDQIPEEDA SAMSEAYAAG AIELSHMCVP ASEGVHFMGG YMQYS                  945

SEQ ID NO: 39          moltype = AA  length = 8
FEATURE                Location/Qualifiers
source                 1..8
                       mol_type = protein
                       organism = synthetic construct
SEQUENCE: 39
GGGGGGGG                                                           8
```

SIDEREAL MYCELIUM FABRICS

CLAIM OF PRIORITY

This patent application claims priority to U.S. provisional patent application No. 63/642,640, titled "SIDEREAL MYCELIUM FABRICS," filed on May 3, 2024, and herein incorporated by reference in its entirety.

REFERENCE TO THE SEQUENCE LISTING

The Sequences included herein (identified by "Seq Id No.") may form a Sequence Listing.

The instant application contains a Sequence Listing which has been filed electronically in ASCII format and is hereby incorporated by reference in its entirety. Said ASCII copy, created on Jul. 25, 2025 is named 14867-703-200 and is 52,434 bytes in size. REFERENCE TO A DEPOSIT OF BIOLOGICAL MATERIAL This application contains a reference to a deposit of biological material, which deposit incorporated herein by reference. Specifically SCC-0006/3.6, a novel and engineered Basidomycota fungal strain, *Cubamyces menziesii*, was deposited under the terms of the Budapest Treaty on the International Recognition of the Deposit of Microorganisms for the Purposes of Patent Procedure at Universidad of Chile, under access code RGM 3586. The deposit of biological material occurred on May 3, 2024.

BACKGROUND

The use of fungi to fabricate textiles provides environmental, economic, and functional benefits. Fungal textiles, often referred to as mycelium-based materials, or "mycotextiles," are inherently sustainable as they can be grown from agricultural waste or other renewable resources in a controlled environment, minimizing reliance on traditional, resource-intensive textile production methods. These materials are biodegradable, ensuring minimal environmental impact at the end of their lifecycle. Furthermore, mycelium textiles may be lightweight, flexible, and durable, making them suitable for a wide range of applications in industries including fashion, construction, and automotive. The cultivation of fungal textiles requires significantly less water and energy compared to conventional textile manufacturing processes, contributing to reduced carbon emissions and overall environmental footprint. Embracing fungal textiles not only promotes eco-conscious practices but also fosters innovation and diversification within the textile industry, paving the way for a more sustainable and resilient future.

While mycelium-based textiles offer numerous advantages, they also come with their set of challenges. One primary challenge is scalability. Scaling up the production of mycelium textiles to meet commercial demands while maintaining quality and consistency can be technically complex and financially demanding. Additionally, the development of standardized production processes and ensuring regulatory compliance can be hurdles. Another challenge is the variability of fungal growth conditions, which can affect the material's properties such as strength, texture, and color. Controlling these variables to achieve desired characteristics consistently is an ongoing challenge for manufacturers. Moreover, although mycelium-based textiles may be fabricated in an ecologically responsible manner, processing of these materials, e.g., to include colors (e.g., dying) and finishing (e.g., shaping, texturing, embossing, coating, etc.) may require resource-intensive steps that may themselves be wasteful and result in pollution.

One potentially valuable processing feature may be the inclusion of nanoparticles into the final textile. As described herein, it would also be particularly useful to provide metallic nanoparticles (MNPs), including methods of making and using them, in processing mycotextiles, which may benefit from the properties of such MNPs.

The idea that fungal spores or other microorganisms might have arrived on Earth from space is known as "Panspermia". The theory of Panspermia encompasses the potential transport of life's building blocks, such as microorganisms, viral particles, organic compounds, or even genetic material (e.g., DNA, RNA, etc.) from space to Earth. Studies have shown that microorganisms can survive extreme conditions in space, such as cosmic radiation levels (e.g., ultraviolet, gamma, ultraviolet radiation, infrared radiation, etc.), vacuum, and extreme temperatures. Some experiments conducted on the International Space Station (ISS) and other space missions have demonstrated the resilience of specific microbes and their abilities to survive in extreme space conditions. Regarding the origin of fungi, it's essential to consider that fungal spores are incredibly resilient and can endure harsh environmental conditions, including those found in space. This resilience has led scientists to consider that spores might have traveled on meteoroids, dust particles, or other celestial bodies through space for an extended time before randomly colliding with planets. Under the proper environmental conditions, these spores could reactivate and colonize their new environment on Earth, contributing to its biological diversity.

On the other hand, the "Late Heavy Bombardment" (LHB) theory states that the Earth and the entire inner solar system suffered through an intense spike in asteroid bombardment roughly 4 billion years ago, at a time corresponding to the Neohadean and Eoarchean eras on Earth. According to this hypothesis, during this interval, a disproportionately large number of asteroids and comets collided with the terrestrial planets and their natural satellites of the inner Solar System, including Mercury, Venus, Earth (and the Moon) and Mars. This hypothesis grew from studies of the Moon's crater record and the hundreds of kilograms of lunar material returned to Earth by the Apollo astronauts. Regarding this hypothesis, the LHB played a significant role in shaping the geology and composition of the inner planets, including Earth, and contributed to the presence of precious metals embedded in the Earth's crust. While the LHB hypothesis primarily focuses on the delivery of water and volatile compounds to Earth, it also implies the influx of a wide gamma of materials, including precious metals (e.g., Au, Ag, Pt, Pd, Rh, Ru, Ir, Os) from outer space. Recently, new features supported by NASA's Planetary Science Division and the Astrobiology Program are shaping our understanding of Earth's early history and its habitability.

Metallic or metal oxide nanoparticles could be obtained by chemical, physical or biological synthetic strategies. Each strategy shows different advantages and disadvantages regarding reaction time, yield, selectivity, costs, and environmental impact. However, the biogenic synthesis through plants, bacteria and fungi, or the byproducts of their metabolisms, may provide both reducing and stabilizing agents, allowing the formation of the nuclei and, at the same time, stabilizing them to avoid aggregation, thus, yielding a stabilized colloidal dispersion of nanoparticles with high biocompatibility. Several microorganisms have been used to synthesize silver and gold nanoparticles (AgNPs and AuNPs) via bioreduction. The reduction of metal complexes by microorganisms is often mediated by enzymes and biomolecules produced by the same microorganisms as a response to external stress. Some examples of microorganisms commonly used for AuNPs synthesis include bacteria, fungi, and algae. Some examples are listed below: algae such as *Chlorella vulgaris, Spirulina platensis*, and *Dunaliella salina*; bacteria include *Pseudomonas aeruginosa, Bacillus licheniformis, Escherichia coli, Acidithiobacillus ferrooxidans* and *Acidithiobacillus thiooxidans*. Fungi such as *Aspergillus niger, Fusarium oxysporum, Fusarium solani, Trichoderma viride, Trichoderma harzianum, Penicillium chrysogenum*, and *Penicillium brevicompactum*, among others.

What is needed are methods and compositions that may address these problems. Described herein are methods and compositions that may address these needs.

SUMMARY OF THE DISCLOSURE

Described herein are methods and compositions (e.g., textiles, as well as components for forming, processing and using such textiles) of mycelium-based materials. In general, these mycelium-based materials, e.g., mycelium-based textiles, may include metallic nanoparticles, and may be configured to have many advantageous properties as compared to traditional textiles, and as compared to previously described mycelium-based textiles.

The materials and methods described herein may be referred to as Sidereal Mycelium Fabrics, as they are inspired by the concepts of Panspermia and the Heavy Late Bombardment. These compositions (e.g., fabrics, materials, and affiliated cell lines) and methods of making and using them represent groundbreaking innovations at the intersection of material biotechnology and nanotechnology, fungal physiology, synthetic biology and genetic engineering, integrating principles of biomimicry, applied mycology, astrobiology, material science, and sustainable fashion. Inspired by Panspermia and the Late Heavy Bombardment theories, these compositions and methods leverage the nano-myco-synthesis potential of extremophilic fungi from celestial precious metals, making it a unique self-nano-synthetized mycelium fabric material for the luxury fashion industry. The Sidereal Mycelium Fabrics described herein are inspired by the theories of Panspermia and the Late Heavy Bombardment and may provide a unique and sustainable mycotextiles for the fashion industry. as schematized in FIG. 1.

The methods described here provide multiple types of sidereal mycotextiles. The methods and compositions described herein may be related to, and may be used with and improve, the methods, compositions, and apparatuses related to mycotextile production described in the each of U.S. Patent Published Application No. US 2023/0356501 (and corresponding International Patent Application No. PCT/IB2023/053847), titled "MYCOTEXTILES INCLUDING ACTIVATED SCAFFOLDS AND NANO-PARTICLE CROSS-LINKERS AND METHODS OF MAKING THEM," filed on Apr. 14, 2023, claiming priority to U.S. provisional patent application No. 63/331,734, filed on Apr. 15, 2022; as well as U.S. Provisional Patent No. 63/520,933 titled "NANOEMULSIONS FOR INTERNAL HUMECTATION OF MYCELIUM-BASED TEXTILES," filed on Oct. 13, 2023 and U.S. patent application Ser. No. 18/595,392 (and corresponding International Patent Application No. PCT/US2024/018434), filed on Mar. 4, 2024 and titled "LARGE-SCALE PRODUCTION OF MYCELIUM-BASED TEXTILES AT MUSHROOM FARM FACILITIES". Each of these patent applications is herein incorporated by reference in its entirety.

The sidereal mycelium fabrics described herein may provide new types of raw material for the fashion industry based on biosynthesized intelligent materials because of the several exploitable properties of the materials at the nanoscale, including the use of metallic nanoparticles. Metals have been part of human development for centuries. At the beginning of human civilization, metals drove significant advancements thanks to the developments in metallurgy (e.g., the Copper Age—III millennium B.C., Bronze Age—II millennium B.C., and Iron Age—I millennium B.C.), giving rise to different revolutionary applications such as pigments, cooking tools, weapons, and coins, among others. In the current era, the applications are much more sophisticated thanks to nanotechnology advancements. Nano-engineered materials are present in many products today. Metallic nanoparticles (MNPs), especially those from precious metals, are the main components of our daily electronic devices. Moreover, MNPs are used in energy applications, such as solar cells, fuel cells, and batteries, to improve efficiency and performance. Likewise, they drive the current energetic transition to clean energy based on H2 production as electrocatalysts. In medical approaches, they have been tested in biosensing, drug delivery systems, imaging agents, and as antimicrobial agents. Also, they are used in environmental remediation processes, such as wastewater treatment and pollution control, due to their ability to catalyze reactions and absorb pollutants.

Also described herein is the use of fungi for metallic nanoparticle (MNP) synthesis and the use of such fungi and/or NMPs derived from these fungi to form mycotextiles having dramatically improved characteristics. The use of fungi for MNP biosynthesis offers several advantages over chemical methods, including lower cost, greater biocompatibility, and reduced environmental impact because it does not require toxic chemicals or high-energy inputs. However, bioreduction depends on the fungal strain (e.g., its extremophilic abilities, cell wall composition, ability to produce polysaccharides and oxidoreductase extracellular enzymes, etc.), the growth conditions (e.g., a liquid, solid, hybrid state fermentation substrate, amendments, static or orbital culture, etc.), and the method of NPs synthesis used. High-quality metal NPs may be obtained and used by careful optimization of the culture conditions and parameters, such as pH, temperature, salinity, and concentration of metal ions, as described herein.

Specifically, extremophile fungi can tolerate high concentrations of heavy metals because of their ability to internalize and bioaccumulate metal ions. This greater fungal power in the synthesis of nanoparticles is due to its extracellular enzymes, proteins, and aromatic compounds (naphthoquinone and anthraquinone) that act as electron shuttles for reducing metal ions. It has been shown that hydroxyl and carboxyl groups on tyrosine and asparagine and/or glutamic residues are used to synthesize nanoparticles. It has been demonstrated that fungi produce nanoparticles intracellularly or extracellularly. In the case of intracellular synthesis, the fungal cell traps ions on the cell surface that are reduced by enzymes (e.g., oxidoreductases, etc.) present in the cell wall or cytoplasmic membrane. In extracellular synthesis, nanoparticles are synthesized and stabilized by proteins and reducing agents secreted by the fungus or contained in its cell wall. Some fungal enzymes can act as reducing agents and play a crucial role in the bioreduction of metal ions to colloidal MNPs for various applications. They can also influence the colloids' size, shape, and stability. Some enzymes have been identified to be involved in the synthesis of MNPs, including, among others, nitrate reductases, cytochrome P450, laccases and xylanases.

The methods and compositions described herein may ensure a homogeneous distribution of the synthesis of extracellular enzymes, proteins, polysaccharides, and aromatic compounds associated with the MNPs mycosynthesis, for example, by stabilizing the phenotypical, biochemical and physiological behavior of the working fungus, which is closely related to its genetic characteristics, including its mycelial stage.

In general, the method and compositions described herein may include the use of dikaryotic Basidiomycota in the formation and processing of mycotextiles. Basidiomycota's life cycle includes three main mycelial stages: heterokaryotic, monokaryotic, and dikaryotic. As described herein, the heterokaryotic and monokaryotic stages radically affect the reproducibility and homogeneity of the materials in the mycotextiles development. The methods and compositions described herein may include one or more strategies to avoid dedikaryotization to prevent the conversion of dikaryotic cells into monokaryotic cells. Thus, the methods and compositions described herein may include one or more dikaryon fungal strain (for example, a dikaryotic Basidomycota strain). Any dikaryon fungal strain (e.g., any dikaryon Basidomycota fungal strain) may be used with the methods and compositions described herein. Also described herein are methods of forming dikaryon fungal strains, including engineered dikaryon strains. The dikaryon fungal strain may be selected and or engineered to have a homogeneous behavior, resulting in nuclear fidelity, reflected in the maintenance of the dikaryotic genotype (diploid) and a more homogeneous phenotype during mycelial development and guaranteeing a successful sidereal mycelium fabric production.

Thus, in general, the Sidereal Mycelium Fabrics (mycofabrics) described herein may include one or more dikaryon fungal strain. In some cases, the dikaryon fungal strain may include nanoparticles that are embedded into the hyphae of the fungi, poetically reflecting the manner in which the noble/precious spatial metals were embedded in the Earth's crust 4 billion years ago, while the living mycelium matrix is submerged in a solution containing specific precious metal ions. This may form a resilient mycotextile that exhibits remarkable properties, such as material reinforcement, an unprecedented and unique look and feel (e.g., fine art materials that are unique and unrepeatable), and a broad palette of smart properties, avoiding the use of petrochemical-based dye or pigment formulations in the post-fermentation stage, as shown schematically in FIG. 1.

In the context of fashion applications, the methods and compositions described herein embrace unique textures by creating myco-inspired embossing and engraving techniques that may satisfy the need to create avant-garde garments that blur the boundaries between science, nature, the sidereal space, and style.

As mentioned above, the mycofabrics described herein may generally be referred to as Sideral Mycelium Fabrics and may be include one or more metal nanoparticles (or their derived compounds) and may form a biotextile obtained by a wild or engineered extremophilic fungal strain, and in particular, a dikaryon fungal strain. These Sideral Mycelium Fabrics described herein may be referred to as sidereal mycelium fabrics to acknowledge that the fungi and metals origins have been intertwined billions of years ago in the stars themselves. As described herein, Sidereal Mycelium Fabrics may have an unprecedented appearance, as well as novel functionalities, and may provide a novel materiality, such as (but not limited to) unrepeatable work arts, for the future textile industry.

For example, described herein are methods of forming a mycotextile, the method comprising: generating a pre-inoculum substrate seeded with a fungal strain; growing a mycelium mat using the pre-inoculum substrate while maintaining the fungal strain as dikaryotic, wherein the mycelium mat is grown around a scaffold layer so that the scaffold layer is incorporated into the mycelium mat; impregnating hyphae within the mycelium mat with functionalized nanoparticles and/or a solution of metallic ions; and processing the mycelium mat to crosslink chitin in the hypha to form the mycotextile, wherein the mycelium mat remains dikaryotic.

The fungal strain may be engineered to be resistant to a drug or other agent (e.g., an antibiotic), further where growing the mycelium mat comprises growing the mycelium mat in the presence of the drug or other agent (e.g., antibiotic) to maintain the fungal strain as dikaryotic. Maintaining the fungal strain as dikaryotic may comprise maintaining the maintaining the fungal strain so that greater than 95% (e.g., 99% or greater, etc.) of the hyphae are dikaryotic.

Processing the mycelium mat to crosslink chitin in the hyphae may comprise covalently crosslinking the scaffold layer to chitin within the mycelium mat and covalently or electrostatically crosslinking the functionalized nanoparticles to chitin/chitosan in the hyphae.

Impregnating the hyphae may comprise exposing the hypha of the mycelium mat with a solution of metallic ions and forming metallic nanoparticles in vivo within hypha (e.g., soaking the mycelium mat, etc.). Impregnating hyphae within the mycelium mat with the functionalized nanoparticles may comprise adding additives as growth inducers containing the functionalized nanoparticles on the growing mycelium mat.

Harvesting may comprise harvesting an elongate length of mycelium mat using an automated system. Generating the pre-inoculum substrate seeded with the fungal strain may comprise generating the pre-inoculum substrate seeded with a dikaryotic Basidomycota strain. Generating the pre-inoculum substrate seeded with the dikaryotic fungal strain may comprise generating the pre-inoculum substrate seeded with a SCC-0006/3.6 fungal Basidomycota strain. The pre-inoculum substrate may comprise a lignocellulosic material. The nanobiocide scaffold layer may contain specific growth inducers and biocide nanoparticles to induce, respectively, a high density and homogeneity of mycelial colonization onto the scaffold and the mitigation of environmental contamination in the fermentation processes. The functionalized nanoparticles may comprise functionalized nanoparticles comprising a protein-functionalized iron oxide nanoparticle.

Also described herein are mycotextiles formed by any of the methods described herein.

For example, a mycotextile may include: a support scaffold layer embedded within a crosslinked mycelium matrix, wherein the support scaffold layer is crosslinked to the mycelium matrix; and a plurality metallic and/or ceramic nanoparticles within the crosslinked mycelium matrix, wherein the mycelium matrix is formed of dikaryotic hyphae. All or most (e.g., greater than 80%, greater than 90%, greater than 95%, etc.) of the hyphae forming the mycelium matrix may be dikaryotic. At least some of the nanoparticles may be functionalized with an organic functionalizing agent adsorbed onto a surface of the ceramic nanoparticles to crosslink chitin and/or chitosan of the hyphae structures. The mycelium matrix may comprise greater than 75% of skeletal hyphae and/or ligative hyphae rather than generative hyphae (e.g., 75% or greater, 80% or greater, 85% or greater, 90% or greater, etc.). For example, the mycelium matrix may comprise greater than 90% of skeletal hyphae and/or ligative hyphae rather than generative hyphae. The percentage of skeletal hyphae and/or ligative hyphae relative to generative hyphae may be determined from the final mycotextile by examining (e.g., using microcopy) the ranges of lengths, branching, and hyphae thicknesses in the final cross-linked mycotextile.

The plurality of metallic and/% or ceramic nanoparticles may comprise both metallic and ceramic nanoparticles. The plurality of metallic and/or ceramic nanoparticles may comprise metallic nanoparticles of silver and/or gold. The plurality of metallic and/or ceramic nanoparticles may comprise both silver and/or gold nanoparticles and ceramic nanoparticles.

Also described herein are the engineered Basidomycota fungal strain that may be kept stably dikaryotic, wherein the engineered fungal strain is SCC006/3.6, and mycotextiles made from this strain (e.g., including one or more genetic markers indicative of the SCC006/3.6 fungal strain, as described herein). For example, described herein are methods of forming a mycotextile using the engineered Basidomycota fungal strain and/or a mycotextile formed using the engineered Basidomycota fungal strain.

For example, described herein are engineered Basidomycota fungal strains that may be kept stably dikaryotic, wherein the engineered fungal strain comprises a hph gene encoding hygromycin B phosphotransferase having an amino acid sequence comprising SEQ ID NO. 25, and methods of forming a mycotextile using the engineered Basidomycota fungal strain as well as mycotextiles formed using the engineered Basidomycota fungal strain.

An of the mycotextiles described herein may be include metallic nanoparticles that are formed in vivo within the mycelium of the fungal strain. For example, a method of forming a mycotextile may include: generating a pre-inoculum substrate seeded with a fungal strain; growing a living mycelium mat using the pre-inoculum substrate, wherein the living mycelium mat is grown around a scaffold layer so that the scaffold layer is incorporated into the living mycelium mat; forming metallic nanoparticles in vivo within the living mycelium mat; and processing the living mycelium mat to crosslink chitin in hypha of the mycelium mat to form the mycotextile. Forming metallic nanoparticles in vivo within the living mycelium mat may comprise incubating the living mycelium mat with a solution of metallic ions. Forming metallic nanoparticles in vivo within the living mycelium mat may comprise exposing the living mycelium mat to a solution of metallic ions and reacting metallic ions in the solution of metallic ions with enzymes present in a fungal filtrate of the living mycelium mat.

Any of these methods may include adding functionalized ceramic nanoparticles to the mycelium mat. Adding the functionalized ceramic nanoparticles to the mycelium mat may comprise adding the functionalized ceramic nanoparticles to the living mycelium mat.

The functionalized ceramic nanoparticles may comprise ceramic nanoparticles that are functionalized by the adsorption of a prolamin (including but not limited to Zein) on their surface. Any of these methods may include adding in vitro biogenically-synthesized metallic nanoparticles to the living mycelium mat.

In general, any of these methods may include irradiating the mycelium mat with ultraviolet (UV) light to modify the metallic nanoparticles. Forming the metallic nanoparticles in vivo within the living mycelium mat may comprise forming the metallic nanoparticles extracellularly within the living mycelium mat. Forming the metallic nanoparticles may comprise forming silver, gold, iron oxide, and/or copper oxide nanoparticles. Forming the nanoparticles in vivo may comprise exposing the mycelium mat to a metal ion solution having a concentration of metal ions between 0.1 mM and 50 mM. Forming the nanoparticles in vivo may comprise exposing the mycelium mat to a metal ion solution between about 40 degrees and 90 degrees C. Forming the nanoparticles in vivo may comprise exposing the mycelium mat to a metal ion solution for between 1 hour and 24 hours. In any of these methods, forming the nanoparticles in vivo may comprise immersing the mycelium mat to a metal ion solution. Forming the metallic nanoparticles in vivo may be used to color the mycotextile. In any of these methods the method may also include drying the mycelium mat (typically after and/or as part of crosslinking), and coating the mycelium mat, e.g., with a prolamine protein (e.g., Zein, such as a solution of Zein and glycerol).

For example, a method of forming a mycotextile may include: generating a pre-inoculum substrate seeded with a fungal strain; growing a living mycelium mat using the pre-inoculum substrate, wherein the living mycelium mat is grown around a scaffold layer so that the scaffold layer is incorporated into the living mycelium mat; exposing the living mycelium mat to a solution of metallic ions and reacting the metallic ions with enzymes present in a fungal filtrate of the living mycelium mat act to form a nanoparticles in vivo within the living mycelium mat; and processing the living mycelium mat to crosslink chitin in hypha of the mycelium mat to form the mycotextile.

Also described herein are mycotextiles comprising: a support scaffold layer embedded within a crosslinked mycelium matrix, wherein the support scaffold layer is crosslinked to the mycelium matrix; a plurality metallic nanoparticles formed in vivo within the crosslinked mycelium matrix, characterized by a distribution of metallic nanoparticles through the hyphae network within the crosslinked mycelium matrix, wherein the color of the mycotextile is determined by the plurality of metallic nanoparticles.

The plurality of metallic nanoparticles may be distributed through the hyphae network both over the hyphae and within the hyphae. Any of these mycotextiles may include a second plurality of (e.g., ceramic) nanoparticles that may have a different distribution than the metallic nanoparticles of the plurality of nanoparticles. For example, the ceramic nanoparticles may be limited to distribution over the hyphae of the hyphae network (or primarily distributed over hyphae of the hyphae network. The ceramic nanoparticles may be functionalized by the adsorption of a prolamin on their surface. The metallic nanoparticles may comprise silver, gold, iron oxide, and/or copper oxide nanoparticles. As mentioned, the mycotextile may be coated with a prolamin.

In any of these materials including metallic nanoparticles, the color of the mycotextile may be determined by the localized surface plasmon resonance (LSPR) of the metallic nanoparticles.

For example, a mycotextile may include: a support scaffold layer embedded within a crosslinked mycelium matrix, wherein the support scaffold layer is crosslinked to the mycelium matrix; a plurality of metallic nanoparticles within the crosslinked mycelium matrix, distributed over the hyphae network, wherein the color of the mycotextile is determined by the localized surface plasmon resonance (LSPR) of the metallic nanoparticles.

A method of forming a mycotextile may include: generating a pre-inoculum substrate seeded with a fungal strain; growing a living mycelium mat using the pre-inoculum substrate, wherein the living mycelium mat is grown around a scaffold layer so that the scaffold layer is incorporated into the living mycelium mat; adding in vitro and biogenically-synthesized metallic nanoparticles to the living mycelium mat; and processing the living mycelium mat to crosslink chitin in hypha of the mycelium mat to form the mycotextile. As mentioned, any of these methods may include adding functionalized ceramic nanoparticles to the mycelium mat. For example, adding functionalized ceramic nanoparticles to the mycelium mat comprises adding the functionalized nanoparticles to the living mycelium mat. The functionalized ceramic nanoparticles may comprise ceramic nanoparticles that are functionalized by the adsorption of a prolamin solution on their surface.

A method of forming a mycotextile may include: generating a pre-inoculum substrate seeded with a fungal strain; growing a living mycelium mat using the pre-inoculum substrate, wherein the living mycelium mat is grown around a scaffold layer so that the scaffold layer is incorporated into the living mycelium mat; adding nanoparticles to the living mycelium mat; engraving the living mycelium mat to form a picture, texture and/or pattern on the living mycelium mat to form regions of different thicknesses; and processing the living mycelium mat to crosslink chitin in hypha of the mycelium mat to form the mycotextile.

Engraving may comprise compressing the living mycelium mat in a predefined pattern to form regions of different thicknesses. The regions of different thicknesses may comprise regions having a thickness that varies between 25%-75% across a length of the mycotextile. Engraving may comprise applying pressure to the living mycelium mat for between about 1-50 $kg/ft^2$. Engraving may comprise applying pressure to the living mycelium mat for between about 4 to 20 $kg/ft^2$. Engraving may comprise applying pressure to the living mycelium mat for between about 10 seconds to 300 seconds.

Any of these methods may include adding nanoparticles to the living mycelium mat by forming metallic nanoparticles in vivo within the living mycelium mat. Adding nanoparticles to the living mycelium mat may comprise forming metallic nanoparticles in vivo within the living mycelium mat by exposing the living mycelium mat to a solution of metallic ions and reacting the metallic ions with enzymes present in a fungal filtrate of the living mycelium mat. For example, adding nanoparticles to the living mycelium mat may comprise forming silver, gold, iron oxide, and/or copper oxide nanoparticles. Adding nanoparticles to the living mycelium mat may comprise adding functionalized ceramic nanoparticles to the mycelium mat. Adding the functionalized ceramic nanoparticles to the mycelium mat may comprise adding the functionalized ceramic nanoparticles that are functionalized by the adsorption of a prolamin on their surface. In any of these methods, adding nanoparticles to the living mycelium mat may comprise adding in vitro biogenically-synthesized metallic nanoparticles to the living mycelium mat.

Any of these methods may include irradiating the mycelium mat with ultraviolet (UV) light to modify the nanoparticles, and/or drying the mycelium mat and/or coating the mycelium mat with a prolamine protein solution.

Also described herein are mycotextile comprising: a support scaffold layer embedded within a crosslinked mycelium matrix, wherein the support scaffold layer is crosslinked to the mycelium matrix; a plurality nanoparticles within the crosslinked mycelium matrix and distributed through the hyphae network within the crosslinked mycelium matrix, wherein the mycotextiles are engraved to form a picture, texture and/or pattern having regions of different thicknesses of the hyphae network within the crosslinked mycelium matrix.

The engraved pattern may have regions of different thicknesses of the hyphae network while a plane of the support scaffold within the mycotextile deviates from a plane of the mycotextile by less than 20%. The engraved pattern may have regions of different thicknesses of the hyphae network while a plane of the support scaffold within the mycotextile deviates from a plane of the mycotextile by less than 10%.

The plurality of nanoparticles may comprise a plurality of metallic nanoparticles formed in vivo within the crosslinked mycelium matrix, characterized by a distribution of metallic nanoparticles within and outside of the hyphae of the hyphae network within the crosslinked mycelium matrix. The color of the mycotextile may be determined by the plurality of nanoparticles. For example, the plurality nanoparticles may comprise metallic nanoparticles that are distributed through the hyphae network both over the hyphae and within the hyphae. Any of these mycotextile may include a second plurality of nanoparticles comprising ceramic nanoparticles. The plurality nanoparticles may comprise metallic nanoparticles and the ceramic nanoparticles may have a different distribution than the metallic nanoparticles of the plurality of nanoparticles.

The ceramic nanoparticles may be distributed primarily or exclusively over the hyphae of the hyphae network (e.g., less than 20%, 15%, 10%, etc.) within the hyphae structures, or residual hyphae structures in the final mycotextile. The ceramic nanoparticles may be functionalized by the adsorption of a prolamin on their surface. The plurality of nanoparticles may comprise metallic nanoparticles and wherein the metallic nanoparticles comprise silver, gold, iron oxide, and/or copper oxide nanoparticles. The mycotextile may be coated with a prolamin. The color of the mycotextile may be determined by the localized surface plasmon resonance (LSPR) of the plurality of nanoparticles.

For example, a mycotextile may include: a support scaffold layer embedded within a crosslinked mycelium matrix, wherein the support scaffold layer is crosslinked to the mycelium matrix; a plurality nanoparticles within the crosslinked mycelium matrix and distributed through the hyphae network within the crosslinked mycelium matrix, wherein the mycotextiles are engraved to form a picture, texture and/or pattern having regions of different thicknesses of the hyphae network within the crosslinked mycelium matrix while a plane of the support scaffold within the mycotextile deviates from a plane of the mycotextile by less than 10%.

All of the methods, compositions and/or apparatuses described herein, in any combination, are herein contemplated and can be used to achieve the benefits as described herein.

BRIEF DESCRIPTION OF THE DRAWINGS

A better understanding of the features and advantages of the methods, compositions, and/or apparatuses described herein will be obtained by reference to the following detailed description that sets forth illustrative embodiments, and the accompanying drawings of which:

FIGS. 13A-13B illustrate hyphal architecture of the SCC-0006 parental strain in two different regions of a given field of view. Arrows point to the septa with clamp connections. The scale is indicated in red (40× lens).

FIGS. 14A-14B illustrate hyphal architecture of the SCC-0006 3.1 transformant in two regions of a given field of view. Arrows point to septa lacking clamp connections. The scale is indicated in red (40× lens).

FIGS. 15A-15B illustrate hyphal architecture of the SCC-0006 3.6 transformant in two regions of a given field of view. Arrows point to the septa with clamp connections. The scale is indicated in red (40× lens).

FIGS. 16A-16B illustrate hyphal architecture of the SCC-0006 3.9 transformant strain in two regions of a given field of view. Arrows point to septa lacking clamp connections. The scale is indicated in red (40× lens).

FIG. 26B shows Ag mapping and FIG. 26C shows a histogram mapping the summed spectrum.

(FIG. 27A), 60° C. (FIG. 27B) or 70° C. (FIG. 27C). Scanning Electron Microscopy (SEM) images of the corresponding samples were taken with secondary electrons at 5 k× magnification. Each scale bar shown as an inset of the images corresponds to 5 micrometers.

FIGS. 31C and 31D illustrate the results of GLCM package measurements for entropy and contrast, respectively. Significant differences were determined using a t-test ****=p-value <0.001.

FIG. 33A shows a photograph of the mycotextile after the mycosynthesis of AuNPs and FIGS. 33B-33C show the corresponding SEM images at 5 and 50 k× magnification, respectively, taken using secondary electrons. The scale bar of the image at 5k× is 5 micrometers, and the image taken at 50 k× is 500 nanometers.

FIGS. 41A-41B show Scanning electron microscopy (SEM) images of the samples obtained with 25 mM of each iron salt taken with secondary electrons at 10 k× magnification. FIG. 41A shows FeCl2, FIG. 41B shows FeSO4. Each scale bar shown as an inset of the images corresponds to 5 micrometers.

FIGS. 42A1-42A2 show photographs of the "Wild-Cu" and "Ag—Cu" mycotextiles, respectively. On the left (FIG. 42A1), the "Wild-Cu" was obtained by immersion of a wild mycotextile in a dispersion of copper oxide nanoparticles obtained by biosynthesis using an extract of *Ilex paraguariensis*. On the right (FIG. 42A2), the "Ag—Cu" mycelium fabric was obtained by immersion of the mycotextile loaded with AgNPs in the same dispersion.

FIGS. 42B1-42B3 show scanning electron microscopy (SEM) images (FIG. 42B1) of the "Wild-Cu" mycotextile at 500× and 10 k× magnifications that were taken with secondary electrons. The images were collected at the interface of the common hyphae network and the thick cracked deposit. The scale bar of the image at 500× is 50 micrometers, and the image taken at 10 k× is 5 micrometers. FIG. 42B2 shows copper mapping and FIG. 42B3 shows an EDS spectrum of the same region that are displayed in the image of FIG. 42B1.

FIGS. 42C1-42C4 show scanning electron microscopy (SEM) images (FIG. 42C1) of the Ag—Cu mycotextile at 500× and 10 k× magnifications, taken with secondary electrons. The images were collected at the interface of the common hyphae network and the thick cracked deposit. The scale bar of the image at 500× is 50 micrometers, and the image taken at 10 k× is 5 micrometers. FIGS. 42C2 and 42C3 show silver and copper mapping, respectively, and FIG. 42C4 shows an EDS spectrum of the same region are displayed in the same figure.

FIGS. 43A-43B show photographs of an aqueous suspension of the stabilized magnetic IO and the dried magnetic IO NPs.

FIGS. 44A1-44A2 show photographs of the "Wild-magnetic IO" (FIG. 44A1) and "Ag-magnetic IO" mycotextiles (FIG. 44A2). The "Wild-magnetic IO" was obtained by immersion of a wild mycotextile in a dispersion of magnetic iron oxide nanoparticles obtained by biosynthesis using an extract of Aloe vera. The mycotextile was obtained by immersion of the mycotextile loaded with AgNPs in the same dispersion. Scanning electron microscopy (SEM) images of the corresponding "Wild-magnetic IO" and "Ag-magnetic IO" mycotextiles at 500χ. The scale bar is 50 micrometers.

FIGS. 44B1-44B3 show Iron mapping (FIG. 44B2) and EDS spectrum (FIG. 44B3) of the sample "Wild-magnetic IO." A scanning electron microscopy (SEM) image (FIG. 44B1) was used as a reference for the mapping, which was obtained using backscattered electrons.

FIGS. 44C1-44C4 show Iron (FIG. 44C2) and Silver (FIG. 44C3) mapping and EDS spectra of the sample "Ag-magnetic IO". A scanning electron microscopy (SEM) image (FIG. 44C1) was obtained using backscattered electrons as a reference for the mapping.

FIGS. 45A1 and 45A2 show photographs of the "Wild-yellow IO" (FIG. 45A1) and "Ag-yellow IO" mycotextiles (FIG. 45A2). At left, the "Wild-yellow IO" was obtained by immersion of a wild mycotextile in a dispersion of rod-like IO NPs in a mixture of water, tween 80 and CMC. On the right, the sidereal mycotextile was obtained by immersion of the mycotextile previously loaded with AgNPs in the same dispersion. Scanning electron microscopy (SEM) images of the corresponding "Wild-magnetic IO" and "Ag-magnetic IO" mycotextiles at 10 k× (BOTTOM). The scale bar is 1 micrometer.

FIGS. 45B1-45B3 show Iron mapping (FIG. 45B2) and EDS spectrum (FIG. 45B3) of the sample "Wild-yellow IO." The scanning electron microscopy (SEM) image (FIG. 45B1) used as a reference for the mapping was obtained using backscattered electrons.

FIGS. 45C1-45C4 show Iron (FIG. 45C2) and Silver (FIG. 45C3) mapping and EDS spectra (FIG. 45C4) of the sample "Ag-yellow IO." A scanning electron microscopy (SEM) image (FIG. 45C1) was used as a reference for the mapping, which was obtained using backscattered electrons.

FIGS. 46A1-46A2 show photographs of the "Wild-red IO" (FIG. 46A1) and "Ag-red IO" mycotextiles (FIG. 46A2). At left, the "Wild-red IO" was obtained by immersion of a wild mycotextile in a dispersion of spherical IO NPs in a mixture of water, tween 80 and CMC. On the right, the sidereal mycotextile was obtained by immersion in the same dispersion as the mycotextile previously loaded with AgNPs.

FIGS. 46B1-46B2 show SEM images of the "Ag-red IO" mycotextile at 2 (FIG. 46B1) and 20 k× (FIG. 46B2). The scale bar is 10 micrometers in the image on the left and 1 micrometer in the right image.

FIGS. 46C1-46C4 show Iron (FIG. 46C2) and Silver (FIG. 46C3) mapping and EDS spectra (FIG. 46C4) of the sample "Ag-RED IO". A scanning electron microscopy (SEM) image (FIG. 46C1) was used as a reference for the mapping and obtained using backscattered electrons.

FIGS. 47A1-47A2 show photographs (top) of the starting IO NPs crosslinked (in situ) mycotextile (FIG. 47A1) and the resulting in situ-Ag mycotextile (FIG. 47A2). FIG. 47A1 is depicted the "in-situ" cross-linked material used as a base for the sidereal mycelium fabric, and FIG. 47A2 is the prototype obtained by immersion of this base in a silver nitrate solution. Scanning electron microscopy (SEM) images of the corresponding "in situ" and "in situ-Ag" mycotextiles are shown at 10 k× (bottom). The scale bar is 1 micrometer.

FIGS. 47B1-47B4 show Iron (FIG. 47B2) and Silver (FIG. 47B3) mapping and EDS spectra (FIG. 47B4) of the sample "in situ-Ag". A Scanning Electron Microscopy (SEM) image (FIG. 47B1) was used as a reference for the mapping and obtained using backscattered electrons.

FIGS. 48A1-48A4 show examples of metallic plates designed with four myco-inspired patterns for conventional embossing approximations.

FIGS. 48B1-48B4 show examples of the myco-inspired embossing patterns in the material loaded with AgNPs.

FIG. 48C1-48C4 show examples of myco-inspired embossing patterns in the material loaded with AuNPs.

FIG. 48D1-48D4 show examples of myco-inspired embossing patterns in the material "Ag—Cu NPs".

FIG. 48E1-48E4 show examples of the myco-inspired embossing patterns in the material "Ag-magnetic IO NPs".

FIG. 48F1-48F4 show examples of the myco-inspired embossing patterns in the material "Ag-yellow IO NPs".

FIG. 48G1-48G4 show examples of the myco-inspired embossing patterns in the material "Ag-red IO NPs".

FIGS. 49B1-49B2 show examples of photographs of patterned materials loaded with AgNPs (left) and AuNPs (right) using the crude engraving technique.

FIGS. 49C1-49C3 compare example sections through an un-engraved mycotextile (FIG. 49C1), a mycotextile compressed after crosslinking and drying to form a surface pattern (FIG. 49C2), and a mycotextile engraved into the living mycelium mat (FIG. 49C3) as described herein.

FIG. 52A shows photographs of the remaining crystal violet solutions after adsorption experiments. The prototypes "wild", "Ag—Au NPs", and "Au biosynthesized NPs" were in contact with a crystal violet solution for 90 min in darkness. The photographs correspond to the solution at 0, 60 and 90 min.

FIGS. 52B1-52B3 show photographs of the prototypes "wild" (FIG. 52B1), "Ag—Au NPs" (FIG. 52B2), and "Au biosynthesized NPs" (FIG. 52B3) before (top) and after (bottom) immersion in the solution of crystal violet for 90 min without photoirradiation with UV light (Adsorption process). The final row corresponds to bleaching experiments in which the adsorbed crystal violet is photodegraded after irradiation with UV light for 150 min.

FIG. 53A. Photographs of the remaining crystal violet solutions after photocatalysis experiments. The prototypes "wild", "Ag—Au NPs" and "Au biosynthesized NPs" were in contact with a crystal violet solution for 90 min under irradiation with UV light. The photographs correspond to the solution at 0, 60 and 90 min.

FIGS. 53B1-53B3 show photographs of the prototypes "wild" (FIG. 53B1), "Ag—Au NPs" (FIG. 53B2), and "Au biosynthesized NPs" (FIG. 53B3) before and after immersion in the solution of crystal violet during 90 min under UV light photoirradiation (Photocatalytic process).

FIGS. 54A-54C show photographs comparing the remaining solution before (FIG. 54A) after adsorption and photocatalysis experiments (90 min, FIG. 54B). The corresponding UV-Vis spectra of the solution for the Ag—Au NPs and Au biosynthesized NPs experiments are shown in FIG. 54C.

FIG. 56A shows an example of the chromatogram of four monokaryotic strains obtained from SCC-0006. FIG. 56B shows the chromatogram of a dikaryotic strain SCC-0006 (parental strain) and SCC-0006/3.6 (engineered strain).

DETAILED DESCRIPTION

Figure 1:
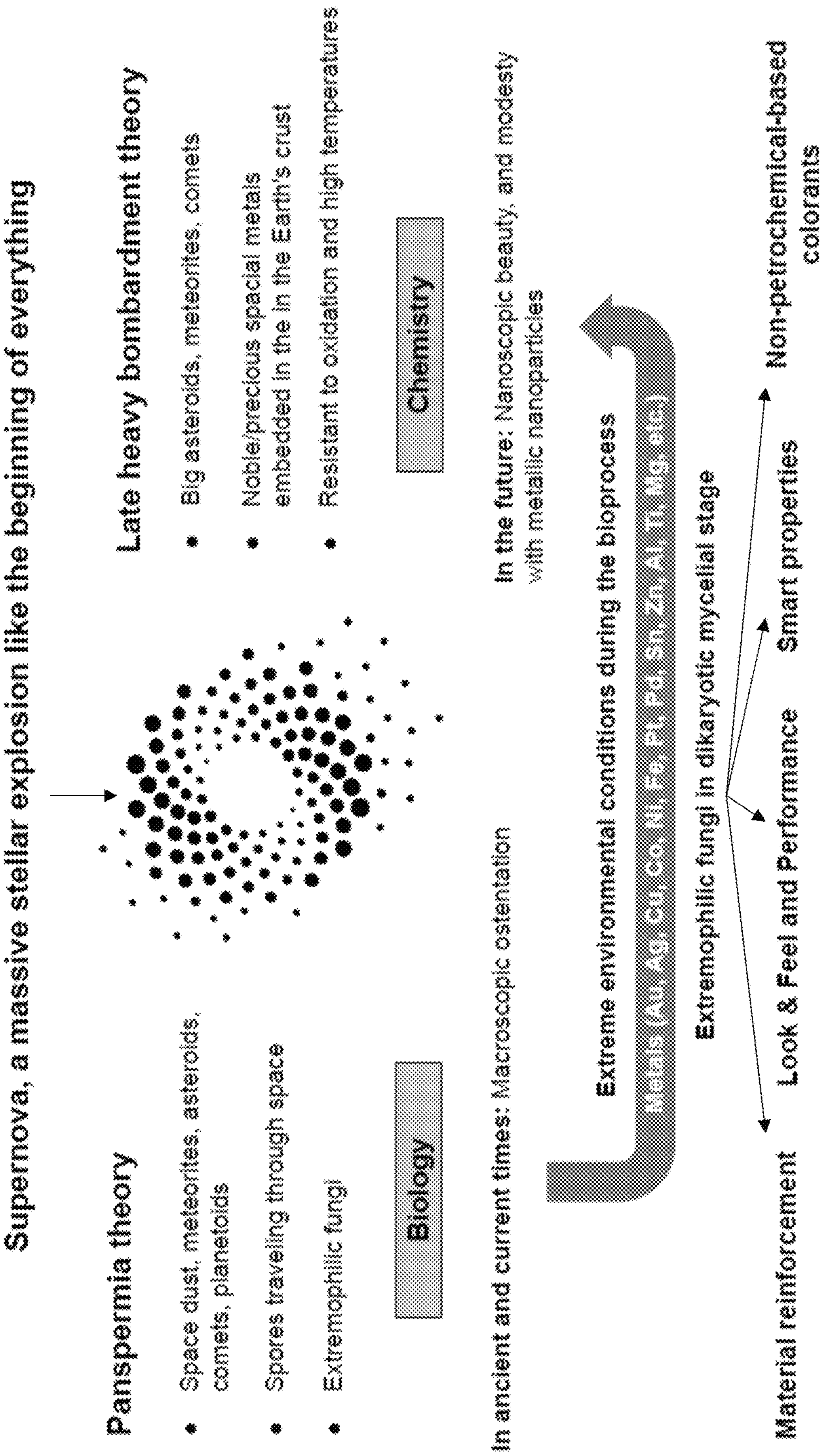
FIG. 1 schematically illustrates the inspiration for the Sideral Mycelium Fabrics described herein, including Panspermia and the Late Heavy Bombardment theories. The Sidereal Mycelium Fabrics described herein may provide a sustainable textile production inspired by cosmic phenomena and the resilience of unique life forms like fungi.

Described herein are mycotextiles having unique and vibrant colors, textures and/or patterns. As described herein, the color, texture and/or patterns of these materials may result from enzymatic processes and/or treatment steps that take advantage of properties of native and/or engineered strains of the fungal strain forming the mycotextile. For example, in general, the methods and compositions (including mycotextiles) described herein may be used with dikaryon fungal strains, including, but not limited to, engineered dikaryon fungal strains. Thus, described herein are dikaryon fungal strains, including dikaryon Basidomycota fungal strains, and in particular, engineered strains and methods of using them to form and/or process mycotextiles.

Following cell fusion in some fungi, the two parent nuclei remain distinct. In many fungi, when two mating partners undergo cellular fusion, the resulting bi-nucleate cell grows filamentously, with each filament cell maintaining two independent nuclei that are replicated in a coordinate fashion. This growth stage is referred to as the dikaryon or dikaryotic filament. The largest and most studied group of organisms with a prolonged dikaryotic stage is the basidiomycete fungi. This phylum includes mushrooms, bracket fungi, and many plant pathogens, including the corn smut *Ustilago maydis.*

Until the present work, it is widely believed that mycelium-based textiles should preferably be formed of monokaryon forms, and not dikaryon forms of a fungal strain. See, e.g., U.S. Pat. No. 11,576,311 ("Monokaryon mycelial material and related method of production"). This is because the cells of the dikaryon undergo a complex form of cell division involving the formation of clamp connections to preserve one copy of each haploid nucleus within every dikaryotic cell, and generate fruiting bodies at any stage that are believed to result in genetic variability, variability in thickness and textures, and may result in blemishes in the final fungal mat, which may require additional post-processing. In contrast, the monokaryotic cell does not go through the normal reproductive process and thus does not generate fruiting bodies. Surprisingly, the inventors have found that maintaining the fungal strain used to form the mycotextile in the dikaryotic form may result in materials having particularly beneficial features and may dramatically simplify some processing, particularly in controlling growth and in some cases, in processing the mycotextile to color (or dye) the mycotextile using one or more elements (including metallic elements) synthesized by the fungi itself during processing.

Thus, in some examples the method and compositions, including textiles, described herein may be limited to the dikaryotic forms of the fungal strains used. Although the methods and examples described herein include engineered dikaryotic strains, described in greater detail below, it should be understood by those of ordinary skill in the art that any appropriate dikaryotic strain may be used, not limited to these specific strains. The benefits and advantages, including improved rates of growth and reproducibility and stability of the resulting textiles, may be achieved with virtually any dikaryotic strain, including strains identified by others as well as the strains explicitly derived herein.

In some cases, dikaryotic fungal strains may be generated or selected to have desired properties. For example, more than 100 fungal strains with mycotextile potential are maintained in a collection curated by the inventors. Dikaryotic strains may be generated from one or more fungal strains selected for one or more properties. These strains may be manipulated as described herein to form a stable dikaryotic line. Although many of the examples described herein focus on particular strains of fungi that are engineered to be stable dikaryotic strains, the techniques described herein may be generally appliable to other fungal strains, including in particular other Basidomycota fungal strains. In some cases, a strain referred to as the SCC-0006 (e.g., the "gold standard") strain, previously referred to as an Unclassified Polyporaceae (see, e.g., U.S. Patent Published Application No. US 2023/0356501 and U.S. patent application Ser. No. 18/595,392) was modified as described herein to form one or more stable dikaryotic strains.

Figure 3:
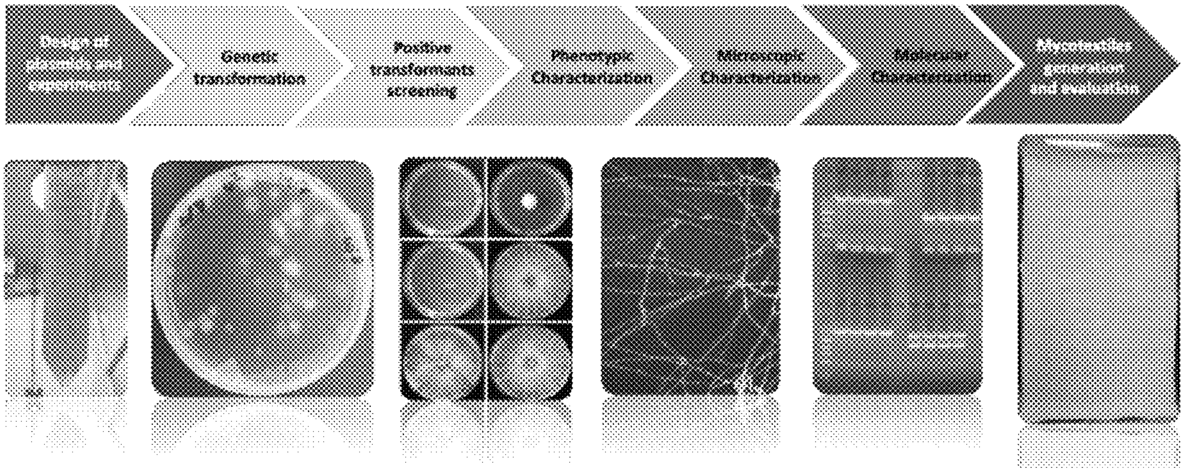
FIG. 3 is a graphical overview of one example of a method of forming a Sidereal Mycelium Fabric as described herein.

As part of this process, gene overexpression, genetic engineering, and genome editing techniques were used to obtaining improved fungal strains and ensure high-performance and reproducible mycelium-based textiles at large-scale production. For this, several tools were used, including the genome DNA sequencing of the strain of interest, the determination of the codon usage, promoters useful for constitutive or inducible gene expression, and functional plasmids. In some cases, the validation of the engineered strain's abilities to produce a high-quality mycotextile was performed using plasmids with selectable markers for positive transformants selection, with a robust gene transformation protocol. Further, systems for positive transformants screening by phenotypical, biochemical, microscopic, enzymatic, and molecular approaches were used. FIG. 3 illustrates an overview of this process.

In some cases, fungal strains having aspects to be improved for mycelium fabric purposes were prepared. For example, to ensure an efficient Sidereal Mycelium Fabric production, stains may be selected and/or engineered having factors directed to enhance the density and homogeneity of mycelium colonization onto the scaffold, the uniformity of the chemical composition of the cell wall facilitating the post-fermentation treatments, and the uniformity of the synthesis of the enzymatic system at the extracellular medium (e.g., oxidoreductase enzymes, etc.).

Processing of Mycelium-Based Fabrics

It is particularly helpful to use strains of fungi that may be efficiently grown at an industrial scale, without requiring sterile, laboratory conditions, despite environmental contamination. Dikarya, the subkingdom of the fungi kingdom that includes Ascomycota and Basidiomycota phylum was found to be a possible source of candidate strains. One strain used herein (e.g., SCC-0006) is a heterokaryon belonging to the Basidiomycota division, which has beneficial characteristics of its life cycle as compared to other organisms. Basidiomycota are dikaryotic, in which each compartment of a hypha contains two haploid nuclei, each derived from a different parent. A dikaryon strain can be formed by mating two compatible monokaryon strains, resulting in plasmogamy but not karyogamy in the fused compartment. When new hyphae grow, the two nuclei synchronously divide, and each new compartment keeps two nuclei. These strains may not normally be stable. In some cases, only plasmogamy is achieved because only the asexual reproduction of the fungus is harnessed. The karyogamy only occurs before the initiation of sexual reproduction.

Basidiomycota fungi germinate from a spore to form a primary monokaryotic mycelium, where each cell compartment contains a single haploid nucleus. During fertilization, the nuclei from one compatible mycelium migrate to the other and are incorporated, forming a secondary mycelium.

Figure 2A:
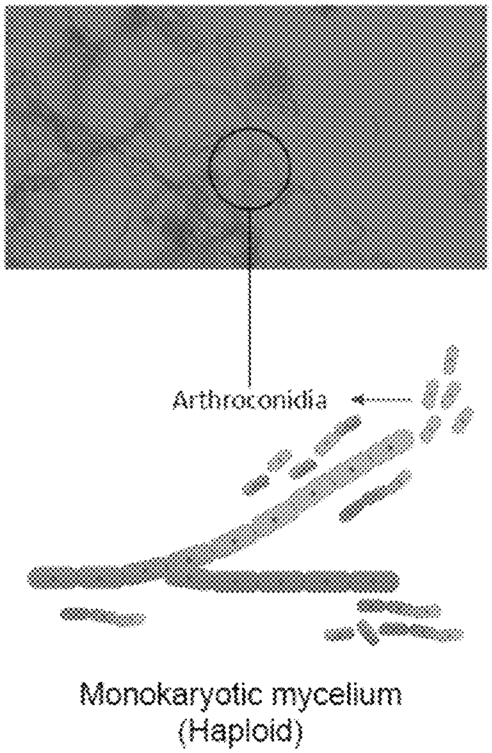
FIGS. 2A-2B illustrate characteristics of monokaryotic (FIG. 2A) and dikaryotic (FIG. 2B) mycelium of fungi.
Figure 2B:
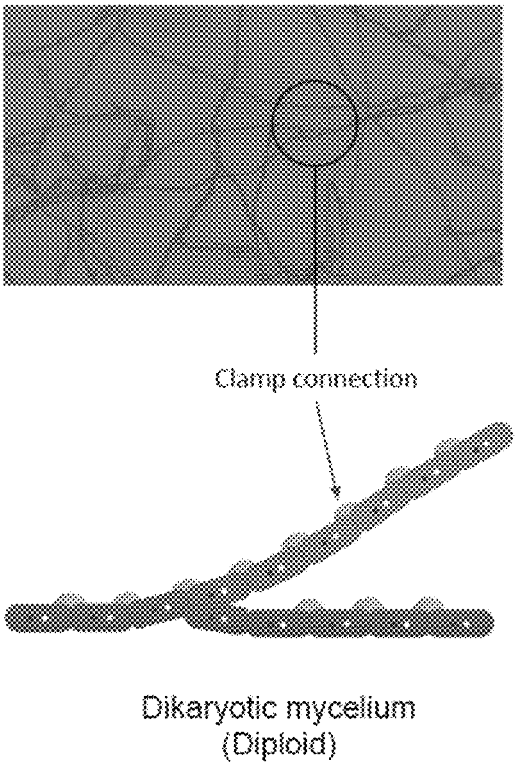

The dikaryon is characterized by the formation of clamp connections, where a regular association of non-fused haploid nuclei occurs, as shown in FIGS. 2A-2B. In dikaryons, the two nuclei coordinate very closely with each other. Functionally, the dikaryon acts like a diploid, meaning both nuclei regulate cell growth, and deficiencies in one nucleus are complemented by the other genome. However, evolutionary forces can still act on individual nuclei since the two nuclei remain separate. If one of the nuclei can increase its own fitness at the expense of the other, it can be selected, even if it has a cost for the dikaryon.

Once the strain establishes itself as a dikaryotic organism, it can no longer incorporate another nucleus, leading to a characteristic phenotype. The gene expression patterns in dikaryons may be similar to that of diploids during vegetative growth. However, the mycelium can still fertilize monokaryons by donating one of its nuclei. These dikaryon-monokaryon (di-mon) matings were first described by Buller in 1930 and are called the Buller phenomenon. This mating in basidiomycetes is regulated by two unlinked mating type loci (matA and matB), which must be different to ensure compatibility. Because many species have multiple alleles at each mating type locus, in most cases, both nuclei in a dikaryon are, in principle, capable of donating nuclei to a monokaryon. However, only one of the two nuclei will successfully fertilize the mycelium for each mating. Thus, the two nuclei of a dikaryon compete to fertilize the monokaryon they encounter.

Normally, fungi do not remain as a dikaryotic organism indefinitely, and it may be difficult to control these organisms in this state. The dikaryon mycelium stage tends to break down, forming monokaryotic hyphae; this phenomenon is called dedikaryotization. This process occurs frequently and can be attributed to environmental factors, such as changes in the surroundings, variations in nutrient availability, temperature, or other conditions, which can influence the stability of the dikaryotic state. If the environment changes in a way that no longer favors the existence of a dikaryotic state, fungi can undergo dedikaryotization. Recombination events during the life cycle of fungi, especially under specific conditions, can lead to genetic recombination between dikaryotic nuclei. This event may result in the fusion of the two nuclei, leading to the loss of dikaryotization and the formation of a monokaryotic mycelium. Finally, genetic instability, as some fungal strains can be genetically unstable, meaning they are more prone to the loss of the dikaryotic condition. Described herein are methods and techniques in which a fungal strain may be maintained as a dikaryotic by maintaining a continuous selection pressure favoring its continued existence, such as antibiotic resistance or auxotrophy.

SCC-0006 is a Basidiomycota heterokaryon strain that is highly promising for mycelium fabric production. However, the homogeneity of mycelium growth, the uniformity of the chemical composition of the cell wall, and the uniformity of the exoenzymes secretion are important to obtaining an efficient Sidereal Mycelium Fabric. Therefore, a dikaryotic SCC-0006 strain was obtained to maintain its phenotypic characteristics for a controllable and defined period of time (e.g., the time that occurs in a batch of mycelium fabric production).

As used herein, maintaining a "fungal fidelity" in a dikaryon can generally be achieved by an infallible selective pressure through antibiotic resistance or auxotrophy strategies. "Nuclear divorce" may be avoided in the dikaryon strain (e.g., a dikaryon strain of SCC-0006 or other appropriate strain), e.g., regeneration into a monokaryon mycelial stage. Note that although the examples described herein include the SCC-0006 strain and derived dikaryon strains, other strains may be used, including other stable dikaryon strains (and specifically other engineered dikaryon strains).

Different selectable markers to identify positive transformants have been described in the genetic engineering of fungi. In some cases, the strains may be engineered to have an antibiotic resistance to a known antibiotic, such as hygromycin, neomycin, geneticin, phleomycin, blasticidin, and nourseothricin. Within the chemical agents are ammonium glufosinate, carboxin, etc. In this case, antibiotic resistance as selective pressure may be used as a strategy to build a stable dikaryon strain (e.g., a stable dikaryon strain of SCC-0006).

Besides enhancing homogeneity, this strategy may also help control of environmental contamination by incorporating a gene that confers resistance to an antibiotic in the working fungal strain. This can favor the development and optimization of production because it may provide greater ease in selecting, maintaining, and growing a resistant strain and better genetic stability. Finally, in the production process, an antibiotic-resistant working strain provides an alternative to creating a selective environment where only the engineered strain can develop and without other contaminants.

Genetic engineering applied to mycelium-based textile development must consider developing an appropriate pipeline to obtain improved strains (see, e.g., FIG. 3), including the use of a toolkit that must support strategies of gene overexpression, genetic engineering, and a functional application of the CRISPR/Cas9 system. One toolkit for engineering strains of SCC-0006 was built is described below.

Whole Genome Sequencing of SCC-0006 Strain and Analysis:

The whole genome DNA of the SCC-0006 was sequenced to understand the capabilities of this gold standard strain from a genomic perspective. The primary objective was to discern key genes, promoters, and terminators, and to provide the background for subsequent genetic transformation. The sequence of the strain (e.g., the SCC-0006 strain) allowed the implementation of sophisticated genetic transformation strategies, ensuring the precision and efficacy of introducing selection markers. The SCC-0006 strain had not previously been sequenced.

Genomic DNA (gDNA) extraction was performed using the Quick-DNA HMW MagBead Kit from Zymo Research (Zymo Research, Irvine, California). This technique ensured the procurement of gDNA characterized by high molecular weight and integrity and subsequent genome sequencing with Nanopore and Illumina technologies. The resulting reads were strategically harnessed for assembly through Flye 2.8v, subsequently annotated with funannotate. The culmination of these processes resulted in the metrics detailed in Table 1.

TABLE 1

General Metrics of the wild strain SCC-0006 genome assembly.

| | |
|---|---|
| Number of contigs | 502 |
| GC (%) | 55.59 |
| N50 | 383,699 |
| L50 | 24 |
| Largest contig | 2,463 Mb |
| Proteins | 11,973 |
| BUSCO: euk_genome_met | 96.60% |
| tRNAs | 371 |

In this example, the assembly, resolving in 502 contigs, reflects a GC content of 55.59%. The L50 index, denoting 24, while the contig itself boasts a substantial length of 383 Kb (N50). The predictive prowess of the assembly pipeline foretells 11,973 CDS or proteins, and a thorough BUSCO completeness analysis, tethered to the euk_genome_met database, yielded a commendable completeness score of 96.60% ([S:95.7%, D:0.9%], F:0.6%, M:2.8%, n:1764). Delving deeper into the genomic landscape reveals 371 tRNA-encoding sequences, where cysteine and tryptophan emerge as the less-represented entities with five copies each. In contrast, the amino acids alanine and arginine dominate, each boasting a presence of 30 copies each. The 11,973 CDS obtained were systematically subjected to codon usage analysis utilizing CodonU.

Genomic DNA sequencing was used for the in silico identification of candidate genes, promoters, and terminators that could work suitably as selectable markers. This allowed the consequent in vivo gene expression analysis and the design and synthesis of the functional plasmids carrying the cassettes of resistance markers' expression. Particular attention was given to optimizing codon usage, facilitating the efficient expression of heterologous genes in the strain of interest. The use of advanced technologies in this comprehensive exploration expanded the understanding of the intricate fungal genome and strategically positions for redesign and refined genetic manipulations within the patented methodologies. This emphasis on codon usage for efficient homologous or heterologous gene overexpression enhanced the translational impact of genetic modifications in various scientific applications described herein.

Figure 4:
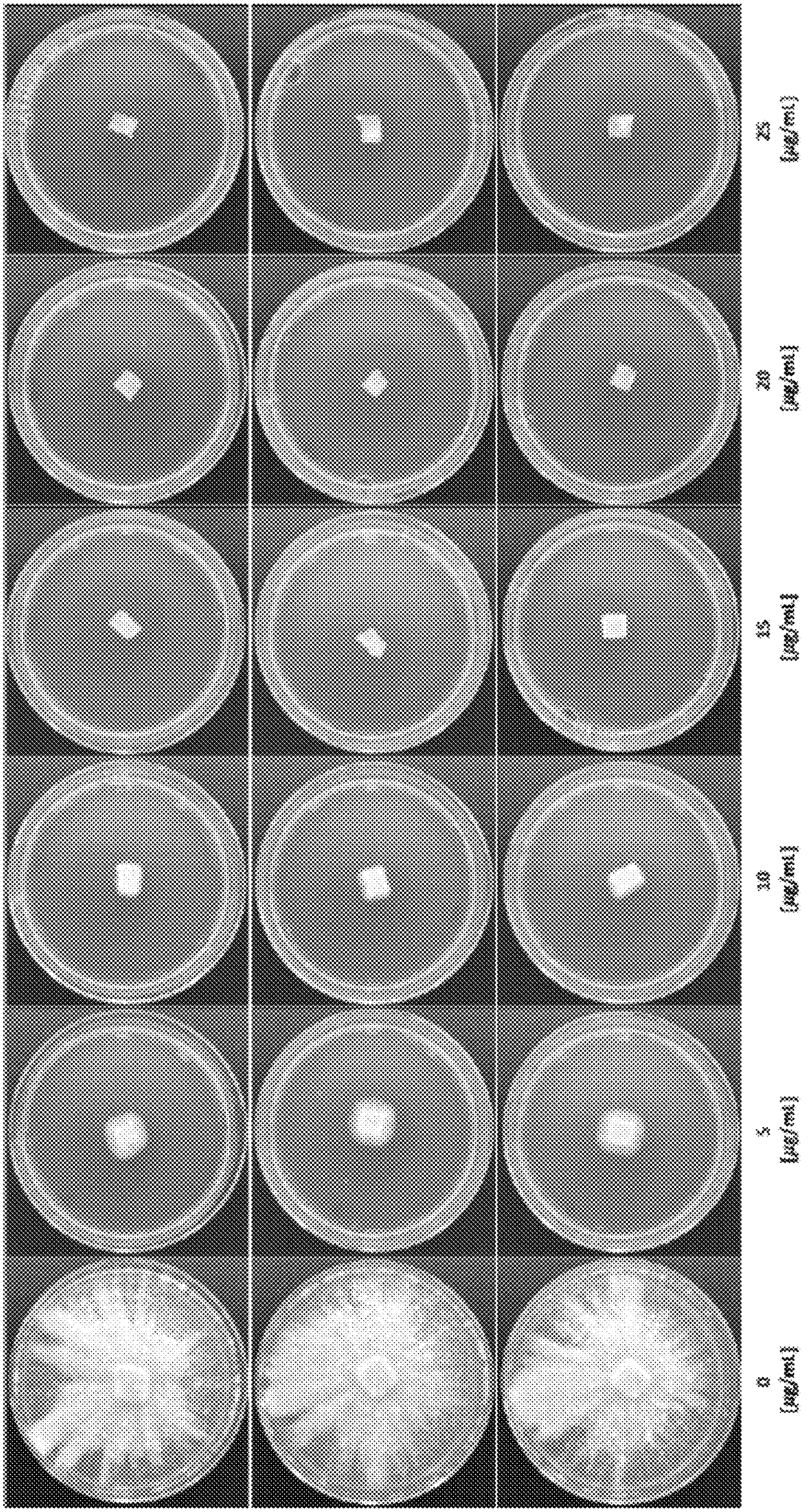
FIG. 4 schematically illustrates the sensitivity of one example strain of fungi (strain SCC-0006) toward hygromycin B. The experiment was performed in triplicate. The photos were taken on day 7 of incubation at 28° C. At 15 μg/mL, there was still some hyphal growth (not visible in the photos), so the complete inhibition concentration was set at 20 μg/mL.

Selection of a Proper Antibiotic as a Selectable Marker in the Transformation Experiments:

Before designing and synthesizing functional plasmids containing the cassettes of resistance marker expression, the first step was to assess the fungus's resistance/tolerance to a specific antibiotic. Different selectable markers to identify positive transformants have been described in the genetic engineering of fungi. The most knowledgeable antibiotics are hygromycin B, neomycin, geneticin, phleomycin, blasticidin, and nourseothricin. The SCC-0006's resistance/tolerance to growth in different concentrations of diverse antibiotics was evaluated. The screening results show a high sensitivity to Hygromycin B, which is widely used as a selectable marker in both prokaryotic and eukaryotic cells. It acts by inhibiting polypeptide synthesis and thereby inhibiting translation in non-resistant strains. The inhibition curve of SCC-0006 with hygromycin B, ranging from 0 g/mL to 25 g/mL, was done in darkness at 28° C. for 7 days (FIG. 4). A 20 μg/mL concentration was determined for complete growth inhibition. Therefore, Hygromycin B was chosen as a dominant selectable marker to build a stable dikaryon strain (in this case, from SCC-0006). For this, an optimized hph gene encoding hygromycin B phosphotransferase was designed using the usage codon of SCC-0006 to confer Hygromycin B resistance into the transformants, which will be called the hph6 gene.

Figure 5A:
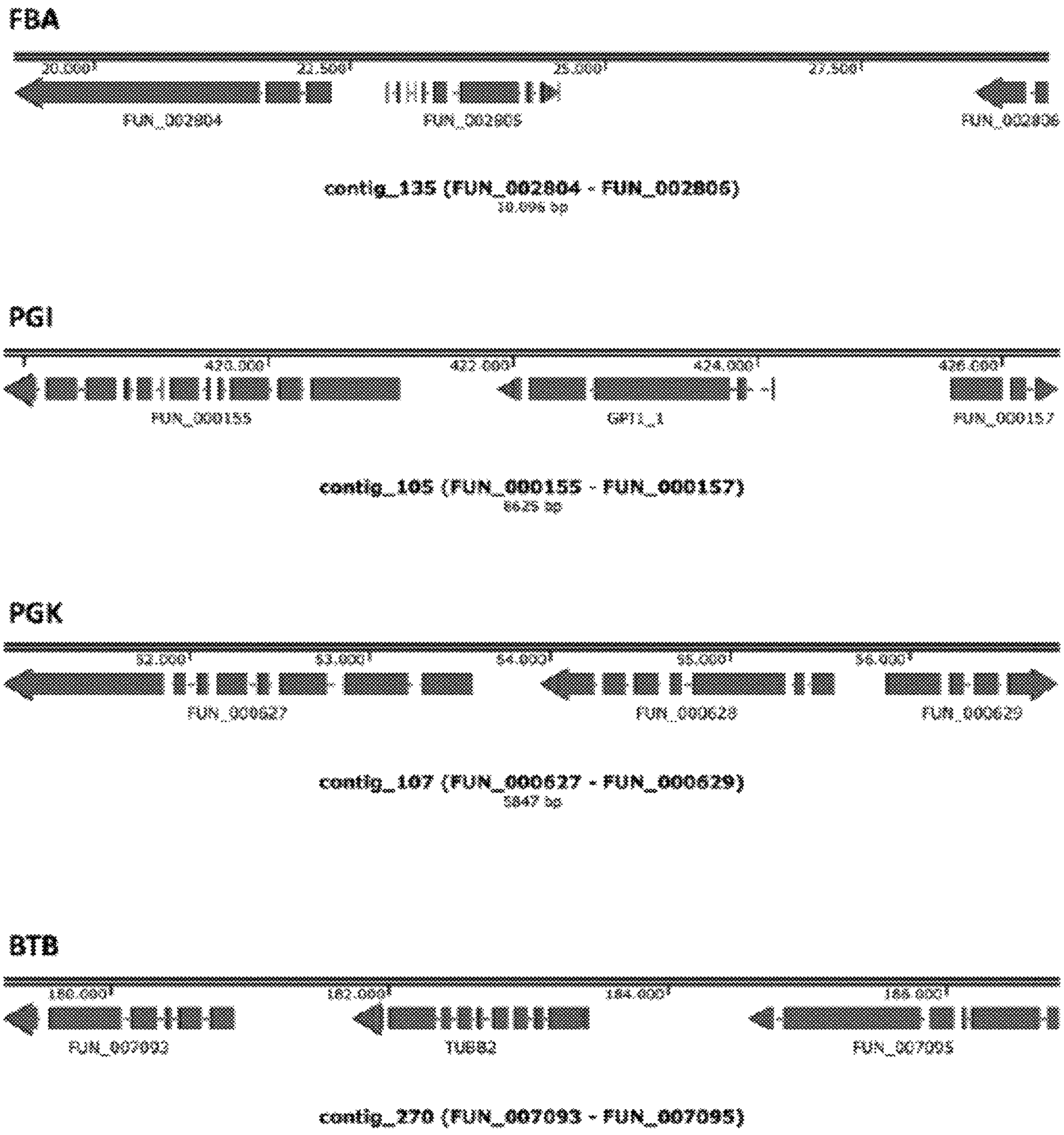
FIGS. 5A-5B show graphical representations of the genomic context of six genes selected from the central metabolism in the example strain of fungi (SCC-0006). The genes include FBA: Fructose-1,6-bisphosphate aldolase (FUN_002805); PGI: Glucose-6-Phosphate Isomerase (FUN_000156); PGK: Phosphoglycerate Kinase (FUN_000628); BTB: Beta-tubulin (FUN_007094); TPI: Triosephosphate isomerase (FUN_000234); GDH: Glutamate dehydrogenase (FUN_005514).
Figure 5B:
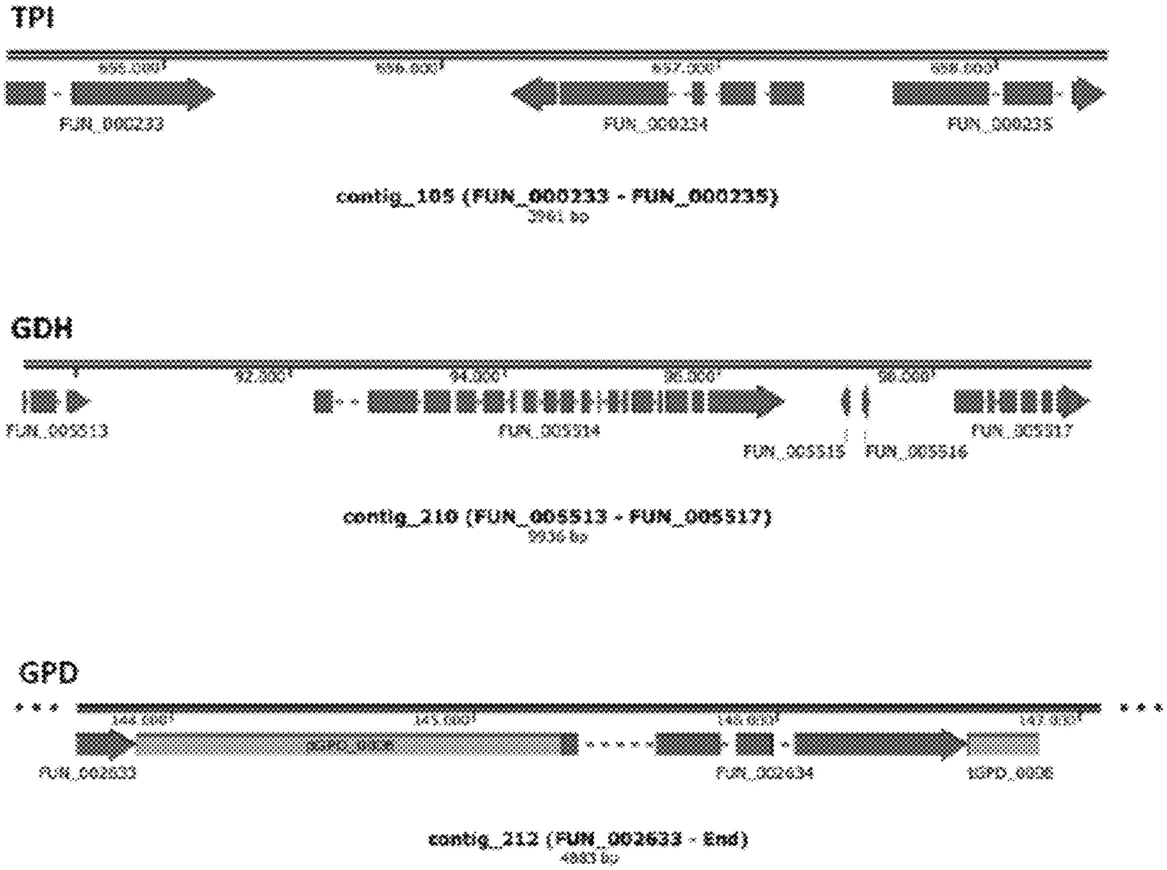

Selection of Native Promoters in the SCC-0006 Genome for Hph Gene Expression:

To determine the best promoter to be used for the optimized hph6 gene expression in the SCC-0006 strain, the transcription levels of six (6) different genes related to the central metabolism, previously described having high levels of constitutive expression in Basiodiomycota species, were qualitatively analyzed using RT-PCR and visualization in agarose gel. For this, previously, an in silico analysis of genome mining was used to identify the chromosomal localization of these genes in the genome of SCC-0006 (FIGS. 5A-5B). As is shown in Table 1, the promoters of the selected genes were the following: FBA: Fructose-1,6-bisphosphate aldolase (FUN_002805); PGI: Glucose-6-Phosphate Isomerase (FUN_000156); PGK: Phosphoglycerate Kinase (FUN_000628); BTB: Beta-tubulin (FUN_007094); TPI: Triosephosphate isomerase (FUN_000234); GPD: glyceraldehyde-3-phosphate dehydrogenase (FUN_002634); GDH: Glutamate dehydrogenase (FUN_005514).

RNA was extracted from samples of living aerial mycelia obtained once the mycotextiles were harvested from the fermentation stage (approx. 7 to 10 days of incubation), using the Quick-RNA Plant Miniprep Kit (Zymo Research, Irvine, California) following the manufacturer instructions. Total RNA was treated with DNAse (New England Biolabs, Ipswich, Massachusetts). Then, cDNA was obtained using an All-In-One 5× RT MasterMix (Applied Biological Materials, Richmond, Canada) following the manufacturer's instructions. RT-PCR was performed using GoTaq® Green Master Mix (Promega, Madison, WI, USA), the cDNA obtained before as a template and the corresponding primers (Table 2). Each primer was designed around an intronic region, and different amplification sizes were obtained from cDNA and gDNA. PCR program: Initial denaturation: 95° C., 3 m; Cycle Denaturation; 95° C., 40 s; Annealing: 58° C., 40 s; Cicle Elongation: 72° C., 1 m; Final Elongation: 72° C., 10 min. The visualization of the PCR products was done in agarose gel 1.5% stained with Safe View Plus.

Figure 6:
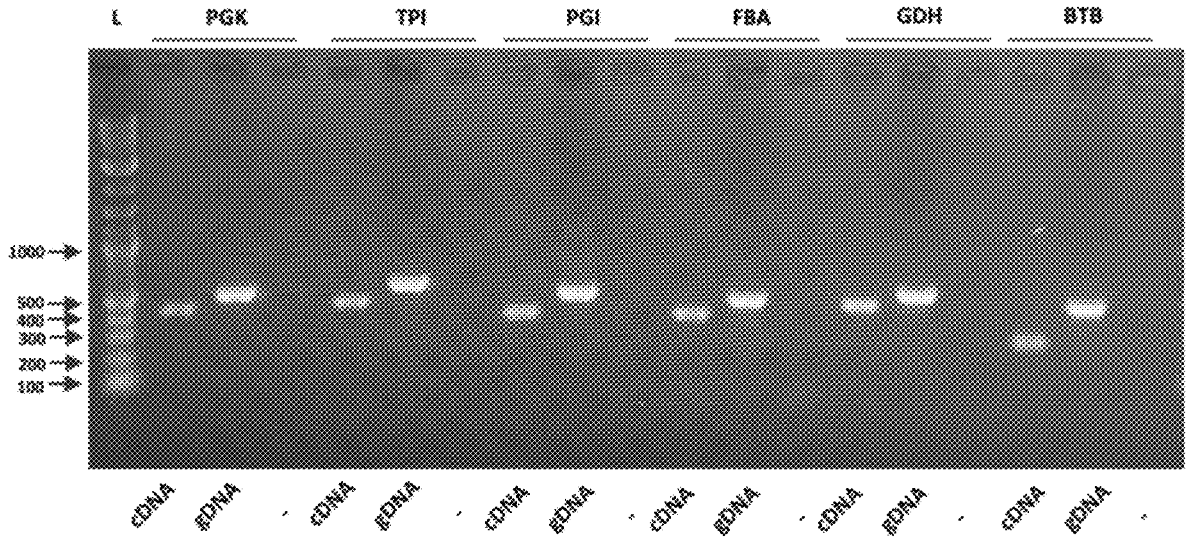
FIG. 6 is an example of an RT-PCR amplification of the six genes selected from the central metabolism from cDNA and gDNA (control) samples obtained from SCC-0006. L: Ladder (1 kb Plus DNA Ladder, NEB): negative PCR controls for each gene. 1% agarose gel electrophoresis.
Figure 7A:
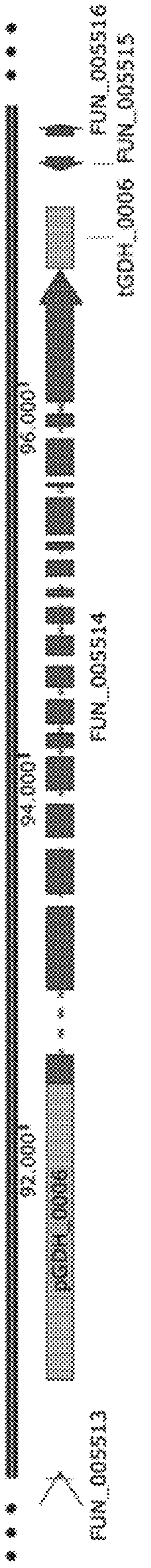
FIGS. 7A-7B illustrate the genomic context and graphic delimitation of the promoters and terminators regions of the glutamate dehydrogenase encoding gene (GDH gene) and glyceraldehyde-3-phosphate dehydrogenase gene (GPD gene) located in the SCC-0006 genome used to design a hygromycin resistance integrative plasmids.
Figure 7B:
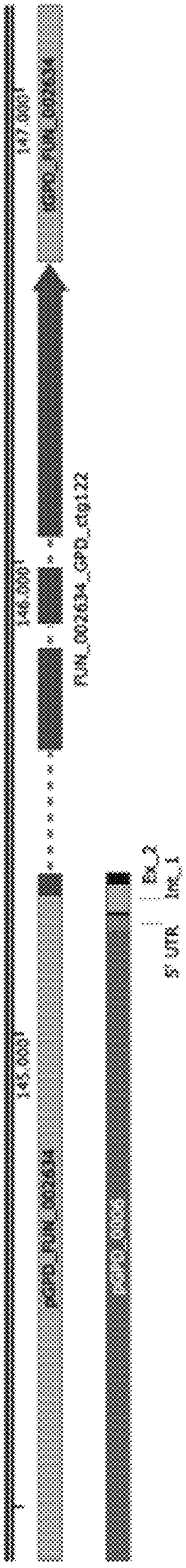

As shown in FIG. 6, all tested genes evidenced similar transcript levels when amplified from cDNA obtained from the tested sample. From these, the glutamate dehydrogenase gene's promoter (pGDH) was selected as one of the most used promoters in fungi for heterologous expression. FIGS. 7A-7B shows the genomic localization of the pGDH promoter (contig_210; 92.241 . . . 96.629; 1.589 pb) and tGDH terminator (contig_210; 96.630 . . . 96.955; 326 pb), with 1589 pb and 326 bp up-stream and down-stream, respectively. Also, the GPD promoter was selected because it is widely used in the genetic engineering of fungi.

TABLE 2

Genomic context information of seven gene promoters analyzed for the hph6 gene expression in SCC-0006. Primers for RT-PCR are shown with the expected amplicon size using gDNA or cDNA as a template.

| Gene | Genome annotation | Genomic localization | | Primer Name | DNA sequence 5'...3' | gDNA (bp) | CDNA (bp) |
|---|---|---|---|---|---|---|---|
| Beta-tubulin (BTB) | FUN_007094 | contig_270 | 183424. 181739 | RT_ tubulin_FW | CGCAAGTGAT GTGTGGTGTT (SEQ ID NO. 1) | 507 | 294 |
| | | | | RT_ tubulin_RV | GTTCCGCCTC TTGTGACG (SEQ ID NO. 2) | | |
| Fructose-1,6-bisphosphate aldolase (FBA) | FUN_002805 | contig_135 | 22870.. 24559 | RT_FBA_ FW | CCTTCCCAAC GACAAGCAG (SEQ ID NO. 3) | 537 | 430 |
| | | | | RT_FBA_ RV | GAAGTTGGGG GAGATCTTGG (SEQ ID NO. 4) | | |
| Glucose-6-Phosphate Isomerase (PGI) | FUN_000156 | contig_105 | 424145.. 421878 | RT_PGI_ FW | CAAGTTCGCG GACTACTTCC (SEQ ID NO. 5) | 572 | 501 |
| | | | | RT_PGI_ RV | ATCAACGAGC CGAGCGTAG (SEQ ID NO. 6) | | |
| Phospho-glycerate Kinase (PGK) | FUN_000628 | contig_107 | 55777.. 53949 | RT_PGK_ FW | GGAAGGAAA GAAGGTCAAG G (SEQ ID NO. 7) | 559 | 449 |
| | | | | RT_PGK_ RV | CCACGGGGAA CACAATCTTG (SEQ ID NO. 8) | | |
| Triosephosphate isomerase (TPI) | FUN_000234 | contig_105 | 657304.. 656255 | RT_TPI_ FW | CTCCGCAAGG AAGTCCAG (SEQ ID NO. 9) | 633 | 483 |
| | | | | RT_TPI_ RV | GGTAACCGAG CCACCATAG (SEQ ID NO. 10) | | |
| Glutamate dehydrogenase (GDH) | FUN_005514 | contig_210 | 92241.. 96629 | RT_GDH_ FW | ACTTACCGGT CCCAAGG (SEQ ID NO. 11) | 596 | 490 |
| | | | | RT_GDH_ RV | AGCAGTAGAG CAGCGAC (SEQ ID NO. 12) | | |
| Glyceraldehyde-3-phosphate dehydrogenase (GPD) | FUN_002634 | contig_122 | 14229.. 147173 | Pgpd-start-FW | GAATTGGGTA CCTGAGTTGA AT (SEQ ID NO. 13) | 1378 | N/A |
| | | | | Pgpd-end-RV | AAGCTTGGTT GAGAGGATG GGATG (SEQ ID NO. 14) | | |

Figure 8A:
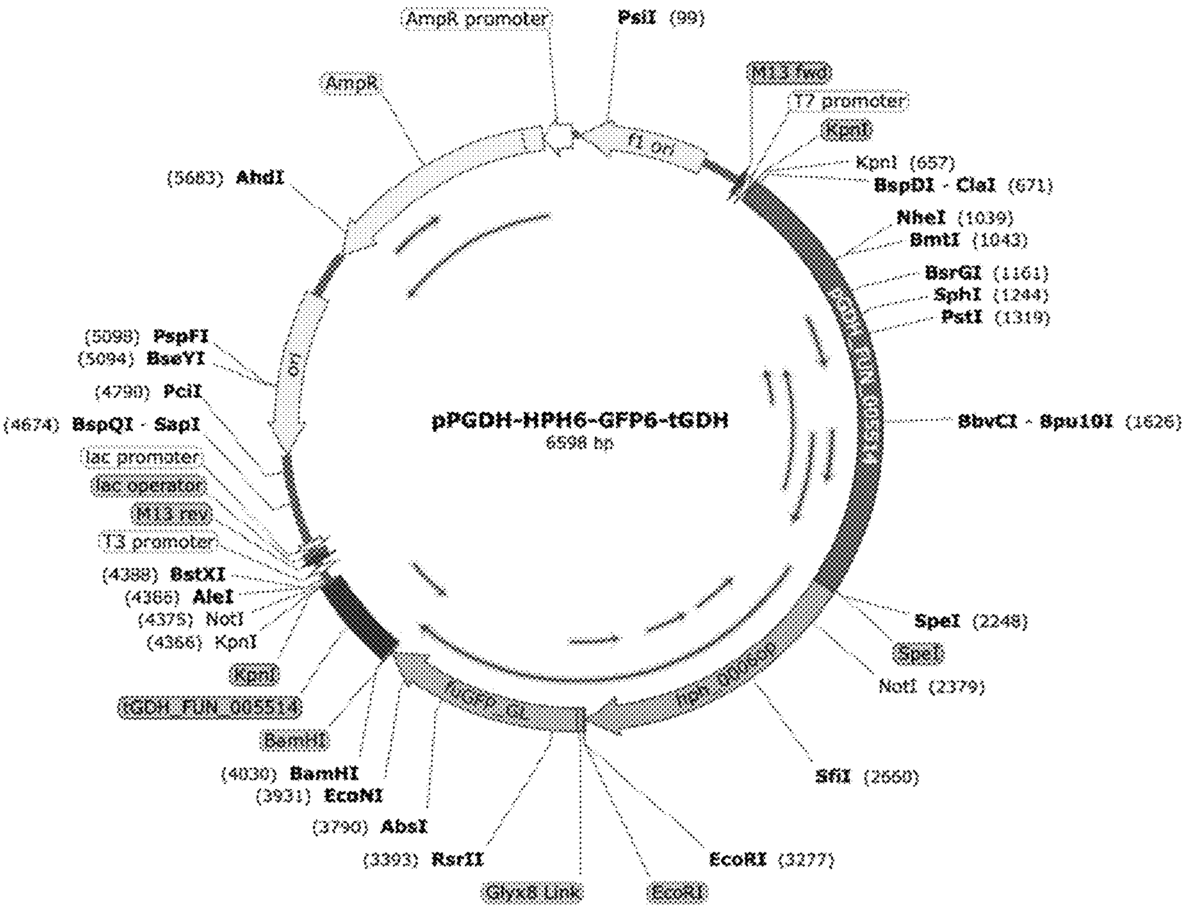
FIG. 8A. is a graphic representation of the pPGDH-HPH6-GFP6-tGDH plasmid. pGDH_0006: Glutamate dehydrogenase gene's promoter (GDH gene). HPH6: Optimized coding sequence of the hygromycin phosphotransferase gene. GFP6: Green fluorescent protein encoding sequence optimized for SCC-0006. tGDH: Glutamate dehydrogenase gene's terminator in SCC-0006.

Design and Synthesis of the Cassette for Hph6 Gene Expression Functional in SCC-0006:

Construction of the pGDH-HPH6-GFP6-tGDH plasmid. Once the pGDH promoter and the tGDH terminator were selected and the hph gene was optimized, the Hygromycin B resistance cassette functional in SCC-0006 using the GDH promoter was designed as follows (FIG. 8A):

pGDH_0006 module: pGDH promoter (1589 bp) with a KpnI restriction enzyme site added upstream from ATG. HPH6 module: hph6 optimized gene functional in SCC-0006 (1023 bp) flanked by SpeI and EcoRI restriction enzyme sites at 5' and 3' ends, respectively. The original coding DNA sequence of the hph gene was obtained from the commercial plasmid pAN7.1. Next, a DNA sequence with Gly-link×8 (SEQ ID NO. 39) polylinker (24 bp) was included. fuGFP6 module: Green fluorescent protein (GFP) encoding gene optimized with the SCC-0006's usage codon (723 bp) and flanked with EcoRI and BamHI restriction enzyme sites at 5' and 3' ends, respectively. tGDH_0006 module: tGDH terminator (326 bp) flanked by BamHI and HindIII at 5' and 3' ends, respectively. The whole construct was synthesized (Genscript, Piscataway, NJ, USA) and cloned in the KpnI restriction enzyme site of the plasmid pBluescript II SK(+), giving rise to the pGDH-HPH6-GFP6-tGDH plasmid (FIG. 8A). The DNA sequence of each module are the following:

>pGDH_0006 module: (SEQ ID NO. 15):
cgccagaaaacatcgatatcgggcccgaatgaaccgcgacatgctcccaagtgactggctggaa
ggtggctccaccgctattctgtcaatgtcacttccaaggagccggcagatctatgcacaagtat
ttgtgactggattgtgagccgtaaatgtggatagcaccaaaatgcgaggccactatgtaagaaa
acctttcggtgggacctgttgagagaatcggcgcttccactcacgcctcccttctgccggaacg
acagtaacaccaacttagcacattcacagctgagatttggagatagaaggtcgcaaagatgtgc
gaatcactgtgagggtggccggcttcatgagcttcagaagtagtctccgcagcgcggggagcta
gcttcgttgcataacggttgtgcgacatcccgcggaggatctacgttgcgcaagatggccccaa
cgttggccgaggacggcacaaggcagcagtctgcacataacgtacgttgtacgttgtacatatg
ccattgggcactcgcaagcgttccccacaaacatacggcttcgagaccggggtaatgtggtggc
acttcgcatgcctccgtgcacagatgcacacgttcgactctagagcagccccttcaaacgttca
ccgcgaacaactaacgctgcagctgactgggcacgccgctccttacgcacgctcggtagggtcg
gtacgagagccgatgaaggggcggacattggggccgtcgggcgtggtgggcaggtgacgcggag
gaagagacgttttgggtgtttggcgagcacgcacctgcgtcgcgagcgtctgggtaattgcgac
cgtcaccaagcatttctcgggggtacacatccgcctggagaggctgtggcatgggacgacatcg
ggcagcttggtatttgtcgcggccagggcagcggcgggggcgccctggagagatcgtggtccga
ccggcggctgaggcggggtcacaagacggatggagagagggagggcatggaccggccgagggag
agacacgtatgtcggggaggggacatcggatcttctgaccctctcaccgcggaaagcaatgatc
gcgagggtattcttgggtgggccaatccatcgcggaggaatgcaagaaattgttgggggccaaa
cgcaagacccggacaggcgcacgcgagcggcgtgcacgggactcgtgagcgcgcgcacgggagt
atggcaacacgaaaggcggtgagaacagggccgtgctcgctgtgctgcgtggtgagaaacgcgc
tggttgcgacgtcctcggccgacggagaatggcatcggacgggtacgaagacgaggatgggatg
caaacgggaggaaggattatcactccgcccaggcaaggacgggcgtctgtgcgattgtctagat
ctggaccataacccaaacgttaatgcagtctcctccgcttgacgtatataaaatgccagggcct
ccccattccattcacttctccctcttccatctcccccatatcttcctcgcgcctctccacactc
acctcacctccgcatagcacacaacgagcgcggtcacatcccccgacgcgacc >HPH6-module: (SEQ ID NO. 16):
atgaagaagcccgagctcacggcgacgtcggtcgagaagttcctcatcgagaagttcgactcgg
tctcggacctcatgcagctctcggagggcgaggagtcgcgcgcgttctcgttcgacgtcggcgg
ccgcggctacgtcctccgcgtcaactcgtgcgcggacggcttctacaaggaccgctacgtctac
cgccacttcgcgtcggcggcgctccccatccccgaggtcctcgacatcggcgagttctcggagt
cgctcacgtactgcatctcgcgccgcgcgcagggcgtcacgctccaggacctccccgagacgga
gctccccgcggtcctccagcccgtcgcggaggcgatggacgcgatcgcggcggcggacctctcg
cagacgtcgggcttcggccccttcggcccccagggcatcggccagtacacgacgtggcgcgact
tcatctgcgcgatcgcggacccccacgtctaccactggcagacggtcatggacgacacggtctc
ggcgtcggtcgcgcaggcgctcgacgagctcatgctctgggcggaggactgccccgaggtccgc
cacctcgtccacgcggacttcggctcgaacaacgtcctcacggacaacggccgcatcacggcgg
tcatcgactggtcggaggcgatgttcggcgactcgcagtacgaggtcgcgaacatcttcttctg
gcgcccctggctcgcgtgcatggagcagcagacgcgctacttcgagcgccgccaccccgagctc
gcgggctcgccccgcctccgcgcgtacatgctccgcatcggcctcgaccagctctaccagtcgc
tcgtcgacggcaacttcgacgacgcggcgtgggcgcagggccgctgcgacgcgatcgtccgctc
gggcgcgggcacggtcggccgcacgcagatcgcgcgccgctcggcggcggtctggacggacggc -continued tgcgtcgaggtcctcgcggactcgggcaaccgccgcccctegacgcgcccccgcgcgaagaag >fuGFP6 module: (SEQ ID NO. 17):
atggtctcgtcgggcgaggacatcttctcgggcctcgtccccatcctcatcgagctcgagggcg acgtcaacggccaccgcttctcggtccgcggcgagggctacggcgacgcgtcgaacggcaagct cgagatcaagttcatctgcacgacgggccgcctccccgtcccctggcccacgctcgtcacgacg ctctcgtacggcgtccagtgcttcgcgaagtaccccgagcacatgcgccagaacgacttcttca agtcggcgatgcccgacggctacgtccaggagcgcacgatctcgttcaaggaggacggcacgta caagacgcgcgcggaggtcaagttcgagggcgaggcgctcgtcaaccgcatcgacctcaagggc ctcgagttcaaggaggacggcaacatcctcggccacaagctcgagtactcgttcaactcgcact acgtctacatcacggcggacaagaaccgcaacggcctcgaggcgcagttccgcatccgccacaa cgtcgacgacggctcggtccagctcgcggaccactaccagcagaacacgcccatcggcgagggc cccgtcctcctccccgagcagcactacctcacgacgaactcggtcctctcgaaggacccccagg agcgccgcgaccacatggtcctcgtcgagttcgtcacggcggcgggcctctcgctcggcatgga cgagctctacaagtcgtga >tGDH_0006 module: (SEQ ID NO. 18):
ggcgcagacgcacccgtcggccctcacgcgtcatagtcacacaaaagctatcgggagactcgtc gaattgaatacagtgtggtaaaaggcaagaatcagcagtaaacctaatacggagccagccgctg ctccgctgtgtaccaagctcccatgtagaagaattgtatgataatataaatagtagattttcgt catcgagattcattcgttagattgtcagtgaggatgtccgacatacaaacgatcgacattgtat gtgccgagggtccaacgttgtgcatatattgtgctcactgctcgtgcgctgaatggaatcgaag ttcaca >GDH-HPH6-GFP6-tGDH_cassette: (SEQ ID NO. 19):
cgccagaaaacatcgatatcgggcccgaatgaaccgcgacatgctcccaagtgactggctggaa ggtggctccaccgctattctgtcaatgtcacttccaaggagccggcagatctatgcacaagtat ttgtgactggattgtgagccgtaaatgtggatagcaccaaaatgcgaggccactatgtaagaaa acctttcggtgggacctgttgagagaatcggcgcttccactcacgcctcccttctgccggaacg acagtaacaccaacttagcacattcacagctgagatttggagatagaaggtcgcaaagatgtgc gaatcactgtgagggtggccggcttcatgagcttcagaagtagtctccgcagcgcggggagcta gcttcgttgcataacggttgtgcgacatcccgcggaggatctacgttgcgcaagatggccccaa cgttggccgaggacggcacaaggcagcagtctgcacataacgtacgttgtacgttgtacatatg ccattgggcactcgcaagcgttccccacaaacatacggcttcgagaccggggtaatgtggtggc acttcgcatgcctccgtgcacagatgcacacgttcgactctagagcagccccttcaaacgttca ccgcgaacaactaacgctgcagctgactgggcacgccgctccttacgcacgctcggtagggtcg gtacgagagccgatgaaggggcggacattggggccgtcgggcgtggtgggcaggtgacgcggag gaagagacgttttgggtgtttggcgagcacgcacctgcgtcgcgagcgtctgggtaattgcgac cgtcaccaagcatttctcgggggtacacatccgcctggagaggctgtggcatgggacgacatcg ggcagcttggtatttgtcgcggccagggcagcggcgggggcgccctggagagatcgtggtccga ccggcggctgaggcggggtcacaagacggatggagagagggagggcatggaccggccgagggag agacacgtatgtcggggaggggacatcggatcttctgaccctctcaccgcggaaagcaatgatc gcgagggtattcttgggtgggccaatccatcgcggaggaatgcaagaaattgttgggggccaaa cgcaagacccggacaggcgcacgcgagcggcgtgcacgggactcgtgagcgcgcgcacgggagt atggcaacacgaaaggcggtgagaacagggccgtgctcgctgtgctgcgtggtgagaaacgcgc -continued tggttgcgacgtcctcggccgacggagaatggcatcggacgggtacgaagacgaggatgggatg caaacgggaggaaggattatcactccgcccaggcaaggacgggcgtctgtgcgattgtctagat ctggaccataacccaaacgttaatgcagtctcctccgcttgacgtatataaaatgccagggcct ccccattccattcacttctccctcttccatctcccccatatcttcctcgcgcctctccacactc acctcacctccgcatagcacacaacgagcgcggtcacatcccccgacgcgaccactagtatgaa gaagcccgagctcacggcgacgtcggtcgagaagttcctcatcgagaagttcgactcggtctcg gacctcatgcagctctcggagggcgaggagtcgcgcgcgttctcgttcgacgtcggcggccgcg gctacgtcctccgcgtcaactcgtgcgcggacggcttctacaaggaccgctacgtctaccgcca cttcgcgtcggcggcgctccccatccccgaggtcctcgacatcggcgagttctcggagtcgctc acgtactgcatctcgcgccgcgcgcagggcgtcacgctccaggacctccccgagacggagctcc ccgcggtcctccagcccgtcgcggaggcgatggacgcgatcgcggcggcggacctctcgcagac gtcgggcttcggccccttcggcccccagggcatcggccagtacacgacgtggcgcgacttcatc tgcgcgatcgcggacccccacgtctaccactggcagacggtcatggacgacacggtctcggcgt cggtcgcgcaggcgctcgacgagctcatgctctgggcggaggactgccccgaggtccgccacct cgtccacgcggacttcggctcgaacaacgtcctcacggacaacggccgcatcacggcggtcatc gactggtcggaggcgatgttcggcgactcgcagtacgaggtcgcgaacatcttcttctggcgcc cctggctcgcgtgcatggagcagcagacgcgctacttcgagcgccgccaccccgagctcgcggg ctcgccccgcctccgcgcgtacatgctccgcatcggcctcgaccagctctaccagtcgctcgtc gacggcaacttcgacgacgcggcgtgggcgcagggccgctgcgacgcgatcgtccgctcgggcg cgggcacggtcggccgcacgcagatcgcgcgccgctcggcggcggtctggacggacggctgcgt cgaggtcctcgcggactcgggcaaccgccgcccctcgacgcgcccccgcgcgaagaaggaattc ggcggtggcggtggcggtggcggtatggtctcgtcgggcgaggacatcttctcgggcctcgtcc ccatcctcatcgagctcgagggcgacgtcaacggccaccgcttctcggtccgcggcgagggcta cggcgacgcgtcgaacggcaagctcgagatcaagttcatctgcacgacgggccgcctccccgtc ccctggcccacgctcgtcacgacgctctcgtacggcgtccagtgcttcgcgaagtaccccgagc acatgcgccagaacgacttcttcaagtcggcgatgcccgacggctacgtccaggagcgcacgat ctcgttcaaggaggacggcacgtacaagacgcgcgcggaggtcaagttcgagggcgaggcgctc gtcaaccgcatcgacctcaagggcctcgagttcaaggaggacggcaacatcctcggccacaagc tcgagtactcgttcaactcgcactacgtctacatcacggcggacaagaaccgcaacggcctcga ggcgcagttccgcatccgccacaacgtcgacgacggctcggtccagctcgcggaccactaccag cagaacacgcccatcggcgagggccccgtcctcctccccgagcagcactacctcacgacgaact cggtcctctcgaaggacccccaggagcgccgcgaccacatggtcctcgtcgagttcgtcacggc gggggcctctcgctcggcatggacgagctctacaagtcgtgaggatccggcgcagacgcaccc gtcggccctcacgcgtcatagtcacacaaaagctatcgggagactcgtcgaattgaatacagtg tggtaaaaggcaagaatcagcagtaaacctaatacggagccagccgctgctccgctgtgtacca agctcccatgtagaagaattgtatgataatataaatagtagattttcgtcatcgagattcattc gttagattgtcagtgaggatgtccgacatacaaacgatcgacattgtatgtgccgagggtccaa cgttgtgcatatattgtgctcactgctcgtgcgctgaatggaatcgaagttcaca >HPH6-GFP6 chimeric protein (aa) (SEQ ID NO. 20):
MKKPELTATSVEKFLIEKFDSVSDLMQLSEGEESRAFSFDVGGRGYVLRVNSCADGFYKDRYVY

RHFASAALPIPEVLDIGEFSESLTYCISRRAQGVTLQDLPETELPAVLOPVAEAMDAIAAADLS

-continued

QTSGFGPFGPQGIGQYTTWRDFICAIADPHVYHWQTVMDDTVSASVAQALDELMLWAEDCPEVR

HLVHADFGSNNVLTDNGRITAVIDWSEAMFGDSQYEVANIFFWRPWLACMEQQTRYFERRHPEL

AGSPRLRAYMLRIGLDQLYQSLVDGNFDDAAWAQGRCDAIVRSGAGTVGRTQIARRSAAVWTDG

CVEVLADSGNRRPSTRPRAKKEFGGGGGGGGMVSSGEDIFSGLVPILIELEGDVNGHRFSVRGE

GYGDASNGKLEIKFICTTGRLPVPWPTLVTTLSYGVQCFAKYPEHMRQNDFFKSAMPDGYVQER

TISFKEDGTYKTRAEVKFEGEALVNRIDLKGLEFKEDGNILGHKLEYSFNSHYVYITADKNRNG

LEAQFRIRHNVDDGSVQLADHYQQNTPIGEGPVLLPEQHYLTTNSVLSKDPQERRDHMVLVEFV

TAAGLSLGMDELYKS*

Figure 8B:
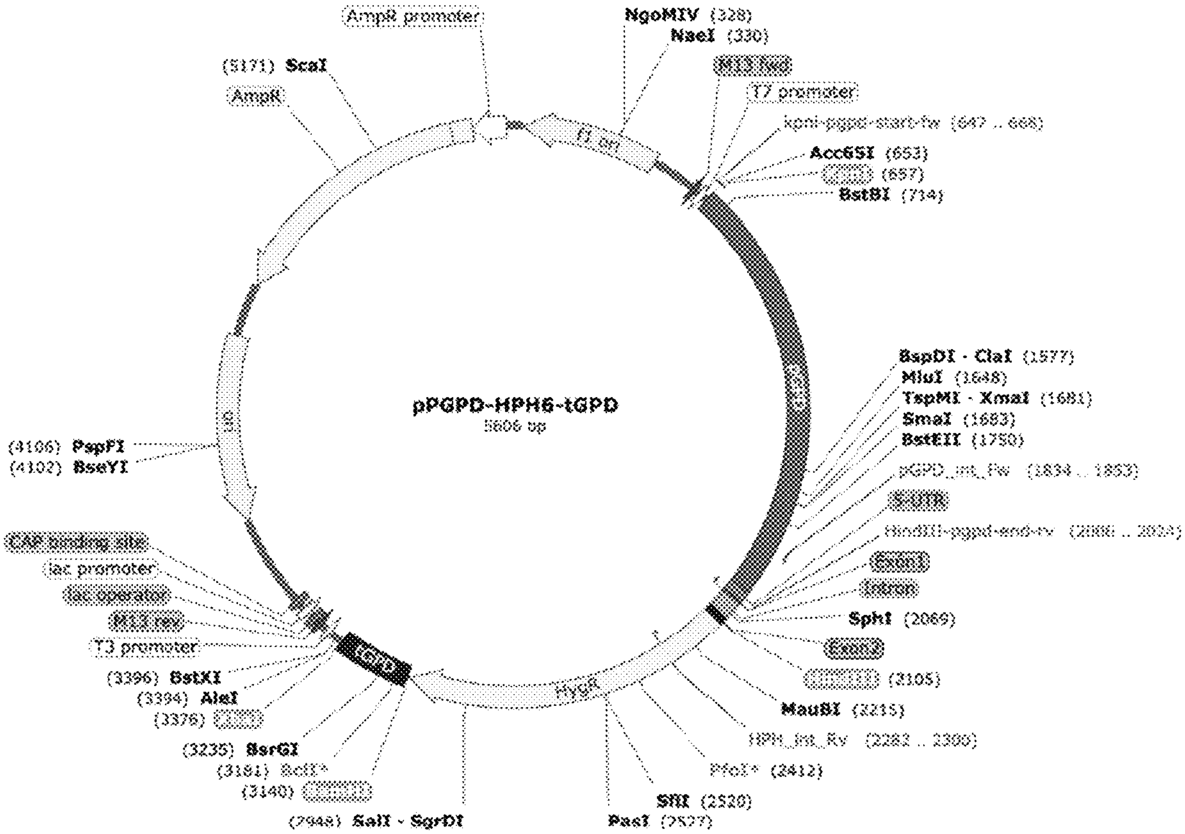
FIG. 8B. Graphic representation of the pPGPD-HPH6-tGPD plasmid. pGPD_0006: glyceraldehyde-3-phosphate dehydrogenase gene's promoter (GPD gene). HPH6: Optimized coding sequence of the hygromycin phosphotransferase gene. tGPD: glyceraldehyde-3-phosphate dehydrogenase gene's terminator in SCC-0006.

Construction of the pPGPD-HPH6-tGPD plasmid. The Hygromycin B resistance cassette functional in SCC-0006 using the GPD promoter was designed as follows (see FIG. 8B): pGPD_0006 module: pGPD promoter (1329 bp) with a KpnI restriction enzyme site added upstream from ATG. HPH6 module: hph6 optimized gene functional in SCC-0006 (1026 bp) flanked by HindIII and BamHI restriction enzyme sites at 5' and 3' ends, respectively. The original coding DNA sequence of the hph gene was obtained from the commercial plasmid pAN7.1. tGPD_0006 module: tGPD terminator (230 bp) flanked by BamHI and XbaI at 5' and 3' ends, respectively. The whole construct was synthesized (Genscript, Piscataway, NJ, USA) and cloned in the plasmid pBluescript II SK(+), giving rise to the pGPD-HPH6-tGPD plasmid (see FIG. 8B). The DNA sequence of each module are the following:

>pgpd_0006 module: (SEQ ID NO. 21):
tgagttgaatggtattatggttgcgcatattatgttgggtttatccgtcgatacttc gaagatatatgtgaacgcttggaatggagagcactgaggatgcaatttcgatgctacggcatca caacgatatgcggacgcaactgctataggggagacacattccctagacagtcaacacatcagcg gtgccataagtagtcaagcaacatatgcgatttcatgacgtacggtcgttgaaagtgattcacg gataccaatgtgcatgtgaaggttcagggcctgggagagttagtagtctagtctgtctgaagag ctgacctggcctacaaatggctgtcatgattgacgtaggaggaggctagtacctacagtgaacg aggcaccggaagagcagagctataagtgggatatgacggatggaaggaattatactgggccact cacgctcgacgcatccaagccgtgtatttcgagaggccgtctccgtctccagcggcagcggaca caagcacacgaacggcgtctgattggtggagtgggattagacgctcgtatgacgtcgtgggatt ggagagcagacacggagaacggatcttgctctcagcattcgagtcagaaaaaacatggggagca tatgtcgcgatatgtacgaacagcgacctgtgcattgctgacgaggacgagacaagtcgctgac agagagggcgcgtacggatctactgtgtcctattagcagtacacttgctagaaggtgccgtcga gacgcgcgaacggaataaggcgattgggagggcgcgtcgcgtccgagtcgcgtccagaccagac ccccgtcaattcggagaacgggccttcggcagccttgcgcgtacattctctctggtaatacacc ccttgcagcccttcgcgccgttcgtcctatcgattgatggccgttggcgagagagagagaggca gtgtgtgccccaaagggcgtcgcgactggtggggagacgcgtcgtacgctcctcctcaaagcaa ccaatcccgggcgggtaaattctggatcggtcgatggctgcgtatcgcccgcacgttcatccct ttcgcccgacggtcaccgcattccgtacagcgcgctgtgccctccgtatggatttgtaacgtgt tcggtctcattatgaacgtctcgcccgtgggcaaatacgccgaagaatgtggagagagggaggag agtaggagaggaaagaggcgccaggagaggacgaggacgagacgacgcggcgatcgaacatctg agatgagataacaatcatccgccccttataaaccctcctcctctccctcctccttc >HPH6-module: (SEQ ID NO. 22):
atgaagaagcccgagctcacggcgacgtcggtcgagaagttcctcatcgagaagttcgactcgg tctcggacctcatgcagctctcggagggcgaggagtcgcgcgcgttctcgttcgacgtcggcgg ccgcggctacgtcctccgcgtcaactcgtgcgcggacggcttctacaaggaccgctacgtctac cgccacttcgcgtcggcggcgctccccatccccgaggtcctcgacatcggcgagttctcggagt -continued cgctcacgtactgcatctcgcgccgcgcgcagggcgtcacgctccaggacctccccgagacgga gctccccgcggtcctccagcccgtcgcggaggcgatggacgcgatcgcggcggcggacctctcg cagacgtcgggcttcggccccttcggcccccagggcatcggccagtacacgacgtggcgcgact tcatctgcgcgatcgcggacccccacgtctaccactggcagacggtcatggacgacacggtctc ggcgtcggtcgcgcaggcgctcgacgagctcatgctctgggcggaggactgccccgaggtccgc cacctcgtccacgcggacttcggctcgaacaacgtcctcacggacaacggccgcatcacggcgg tcatcgactggtcggaggcgatgttcggcgactcgcagtacgaggtcgcgaacatcttcttctg gcgcccctggctcgcgtgcatggagcagcagacgcgctacttcgagcgccgccaccccgagctc gcgggctcgccccgcctccgcgcgtacatgctccgcatcggcctcgaccagctctaccagtcgc tcgtcgacggcaacttcgacgacgcggcgtgggcgcagggccgctgcgacgcgatcgtccgctc gggcgcgggcacggtcggccgcacgcagatcgcgcgccgctcggcggcggtctggacggacggc tgcgtcgaggtcctcgcggactcgggcaaccgccgcccctcgacgcgcccccgcgcgaagaagt ga tGPD_0006 module: (SEQ ID NO. 23):
gccaacgacgatggacttgtgtggtctgtacccgatgatcagtaggaacggaagaagtatctcg tgtgtatgacgcctgtgtggaaacgtgtacatgtacttgtactctgctgcgtgcgtcgtgtagc gagacgattgtaatcataaaatgccatagacgtgcctcgtatctgtccctcgtgtgcgatgcga gactttcgagtacaagacaagcatggtgccagtggagg >GDH-HPH6-GFP6-tGDH_cassette: (SEQ ID NO. 24):
tgagttgaatggtattatggttgcgcatattatgttgggtttatccgtcgatacttcgaagata tatgtgaacgcttggaatggagagcactgaggatgcaatttcgatgctacggcatcacaacgat atgcggacgcaactgctataggggagacacattccctagacagtcaacacatcagcggtgccat aagtagtcaagcaacatatgcgatttcatgacgtacggtcgttgaaagtgattcacggatacca atgtgcatgtgaaggttcagggcctgggagagttagtagtctagtctgtctgaagagctgacct ggcctacaaatggctgtcatgattgacgtaggaggaggctagtacctacagtgaacgaggcacc ggaagagcagagctataagtgggatatgacggatggaaggaattatactgggccactcacgctc gacgcatccaagccgtgtatttcgagaggccgtctccgtctccagcggcagcggacacaagcac acgaacggcgtctgattggtggagtgggattagacgctcgtatgacgtcgtgggattggagagc agacacggagaacggatcttgctctcagcattcgagtcagaaaaaacatggggagcatatgtcg cgatatgtacgaacagcgacctgtgcattgctgacgaggacgagacaagtcgctgacagagagg gcgcgtacggatctactgtgtcctattagcagtacacttgctagaaggtgccgtcgagacgcgc gaacggaataaggcgattgggagggcgcgtcgcgtccgagtcgcgtccagaccagacccccgtc aattcggagaacgggccttcggcagccttgcgcgtacattctctctggtaatacaccccttgca gcccttcgcgccgttcgtcctatcgattgatggccgttggcgagagagagagagaggcagtgtgtg ccccaaagggcgtcgcgactggtggggagacgcgtcgtacgctcctcctcaaagcaaccaatcc cgggcgggtaaattctggatcggtcgatggctgcgtatcgcccgcacgttcatccctttcgccc gacggtcaccgcattccgtacagcgcgctgtgccctccgtatggatttgtaacgtgttcggtct cattatgaacgtctcgccgtgggcaaatacgccgaagaatgtggagagagggaggagagtagga gaggaaagaggcgccaggagaggacgaggacgagacgacgcggcgatcgaacatctgagatgag ataacaatcatccgccccttataaaccctcctcctctccctcctccttccgcatctcctcctct ctccatcccatcctctcaaccatgtctgtgcgtaccatccatacccgtctcctttccgtgtcgc -continued

```
atgctgatcgccctccacatgcagcaagtcaaggtcggaagcttcggatgaagaagcccgagct

cacggcgacgtcggtcgagaagttcctcatcgagaagttcgactcggtctcggacctcatgcag

ctctcggagggcgaggagtcgcgcgcgttctcgttcgacgtcggcggccgcggctacgtcctcc

gcgtcaactcgtgcgcggacggcttctacaaggaccgctacgtctaccgccacttcgcgtcggc

ggcgctccccatccccgaggtcctcgacatcggcgagttctcggagtcgctcacgtactgcatc

tcgcgccgcgcgcagggcgtcacgctccaggacctccccgagacggagctccccgcggtcctcc

agcccgtcgcggaggcgatggacgcgatcgcggcggcggacctctcgcagacgtcgggcttcgg

ccccttcggcccccagggcatcggccagtacacgacgtggcgcgacttcatctgcgcgatcgcg

gacccccacgtctaccactggcagacggtcatggacgacacggtctcggcgtcggtcgcgcagg

cgctcgacgagctcatgctctgggcggaggactgccccgaggtccgccacctcgtccacgcgga

cttcggctcgaacaacgtcctcacggacaacggccgcatcacggcggtcatcgactggtcggag

gcgatgttcggcgactcgcagtacgaggtcgcgaacatcttcttctggcgcccctggctcgcgt

gcatggagcagcagacgcgctacttcgagcgccgccaccccgagctcgcgggctcgccccgcct

ccgcgcgtacatgctccgcatcggcctcgaccagctctaccagtcgctcgtcgacggcaacttc

gacgacgcggcgtgggcgcagggccgctgcgacgcgatcgtccgctcgggcgcgggcacggtcg

gccgcacgcagatcgcgcgccgctcggcggcggtctggacggacggctgcgtcgaggtcctcgc

ggactcgggcaaccgccgcccctcgacgcgcccccgcgcgaagaagtgaggatccgccaacgac

gatggacttgtgtggtctgtacccgatgatcagtaggaacggaagaagtatctcgtgtgtatga

cgcctgtgtggaaacgtgtacatgtacttgtactctgctgcgtgcgtcgtgtagcgagacgatt

gtaatcataaaatgccatagacgtgcctcgtatctgtccctcgtgtgcgatgcgagactttcga

gtacaagacaagcatggtgccagtggagg

>HPH6 protein (aa): (SEQ ID NO. 25):
MKKPELTATSVEKFLIEKFDSVSDLMQLSEGEESRAFSFDVGGRGYVLRVNSCADGFYKDRYVY

RHFASAALPIPEVLDIGEFSESLTYCISRRAQGVTLQDLPETELPAVLQPVAEAMDAIAAADLS

QTSGFGPFGPQGIGQYTTWRDFICAIADPHVYHWQTVMDDTVSASVAQALDELMLWAEDCPEVR

HLVHADFGSNNVLTDNGRITAVIDWSEAMFGDSQYEVANIFFWRPWLACMEQQTRYFERRHPEL

AGSPRLRAYMLRIGLDQLYQSLVDGNFDDAAWAQGRCDAIVRSGAGTVGRTQIARRSAAVWTDG

CVEVLADSGNRRPSTRPRAKK*
```

Obtaining transformant strains and initial selection: A genetic transformation technique was designed and validated. This technique allowed the insertion of DNA fragments (e.g., promoters, genes, terminators, cassettes, constructions, sgRNAs, etc.) in an aleatory or directed way in the genome (e.g., using integrative plasmids). It is also possible to introduce genetic information to be expressed in a non-integrated way into the genome, acting as an extra-chromosomal element (e.g., using replicating plasmids with the useful AMA1 region).

The genetic transformation protocol developed for the SCC-0006 gold standard strain allowed various strategies to improve product performance and/or scaling-up bioprocess: I) homologous or heterologous gene overexpression (e.g., synthetic biology), II) genetic engineering, and III) genome editing using the CRISPR/Cas9 system. The transformation protocol described herein was used for the nonreferenced Unclassified Polyporaceae SCC-0006 strain, resulting in improvements in transformation efficiency, as described below.

Figure 9A:
FIGS. 9A-9B show examples of homogenized mycelium in a mortar (FIG. 9A) and resuspended in MgOsm buffer (FIG. 9B), shown against a light.

Genetic Transformation Protocol:

Mycelial growth: Two 500 mL flasks with 100 mL of modified PDB media were inoculated with 4-8 blocks of mycelium grew for 5-7 days in agar medium (1 $cm^2$ each) and incubated for 48-72 h at 25-28° C. and 200-250 rpm. The grown mycelium was double-filtered with a sterile nylon cloth (35 μm) and Miracloth® (Millipore). Then, the filtered mycelium was collected and homogenized in a sterile mortar (FIG. 9A) and transferred to a 50 mL Falcon tube; the mycelium was resuspended in 30 mL of PDB medium and then disaggregated. Finally, the disaggregated mycelium was incubated for 24 h at 25-28° C. in static condition (regeneration step).

Figure 9B:
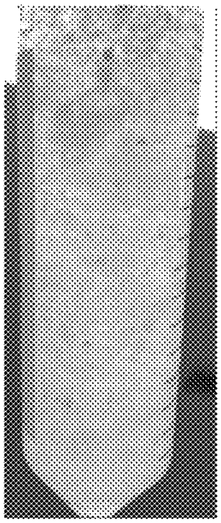

Protoplast liberation: To prepare the lytic enzymes, a solution of Vinotaste® Pro (Novozymes) was prepared in MgOsm buffer (0.5-1M $MgSO_4$, 15-25 mM MES, pH 4.2-6.2). The lytic enzymes solution was sterilized by filtration with two syringe filters (0.45 μm and then 0.22 μm) compatible with aqueous solutions. The regenerated mycelium was filtered with a sterile nylon cloth (35 μm) or Miracloth® (Millipore) and washed with 400 mL of NaCl 0.9%. The mycelium was collected with a spatula and transferred to a 50 mL tube. The mycelium was suspended in 20 mL of MgOsm buffer and vortexed until disaggregated (see, e.g., FIGS. 9A-9B). The mycelium resuspended in MgOsm buffer, and the sterile lytic enzymes solution were mixed in a 1:1 volume ratio. The mycelium with the lytic enzymes mix was incubated overnight in a shaker at 25-30° C. at 200-250 rpm (cell wall lysis and protoplast liberation step).

Figure 10A:
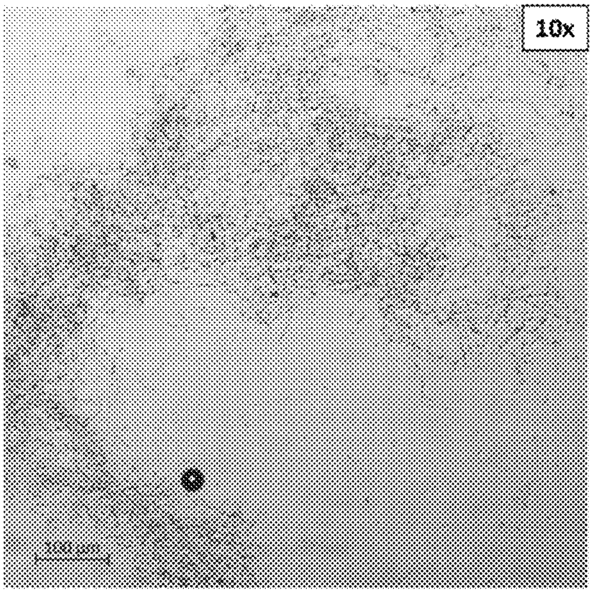
FIGS. 10A-10B illustrate confirmation of protoplast liberation by optical microscope using 10× (FIG. 10A) and 40× (FIG. 10B) magnifications.
Figure 10B:
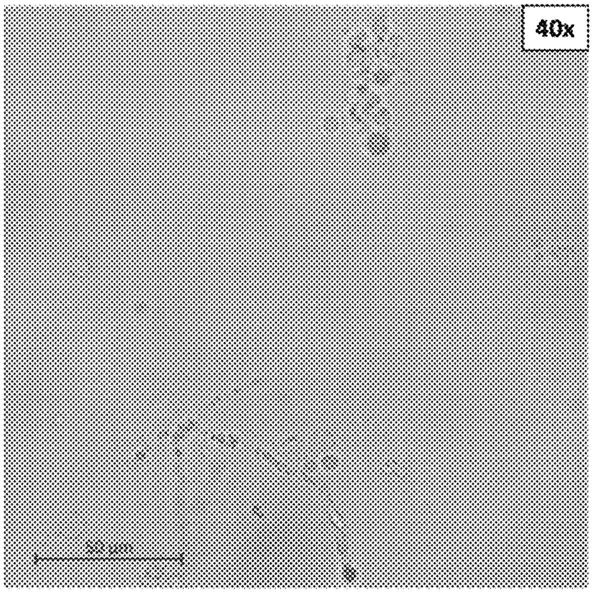
Figure 11A:
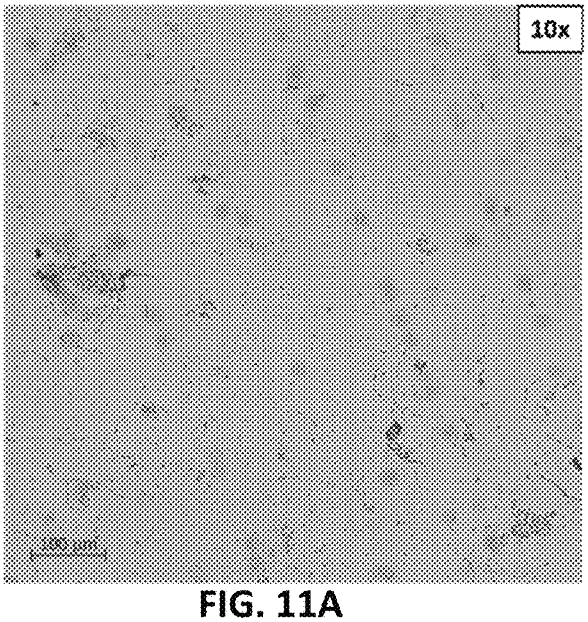
FIGS. 11A-11B show an example of a protoplast solution used for transformation using 10× (FIG. 11A) and 40× (FIG. 11B) magnifications.
Figure 11B:
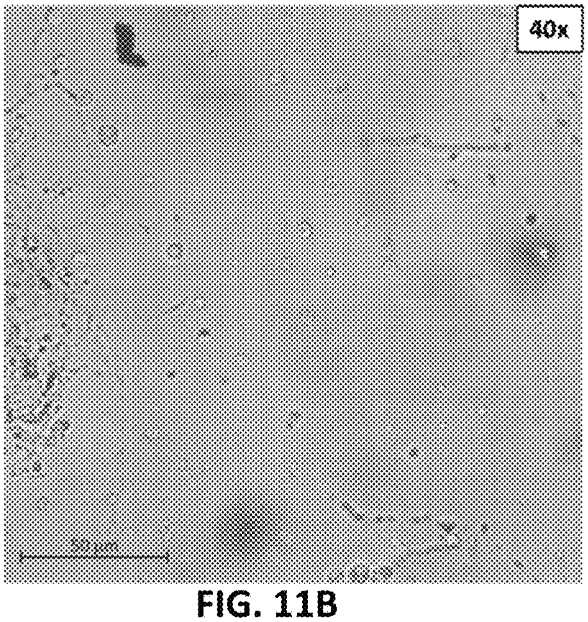

Filtration of protoplasts and washing: Once the mycelium was incubated with the lytic enzymes, a sample was taken to confirm the protoplast liberation by optical microscope (FIGS. 10A-10B). After the confirmation of the protoplast liberation, the mycelium was filtered using a sterile 100 μm pore size filter and the filtrate was collected in 50 mL tubes. The filtrate was re-filtered using a sterile nylon cloth (35 μm) and collected in a new 50 mL tube. The filtrate was distributed in 25 mL volumes, each in a different tube. Then, an equal volume (ratio 1:1) of buffer SorbOsm (0.5-1M Sorbitol, 15-25 mM MES, pH 4.2-6.2) was added to each tube and mixed by immersion gently. The protoplasts were centrifuged with a swing bucket at 1500 g for 20 min. Buffer Sorb/CaOsm (0.5-1M Sorbitol, 35-50 mM $CaCl_2$), 5-15 mM MES, pH 4.2-6.2) was added to reach 30 mL of solution, and then the protoplasts were pelleted by centrifugation with swing-bucket at 1500 g for 15 min. Then, the supernatant was carefully collected with a micropipette from the top. Buffer Sorb/CaOsm was added to the protoplast suspension until reaching 30 mL, and then the protoplasts were pelleted by centrifugation at 1500-2500 g for 10-15 min. The supernatant was collected with a micropipette from the top, leaving around 5 mL of the remaining supernatant. Then, a sample was taken to estimate the protoplast concentration by counting using a Neubauer chamber. Buffer Sorb/CaOsm was added to the protoplast suspension until reaching 30 mL, and then the protoplasts were centrifuged at 1500-2500 g for 10-15 min. Finally, the supernatant was carefully collected with a micropipette from the top to avoid cell debris or partially degraded hyphae, leaving around 1 mL of remaining buffer or the amount needed for the protoplast concentration to achieve between $1\times10^7$ and $2.5\times10^8$ protoplasts/mL. The protoplasts were resuspended gently, and the integrity of the protoplasts was checked by optical microscopy, as evidenced in FIGS. 11A-11B.

Protoplast transformation: the DNA mix was prepared in sterile 2 mL Eppendorf tubes containing: 10 μL 0.01-0.1 M aurintricarboxylic acid (ATA) solution (Sigma-Aldrich, USA); 10 μL PCM buffer (20-40% PEG 3350, 25-50 mM $CaCl_2$), 5-10 mM MES, pH 5-6); 10-20 μL concentrated plasmid (2-10 μg plasmidic DNA).

100 μL of the protoplast solution was added to the DNA mix and homogenized using gentle finger touches. It was then incubated at 4° C. for 40-60 min. 50 μL of protoplast was separated for positive and negative controls.

500 μL of PCM buffer was added to the previous mixture, homogenized using gentle finger touches and inversion, and then incubated at room temperature for 30 min.

600 μL of Sorb/CaOsm buffer was added to the previous mixture and homogenized using gentle finger touches and inversion.

For the recuperation step, the protoplast solution was mixed with 2 mL of PDB 1 M Sorbitol in a 15 mL tube and incubated horizontally for 1 hour at 30° C. in a rotator.

A two-layer method was used to plate the transformed protoplasts. The bottom layer was prepared with PDA 1M Sorb (2% agar) and supplemented with antibiotics (60 μg/mL hygromycin B). For the top layer, PDA 1M Sorb (1% agar) was melted and tempered in a water bath at 55° C. for at least 1 hour. Once completed the protoplast's recuperation time, the whole 3 mL of protoplast mixtures were mixed with melted PDA 1M Sorb (1% agar), supplemented with antibiotics when needed (e.g., 60 μg/mL hygromycin B), and distributed in petri dish with PDA base (2% agar).

As a control, the same protocol was used without the plasmidic DNA. Only 2 Petri dishes were used to plate the control, one with antibiotics (e.g., 60 μg/mL hygromycin B) and the other without them. Instead of using the whole 3 mL of the protoplast's mixture, as shown above, 1.2 mL was mixed with 20 mL of PDA and then plated. The resulting plates were incubated at 28° C. for 1 week or until the appearance of transformant colonies (protoplast regeneration step).

Figure 12:
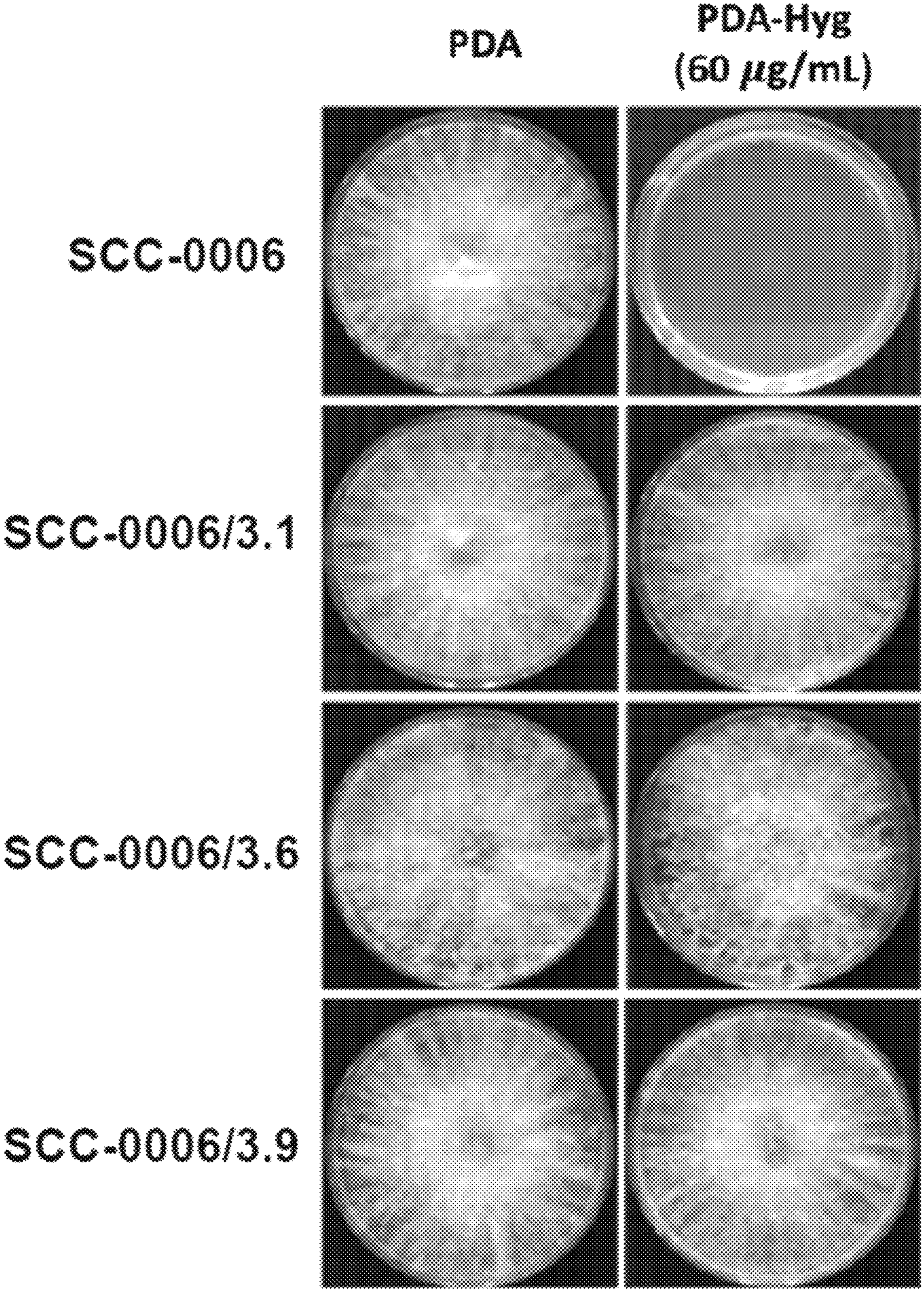
FIG. 12 shows examples of growth of SCC-0006's transformant strains in PDA media supplemented with 60 μg/mL. SCC-0006 parental strains are used as control.

Phenotypic screening of positive transformants $HPH^+$: From several rounds of transformation experiments and later preselection of transformants obtained, nine colonies were obtained using the pGDH-HPH6-GFP6-tGDH plasmid, achieving a transformation efficiency of 0.9 transformants/μg plasmidic DNA). These strains underwent three growth rounds under selective pressure (e.g., 60 μg/mL hygromycin B), and finally, only three transformants were able to grow in the presence of hygromycin B without losing the cassette of hygromycin resistance (FIG. 12).

Microscopic analysis of the selected positive transformants $HPH^+$: The hyphal architecture of these three strains, SCC-0006/3.1, SCC-0006/3.6, and SCC-0006/3.9, were analyzed by optical microscopy and compared to the parental strain (wild strain). As a result, it was found that the SCC-0006/3.6 transformant best kept the hyphal architecture observed in the native SCC-0006 strain (FIGS. 13A-13B and FIGS. 15A-15B) and showed the presence of clamp connections. In contrast, both SCC-0006/3.1 (FIGS. 14A-14B) and SCC-0006/3.9 (FIGS. 16A-16B) presented hyphae with a high degree of fragmentation (arthroconidia formation) and septa lacking clamp connections (see FIG. 2).

Figure 17A:
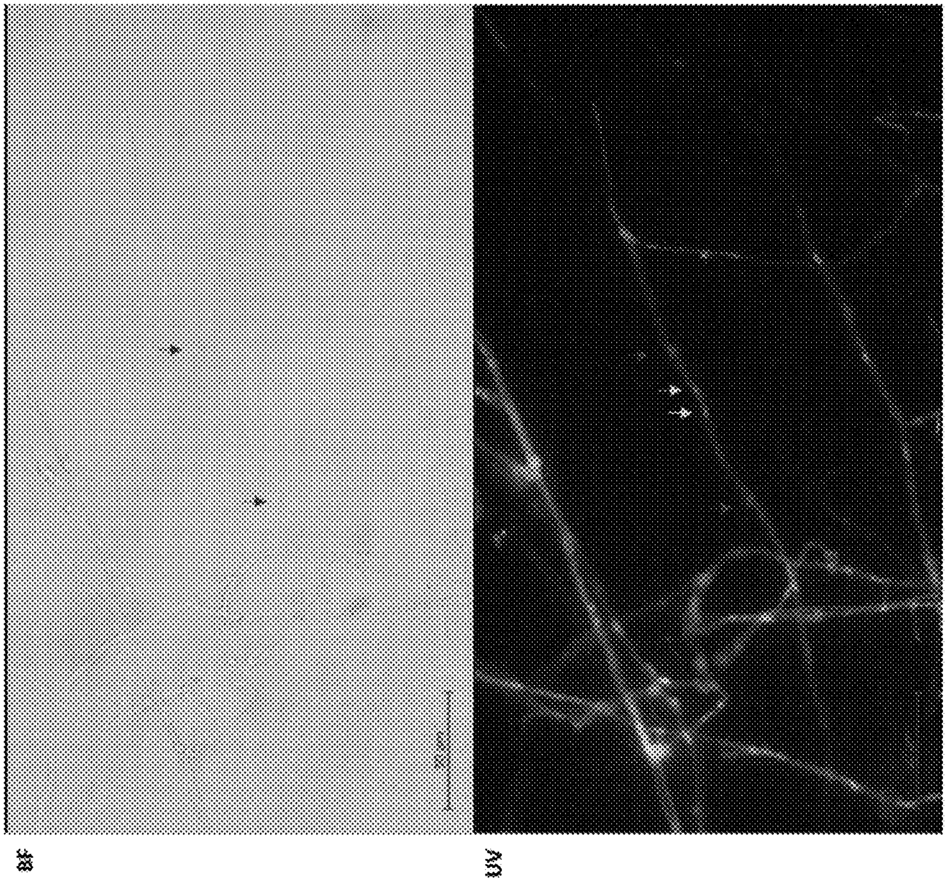
FIGS. 17A-17B illustrate hyphal architecture and nuclei localization in the parental SCC-0006 strain (FIG. 17A) and the SCC-0006/3.6 transformant (FIG. 17B). Arrows point to the septa with clamp connections. Green arrows point to nuclei stained with DAPI. BF: Bright field (top); UV: UV 385 nm (down). The scale is indicated in red (40× lens).
Figure 17B:
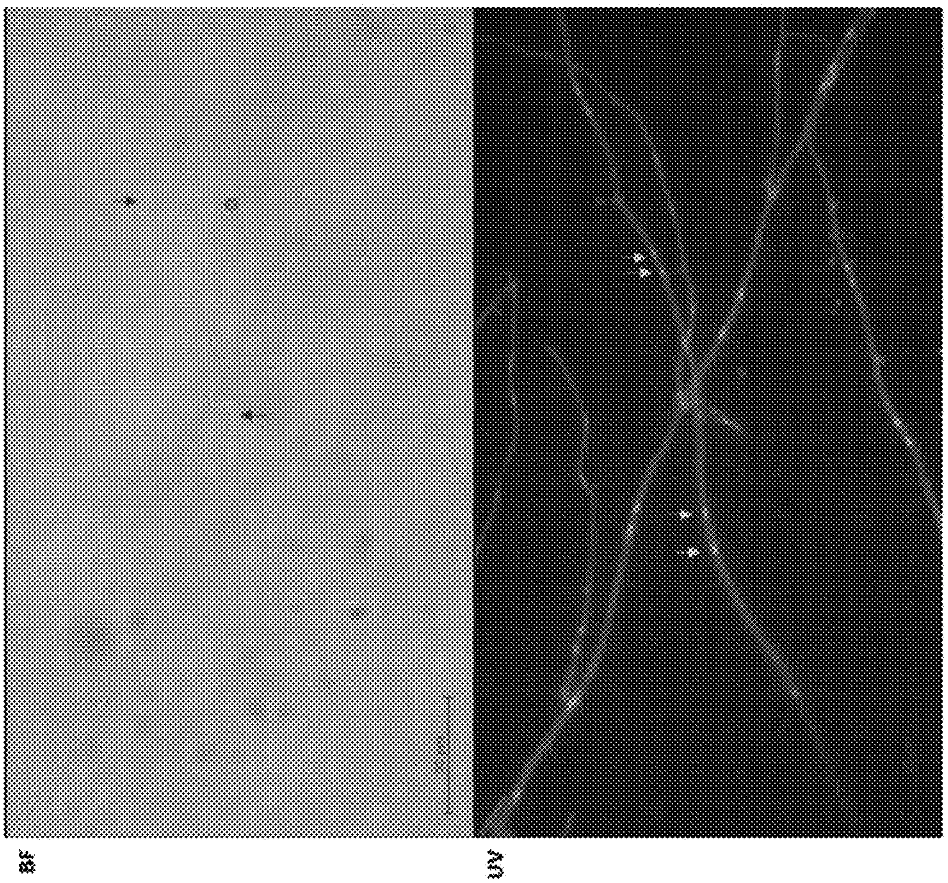
Figure 18B:
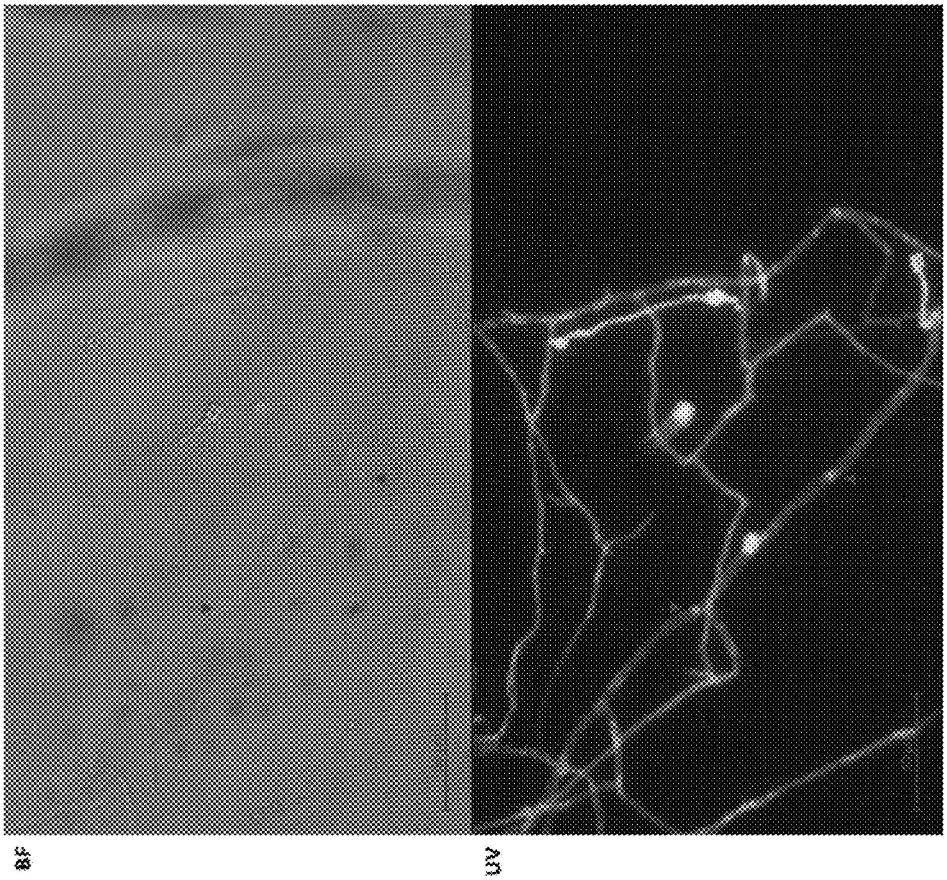
FIGS. 18A-18B illustrate hyphal architecture and absence of visible nuclei in the transformants SCC-0006 3.1(FIG. 18A) and SCC-0006/3.9 (FIG. 18B). Arrows point to septa lacking clamp connections. Bright field (top); UV FILTER: UV 385 nm (down). The scale is indicated in red (40× lens).
Figure 18A:
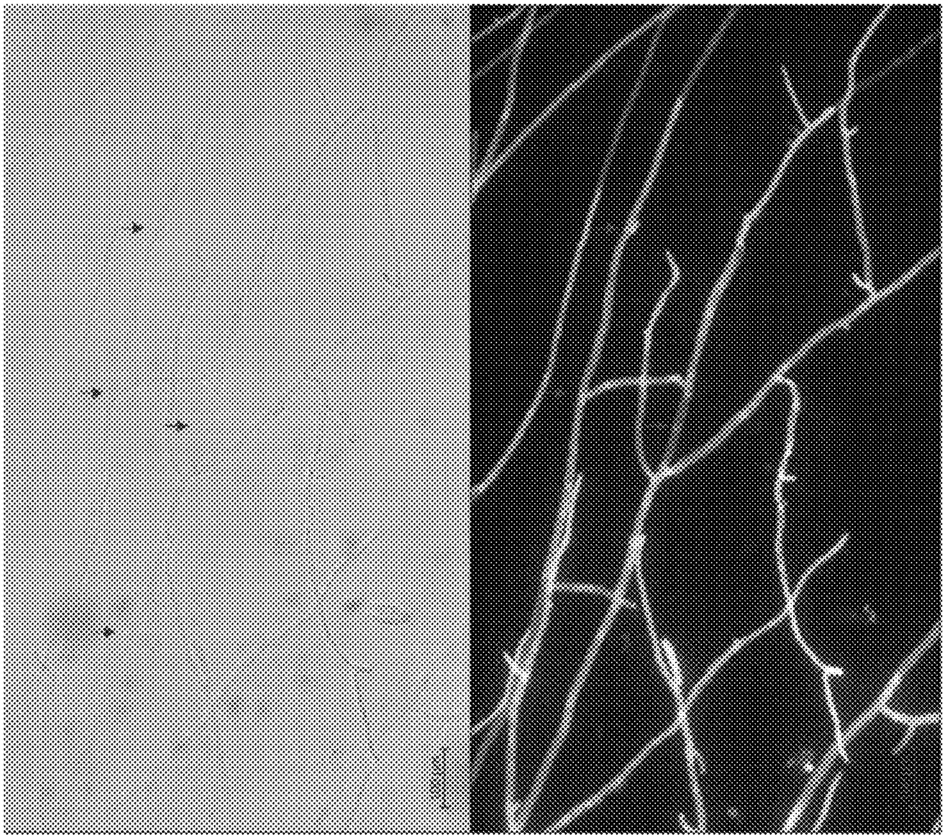

As discussed above, it is known that fungi possess different states concerning their ploidy. Monokaryotic strains possess one nucleus, and their hyphal architecture is characterized by septa that do not have clamp connections. On the other hand, dikaryotic strains (e.g., SCC-0006 and SCC-0006/3.6) possess two nuclei and their hyphal architecture is characterized by presenting septa with clamp connections. Based on this, it was proposed that the parental and SCC-0006/3.6 may form stable dikaryotic strains, and SCC-0006/3.1 and SCC-0006/3.9 are primarily monokaryotic strains. The proposal was tested by staining microcultures of each strain with DAPI to visualize the nuclei in the hyphal structure. Both the parental strain SCC-0006 and the SCC-0006/3.6 transformant presented cells delimited by septa with clamps and two visible nuclei (FIGS. 17A-17B). On the contrary, in SCC-0006/3.1 and SCC-0006/3.9 transformants, the nuclei couldn't be visualized, the septa lacked clamp connections, and a high amount of fragmented arthroconidia was evidenced (FIGS. 18A-18B).

Molecular Screening of Positive Transformants HPH+

Figure 19A:
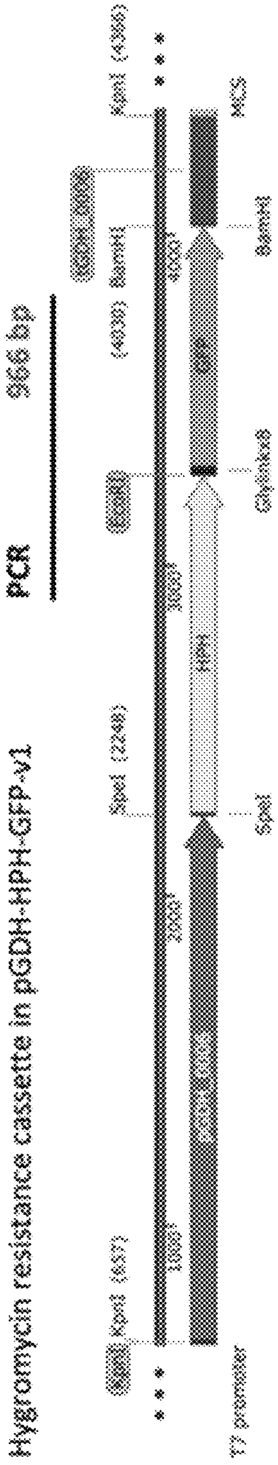
FIGS. 19A-19B show a PCR amplification of a 966 bp fragment from the HPH6:GFP6 cassette present (FIG. 19A) in the pGDH-HPH6-GFP6 v1.0 plasmid from a gDNA sample obtained from the parental and SCC-0006 3.6 strain.
Figure 19B:
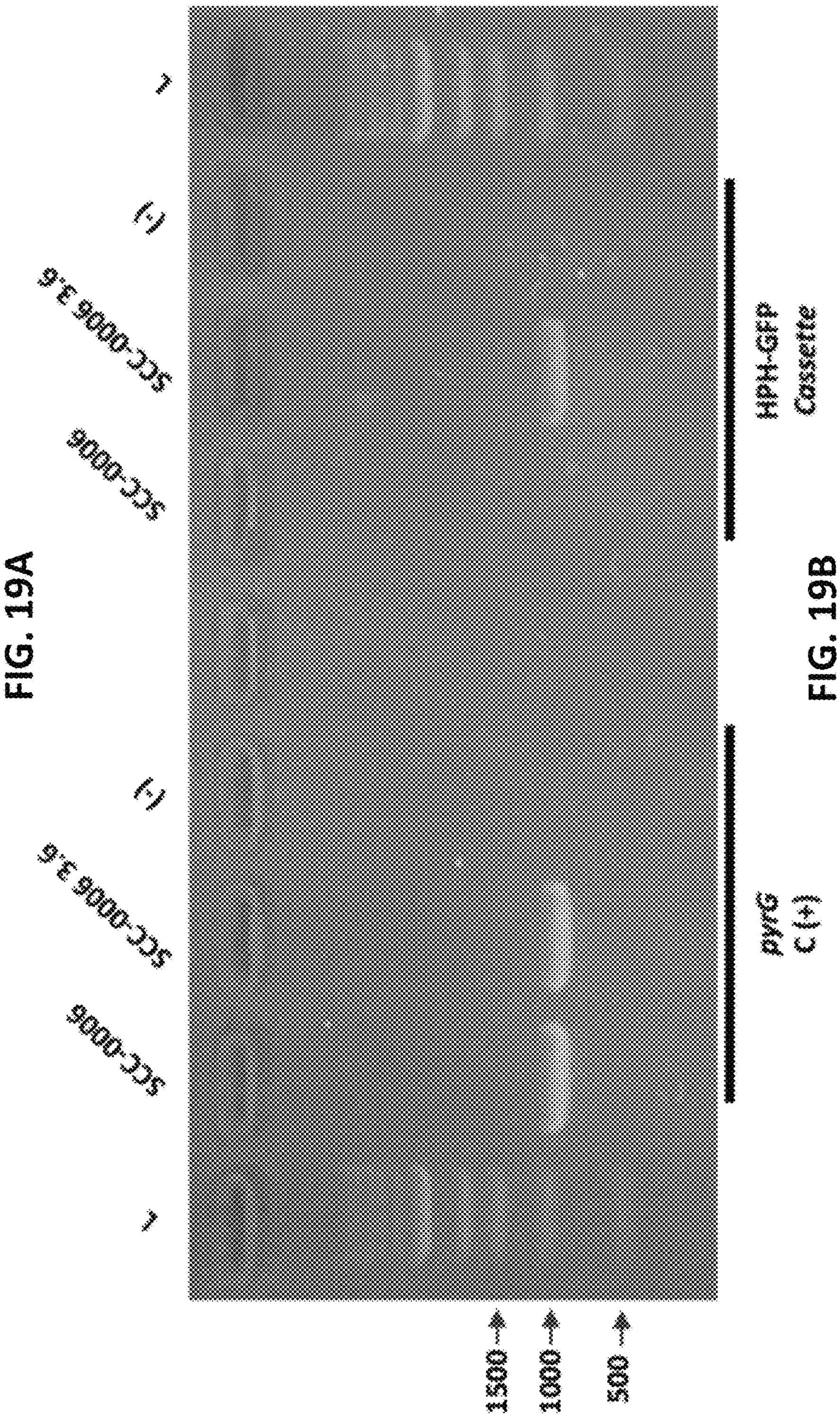

To determine if the construction (e.g., GDH-HPH6-GFP6-tGDH cassette) was adequately integrated into the genome of the SCC-0006/3.6 transformant, PCR amplification and sequencing of the amplified DNA fragments was carried out using the parental strain SCC-0006 as the negative control, and the pyrG gene encoding orotidine-5'-decarboxylase (FUN_004118) as an internal positive control. FIGS. 19A-19B show the presence of the pGDH-HPH6-GFP6-tGDH plasmid in the genome of SCC-0006/3.6. As expected, a 966 pb-PCR product of the HPH6:GFP6 resistance cassette was amplified using the genomic DNA from SCC-0006/3.6 as template, and the primers pairs: HPH6_int_Fw (5' . . . TGGTCGGAGCGCGATGTTC . . . 3', SEQ ID NO. 26) and GFP6_int_Rv (5' . . . CGTGTTCTGCTGGTAGTGGTC . . . 3', SEQ ID NO. 27). This PCR product was sequenced to confirm the presence of the construct. No band was generated with this PCR amplification in the SCC-0006 parental strain. In both cases (e.g., parental SCC-0006 and SCC-0006/3.6), a 953 bp fragment of the pyrG gene used as a positive control was amplified using the primers pairs: pyrG_Fw (5' . . . ATGGCGTCGATCCTTAAGCA . . . 3', SEQ ID NO. 28) and pyrG_Rv (5' . . . CTATGCGCTCGAGCCAATGC . . . 3', SEQ ID NO. 29). Besides, the whole genome sequencing of the SCC-0006/3.6 transformant was performed to identify the specific locus where the cassette was integrated into its genome (data not shown).

In some cases, it may be desirable for a fungal strain used for the large-scale production of mycotextiles to allow traceability to the identity of the strain during and after the industrial process. This traceability can be performed using a unique DNA barcode inserted into the fungal strains' genomic DNA, as shown in FIGS. 19A-19B. For example, the transformant SCC-0006/3.6 results from integrating the pGDH-HPH6-GFP6-tGDH plasmid in its genome. Because of this, it is possible to amplify by PCR and sequence this unique DNA barcode that is only present in this engineered strain (e.g., the resistance cassette carrying the HPH6 and/or GFP6 genes, which were designed using the own usage codon of the SCC-0006 strain).

Figure 20A:
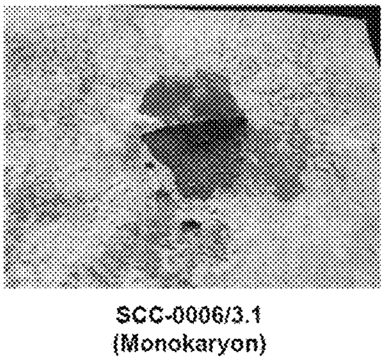
FIGS. 20A-20C illustrate resulting mycelium fabrics (mycotextiles) using monokaryon and dikaryon strains.
Figure 20B:
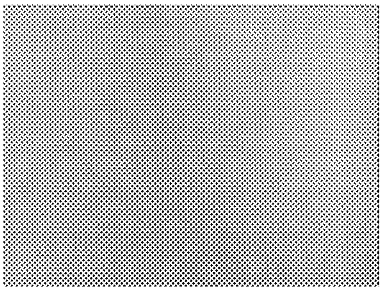
Figure 20C:
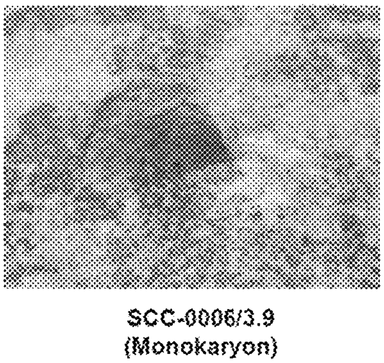

Effect of the Monokaryon and Dikaryon Fungal Strains on Mycelium Fabrics Development To evaluate the abilities of the monokaryon and dikaryon strains to obtain well-colonized, dense and homogeneous mycelium fabrics, spawn of the transformants SCC-0006/3.1, SCC-0006/3.6, and SCC-0006/3.9 were used in the fermentation process as previously described, using the parental strain SCC-0006 as control. As observed, the mycelium of the monokaryon strains is relatively weak, fragmented (forming a fine powder), and easily detached from the scaffold. In the SCC-0006/3.6 dikaryon strain, the mycelium showed greater density, more vigorous, homogeneous growth, and the most adherence to the scaffold (FIGS. 20A-20C, FIG. 20B shows the dikaryon strain as compared to the monokaryonic strains of FIGS. 20A and 20C).

Figure 21:
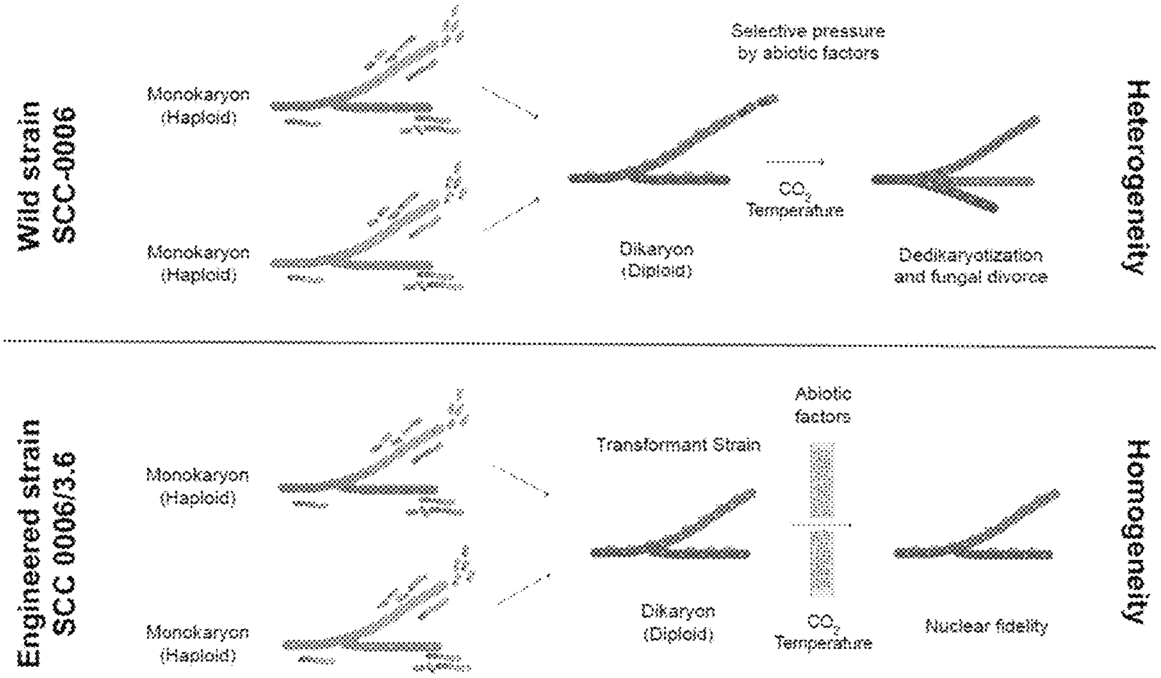
FIG. 21 schematic illustrates how the selective pressure introduced in the engineered fungal strain (e.g., SCC0006/3.6 in this example) does not undergo the process of dikaryotization, leading to homogeneity in the mycotextiles.

One possible theory to explain these results is represented in FIG. 21. The vegetative mycelial cells contain two different nuclei with compatible mating types, leading this organism to be diploid and generate a more robust mycelium due to the action of the two nuclei on the phenotype. In the case of SCC-0006/3.1 and SCC-0006/3.9, both monokaryon strains, the observation under a microscope of the mycelium detached from the mycotextile, it was observed that the hyphae were smaller in size and presented abundant fragmentation, which gave rise to arthroconidia (oidium), which is compatible with strains with monokaryon (haploid) characteristics. In SCC-0006/3.6, a dikaryon strain with diploid characteristics, the mycotextiles are characterized by a mycelium with the desired characteristics (robust, homogeneous, vigorous). This improved behavior is attributed to the insertion of the integrative plasmid with the selective pressure (e.g., antibiotic resistance), which prevents the dedikaryotization process, and the phenotype is maintained by the action of the nuclei during the growth and colonization of the mycotextile. In general, these experiments and others support the use of dikaryotic strains of fungi for the fabrication and resulting textiles.

FIG. 21 illustrates one example of how the selective pressure introduced in the engineered strain SCC0006/3.6 does not undergo the process of dikaryotization, leading to homogeneity in the mycotextiles. Under normal conditions, as observed in the native strain SCC 0006, during the initial stages, two compatible hyphae with monokaryotic characteristics (haploid) fuse in plasmogamy, the first step in sexual reproduction. It is important to note that the nuclei of the hyphae do not fuse immediately, resulting in the formation of a dikaryotic cell (diploid). This stage is called dikaryotization, characterized by the presence of two different nuclei, one from each parent, in each hypha. From a phenotypic point of view, this state provides advantages such as more excellent genetic stability due to genetic redundancy provided by two copies of each gene. This allows for better adaptation to the changing environment due to the genetic variability provided by the two sets of chromosomes, avoiding the loss of beneficial adaptations due to genetic drift.

This mycelial stage in fungi can be preserved for long periods. Finally, two events can be observed: the first is to continue with the sexual reproduction cycle by the fusion of nuclei (karyogamy), culminating in the formation of fruiting bodies, and the second is to undergo a process called dedikaryotization, which converts dikaryotic cells into monokaryotic cells. This dedikaryotization process can be favored by environmental factors such as stress, nutrient availability, temperature, humidity, and $CO_2$, among others, influencing the stability of the dikaryotic state in fungi and, therefore, changes in phenotype.

In the case of mycotextiles, dedikaryotization affects the homogeneity of the materials, as it can be observed that these will be composed of hyphae with different nuclear characteristics (dikaryotic and monokaryotic), each with its characteristic phenotype and therefore heterogeneity in the material. To regulate this heterogeneity in the SCC-0006 strain, the engineered strain SCC-0006/3.6 was created, which, thanks to the introduction of a resistance marker, exerts a selective pressure that prevents hyphae from undergoing dedikaryotization processes, thus resulting in nuclear fidelity, reflected in the maintenance of the dikaryotic genotype (diploid) and a more homogeneous phenotype during mycelial development.

Wild-type Basidiomycete fungi typically undergo dedikaryotization processes. This phenomenon can be attributed to environmental factors such as nutrient availability, pH, temperature and other factors that can trigger transitions between dikaryotic and monokaryotic states. Another factor that may be responsible for this process is mutation or epigenetic changes within the nuclei, which may cause a loss of heterokaryotic compatibility, leading to dedication. When comparing the mycotextiles generated by the SCC-0006 parental strain, the mycelium may lose homogeneity due to dedikaryotization processes; this has been verified by the presence of arthroconidia, a reproduction structure of monokaryotic cells. The mycelium of the stable dikaryotic strain SC0006/3.6 tends to be more homogeneous, robust and vigorous, which when observed under a microscope shows the presence of generative hyphae with fibulas which is an indicator of a dikaryotic state.

In general, mycotextiles formed using a dikaryotic strain, and particularly a strain which is grown under conditions maintaining the dikaryotic state, may result in superior properties, and further the resulting mycotextile may be readily identified as arising from a dikaryotic strain by the presence of one or more easily identified markers, including clamp connections, and/or an enrichment for molecules related to clamp connections.

The mechanical properties of the resulting mycelia, hence the overall quality of the final mycotextile product, depend on hyphal architecture. SCC-006 possesses a trimitic hyphal system composed of generative hyphae, skeletal hyphae and ligative hyphae, the latter two being the most relevant for better mechanical properties. In monokaryotic mycelium, generative hyphae is predominant, and it is also prone to reproduce asexually by generating arthroconidia, fractioning generative hyphae and generating mycelia that is easily washed out during post-fermentation processes when growing the fungus to produce the mycotextile.

In contrast, dikaryotic mycelia may possess higher proportions of skeletal hyphae and ligative hyphae (e.g., greater than 50%, of the hyphal architecture may be skeletal hyphae and ligative hyphae, 55% or greater, 60% or greater, 65% or greater, 70% or greater, 75% or greater, 80% or greater, 85% or greater, 90% or greater, 95% or greater, 96% or greater, 97% or greater, 98% or greater, 99% or greater, etc.), which may be related to natural processes of fruiting bodies generation where their outstanding mechanical properties are due to the combination and interaction of the three types of hyphae. Dikaryotic strains may be better suited than a non-dikaryotic strain to obtain high-quality mycotextiles.

One advantage mentioned above is that the dikaryotic hypha may be produced by the actions of two nuclei on one phenotype. If, for example, one of the nuclei has a defective gene, the other can replace the function and if this type of genetic variation is not present, the phenotype is due to the additive action of the gene products of two nuclei.

The dedikaryotization phenomenon has been widely observed in fungi, but the environmental cues that trigger this event are not completely understood, making it particularly difficult to reliably control in manufacturing processes. It is unknown whether there is a basal dedikaryotization rate in the growing hyphae or whether that is influenced by conditions such as temperature, $CO_2$ levels, humidity, etc. Further, such factors or conditions may be different for different fungal strains or species and may need to be determined for each fungal species.

For example, initial work has shown that the native strain SCC-006 is prone to developing monokaryotic growth areas during both pre-fermentation and fermentation processes. These areas usually coexist with dikaryotic mycelia, which may result in irregular growth. In the pre-fermentation stage, especially during plate propagation, the dedikaryotization phenomenon may be observed even when incubation conditions are maintained constant. Thus it may be particularly helpful to provide and/or use strains (dikaryotic fungal strains) that include a selective driver (such as antibiotic resistance) to help maintain selective pressure to remain dikaryotic. In fermentation processes, such as mycelia growth on mats, higher proportions of monokaryotic mycelium may result in deficient materials that do not endure post-fermentation treatments, resulting in loss of mycelia and poor-quality mycotextiles.

Although the fermentation processes may have growth conditions that are optimized to ensure fast substrate and mat colonization, these conditions have also been found to be suitable for dedikaryotization. At low-scale fermentation, environmental conditions are easier to control than large-scale processes, resulting in more regular-quality mats at low-scale. Concerning large-scale fermentation, complete control of this phenomenon is hard to ensure only by addressing environmental growth conditions. Thus, large-scale growth needed for mycotextiles may require the use of stable dikaryotic fungal strains and/or strains including a driver (such as chemical resistance and growth in the chemical) to help maintain the fungal strain in the dikaryotic state. As described above, the two separate haploid nuclei of the dikaryon are genetically similar to a diploid by having two copies of the nuclear genome per cell, so all gene products are duplicated, which gives an advantage in the phenotype, homogeneous behavior in growth, homogeneous behavior in the cell wall chemical composition, and homogeneous behavior related to the extracellular synthesis of enzymes associated to the nanoparticles mycosynthesis processes.

Detection of Dikaryotic Fungi in Mycotextile

A mycotextile formed using the methods and compositions described herein in which the fungal strain used is dikaryotic may include one or more characteristics indicating or confirming the use of the dikaryotic strain. For example, these compositions (mycotextiles) may have an ultrastructure visible by microscopy (including electron microscopy) unique to dikaryotic strains. In some cases, the mycotextile may include clamp connections or residue (e.g., proteins) correlated with clamp connections such as septins (e.g., one or more of CcCdc3, CcCdc10, CcCdc11a, CcCdc11b, and CcCdc12), cell end markers (e.g., TeaA, TeaB, Formin SepA, etc.), and proteins associated with mating and cell polarity (e.g., Pec1, Prf1, etc.) or other proteins (e.g., MAK-1, Thn1, etc.). Proteins/protein residues may be identified using, e.g., antibodies or immunohistochemical means.

In the final mycotextile, a genetic test may be used to verify the mycelium is dikaryotic. For example, genomic DNA may be extracted from the mycotextile and amplified (e.g., by PCR amplification) and sequenced to confirm the identity of the fungal strain used to form the material (e.g., the use of one of the strains identified herein), and in some cases, to identify that the stain include a sequence corresponding to resistance to the compound (e.g., drug, antibiotic, etc.). In any of these compositions the fungal strain may be identified by sequencing of a key gene (e.g., transcription factors, etc.) correlated with the fungal strain. For example, it may be reasonably concluded that the fungal strain used to form the mycotextile was in a dikaryotic state by confirming that the strain corresponds to SCC-006/3.6, e.g., by identifying the HPH:GFP cassette described above based on its sequence, e.g., using molecular markers such as ITS or RPB2. HPH:GFP cassette can allow differentiation between the SCC_0006/3.6 transformant from the SCC-0006 parental strain because the genes that code for resistance to hygromycin and the Green Fluorescent protein are naturally absent in the wild strain.

For example, the ITS region sequence of SCC-0006/3.6 (Seq. ID no.: 30) may be used to identify this and related fungal strains configured to be dikaryotic:

```
TTAGAGGAAGTAAAAGTCGTAACAAGGTTTCCGTAGGTGAACCTGCGGA
AGGATCATTAACGAGTTCTGACATGGGTTGTAGCTGGCCTCACGAGGCA
TGTGCACGCCCTGCTCATCCACTCTACACCTGTGCACTTACTGTAGGTT
TGGCGTGGGCTTCGAGGGCCTTCACGGGCTTTTGAGGCATTCTGCCTGC
CTATGTATCACTACAAACACTATAAAGTAACAGAATGTAATCGCGTCTA
ACGCATCTTAATACAACTTTCAGCAACGGATCTCTTGGCTCTCGCATCG
```

-continued

```
ATGAAGAACGCAGCGAAATGCGATAAGTAATGTGAATTGCAGAATTCAG

TGAATCATCGAATCTTTGAACGCACCTTGCGCTCCTTGGTATTCCGAGG

AGCATGCCTGTTTGAGTGTCATGGTATTCTCAACCCACACATCCTTGTG

ATGCTTGTGAGGCTTGGACTTGGAGGCTTGCTGGCCCGTCGCGGTCGGC

TCCTCTTGAATGCATTAGCTTGGTTCCTTGCGGATCGGCTCTCAGTGTG

ATAATTGTCTACGCTGTGACCGTGAAGCGTTTGGCGAGCTTCTAACCGT

CCTGCTAGGGACAACTTACTTGACATCTGACCTCAAATCAGGTAGGACT

ACCCGCTGAACTTAAGCATATCAATAA
```

All or a region of this sequence may be identified (e.g., 10 bp or more, 12 bp or more, 13 bp or more, 15 bp or more, etc.).

As mentioned, the strain used to form the mycotextile may include a gene for resistance to a drug or other agent. As mentioned, the resistance may be to Hygromycin B (hph gene) as the antibiotic resistance to allow selection of the dikaryotic strain. Other resistances may include Nourseothricin, Carboxin are other antibiotics that have an inhibitory effect on the growth of the native fungal strain (e.g., a native SCC-006 strain) in an acceptable concentration range. For Nourseothricin the fungal strain may include a plasmid for the expression of the nat gene (Nourseothricin N-acetyl transferase) that confers resistance to the antibiotic.

In some cases, an engineered dikaryotic fungal strain, such as, but not limited to SCC-0006/3.6, may include genetic material conferring resistance to a drug (e.g., an antibiotic). In some examples the resistance results from integrating the pGDH-HPH6-GFP6-tGDH plasmid in its genome (see in the Annex). Therefore, it is possible to amplify by PCR and sequence a fragment of this unique DNA barcode that is only present in this engineered strain (e.g., the resistance cassette carrying the HPH6 and/or GFP6 gene, which were designed and synthesized using the own usage codon of the SCC-0006 strain).

In one example a molecular marker may be used to verify that the mycelium of the mycotextile was in the dikaryotic state. In this example, genetic material from the formed and completed mycotextile (which may be present but fragmented) may be amplified from the mycotextile by PCR and sequenced to identify the Hom2 gene (transcription factor). In some cases, the presence of a single nucleotide polymorphism (SNP) can feasibly indicate if the strain is in a dikaryotic state. For example, genomic DNA may be isolated from the mycotextile (fabric), and multiple (e.g., four) PCR reactions can be performed with different combinations of primer pairs (forward and reverse) as indicated: i) M13F+M13R: Amplification with universal primers; ii) M13F+HPH_int_R: Amplification of a region of the pHPH_GFP V1 plasmid for the identification of the transformant; iii) gfpF+M13R: Amplification of a region of the pHPH_GFP V1 plasmid for the identification of the transformant; and iv) ITS1 and ITS4: Amplification of the intergenic spacer sequence (ITS), as a positive control. Also, the parental SCC-0006 strain is used as a control in all the PCR reactions. The conditions for amplification using the PCR technique (e.g., thermocycler conditions) may include: Initial Denaturation: 95° C.—3'; Denaturation: 95° C.—45"; Annealing: 58° C.—45"; Extension: 72° C.—1'; Final Extension: 72° C.—10'.

The amplification of the PCR product with the universal primers M13 Forward and M13 Reverse will only be positive in the pHPH-GFP V1 plasmid used as a control, yielding the expected sizes, as shown in Table 2:

TABLE I

PCR reaction results as shown in FIG. 1.

| Primers Pairs | gDNA SCC-0006 (A) | gDNA SCC-0006/3.6 (A) | pHPH-GFP V1 | Expected size |
|---|---|---|---|---|
| M13F + M13R (i) | Not amplified | Not amplified | ≅3938 bp | 3938 bp |
| M13F + hph_int_R (ii) | Not amplified | ≅1824 bp | ≅1824 bp | 1824 bp |
| gfp_F + M13R (iii) | Not amplified | ≅652 bp | ≅652 bp | 652 bp |
| ITS1 + ITS4 (control) | ≅643 bp | ≅643 bp | Not amplified | 643 bp |

Table 2: PCR Reaction Results

Figure 55:
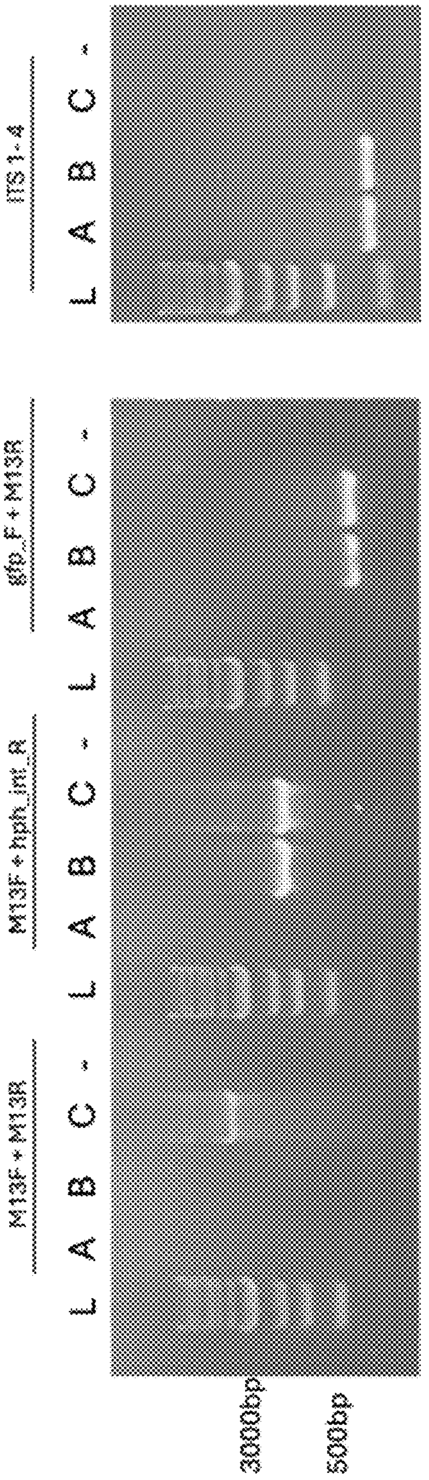
FIG. 55 shows an example of a gel showing the detection of the engineered SCC-0006/3.6 strain.

In one example, amplification with the universal primers M13 (Forward or Reverse)+specific primers (ii and iii) was positive in the SCC-0006/3.6 strain and the pHPH-GFP V1 plasmid. Notably, to obtain PCR amplifications using primer pairs ii and iii using genomic DNA of SCC-0006/3.6 DNA as a template, the internal DNA sequence of the hygromycin resistance cassette (HPH) is known (see above). The PCR products may be generated using primers ITS1 and ITS4, used as an internal control, were positive in the genomic DNA samples from both the parental strain SCC-0006 and SCC-0006/3.6. Table 2 presents the expected sizes in base pairs for each of the PCR products, which are consistent with the results obtained and shown in FIG. 55. FIG. 55 shows an example of a gel visualization for the detection of an engineered strain (e.g., the SCC-0006/3.6 strain). Lanes L corresponds to the kb DNA Ladder (New England BioLabs), lanes A: gDNA SCC-0006, B: gDNA SCC-0006/3.6, C: pHPH-GFP V1, and "-": corresponds to the negative control for each reaction. The expected sizes for each reaction are found in Table 2.

Figure 56A:
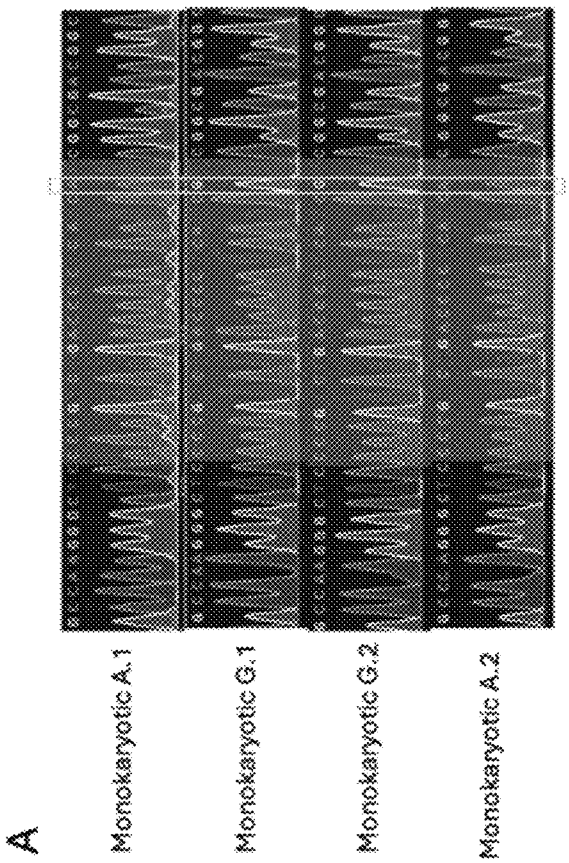
FIGS. 56A-56B illustrate one example of a method of identifying SNPs in monokaryotic and dikaryotic strains.
Figure 56B:
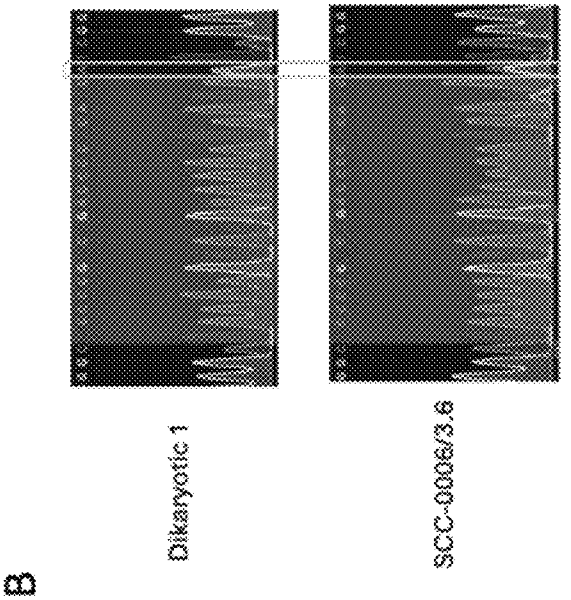

Also described herein are methods and apparatuses (e.g., systems, including reagents) for detecting that the mycotextile was formed using a dikaryotic fungal strain. For example, in some cases, an analysis of a mycotextile may include determining if the mycotextile can be sequenced to identify the presence of a drug resistance gene; in some cases, the test may sequence genetic material (residual genetic material) from the mycotextile including the Hom2 (a transcription factor gene) which is correlated with the presence of dikaryotic fungal strains. Dikaryotic strains in fungi, especially in basidiomycetes, are characterized by having two haploid nuclei (n+n) coexisting within the same cell without fusion. Unlike monokaryotic strains, which contain a single haploid nucleus (n) per cell and represent the initial phase of mycelium after spore germination, dikaryotic strains form when two compatible monokaryotic mycelium fuse, sharing their nuclei but without immediate karyogamy. This dikaryotic condition allows for developing advanced reproductive and differentiating structures for the mycelial network. To differentiate monokaryotic from dikaryotic strains, tools such as Single Nucleotide Polymorphism (SNP) identification can be employed, distinguishing specific genetic sequences of each nucleus in dikaryotic. Due to the presence of these polymorphisms in specific genes between heterokaryons, it is possible to distinguish them molecularly. In the SCC-0006 species, a polymorphism has been found in the FUN_010251 gene that encodes a putative transcription factor Hom2. This transcription factor is crucial for regulating genes involved in fungal development and morphogenesis. The SNP identified in the Hom2 gene can be used as an effective tool to distinguish between monokaryotic and dikaryotic strains, as is shown in FIGS. 56A and 56B. In this example, for SNP identification, a PCR was performed using the primer pairs Hom_F_Out+Hom_R_Out, followed by sequencing of the PCR product. At position 186 of the Hom2 gene, monokaryotic strains show Guanine (G) or Adenine (A). In contrast, dikaryotic strains display both signals in the chromatogram (A/G), indicating the presence of both nuclei (FIG. 56B). Therefore, similar to the previous method, once gDNA samples are isolated from mycotextile, a PCR and sequencing can be performed on Hom2 to determine if it corresponds to a dikaryotic strain.

For this example, this technique may use primers including:
M13F, e.g.,

SEQ ID No.: 31

(5'...GTAAAACGACGGCCAGT...3';

M13R,

SEQ ID No.: 32

(5'...CAGGAAACAGCTATGAC...3');

gfpF,

SEQ ID No.: 33

(5'...GGACCACTACCAGCAGAACA...3');

hph_int_R,

SEQ ID No.: 34

(5'...CGTAGCGGTCCTTGTAGAA...3');

ITS1,

SEQ ID No. 35

(5'...TCCGTAGGTGAACCTGCGG...3');

ITS4,

SEQ ID No. 36

(5'...TCCTCCGCTTATTGATATGC...3')

>gDNA_Hom2

(SEQ ID No.: SEQ ID No. 37

ATGCTACCCACCACTCACGATCCTTCCTCCTCCGCACTCAACCACCAGCCCTCCCTCTACCCCG

TCGTCCCCCACCACTCCCTCCCACAGAACCCCGTTCACCACCATCCTTATCCTATTCCCCCTCA

GAACCCTCCCTTTGATCACCACCAGCAACTCCAGCAGCTGCACCCCGCCCTCTCCCATCCTCAC

AACCACCACCCACACATCCACCACCTCCAGCAGAACCAGACTTGCGTACCCGCTCTCATCCCAC

CAGGCATGGACCCTTCCCAGGTCGACATCCGCACCTTCTATCCCTACACCCCAAACGAAGTAAA

GCACAGAAAGCGCACCACCCGCGCTCAGCTCAAGGTCCTCGAGGGTGTCTACAAATATGACACA

AAGCCCAACGCCTCCCTTCGCAAGAAACTCGCGGCAGAGCTCGACATGACTCCCCGCGGTGTCC

AGGTACTTGCCTTCCTCGATTGCAACCCGTTCCCTTCTATCTCCTCTCCCTCTGTCATTGTCCC

GTGCTTATCTGGTCCTTCCTTCCTCTCTTCCTCCAGGTCTGGTTCCAGAATCGCCGTGCCAAAA

CAAAACAGCAAGCCAAGAAGGCGGAGGCCGCCAACGCCGCCAAGGGCTCCCCGTCTGACCCCTC

ATC(G/A)TCGGCGACGGCAGCAGCAGCCGCCTCCAACCCCCCGATAGCACCTCGTCCTACCGA

AGACGCGGCAGACGACGACGACAACGACAACGACGATCCAGACGAGCCATGTGCATTGGCGCCT

CCGTCTCCCAAGCAATCGGAGGACGCAACACCGGAAAACGCTGCAACAGCTGACGGCACCGTTC

CCGCTTCCTCAAACGCAAACCCGAACGCCAGTGCACAGCAGGACAACGAACAGGCCCACCTAAC

GCCTGATAGCCGCCGCTCCTCCATGGCCCCTCCCCTTCCTCGGTCCCCCGCTTGGTCATCGTCT

TCTCCCTCGGTCTCCACGGCGCCTGCCCCCTCTTCAACCGCTCCCTCGTCCGCACTCAGCAGTC

CCAATCCCGCGAATCATGCGAACAGTTCCCACGTTCGTCTCTCCACTCACCCGCCCTCCGCCAC

CTCTTCCTACTCGCACAACCACCTCGCGCCCACCGACATTTACTCGCAGCGACGCACCTCTCTC

CCGCCTTCCCTTTCCTCCACATCTGGTCATGCCCCCGGCATGCTGAGTACCCTCCGTCGACGCG

-continued

GCTATGACGACACCCGCCGACGCTCGACAGACATGGGCGGTCACCGCATCGTCGCCCATCCGTA

CATCTCTGTCGCCCAGAGCGCCAACGGCCCGCATAATATATACGGCGATGGTGACGACGCTCCG

CCTGCCAGGCGTCCCATGCTCATGCAGCGTATGACCGCACCCTACGCTTCGAACCACCACTCGC

AAGGGACGCAAGCGATGCACTCTCCGCAGGCGCATTCTCAACATGCCCACTCCCAGTCGATCTT

GCCCTCCCAGGCGCAGCAACAGCGAGCGCAGCACCTGGGACAGCAGCGCCAGCACTACGACATC

TCGCCCATTCAGGTGTCCATCTCCCATTCGCAGGGCTACAACCAGCCGCCAAACCACCCGGGCA

GTCACGGCTACGATCTGTTCGCGCCCCGACATTCGATCGACGGCAGCGCGCTCGGCCTGACCCA

AGCGCACGCACAGATGAGCATGGGCCTGTCTCCCTTGCACCCTGCGCCTGGCACAGGAATGGAC

AACGACGCGTTTAGCATGGGTCTCGGGATGAGCAGCCACTACGCTGTGTCGCAGCGTCCACTAC

CCCCTACCATACCTGGACCGCTTCCCTCTCCCAACTATCAGTTCGGGAACCCGTTCGTACCTGC

CCCGAACGACTCGTCTTCTAGCTCTTCCATGAGCAACTCTGCGTCGGGCACGCCTCCCAATGGC

GCTTCGCCGCCATTGCTCAGCCTGCGGCGTACAAGCGAGAGCGCATTGTCAGATGGAGACACGG

AGGAGAGCAGCGGCGCGCCTCTGTCCAGATTTGGCAGTATTGCGAGTATCAACGGC

>Hom2 protein (SEQ ID NO. 38)

MLPTTHDPSSSALNHQPSLYPVVPHHSLPQNPVHHHPYPIPPQNPPFDHHQQLQQLHPALSHPH

NHHPHIHHLQQNQTCVPALIPPGMDPSQVDIRTFYPYTPNEVKHRKRTTRAQLKVLEGVYKYDT

KPNASLRKKLAAELDMTPRGVQVWFQNRRAKTKQQAKKAEAANAAKGSPSDPSSSATAAAAASN

PPIAPRPTEDAADDDDNDNDDPDEPCALAPPSPKQSEDATPENAATADGTVPASSNANPNASAQ

QDNEQAHLTPDSRRSSMAPPLPRSPAWSSSSPSVSTAPAPSSTAPSSALSSPNPANHANSSHVR

LSTHPPSATSSYSHNHLAPTDIYSQRRTSLPPSLSSTSGHAPGMLSTLRRRGYDDTRRRSTDMG

GHRIVAHPYISVAQSANGPHNIYGDGDDAPPARRPMLMQRMTAPYASNHHSQGTQAMHSPQAHS

QHAHSQSILPSQAQQQRAQHLGQQRQHYDISPIQVSISHSQGYNQPPNHPGSHGYDLFAPRHSI

DGSALGLIQAHAQMSMGLSPLHPAPGTGMDNDAFSMGLGMSSHYAVSQRPLPPTIPGPLPSPNY

QFGNPFVPAPNDSSSSSSMSNSASGTPPNGASPPLLSLRRTSESALSDGDTEESSGAPLSRFGS

IASINGSEASWTSAYVSDSAAEGEEGDGSASRKMSCASEFLGMFSGLDVGSNGGTPAPHGLQES

HPLRQSRSSSHLSPNAFVPHHMQAPAPTPPDSMGADQQQQQHIHMQAPSDADGYPSPSSASTVS

AGSNHGNGGSHTHILSHDTTPSHTTVGNGNGGHLQQQGANSMRNHSSSELAYALQGEPEPPRGY

QQHPPAGAKEELQYPMYVSQEASETDAGDAAAYGYAQEQGHHDAREYAKAQMGHFPTLYEGYVY

PHGNVNDQIPEEDASAMSEAYAAGAIELSHMCVPASEGVHFMGGYMQYS*

In any these cases, microscopy (e.g., light microscopy, electron microscopy, etc.) may be used to analysis the mycotextiles, including newly harvested mycotextiles. For example, in basidiomycete fungi, monokaryotic organisms are characterized by having a single nucleus in their hyphae; therefore, these cells are haploid. They originate from a basidiospore or arthrospore that germinates to form a hypha, which expands and grows. The monokaryotic mycelium generally cannot form fruiting bodies by itself. It needs to be fused with another compatible mycelium to generate a dikaryotic (diploid) organism and advance in its life cycle. Therefore, asexual reproduction mediated by arthroconidia predominates in them. Dikaryotic hyphae contain two haploid nuclei (n+n) of different origins in each cell. These nuclei do not fuse immediately and coexist in the cell. One of the distinguishing characteristics between dikaryotic and monokaryotic mycelia is the presence of clamp connections in the dikaryotic mycelium, as discussed above. This structure ensures that each daughter cell receives one of the two haploid nuclei, maintaining the dikaryotic state in the hyphae. Optical microscopy was used to observe the dikaryotic state in the transformant strain SCC-0006/3.6. The search for clamp connections in the final product (mycotextile) is complicated due to post-harvest treatments applied to the material, which hinder the observation of this structure. However, during the fermentation stages, its identification is clear and serves as an indicator of the dikaryotic composition of the hyphae.

Redox Potential of Different Fungal Strains

Also described herein are methods, compositions and systems for forming nanoparticles as part of the fungal growth. Nanomaterials are synthesized using a variety of methods, both physical and chemical. In the chemical method, the synthesis of nanoparticles is based on an oxidation/reduction process, in which metal ions present in the precursor are reduced by certain compounds, generating nucleation centers, from where the nanoparticles emerge and grow until reaching a size at the nanoscale. In this method, the reducing agent is crucial in the synthesis process because it delivers the electrons to the ions to form (e.g., to accumulate) atoms. It is known that the reducing power of a compound is related to its electron transfer capacity, which is linked to its potential antioxidant activity. It is known that certain natural products with high antioxidant ability can synthesize metallic nanoparticles because they not only effectively reduce metal salts but also act as stabilizing agents. In order to evaluate the antioxidant capability of certain compounds, some spectrophotometrically quantifiable model molecules could be used. In this case, the stable free radical 2,2-diphenyl-1-picrylhydrazyl (DPPH•, $C_{18}H_{12}N_5O_6$) was used to evaluate different fungal strains and determine their potential to synthesize metal nanoparticles. DPPH• is characterized as a stable free radical because of the delocalization of the unpaired electron on the whole molecule. Antioxidants (AH) or other radical species (R) can react with this stable radical, providing an electron or a hydrogen atom, thus reducing it to 2,2-diphenyl-1-hydrazine (DPPH-H) or a substituted hydrazine analog (DPPH-R) characterized by the color change from dark violet to colorless or pale yellow. The resulting discoloration is stoichiometric concerning the number of electrons absorbed that could be followed spectrophotometrically.

Materials and Methods for Determining Antioxidant Activity by the DPPH• Method

A solution of DPPH• (600 µM) in 80% ethanol was prepared and diluted until an absorbance of 0.7±0.02 units was obtained at 517 nm. A 0.1 g mycelium mass from each strain was weighed and introduced in an amber Eppendorf tube. Then, 1000 µl of the DPPH• solution was added. In parallel, a control sample (without mycelium) was prepared. Each tube was incubated in the dark, and samples were taken every 15 minutes for 1 hour to measure the absorbance at 517 nm. The % of DPPH• consumed was determined as follows: DPPH• consumed (%)=$[(\text{Absorbance}_{Control}-\text{Absorbance}_{Sample}/\text{Absorbance}_{Control})\times 100]$. Knowing the initial amount of DPPH and the calculated consumed percentage, the mg of DPPH• consumed was normalized by the mg of mycelium.

Results of the antioxidant activity of selected fungal strains: FIG. 22A to FIG. 22D shows the antioxidant activity results of several fungal strains, as shown in Table 3. All the strains presented in this example were previously described in both U.S. patent application No. US 2023/0356501-A1 and the recent U.S. patent application Ser. No. 18/595,392, filed on Mar. 4, 2024. SCC-0006 was previously referred to as Unclassified Polyporaceae strain SCC-0006.

TABLE 3

The list of fungal strains selected to determine antioxidant activity by the DPPH• Method.

| SCC No. | Family | Genus | Species | Source |
|---|---|---|---|---|
| 0002 | Polyporaceae | N.A | N.A | MYCOTEXTILES INCLUDING |
| 0006 | | N.A | N.A | ACTIVATED SCAFFOLDS |
| 0013 | | *Lentinus* | sp. | AND NANO-PARTICLE |
| 0028 | | N.A | N.A | CROSS-LINKERS AND |
| 0046 | | *Polyporus* | sp. | METHODS OF MAKING THEM U.S. patent publication No. US 2023/0356501-A1 |
| 0053 | Ganodermataceae | *Ganoderma* | *resinaceum* | LARGE-SCALE PRODUCTION |
| 0066 | | *Ganoderma* cf. | *australe* | OF MYCELIUM-BASED |
| 0067 | | *Ganoderma* cf. | *australe* | TEXTILES AT MUSHROOM |
| 0075 | | *Ganoderma* cf. | *australe* | FARM FACILITIES |
| 0076 | | *Ganoderma* cf. | *australe* | U.S. patent application |
| 0078 | | *Ganoderma* cf. | *australe* | Ser. No. 18/595,392 |
| 0079 | | *Ganoderma* cf. | *australe* | |
| 0080 | | *Ganoderma* cf. | *australe* | |
| 0054 | Fomitopsidaceae | *Fomitopsis* | *abieticola* | |
| 0059 | Meruliaceae | *Bjerkandera* | *adusta* | |

The figures are discussed according to the families to which fungal strains belong. These results refer to the capacity of each of these strains for the biosynthesis of metallic nanoparticles since it also requires the transfer of electrons from the biological entity to the metallic ion dissolved in water.

Figure 22A:
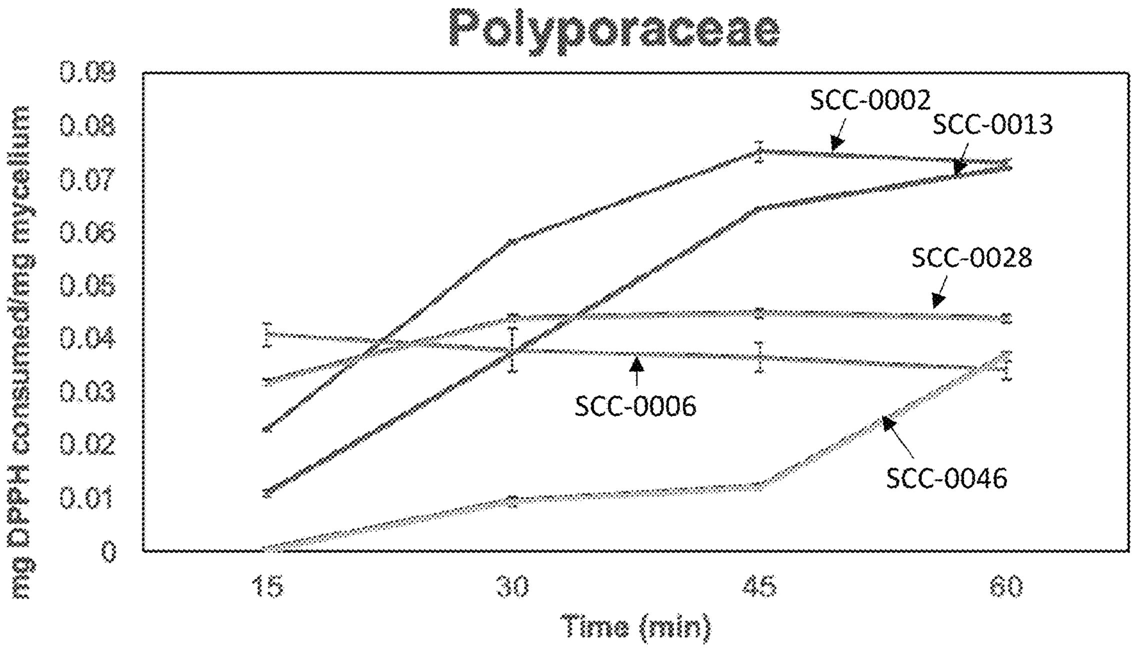
FIG. 22A is a graph showing consumed DPPH in time normalized by the mycelium mass for SCC-0002, SCC-0006, SCC-0013, SCC-0028 and SCC-0046 fungal strains belonging to the Polyporaceae family.

The antioxidant activities measured in the five fungal strains belonging to the Polyporaceae family are displayed in FIG. 22A. SCC-0002, SCC-0028 and SCC-0006 strains have been referenced previously as Unclassified Polyporaceae in the U.S. patent application No. US 2023/0356501-A1, while the SCC-0013 and SCC-0046 have been identified as a new species of Lentinus and Polyporus genus, respectively. However, all strains in this group belong to the Polyporaceae family. The SCC-0002 strain showed higher activity compared to the other strains and shows a linear increase of the consumed DPPH• molecules up to 45 and 60 minutes of reaction, reaching a plateau of around 0.075 mg of DPPH•/mg mycelium. The SCC-0013 strain activity was the second-highest activity of all analyzed strains. However, at the end of the reaction (e.g., 60 minutes), it reaches the same activity level as the SCC-0002 strain. In this group, the strains SCC-0006 and SCC-0028 show comparable activity levels, with the activity of the SCC-0006 strain almost invariant over time and fixed around 0.03 and 0.04 mg DPPH•/mg mycelium. In this case, it is interesting to observe that both Unclassified Polyporaceae SCC-0006 and SCC-0028 showed constant behavior during all the experiments. Finally, the SCC-0046 strain revealed the lowest activity of this group at the first 45 minutes, but its activity turned equal to that of SCC-0006 at 60 minutes of reaction.

Figure 22B:
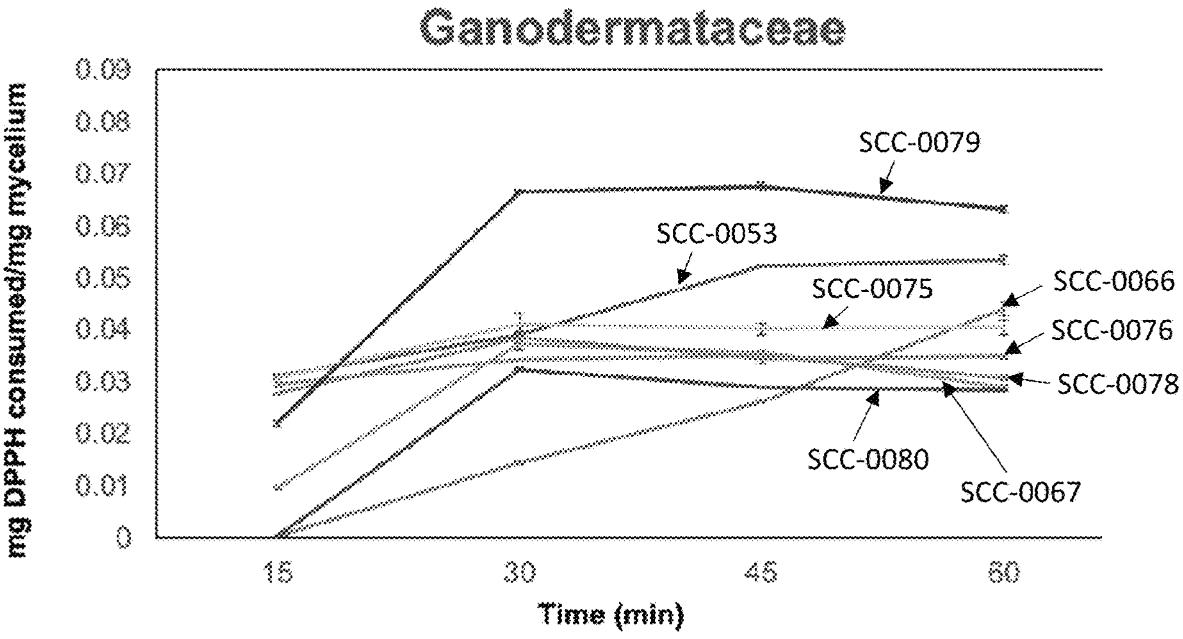
FIG. 22B is a graph showing consumed DPPH in time normalized by the mycelium mass for SCC-0053, SCC-0066, SCC-0067, SCC-0075, SCC-0076, SCC-0078, SCC-0079 and SCC-0080 strains belonging to the Ganodermataceae family.

Likewise, eight fungal strains from the Ganodermataceae family, one of them belongs to *G. resinaceum* (e.g., SCC-0053) and seven to *G. australe* (e.g., SCC-0066, SCC-0067, SCC-0075, SCC-0076, SCC-0078, SCC-0079 and SCC-0080) species, were evaluated according to their antioxidant capabilities. It is essential to mention that *G. australe* native strains were isolated from different sampling sites and do not correspond to the same strain. As shown in FIG. 22B, SCC-0053 and SCC-0079 were the strains that presented the best capacity as effective reducers in the synthesis of nanoparticles. Here, the strain SCC-0079 showed maximum activity after 30 min of reaction, while the plateau in SCC-0053 was reached after 45 min, with around 0.068 and 0.053 mg of DPPH•/mg mycelium, respectively. In the case of strains SCC-0067, SCC-0075, SCC-0076, SCC-0078 and SCC-0080, they presented a medium activity between 0.03 and 0.04 mg DPPH/mg mycelium, all of them, reaching a plateau after around 30 min reaction. Finally, the strain SCC-0066 showed a linear trend, which differs from the other strains, reaching 0.044 mg of DPPH•/mg mycelium at the end of the reaction (60 min). Despite the lower activity of SCC-0066 before 60 min of reaction, it reached a final value equal to the rest of the strains studied in this group (around 0.04 mg DPPH/mg mycelium).

Figure 22C:
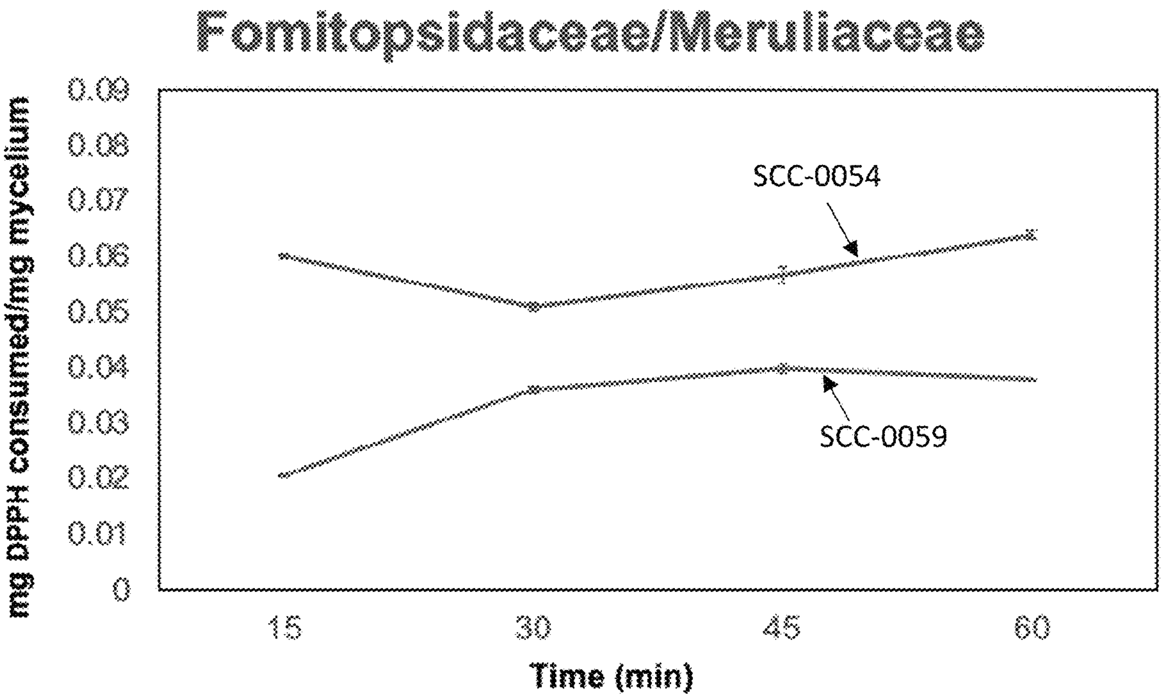
FIG. 22C is a graph showing consumed DPPH in time normalized by the mycelium mass for the species SCC-0054 of the Fomitopsidaceae family and SCC-0059 of the Meruliaceae family.

In FIG. 22C shows the antioxidant abilities of two strains from different families than Polyporaceae and Ganodermataceae, which were used as controls. One strain belongs to the Fomitopsidaceae family (*Fomitopsis abieticola* SCC-0054), and one strain belongs to the Meruliacae family (*Bjerkandera adusta* SCC-0059). SCC-0054 shows a constant behavior over time, reaching an average of 0.063 mg DPPH/mg mycelium between 15 and 60 minutes of reaction, while the SCC-0059 strain showed a modest increase from 0.02 to 0.04 (mg DPPH/mg mycelium) reaching a plateau after 45 min of reaction.

Figure 22D:
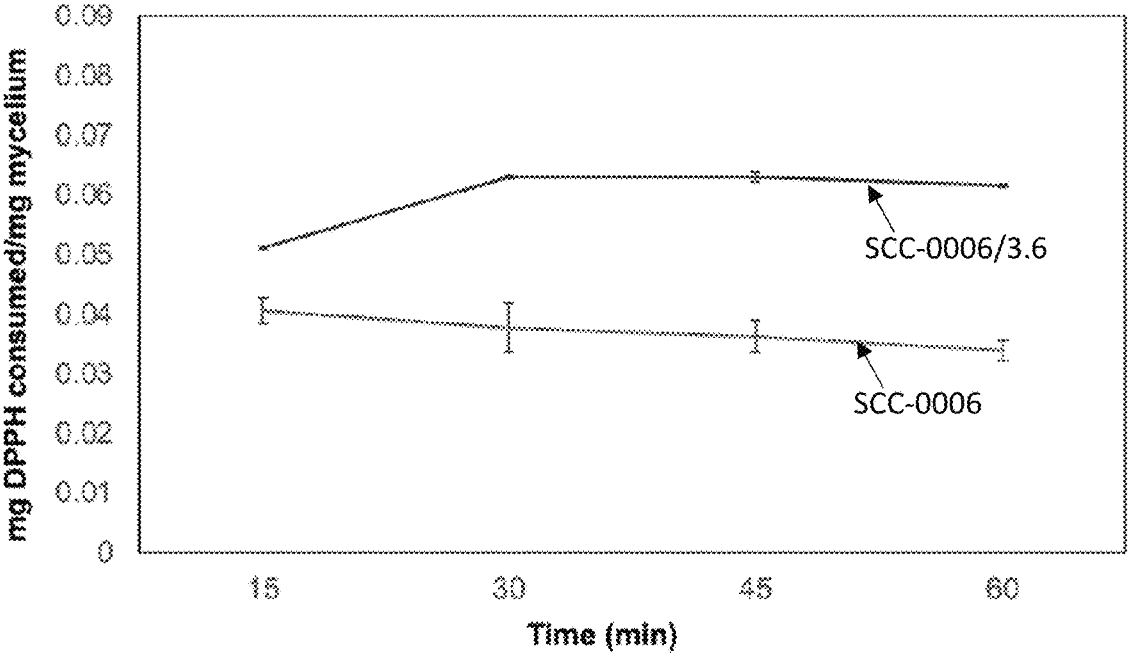
FIG. 22D is a graph showing a comparison of the antioxidant activity of the strain SCC-0006 with the transformant strain SCC-0006/3.6

Regarding the comparison between the transformant SCC-0006/3.6 and its parental strain SCC-0006, the transformant shows an increase that almost doubles the antioxidant activity of its parental strain (FIG. 22D). SCC-0006/3.6 shows constant behavior during the entire reaction time (from 15 min to 60 min) with an average of 0.06 mg DPPH/mg mycelium, while SCC-0006 showed the lowest activity with an average of 0.037 mg DPPH/mg mycelium, evidencing to be a better-reducing agent for synthesizing metallic nanoparticles with respect to its parental strain.

As mentioned above, the SCC-0002 and SCC-0013 strains in the Polyporaceae group showed a higher antioxidant activity after 45 and 60 minutes of reaction, respectively, reaching a plateau of around 0.075 mg of DPPH•/mg mycelium. In addition, the *Ganoderma australe* SCC-0079 was the Ganodermataceae strain with higher antioxidant activities after 30 minutes of reaction with 0.068 mg of DPPH•/mg mycelium and *Fomitopsis abieticola* SCC-0054 belonging to the Fomitopsidaceae family showed a uniform behavior over time, reaching an average of 0.063 mg DPPH/mg mycelium during all reactions. Also, the SCC-0006/3.6 transformant, a stable dikaryon transformant derived from SCC-0006, reached an average of 0.06 mg DPPH/mg mycelium from the beginning and during the entire reaction time (from 15 to 60 minutes).

It is clear that the high antioxidant activity, the speed of the enzymatic reaction from the beginning, and its uniformity during the time (e.g., without decay or decrease during the treatment) are aspects that evidence the adequate presence of reductase enzymes in the extracellular medium, which may promote a more efficient synthesis of nanoparticles throughout the whole treatment and, finally, ensuring a sidereal mycotextile with a modulated homogeneous and uniform pattern.

Considering the improved and homogenized properties of the dikaryon SCC-0006/3.6 regarding its high antioxidant activity, speed, and stability of the enzymatic reaction, as well as its high skills, the reproducible and scalable potential to produce a mycotextile with appropriate quality and performance, it was selected as a promising strain to continue the experiments, however the methods and compositions for in vivo formation of metallic nanoparticles (and subsequent coloring of the mycotextile) described herein may be used (and adapted for use) with virtually any fungal strain.

Sidereal Mycotextiles and Method of Forming them

Described herein are sidereal mycotextiles including at least some of the nanoparticles formed by an in vitro process and methods to obtain sideral mycelium fabrics according to the metallic species employed in each approximation. Mainly three approaches are described in this patent and may include the in vivo mycosynthesis of nanoparticles, including nanoparticles of silver, gold and iron oxide by directly incubating a freshly harvested crude mycotextile with the solution of each metallic salt made from raw mycotextile. In this case, the same living fungus performs the NP's mycosynthesis as well as forming the bulk of the mycotextile. Thus, additional nanoparticles (referred to as "in vitro" nanoparticles, typically ceramic nanoparticles, and/or "ex vivo" nanoparticles, typically metallic nanoparticles) optionally be included. The in vivo formation of nanoparticles by the activity of the fungus itself may be related to the antioxidant potential of the fungus used. The in vitro NPs biosynthesis methods described herein may be based on the biological synthesis of nanoparticles mediated by an organism different from the fungus (e.g., plants, prokaryotic or eukaryotic microalgae, etc.) and the addition of these NPs to the mycotextiles (containing the inactivated fungus), e.g., at a post-fermentation stage. Also described herein is the combination of both in vivo NPs mycosynthesis and in vitro NPs biosynthesis (e.g., "ex vivo" nanoparticles), which may include a first step of NP's mycosynthesis made by the same living fungus and a subsequent treatment with NPs biosynthesized by other organisms and its application in the post-fermentation stage. A graphical guide of the examples developed herein is displayed in FIG. 23.

The In Vivo Mycosynthesis of Silver, Gold and Iron Oxide Nanoparticles

Silver nanoparticles (AgNPs) exhibit various biological activities, including antibacterial, antifungal, antiviral, hepatoprotective, and hypotensive properties. Extracts from the fungal fruiting body and mycelium may be used for AgNP mycosynthesis. In contrast, biomass, live cultures, and fungal metabolites of different purity (including enzymes, polysaccharides, and phenolic compounds) have been less explored. Moreover, additional external physical influences combined with the mycosynthesis methods have been developed to improve the characteristics of the nanoparticles. Likewise, gold nanoparticles (AuNPs) have been used in chemical and biological sensing, bioimaging, nonlinear optics, catalysis, targeted drug delivery, as antimicrobial and antioxidant agents, and in treating cancer, Alzheimer's, and cardiovascular diseases. On the other hand, iron oxides (IO NPs) have one of the most outstanding biocompatibilities because of their magnificent physical characteristics, such as superparamagnetism, low susceptibility to oxidation and long half-lives in blood. These nanoparticles have a wide range of applications, such as antibiotic degradation, dye adsorption, food-related processes, biomedical (drug delivery, magnetic cell sorting, magnetic resonance imaging, immunoassays, tissue engineering, tracking of stem cells, and cancer hyperthermia treatment).

Methods for the In Vivo NPS Mycosynthesis of Ag, Au, and IO NPs

In general, any of the methods and compositions described herein may include the formation of in vivo nanoparticles by incubating the live mycelium mat with a solution including the metallic salt (salts of one or more of:

Au, Ag, and iron oxide) so that endogenous activity of the fungi within the mycelium mat may form nanoparticles by a redox reaction to synthesize nanoparticles. The time, temperature and concentration of the metallic salt solution may be adjusted within the parameters described herein in order to effect the final concentration, localization/distribution and size of the resulting nanoparticles, which may in turn modulate the color of the resulting mycotextile. Any of the mycotextiles described herein may be colored ("dyed") by the inclusion of one or more nanoparticle (e.g., metallic nanoparticles) without the addition of a chemical dye, such as an alcohol-based and/or oil-based dye (as may be used with traditional leathers) or synthetic dyes, pigment dyes or water-based dyes. Thus the methods and compositions (mycotextiles) may be substantially free of these dyes. However, in some cases, it may be desirable to include one or more additional dyes (e.g., water based dyes, pigment dyes, alcohol-based dyes, and/or oil-based dyes).

When generating materials loaded with silver nanoparticles (AgNPs), the concentration of the precursor may affect the synthesis of AgNPs, as described herein. For this, a freshly harvested mycotextile was incubated with a specific volume of silver nitrate ($AgNO_3$) solution with different concentrations (e.g., 1, 2, 3, 5, 10 and 15 mM). In some examples every 30×40 cm mycotextile was completely immersed in the dark in a container with 500 ml of the corresponding solution. The temperature may affect parameters such as the speed of synthesis and the size and stability of the nanoparticles; incubations at 50, 60 and 70° C. were also evaluated. The incubation may be between about 40 degrees and 90 degrees C. (e.g., between about 45 degrees C. and 75 degrees C., between about 40 degrees C. and 80 degrees C., etc.). Thus, these methods may include incubating at between 0.1 mM and 50 mM of the metallic ion in solution. the mycelium mat may be incubated for between about 1 hour and 36 hours. For example, after an overnight incubation (e.g., between 2 hours and 30 hours, between 4 hours and 24 hours, between 12 and 24 hours, etc.), the mycotextiles may be removed from the metallic salt (e.g., $AgNO_3$) solution, and the excess of liquid drained off (at this point, for $AgNO_3$ salt solutions, the mycotextile will acquire a brownish color). The mycelium mat may be crosslinked (in some cases, including the application of a ceramic nanoparticle). The mycotextiles may then be dried in an oven, e.g., at 70° C. In any of these examples, once dry, each mycotextile may be immersed, e.g., for 10 min, in 1% nanoemulsion as described in U.S. patent application No. US 2023/0356501, International patent application No. PCT/IB2023/053847, U.S. provisional patent No. 63/520,933 and U.S. provisional patent No. 63/590,397, each of which is herein incorporated by reference in its entirety. The putative mycotextiles may then be drained (e.g., at room temperature) and then dried, e.g., at 70° C. Once dried, a solution of prolamine protein (e.g., a zein solution) in glycerol (e.g., 30% glycerol, pH 12) may be applied, e.g., by spraying, and the final material may be allowed to dry at room temperature. Finally, each prototype was exposed to ultraviolet light (8 W, 254 nm) for 10 min. The timing and temperature of the incubation may be adjusted, as will the use of UV irradiation (energy applied, duration, etc.) to adjust the final color of the material. Similar processes may be used for any of these in vivo metallic nanoparticles.

To obtain materials loaded with gold nanoparticles (AuNPs), two main strategies were followed: (i) direct mycosynthesis from a crude mycotextile (freshly harvested) and (ii) from the spontaneous redox reduction of AgNPs present in a mycotextile prepared as described above. In any of the cases, the gold starting solution was prepared as follows: lg of pure metallic gold was weighed and digested with 20 ml of boiling aqua regia (HCl with $HNO_3$ in a 3:1 ratio) for 30 min. Upon completion of the chemical digestion, the solution was allowed to cool to room temperature and analytically transferred to a 100 ml volumetric flask and completed with distilled water (this "mother" solution remains at a concentration of 1 mM). For each reaction, the proper volume was diluted using a 1:100 ratio. For the first approximation, each 30×40 cm mycotextile was fully immersed in a glass container containing 600 ml of gold solution (0.01 mM) and incubated overnight (e.g., between 12 to 24 h) at 60° C. After the incubation, the mycotextiles were removed from the gold solution, and the excess liquid was drained off (at this point, the mycotextile will turn purple). The resulting material was processed as described above for the mycosynthesis of AgNPs: immersion in the nanoemulsion, drying, coated with a prolamin:glycerol (e.g., zein:glycerol) solution. For the second approximation, the resulting material of the AgNPs mycosynthesis was dipped in 600 ml of gold solution (0.01 mM) and allowed to react for 5, 10 and 20 min. A color change from brownish to purple was observed here and in the remaining liquid. The evidence of this chemical transformation was recorded in the remaining liquid, employing the analysis of the plasmon light absorption using UV-Vis spectroscopy in solutions containing both silver and gold.

Regarding the myco-synthesis of iron oxide (IO NPs), a determined concentration of iron salts solutions. Iron (II) chloride (FeCl2) and iron (II) sulfate ($FeSO_7{*}7H_2O$) were tested. For these experiments, iron starting concentrations were 10, 15, 20 and 25 mM. The mycotextiles were completely immersed in a container with 500 ml of the corresponding solution with the precaution that the mycelium remained in contact with them. Each container was sealed and incubated at 60° C. overnight. The next day, the mycotextiles were removed from the solutions, and the excess was drained off (at this point, the mycotextile will acquire a yellowish color). The resulting materials were processed as described above for silver and gold mycosynthesis.

Results on A2NP Mycosynthesis

There are several factors determining the effectiveness of mycosynthesis, mainly the initial concentration of the precursor, the incubation time, and the incubation temperature. Exploratory tests using incubations in stirred liquid medium (e.g., potato dextrose broth) revealed that the range of the parameters that could be tested are the following: silver nitrate concentration between 1 and 20 mM; incubation times between 4 and 24 h and temperatures between 25 to 80° C. The effect of the concentration of the silver nitrate was visually observed that the brownish color developed in the mycotextile, which increases the intensity with the silver concentration when evaluated from 0 to 15 mM (FIGS. 24A-24D). In the same figure, it is possible to observe the corresponding microstructure of the material using a Scanning Electron Microscopy (SEM). The comparative images taken at the same magnification (5 kx) suggest that the hyphae are thickened after the mycosynthesis, which could be attributed to the presence of a coating of nanoparticles together with the proteins secreted by the fungus during the process. Depending on the region, it could be observed that the coating is more dense in those areas with higher darkening. After observing several representative regions, the samples obtained at 60° C. with an initial concentration of silver nitrate of 5 mM showed a more homogenous microstructure.

Figure 25A:
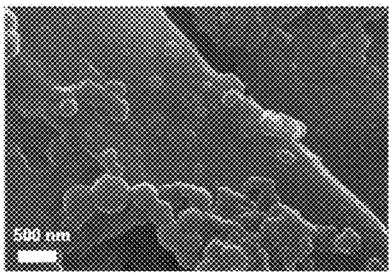
FIGS. 25A-25C illustrate scanning electron microscopy (SEM) images of three samples synthesized with 5 mM of silver nitrate solution taken with secondary electrons at 50 k× magnification. Each scale bar shown as an inset of the images corresponds to 500 nanometers.
Figure 25B:
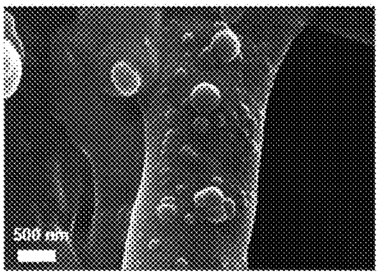
Figure 25C:
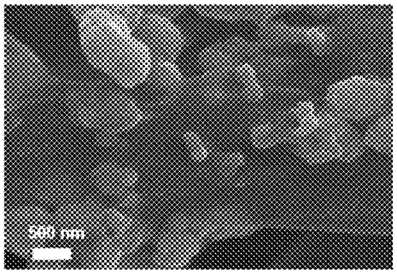
Figure 26A:
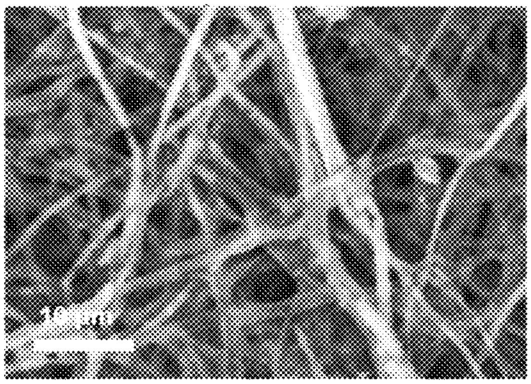
FIGS. 26A-26C show silver mapping and EDS spectrum obtained at 5 mM of silver nitrate and 60° C. The scanning electron microscopy image (FIG. 26A) used as a reference for the mapping was obtained using backscattered electrons.
Figure 26B:
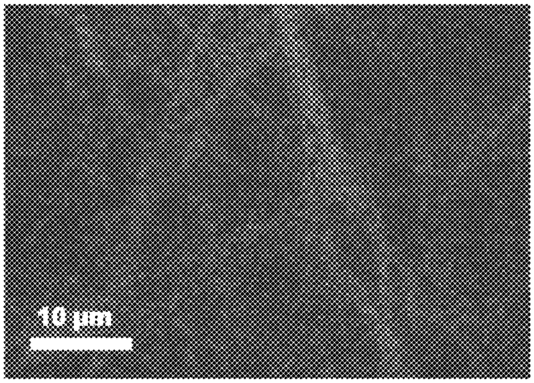
Figure 26C:
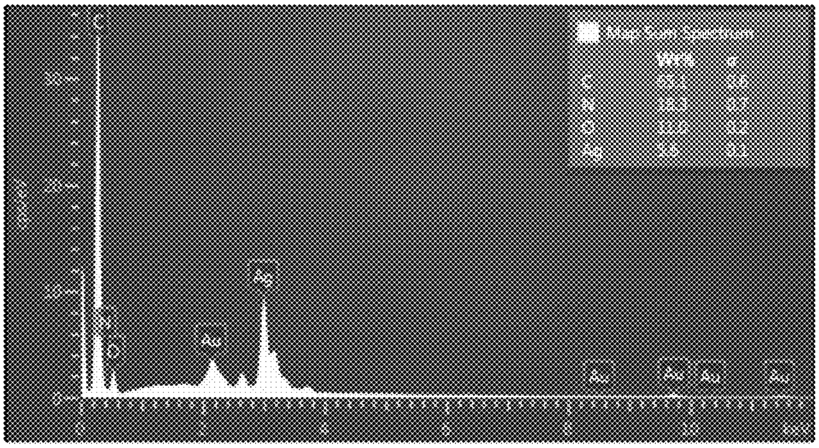

FIGS. 25A-25C displayed SEM taken with 50k× magnification in three different samples, revealing spheroid-like morphologies and high polydispersity in the particle sizes. The mean particle size range covers from below 100 nm to 600 nm. These particles are formed on the surface of the mycelium, but the color change in the remaining solution after the synthesis is completed suggests that the particles are also suspended in the solution. The EDS spectrum and silver mapping in a determined region of a representative material revealed that the silver nanoparticles are distributed along the hyphae, as observed in FIGS. 26A-26C. The approximate concentration in the tested area was 5.6 wt. %.

It is known that higher concentrations of silver nitrate may lead to larger nanoparticles. The nucleation and growth of nanoparticles are influenced by the availability of silver ions, and higher concentrations result in increased nucleation events. Higher nucleation sites lead to a higher density of nanoparticles. High silver concentrations also increase the reduction reaction's overall yield, which was observed in the intensification of the color. Reaction kinetics may also be affected by higher concentrations of the precursors because the reduction process occurs faster. Finally, the shape and size dispersion of the nanoparticles may also be affected by concentration, leading to variations in shape (spherical, triangular, hexagonal, etc.) and agglomeration.

Figures 27A, 27B, 27C:
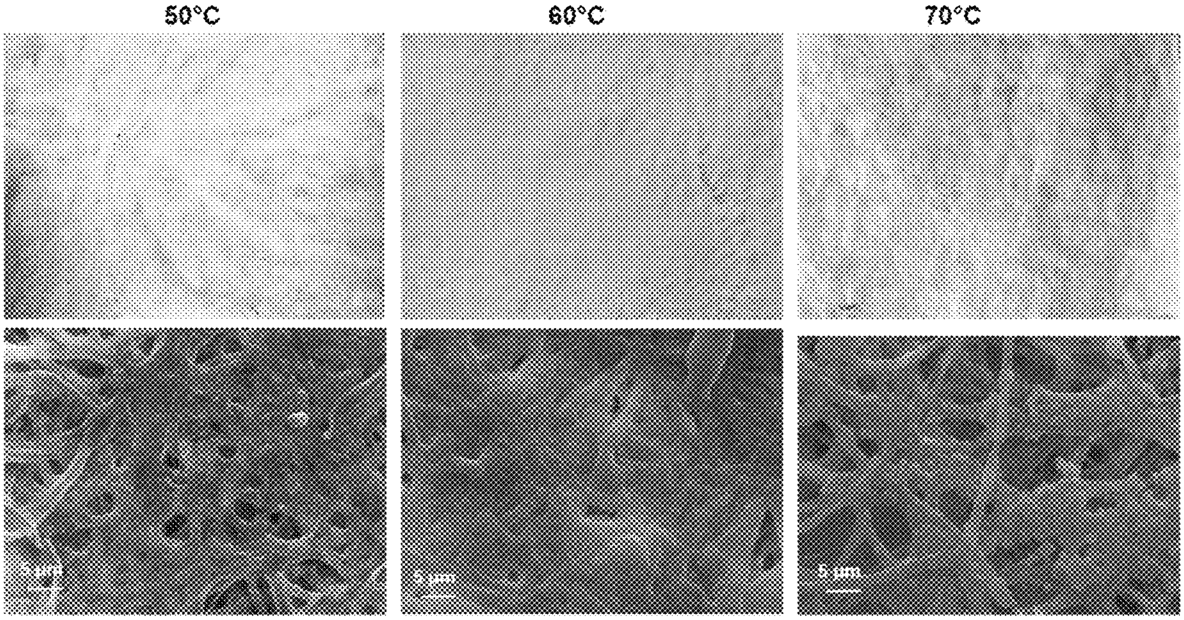
FIGS. 27A-27C show photographs and corresponding SEMs of several mycotextiles after the mycosynthesis of silver nanoparticles were obtained by changing the temperature at 50° C.

Regarding the effect of the temperature, FIGS. 27A-27C exposes the photographs and the corresponding SEM image (5k× magnification) for mycotextiles obtained by incubating the crude materials in silver nitrate solution (5 mM) at different temperatures. From SEM images, it is possible to infer that particle size increases with temperature and aggregation; this behavior is reflected in the color distribution on the material surface. Higher particle size and lower distribution are consistent with expected for this type of reaction. It is well known that reaction rates increase with temperature; at higher temperatures, higher mass and charge transfer. According to the Arrhenius equation, the increase in the kinetic energy also favors the reactions catalyzed by enzymes. However, enzymes can denature and lose their three-dimensional structure at extreme temperatures. Each enzyme has an optimal temperature it works most efficiently, which is related to its structure and stability. Moreover, in the synthesis of nanoparticles, high temperatures may increase particle size, attributed to nanoparticle aggregation. This observation indicates that the optimal temperature for this experiment using $AgNO_3$ 5 mM and overnight incubation is around 60° C.

Figure 28:
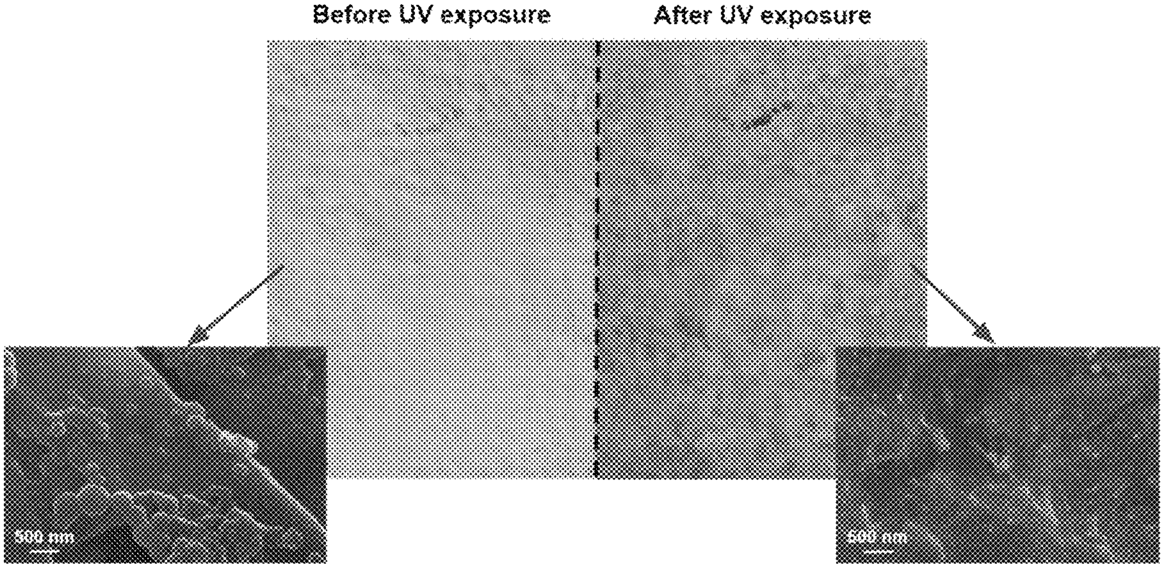
FIG. 28 shows the effect of the photoirradiation on the color of the mycelium fabric, the morphology and distribution of AgNPs on the surface of the hyphae on the sample obtained at 5 mM of silver nitrate and 60° C. On the left is shown the material after UV source irradiation, and on the right is after 10 min of UV irradiation.
Figures 29A, 29B, 29C:
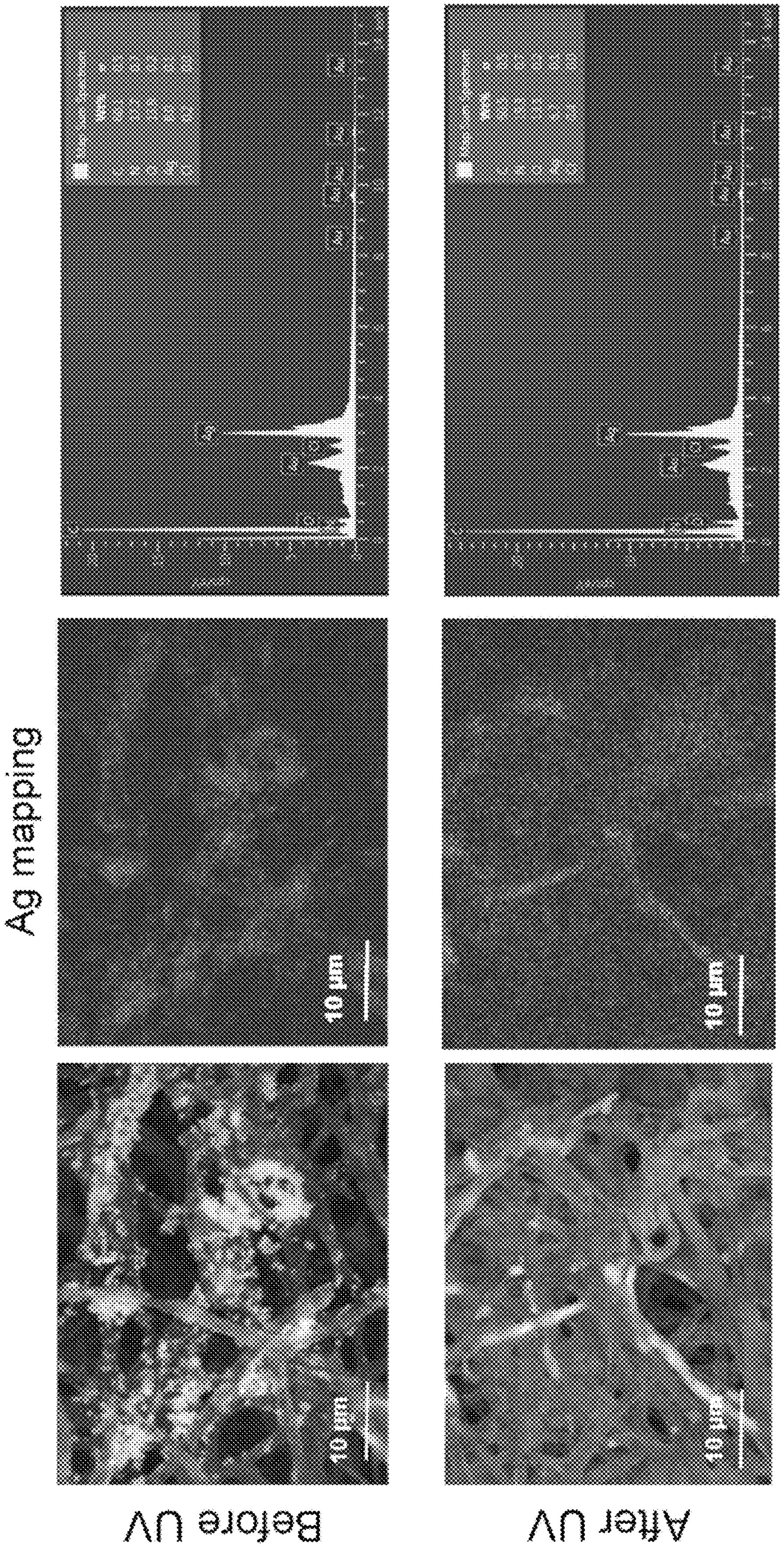
FIGS. 29A-29C show SEM images (FIG. 29A), Silver mapping (FIG. 29B) and EDS spectrum (FIG. 29C) of samples before (top) and after (bottom) UV irradiation. The SEM images used as references for the mapping were obtained using backscattered electrons.

The processed mycotextiles were exposed to UV irradiation for an appropriate period of time (e.g., between 1 minute and 120 minutes, between 1 minutes and 60 minutes, between 3 minutes and 30 minutes, between 5 minutes and 14 minutes, between 7 minutes and 12 minutes, about 8 minutes, about 10 min, about 12 minutes, etc.) to complete the process. The light source may be placed on the top of the surface at a distance of, e.g., between 1 cm and 30 cm (e.g., between 1 cm and 25 cm, between 5 cm and 25 cm, between 10 cm and 20 cm, about 15 cm, etc.). After the photoirradiation, an increase in the intensity of the brownish color of the material was observed (FIG. 28). The resulting microstructure, revealed by SEM, shows a change in the size and distribution of the nanoparticles previously observed in the material. The nanoparticles appear more distributed on the surface, with sizes lower than the ones obtained before irradiation, suggesting that the photoirradiation caused a fragmentation of the aggregates. It has been reported that photolysis causes electron loss in silver nanoparticles because of surface plasmon resonance, which produces a transient state that precedes the complete fragmentation of larger particles. Laser irradiation causes AgNPs to break down into smaller fragments. FIGS. 29A-29C shows the silver mapping and the respective EDS spectra for a given sample before and after UV irradiation. As observed, silver distribution increases after the irradiation and a diminution in the silver concentration in the tested area from 8.0 wt. % to 6.7 wt. % could be related to the higher metal dispersion in the material.

The in vivo nanoparticles formed as described herein may have a range of particle diameters, e.g., between about 10 nm and 900 nm, between about 50 nm and 800 nm, etc. In some cases, the use of UV irradiation may reduce the size range to approximately half (or less) than the original size range (e.g., between 5 nm and 500 nm, etc.).

Figure 30A:
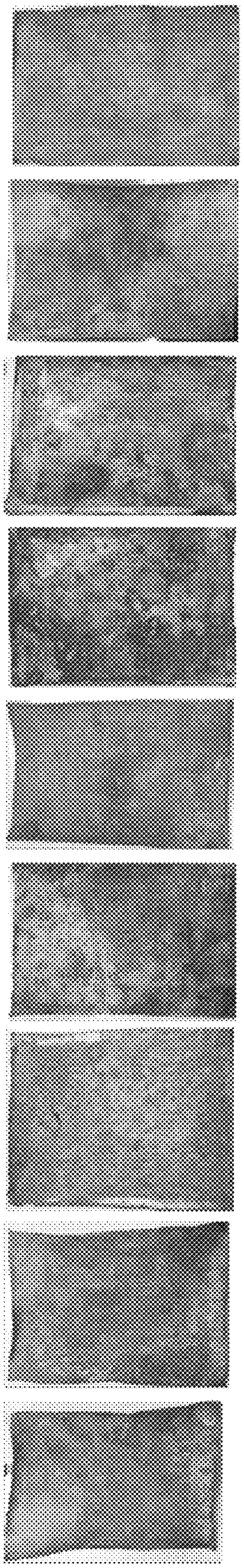
FIGS. 30A-30B show examples of photographic records of nine silver prototypes produced in the SCC-0006 strain (top) and the dikaryotic SCC-0006/3.6 strain (bottom) strains.
Figure 30B:
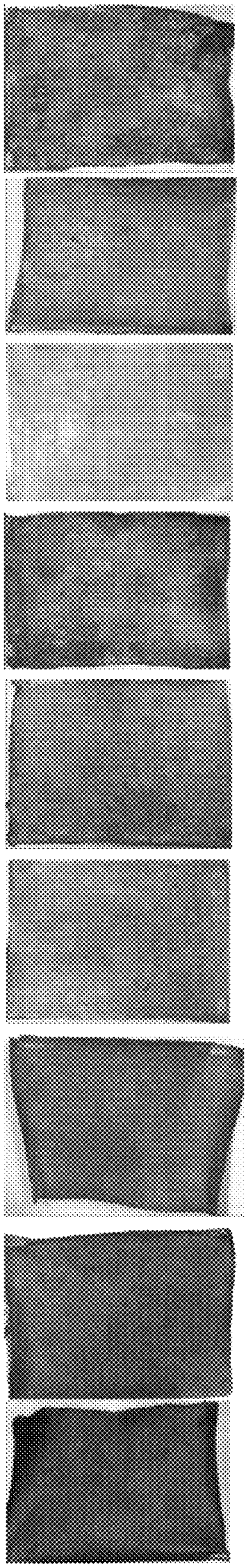

Comparison of the Homogeneity and Entropy Derives from the AgNPs Mycosynthesis Capabilities Between the Wild Type SCC-0006 vs. SCC-0006/3.6 Improved Strain As discussed above, the heterokaryon wild-type SCC-0006 strain has an inherent ability to biosynthesize metallic nanoparticles such as AgNPs and AuNPs. To evaluate the effect of the introduced dikaryon condition into SCC-0006/3.6 on the homogeneity of the AgNPs mycosynthesis, the photographs of several prototypes loaded with AgNPs obtained using both SCC-0006 and SCC-0006/3.6 strains were analyzed using the processing software ImageJ (public domain programmed in java). The nine images shown in FIG. 30A correspond to the prototypes obtained with the native strain SCC-0006 and the nine images in FIG. 30B correspond to the SCC-0006/3.6 transformant.

Figure 31A:
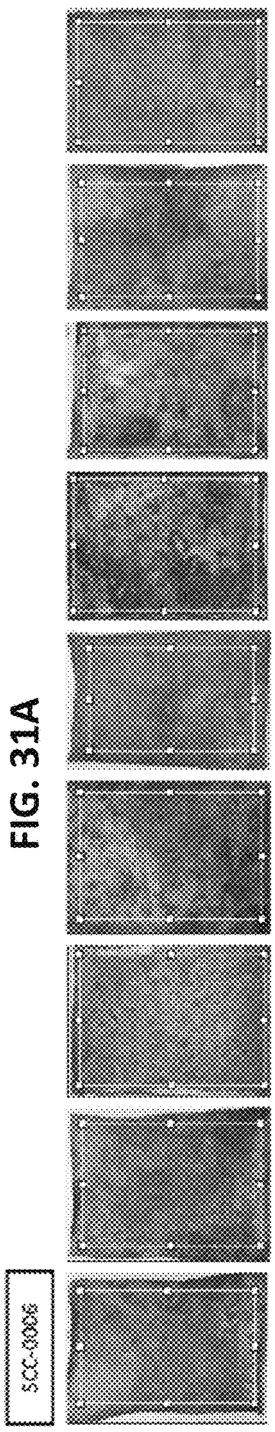
FIGS. 31A-31D illustrate homogeneity measurements in silver prototypes of SCC-0006 and SCC-0006 3.6 strains. Photographic records from FIGS. 30A-30B were converted to 8-bit images using ImageJ. The measurement zones were delineated with the GLCM package in boxed regions for the SCC-0006 strain (FIG. 31A) and, for the SCC-0006 3.6 strain (FIG. 31B).
Figure 31B:
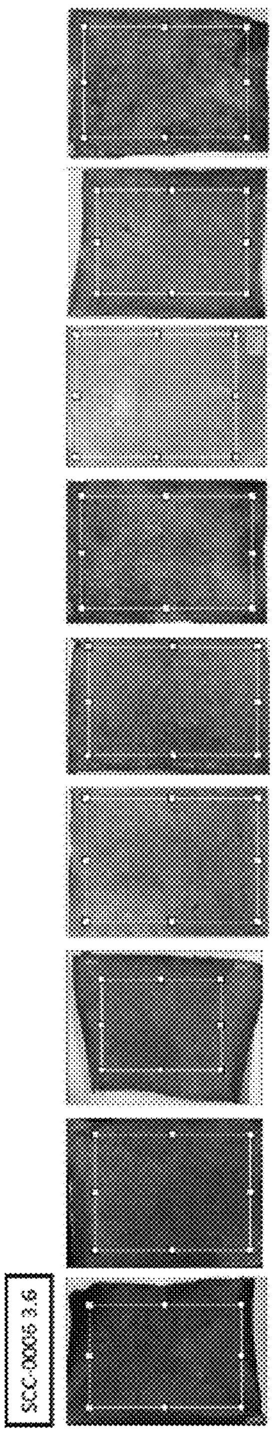

Under the naked eye view, an astonishing effect on the homogeneity was observed in those prototypes obtained with the modified strain, with the SCC-006/3.6 (dikaryotic) strain having a much more homogeneous appearance. To evaluate the qualitative change observed, the homogeneity was analyzed quantitatively. The images shown above were transformed into 8-Bit images. Subsequently, they underwent digital analysis using the Gray Level Co-occurrence Matrix (GLCM) toolkit, a statistical method employed in image processing and computer vision to analyze spatial relationships among pixel intensities in a grayscale image. The central areas of each material for strains of study were delineated for this purpose, demarcated by rectangles shown in FIG. 31A for SCC-0006 and in FIG. 31B for SCC-0006/3.6. Two parameters were measured from these photographs to correlate the material homogeneity with a numerical value. Firstly, the Entropy (the coating is denser) was calculated using the following formula:

$$H(x) = -\sum i = 1N\sum j = 1NP(i, j)\cdot \log 2\,[P(i, j)]$$

Where, P(i,j) represents the probability of co-occurrence for the pixel value pair (i,j) in the GLCM matrix. This calculation is performed for each pair of pixel values in the image. The Entropy function quantitatively measures the variability (or disorder) in the co-occurrence relationships of pixel value pairs in the image. A higher entropy value indicates a minor uniform and disorderly distribution of value pairs, suggesting greater textural complexity. Conversely, lower entropy reflects a more organized and predictable distribution, indicating a more homogeneous texture. Entropy, derived from the GLCM, emerges as a sensitive and valuable indicator for characterizing image textural complexity.

Additionally, the Contrast was used as a secondary parameter to analyze the images, whose calculation formulae run as follows:

$$\text{Contrast} = \sum i, j\,(|i - j|)\,2 \cdot P\,(i, j)$$

Contrast measures the intensity difference between adjacent pixels. A higher contrast value indicates a more significant variation between pixel values in the image, suggesting a more pronounced texture. Conversely, a lower contrast value indicates smoother variation in pixel values, indicating a more uniform texture.

Figure 31C:
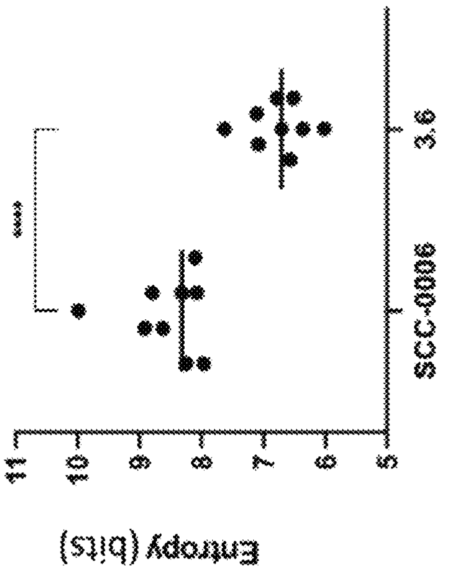
Figure 31D:
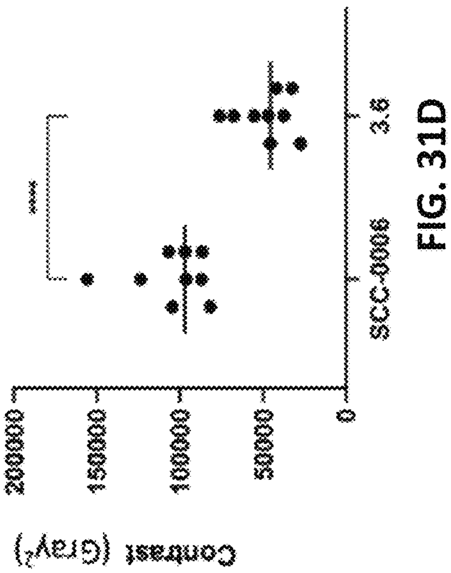

Both values were graphed using GraphPad Prism version 10.0.0, and the results are displayed in FIG. 31C for the entropy and in FIG. 31D for the contrast. A significant difference was observed (*: p-value<0.001). The prototypes derived from the SCC-0006/3.6 strain exhibited a greater homogeneity in the AgNPS distribution than the SCC-0006 strain. This tool could transform the qualitative observation (e.g., as in FIGS. 30A-30**B) into a quantitative parameter.

Figure 32B:
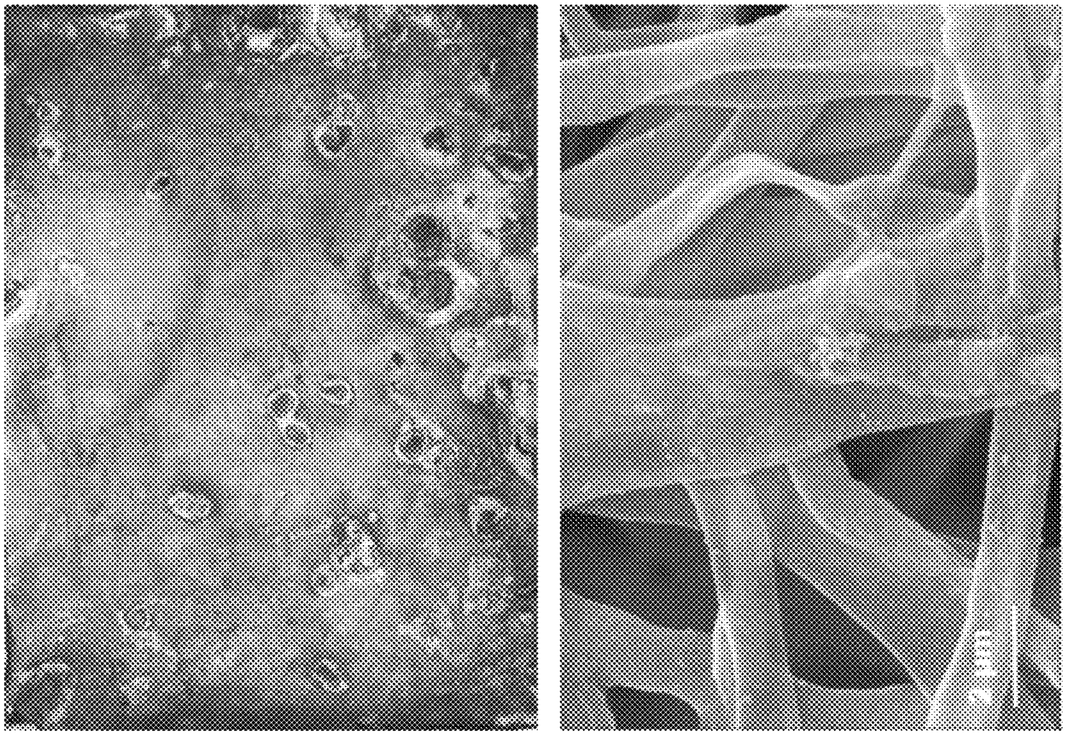
FIGS. 32A-32B show photographs (top) and SEM images (bottom) of several mycotextiles after the mycosynthesis of silver nanoparticles obtained by modifying the fungal strains: SCC-0002 (FIG. 32A) and SCC-0013 (FIG. 32B). Scanning electron microscopy (SEM) images of the corresponding samples (SCC-0002 and SCC-0013) were taken with secondary electrons at 20 k× magnification (BOTTOM). Each scale bar shown as an inset of the images corresponds to 2 micrometers.
Figure 32A:
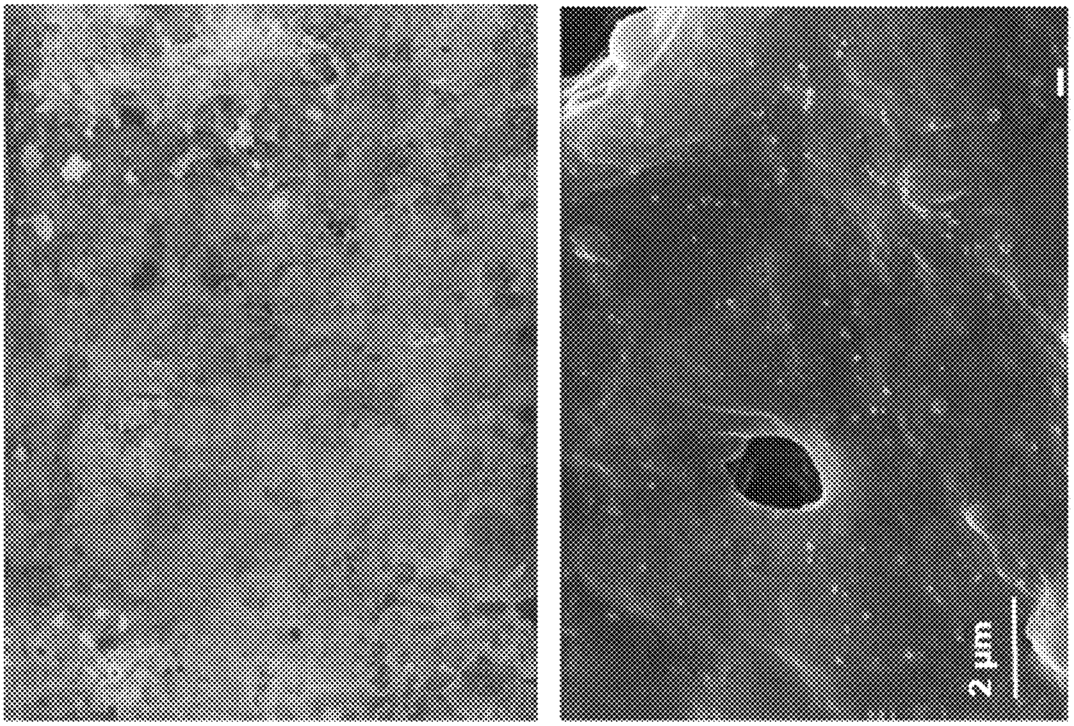

To compare the homogeneity and the distribution of the AgNPs, the strains with the highest antioxidant activities in the Polyporaceae family (SCC-0002 and SCC-0013), were used to obtain silver-loaded mycotextiles using the direct mycosynthesis. The photographs of the obtained prototype and the corresponding SEM images (magnification 20k×) are shown in FIGS. 32A-32B. Although the biosynthesis of AgNPs was successful with these strains, several differences could be highlighted regarding the results previously with the transformant SCC-0006/3.6. Regarding the look and homogeneity, the transformant strain provided a material with the expected look. As observed, the other strains yield sections of the material with irregular growth. When observed by electron microscopy, these differences are evident. In the case of the resulting AgNPs loaded in the prototype from SCC-002, the hyphae network cannot be distinguished; instead, it is observed as an amorphous mass decorated with spherical shiny particles.

The specific mechanisms involved in the biogenic synthesis of silver nanoparticles using fungi have not been fully elucidated. It is known that extracellular synthesis of nanoparticles occurs according to reactions in which the enzymes present in the fungal filtrate act to reduce silver ions, producing elemental silver ($Ag^0$) at a nanometric scale. Many biomolecules can react with silver ions, such as those associated with the complex pathways involving electron transfer during the conversion of NADPH/NADH to $NADP^+/NAD^+$. Nicotinamide adenine dinucleotide (NADH) and NADH-dependent nitrate reductase enzymes are considered the most important in the biogenic synthesis of metallic nanoparticles.

Results on AuNPs Mycosynthesis

The ability to biosynthesize silver and gold nanoparticles was studied mainly in two groups of fungi: Ascomycota and Basidiomycota. Mycogenic AuNPs are usually spherical, but other shapes have also been found. For the obtention of AuNPs loaded mycotextiles, two strategies were used: (i) direct biosynthesis and (ii) the spontaneous redox reaction between the as-synthetized AgNPs and chloroauric ions.

Figure 33B:
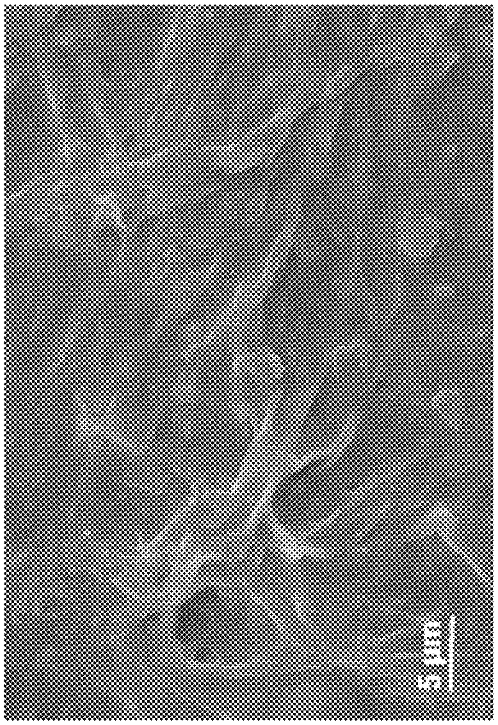
FIGS. 33A-33C show an example of a mycotextile after the mycosynthesis of AuNPs.
Figure 33C:
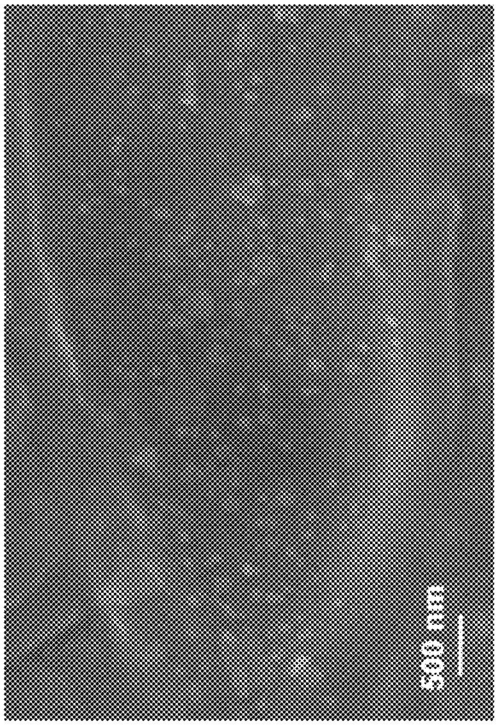
Figure 33A:
Figure 34B:
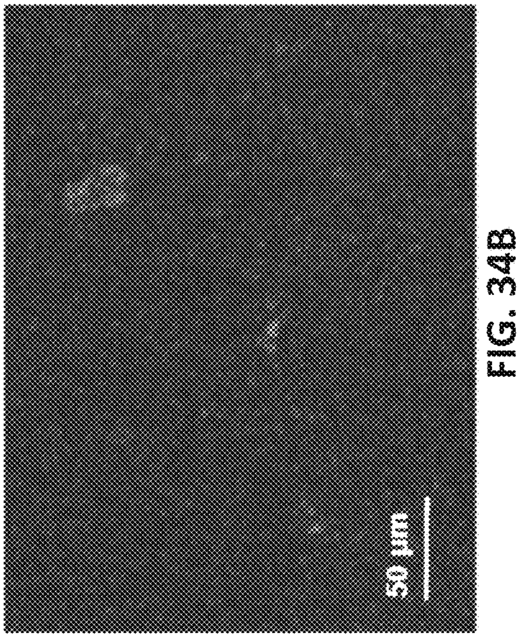
FIGS. 34A-34C illustrate gold mapping (FIG. 34B) and EDS spectrum (FIG. 34C) of the samples before and after UV irradiation. The Scanning electron microscopy (SEM) image (FIG. 34A) used as a reference for the mapping was obtained using backscattered electrons.
Figure 34A:
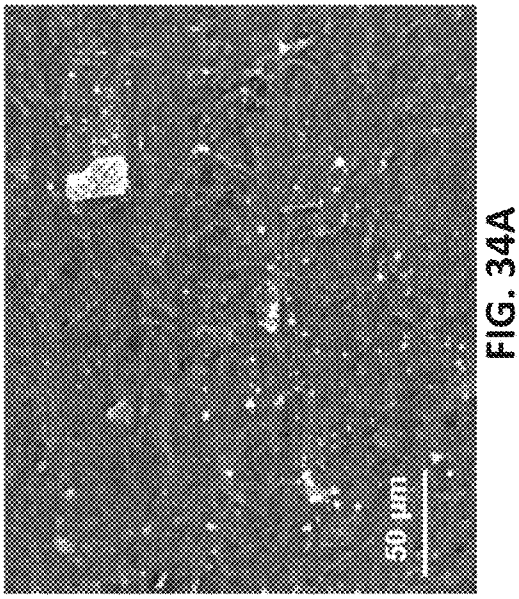
Figure 34C:
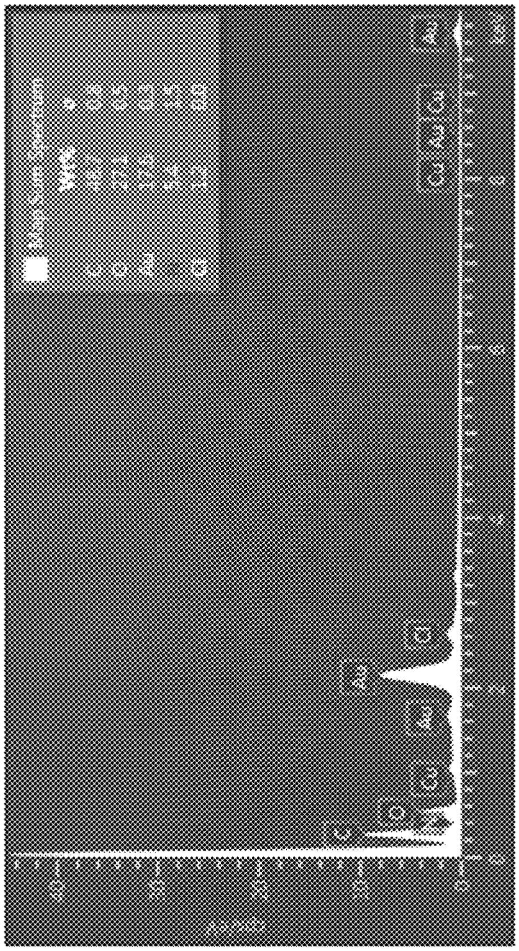
Figures 35A, 35B, 35C, 35D:
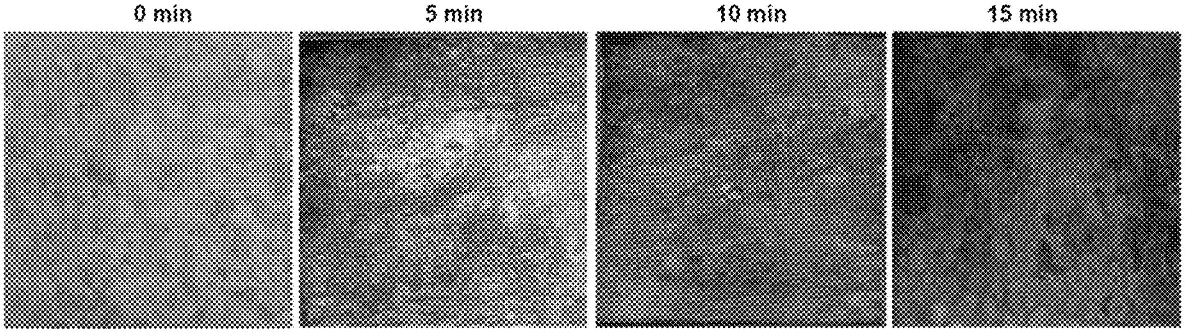
FIGS. 35A-35D show examples of photographs of the mycotextiles after the chemical reduction after 0 min (FIG. 35A), 5 min (FIG. 35B), 10 min (FIG. 35C) and 20 min (FIG. 35D) to obtain AuNPs by spontaneous oxidation of AgNPs.

A prototype obtained by direct mycosynthesis requires an overnight incubation in the gold solution (pH below 1). After that, the material is removed from the acidic solution and then treated with the nanoemulsion and prolamine protein (e.g., zein) coating, as mentioned above, for AgNPs. FIGS. 33A-33C shows a photograph of the resulting prototype with the corresponding SEM images at 5 and 50k×. It is possible to observe that the surface has yellow-colored regions as well as regions colored in purple. The corresponding SEM image at 5k× shows a dense coating with dispersed nanoparticles of around 60 to 100 nm. However, a higher magnification (50k×) revealed a higher size dispersion. The elemental mapping of this region is shown in FIGS. 34A-34C and reveals the aggregation of the gold nanoparticles (gold weight percentage is around 17.6%, assigned to these big particles (around 100 nm).

A strategy to avoid aggregation is the spontaneous redox reactions of metallic silver and gold ions. A spontaneous redox reaction is associated with positive cell potential that imparts a negative Gibbs free energy change during a chemical reaction. Hence, a positive cell potential determines the spontaneity of a redox reaction. In the case of the gold reduction at the expense of silver oxidation, the standard cell potential is equal to 0.5 V. It could be calculated from the following net redox reaction: $Au^{3+}(aq)+3Ag(s) \rightarrow Au(s)+3Ag^+(aq)$ ($E^0$=0.5 V).

As observed in FIGS. 35A-35D, the immersion of the prototype previously loaded with silver nanoparticles in a gold solution between 5 to 15 min yields a more homogenous color change. This strategy provides a better environment in which to perform the redox reaction because the AgNPs are already immobilized on the surface of the hyphae, which guarantees a lower dispersion in the particle size of the obtained AuNPs. Silver ions resulting from this reaction are expected to release the material, or probably some of the ions may remain adsorbed of the hyphae.

Figure 36:
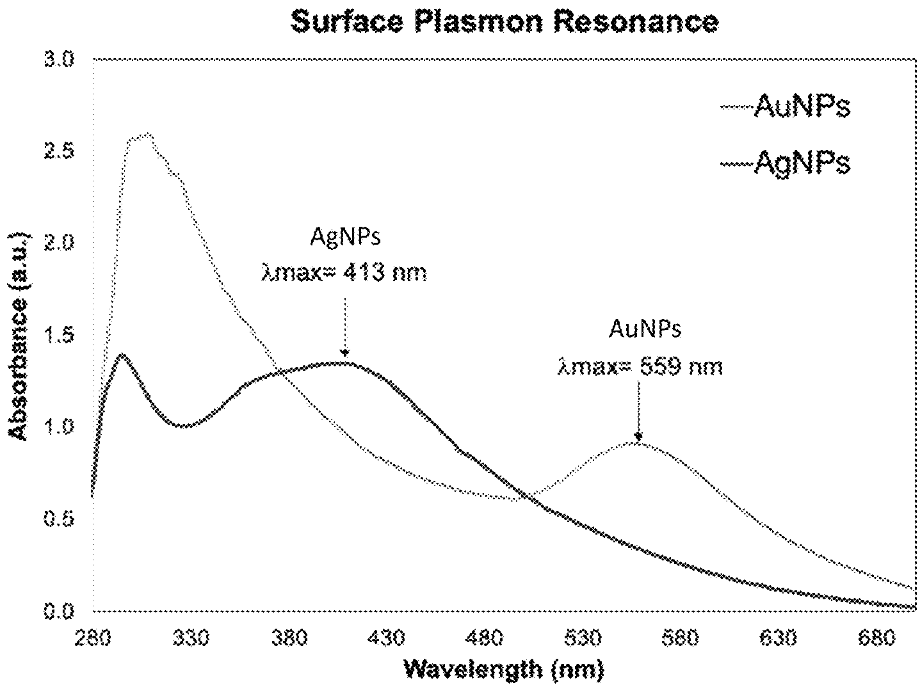
FIG. 36 shows a UV-Vis spectra of i) the residual solution of the AgNPs mycosynthesis and ii) the residual solution of the chemical reduction of the AuNPs synthesis. Each spectrum highlights the surface plasmon resonance band at 413 and 559 nm for AgNPs and AuNPs, respectively.

Nanosized gold has some unexpected optical properties. For example, Au NPs colloids may look red, orange, or even blue. The color depends on the size and shape of the nanoparticles and also on the distance between them. The different colors of Au NPs arise from a physical phenomenon named localized surface plasmon resonance (LSPR). When light interacts with the surface of a metal, it creates a surface plasmon, which is a group of electrons moving back and forth in a synchronized feature across the surface of the metal. When the electrons are moving at the same frequency as the incident light, the plasmon is said to be in resonance. At this stage, the electrons absorb and scatter light (according to Mie's theory), producing the colors we can see. The LSPR of 5-10 nm spherical Au NPs ranges from 520 to 580 nm, which means they absorb green or yellow light. As a result, they show the complementary color of green or yellow, which is red or purple. In the case of AgNPs, the LSPR peak is exhibited at 380 to 460 nm for monodispersed colloidal dispersion with spherical particles with an average diameter of less than 100 nm. The occurrence of the LSPR phenomena could be measured utilizing UV-visible spectroscopy. As observed in the UV-visible spectrum (FIG. 36) of the remaining solution after the incubation in $AgNO_3$, a broad band around 413 nm accounts for the presence of colloidal AgNPs, evidencing that the synthesis occurs extracellularly. On the other hand, after 15 min of reaction with the gold solution, the remaining solution provokes a change in the spectrum with a broad peak around 559 urn, indicating that the previously mentioned redox reaction occurred. Hence, AuNPs are now present in the material.

Figure 37A:
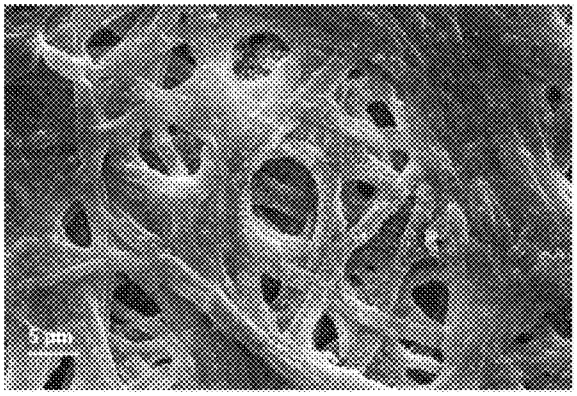
FIGS. 37A and 37B show scanning electron microscopy (SEM) images at 5 and 50 k× magnification, respectively, taken using secondary electrons of the AuNPs loaded mycotextile. The scale bar of the image at 5k× is 5 micrometers, and the image taken at 50 k× is 500 nanometers.
Figure 37B:
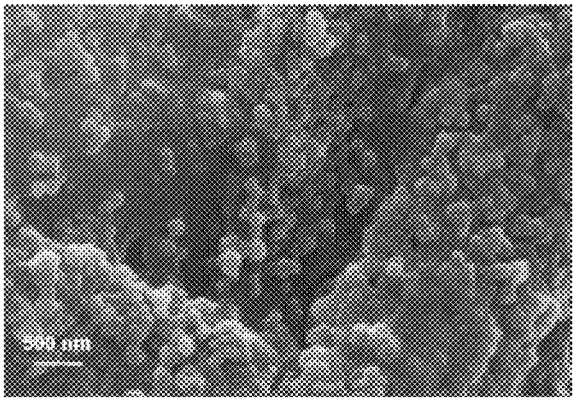
Figure 38A:
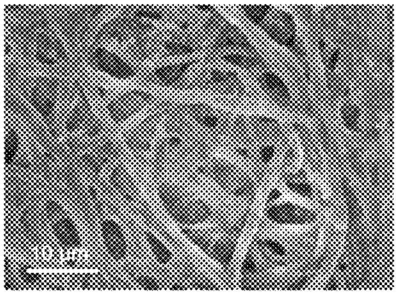
FIGS. 38A-38D illustrate gold and silver mapping (FIGS. 38B and 38C, respectively) and EDS spectra (FIG. 38D) of the sample obtained by chemical synthesis. The Scanning electron microscopy (SEM) image (FIG. 38A) used as a reference for the mapping was obtained using backscattered electrons.
Figure 38B:
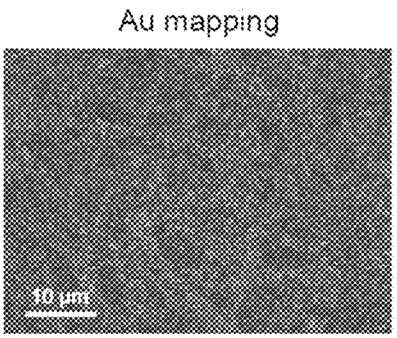
Figure 38C:
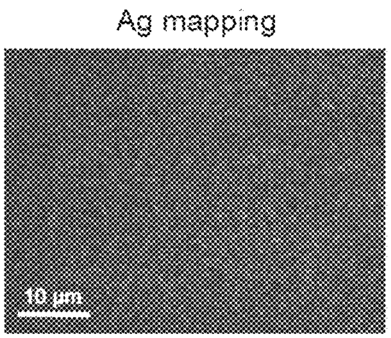
Figure 38D:
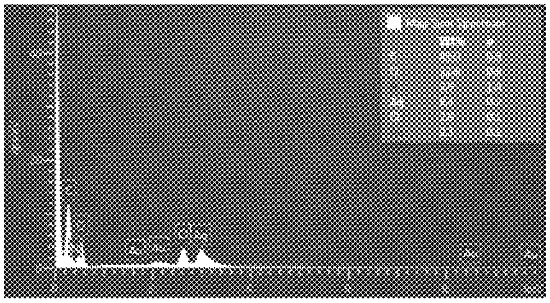
Figures 39A, 39B, 39C, 39D:
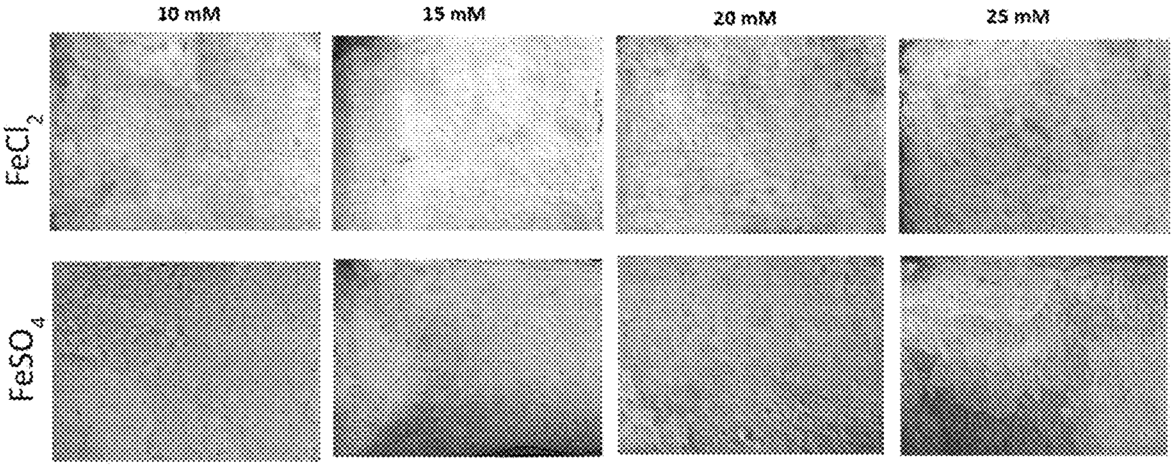
FIGS. 39A-39D show examples of photographs of the mycelium fabrics after the mycosynthesis of IO NPs using two different salts as precursors (top: FeCl2, bottom: FeSO4) at concentrations of 10 mM (FIG. 39A), 15 mM (FIG. 39B), 20 mM (FIG. 39C) and 25 mM (FIG. 39D) of each salt.
Figures 40A, 40B, 40C:
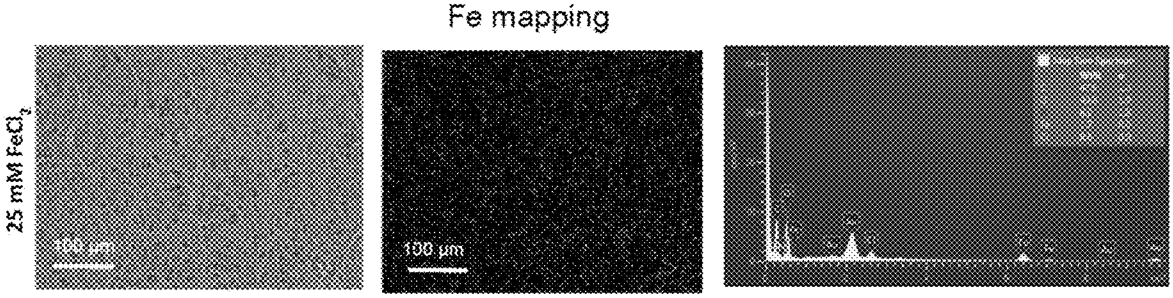
FIGS. 40A-40C show an example of Iron (Fe) mapping (FIG. 40B) and EDS spectra (FIG. 40C) obtained with 25 mM of FeCl2. The scanning electron microscopy (SEM) image (FIG. 40A) used as references for the mapping was obtained using backscattered electrons.
Figures 40D, 40E, 40F:
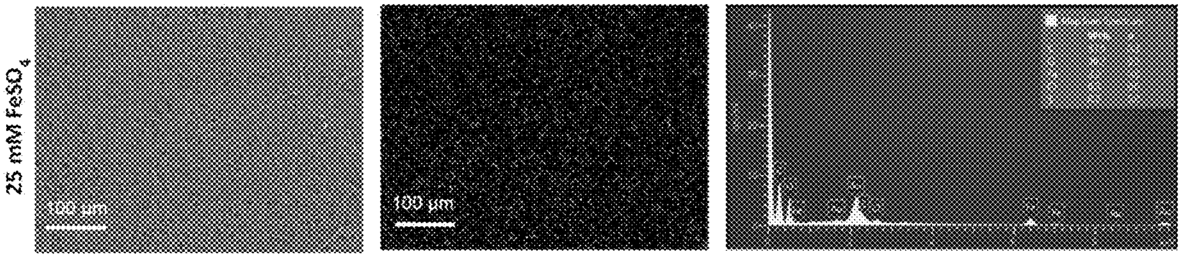
FIGS. 40D-40F show an example of Iron (Fe) mapping (FIG. 40E) and EDS spectra (FIG. 40F) obtained with 25 mM of FeSO4. The scanning electron microscopy (SEM) image (FIG. 40D) used as references for the mapping was obtained using backscattered electrons.

SEM images taken with magnifications of 5 and 50 k× (FIGS. 37A-37B) reveal that the hyphae network is fully covered by spherical nanoparticles of around 100 nm. Gold and silver mapping on a determined sample region shows a very high and homogenous distribution over the tested surface. EDS analysis in FIGS. 38A-38D reveals a gold mean content of 0.3 wt. %. When the starting gold concentration is 0.01 mM, the maximum expected gold loading in the prototype is 0.4 wt. %, as the experimental value is very close to the theoretical value, which means that the gold is highly dispersed in the material. Considering that in previous analyses of surfaces with the same dimensions (spectrum taken at the same magnification and under equivalent conditions), the silver concentration ranges between 7 and 8 wt. %, the quantification of an equivalent silver content suggests that the oxidized silver ions remain adsorbed in the surface instead of being released to the aqueous medium. The observed color change accounts for the presence of sufficient Au NPs to provoke a change in the appearance and texture of the material, as well as to induce functionality, as will be seen below.

Results on IO NPs Mycosynthesis0260

The materials resulting from the incubation with $Fe^{2+}$ salts are shown in FIGS. 39A-39D. Changing the initial concentration from 10 to 25 mM did not cause a marked difference in the appearance of the material. All developed a yellowish color regardless of the precursor used or the starting concentration. SEM images of the material obtained with the highest concentration (i.e., 25 mM) were taken at a magnification of 500× do not show big differences in the mycelium networks. Likewise, the iron mapping and EDS spectra do not show a marked difference regarding the iron source used. Iron content measured in the selected area was 1.7 and 2.2 wt. % when starting with chloride or sulfate salts, respectively (FIGS. 40A-40F). By increasing the magnification of the images to 10k× (FIGS. 41A-41B), it is possible to distinguish that the hyphae are more homogeneously covered by the nanoparticles when ferrous chloride is used as precursor.

In the case of iron species, it is well known that extracellular enzymes produced by some fungal species can catalyze the breakdown of anionic iron complexes of ferric and ferrous salts. Moreover, under aerobic and moderate pH conditions, ferrous iron ($Fe^{2+}$) is oxidized spontaneously to the ferric ($Fe^{3+}$) form and is hydrolyzed (abiotically) to insoluble ferric hydroxide ($Fe(OH)_3$). This process is the opposite of the one observed with silver and gold, where electrons are needed to transform the oxidized ions to zero valent atoms and, therefore, metallic nanoparticles. In this example, ($Fe^{2+}$) ions must gain one electron to transform into ($Fe^{3+}$) ions that further precipitate as a hydroxide or an oxyhydroxide; therefore, the metabolic pathway and involved proteins in this case should be different.

In Vitro Biosynthesis and Combination with In Vivo Mycosynthesis

In an example of an ex situ approach, nanoparticles were synthesized using biological methods since the reducing agents derived from natural resources such as plants, algae, microalgae, and microorganisms are more efficient and environmentally friendly. For instance, plant extracts contain different phytochemicals that stabilize or reduce metal ions to metal nanoparticles (e.g., phenolic compounds, terpenoids, flavones, ketones, amides, aldehydes and carboxylic acids). The resulting colloidal suspension can be incorporated either by immersion or spray-dry techniques. In the case of immersion, the mycotextiles were dipped in the colloidal dispersion of the nanoparticles for 15 min, ensuring that the side with the mycelium was facing up to induce the penetration of the liquid dispersion mechanically. The prototype is disposed horizontally for the spray-dry method, controlling the liquid flow and flow speed to ensure the mycelium is well-soaked. Then, the mycotextiles were dried at room temperature. For these examples, copper oxide, magnetic iron oxide, and yellow and red iron oxide pigments were used in several combinations as described below:

Biosynthesis of Copper Oxide Nanoparticles

Copper can be considered an important antimicrobial agent because they are effective against many microorganisms, including fungi, viruses, and multidrug-resistant bacteria. An extract of *Ilex paraguariensis* (yerba mate) was prepared at 5 w/v % in distilled water at 85° C. for 10 min with constant stirring. The extract is filtered by gravity at room temperature using a proper porous material. A 0.1M copper sulfate ($CuSO_4$ $5H_2O$) solution was prepared in parallel. The yerba mate extract was slowly added dropwise to copper sulfate solution in a volume 1:5 ratio and kept under constant stirring; after adding the extract, the pH was adjusted to 9 units using a 3M NaOH solution. Finally, the synthesis was left under stirring for 1 h, and the resulting deep grass green colored suspension was reserved for its application. This synthesis process can be carried out using extracts from different plants that have high antioxidant activities, including native trees, such as *Ilex guayusa, Peumus boldus, Schinus molle, Quillaja saponaria, Cryptocarya alba*, among others. In addition, macro and microalgae, such as *Ulva compressa, Spirulina platensis, Spirulina maxima, Arthrospira platensis, Chrorella* sp., *Euglena gracilis, Euglena* sp., *Nannochloropsis* sp., *Phaeodactylum tricornutum, Asterarcys* sp., *Scenedesmus* sp., *Uronema* sp., etc.

Biosynthesis of Magnetic Iron Oxide Nanoparticles

Iron oxide nanoparticles have attracted great interest in recent times due to their magnetic nature, biocompatibility, of these metal oxide nanoparticles, one of them, low susceptibility to oxidation, immunoassays and antimicrobial activity against various pathogens such as fungi and bacteria, and viral particles. Furthermore, iron oxide nanoparticles have been used for their different coloring tissues. An Aloe vera extract was prepared at 1% w/v in distilled water at 85° C. for 10 min with constant stirring. The extract is filtered by gravity at room temperature using a proper porous material. A solution of 0.1 M of iron sulfate ($FeSO_4$*$7H_2O$) was prepared in parallel. Aloe vera extract was slowly added to the $FeSO_4$ $7H_2O$ solution in a volume ratio of 1:2 (with constant stirring). Once this was finished, the pH was adjusted to 12 units with a 3M NaOH solution. Finally, the synthesis was left stirring for 2 h, and the resulting deep brownish suspension was reserved at room temperature for the application.

Formulations of Yellow and Red Nano Pigments of Iron Oxide

Iron oxides have been widely used in the textiles industry to impart novel properties, such as antibacterial and antifungal activity, removal of adsorbed dyes, thermal stability, mechanical properties and other functions. Moreover, iron oxides are the most abundant minerals in the earth's crust, allowing its utilization as pigments in prehistoric ages. Iron oxides exist in a wide range of colors, from yellow to black. The most common are yellow, corresponding to goethite (FeOOH); red, corresponding to hematite ($Fe_2O_3$); and black, corresponding to hematite ($Fe_3O_4$). The colloidal dispersion of yellow and red iron oxides was obtained by dispersing the proper amount of the corresponding solid in water (the concentration of yellow IO was 0.125% w/v, and the red IO was 0.25% w/v). Also, a dispersing agent such as polysorbates (e.g., tween 20, tween 80), polyacrylic acid (PAA), polyethylene glycol (PEG), polyvinylpyrrolidone (PVP), ionic liquids (IL), among others; in concentrations around 1 and 10% w/v; and, a thickener such as polyvinyl alcohol (PVA), carboxymethylcellulose (CMC), Xanthan Gum (XG), Guar Gum (GG), alginate (A), among others in concentrations around 0.01 and 0.1% w/v. These mixtures were formulated to reach viscosities between 100 to 1000 cps.

Starting Mycomaterials and Combinations

Figure 23:
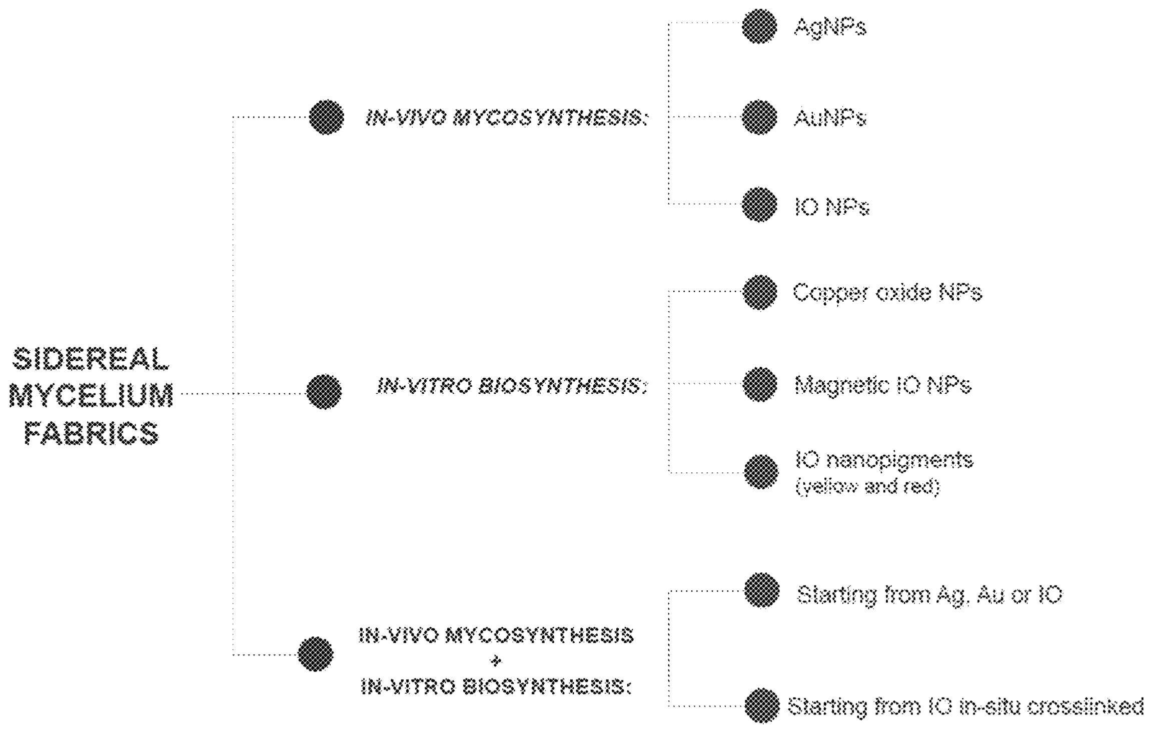
FIG. 23 illustrates an example of a scheme describing some examples of sidereal mycelium fabric according to the in vivo mycosynthesis, in vitro biosynthesis or the combination of both.
Figures 24A, 24B, 24C, 24D:
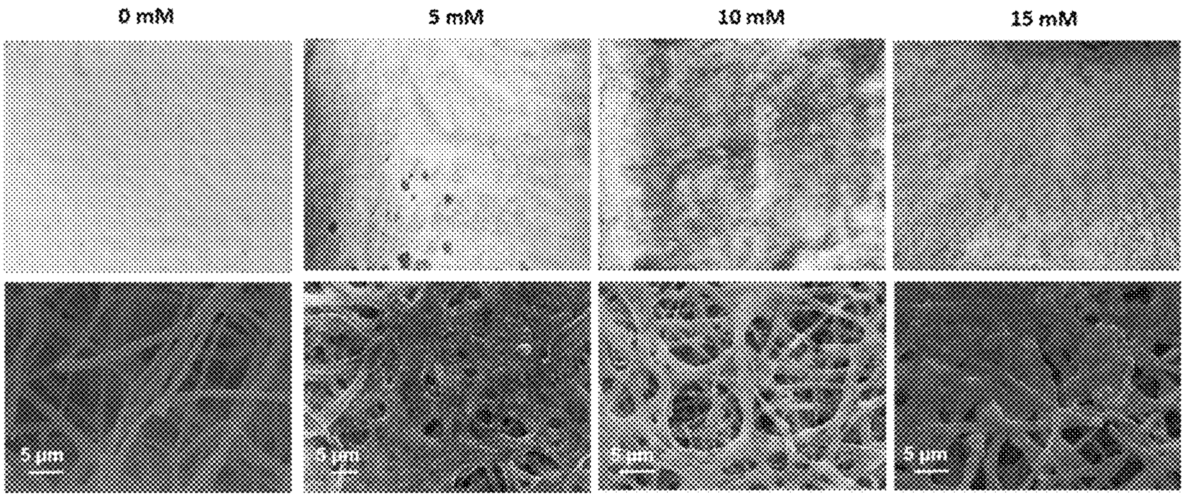
FIGS. 24A-24D show examples of light images and scanning electron microcopy (SEM) images of several mycotextiles after the mycosynthesis of silver nanoparticles were obtained by changing the silver concentration in 0 (FIG. 24A), 5 (FIG. 24B), 10 (FIG. 24C) and 15 mM (FIG. 24D). Scanning electron microscopy (SEM) images of the corresponding samples are shown using secondary electrons at 5 k× magnification. Each scale bar shown as an inset of the images corresponds to 5 micrometers.

The bases for these approximations are any of the following materials: 1) a wild mycotextile, 2) an Ag NPs loaded mycotextile or, 3) an in-situ crosslinked mycotextile (for a graphic reference see FIG. 23 above). The following combinations could be achieved: (i) Wild-Cu, (ii) Wild-magnetic IO, (iii) Wild-yellow IO, (iv) Wild-red IO, (v) Ag—Cu, (vi) Ag-magnetic IO, (vii) Ag-yellow IO, (viii) Ag-red IO, (ix) Au—Cu, (x) Au-magnetic IO, (xi) Au-yellow IO, (xii) Au-red IO, (xiii) in-situ-Cu, (xiv) in-situ-Ag, (xv) in situ-Au, (xvi) in-situ-magnetic IO, (xvii) in-situ-red IO.

First, a "Wild" mycotextile is obtained by adding the nanoparticles as part of the post-processing steps (see, e.g., the post-treatment described in U.S. patent application No. US 2023/0356501-A1, and U.S. provisional patent No. U.S. 63/590,397). The mycelium is grown onto the scaffold for 7-10 days, preferably in fermentation conditions as encountered in a mushroom farm. Then, the harvested material is dried and immersed in an O/W nanoemulsion. The greased and dried material is immersed in the colloidal suspension of functionalized (e.g., ceramic) nanoparticles. Finally, the mechanically reinforced material is dried and coated with a prolamine protein (e.g., zein) solution. From this point, copper or iron oxide nanoparticles are incorporated.

Any of these apparatuses may include one or more types of ceramic nanoparticles. Ceramic nanoparticles may include oxide and non-oxide types. Common examples of oxide ceramic nanoparticles include silica ($SiO_2$), alumina ($Al_2O_3$), titania ($TiO_2$), and zirconia ($ZrO_2$), while non-oxide examples include silicon carbide (SiC) and boron nitride (BN). Hydroxyapatite (HA), calcium phosphate (CP), and calcium carbonate ($CaCO_3$) are also ceramic nanoparticles.

Second, the Ag or Au NPs (nanoparticle) loaded mycotextiles may be obtained as described above by mycosynthesis, e.g., forming the nanoparticles in vivo, following fermentation but prior to post-fermentation processing, by incubating in the appropriate (e.g., metallic ion) solution.

Third, "in-situ" crosslinked materials may be obtained by adding nanoparticles during growth of the mycelium mat (e.g., see U.S. patent application Ser. No. 18/595,392, field Mar. 4, 2024). Here, the ceramic nanoparticles used for the reinforcement are the yellow-iron oxide (yellow IO). The nanoparticles were added when the mycelium was self-generated in the fermentation room. Therefore, the harvested material already possesses the functionalized nanoparticles. The harvested material may be dried and greased with the O/W nanoemulsion. Finally, the material is coated with a prolamine protein (e.g., zein-protein) and is ready to incorporate the biosynthesized nanoparticles.

Results of the Reinforcement with Copper Oxide Nanoparticles

The advantage of combining different types of nanomaterials includes the possibility of achieving a synergistic activity. For example, combinations of silver and copper nanoparticles increase antibacterial efficacy against a wide range of bacteria, including antibiotic-resistant strains such as the gram-negative *Escherichia coli* and *Pseudomonas aeruginosa*, as well as the gram-positive *Staphylococcus aureus, Enterococcus faecalis*, and *Streptococcus disgalactiae*. Likewise, nanostructures based on zinc, copper, aluminum and titanium could be assembled into the collagen fibers of leather or sprayed to improve rub fastness, color fastness and adhesion strength. As seen in FIG. 42A1-42A2, either when the starting mycotextile is the wild prototype (left, FIG. 42A1) or the AgNPs loaded mycotextile (right, FIG. 42A2), the copper oxide nanoparticles exist at the surface in the form of deep green grass-like regions that apparently did not penetrate the mycelium network. SEM images in FIGS. 42B1 and 42C1 show the microstructure of the corresponding materials at the interface of these "green spots" at 500× magnification for each material. In both cases, two regions are clearly observed: a region on the left corresponding to the common hyphae network and a region at the right of the image that could be described as a thick cracked deposit. Furthermore, when zooming in on both sides at 10k× magnification, it could be observed the ceramic nanoparticles used for the mechanical reinforcement during the post-fermentation stage in the "wild-Cu" prototype and the cracked thick coating is composed of aggregates of tiny spheroidal nanoparticles. In the case of the EDS spectrum and copper mapping, it was confirmed that these agglomerates on the mycelium surface are copper nanoparticles. The approximate concentration in the analyzed area was 4.3 and 10.9 wt. % for "wild-Cu" and "Ag—Cu", respectively. This difference could be explained by the aggregation that does not provide a homogenous distribution of the copper at the surface. This accumulation in the surface could result from the previous loading with AgNPs, limiting the interaction between the hyphae and the nanoparticles introduced in this step.

Results of the Material Reinforcement with Magnetic Iron Oxide Nanoparticles

Magnetic properties are highly desirable for novel applications in the textile industry. For instance, they provide conductive or antistatic properties, electromagnetic shielding, radar-absorbing capabilities, soft keyboards, magnetic heating, etc. Different types of magnetic nanostructures, such as iron oxides (e.g., magnetite, maghemite), cobalt, nickel, ferrites, and metallic alloys, could be obtained by biological routes. The biosynthesis of magnetite has been reported. An efficient approach is using Aloe vera extract as a stabilizing agent as it provides chromones, anthrones and phenolic compounds, leading a green and environmentally friendly synthetic route. The brownish colloidal suspension in the aqueous media of the stabilized magnetic-IO nanoparticles presents a viscosity slightly higher than that of pure water at the same temperature due to the mucilaginous substances existing in Aloe vera. However, dried magnetite separated by centrifugation is black-colored. The obtained solid exhibits a magnetic response close to the magnetic field of a magnet, as illustrated in the photographs in FIGS. 43A-43B. Moreover, as seen in FIGS. 44A1-44A2, the iron oxide nanoparticles pigmented both the wild prototype (FIG. 44A1) and the AgNPs-loaded mycotextile (FIG. 44A2) in brown color. The coating seems more homogenous in the material "Ag-magnetic IO" with some isolated darker regions. In "wild-magnetic IO", these darker areas are more evident, suggesting a less homogeneous coating distribution. SEM images with a magnification of 500× that accompany these photos show a landscape of the material's surface in which it can be distinguished that the coating on the wild material is more homogeneous and denser. In the case of the mycotextile previously loaded with Ag NPs, the nanoparticle aggregates seem much more minor, yielding a more homogenous coating onto the hyphae. In the case of the EDS spectrum of the "wild-magnetic IO" collected in a region where a dense coating is clearly distinguished, the approximate iron concentration in the analyzed area was 4.6% by weight, as seen in FIG. 44B1-44B3. Meanwhile, elemental mapping confirms that this coating is formed of iron oxide and distributed inhomogeneously throughout the mycelium. Elemental mapping in "Ag-magnetic IO" collected in a region where a dark area was observed reveals the presence of silver in all the analyzed surfaces, while iron clearly is present in the coating. The approximate iron concentration in the tested area coincides with 4.6 wt. %, while silver content is around 2.9 wt. % (FIG. 44C1-44C4). This diminution in silver content could be related to the selected region where an iron oxide coating is presented. Thus, this iron oxide layer restricts the X-ray emission of the silver nanoparticles existing below this coating. On the other hand, the magnetic response of the material containing the nanoparticles will be discussed below.

Results of Yellow and Red Nanopigments

The wild and Ag-loaded prototypes immersed in a suspension of the yellow-IO nanopigments are shown in FIG. 45A1-45A2. They appear more homogenous than previous examples. When the initial mycotextile is the wild-yellow IO (FIG. 45A1), iron oxide nanoparticles are present on the surface, giving the prototypes an intense yellow color. However, in the case of the mycotextile loaded with Ag-yellow IO (FIG. 45A2), this intense yellow coloration was not observed. The microstructure observed using the SEM images (FIG. 45A1) at 10k× magnification for each material), reveals that the iron oxide nanopigments comprise nanorods around 200×500 nm, more extensive than copper and magnetic IO nanoparticles. They tend to agglomerate instead of forming a continuous coating on the material. In the case of the EDS spectrum and iron mapping (FIG. 45B1-45B3), the presence of iron oxide nanoparticles distributed homogeneously throughout the hyphae was confirmed; the approximate concentration in the analyzed area was 2.5% by weight. In the case of mycotextile, which has silver nanoparticles, it was confirmed that the rod structures incorporated in the hyphae of the mycelium are iron oxide nanoparticles. The approximate concentration in the analyzed area was 9.9% and 0.4% in weight for silver and iron, respectively (FIG. 45C1-45C4). This difference regarding the iron loading in the wild prototype could indicate some incompatibility between the surface charge of these particles and the surface of the materials, leading to a lower distribution of the nanopigments. In the case of the resulting materials by immersion in the red IO NPs formulation (shown in FIG. 46A1-46A2), these nanoparticles remain on the surface of the hypha in a similar way to what was observed with the yellow IO nanoparticles but turning the surface of the mycotextile into red color. As observed in both SEM images shown in FIG. 46B1-46B2 (taken at 2 and 20 Kx, respectively) for the "Ag-red IO" prototype, these nanoparticles show a more heterogeneous distribution in size and yield a higher covering of the hyphae network than those obtained with the same concentration of yellow IO NPS. A closer look at a single hypha shows that these particles are heterogeneous in shape and range around 100 nm. Elemental mapping in a given region using EDS reveals that the aggregates on the surface are composed of iron and oxygen, confirming the presence of iron oxide nanoparticles. The iron and silver content in the analyzed region is 8.2 and 1.7 wt. %, respectively. See FIGS. 46C1-46C4.

In-Situ Nano Crosslinking and Silver Nanoparticles

Prolamine protein (e.g., zein-) functionalized IO NPs nanoparticles were dispersed in a BIOrganic CHAI solution; the mixture was sonicated (60 Hz for 1 h) and sterilized before application onto the growing mycelium during the fermentation process using a spraying gun. The details of formulations and application schemes for this colloidal dispersion are described in the provisional patent No. U.S. 63/520,933.

FIGS. 47A1-47A2 show at the left (FIG. 47A1) the starting prototype obtained with yellow IO NPs where a yellowish surface is observed, being characteristic of the ocher-colored solid used as a crosslinker. The observation of the SEM image at 10 k× magnification, present in the same figure (bottom), revealed that the nanoparticles are in intimate contact with the hyphae but also tend to be more aggregated in some areas of the network; however, the morphology of each hypha could be clearly distinguished. After immersing this material in the silver nitrate solution overnight at 60° C., the material took the expected brownish color given by the silver, and the microstructure changed. Here, the hyphae appear highly interconnected and also covered by a dense layer, which agrees with the result in FIG. 28 (AgNPs loaded prototype after exposure to UV light). EDS spectrum and elemental mapping in FIG. 47B1-47B4 show a homogeneous distribution of silver along the tested surface with a weight content of 5.6%. In contrast, iron distribution is less homogenous, being identified as a small cumulus of rod-like nanoparticles with weight contents around 0.3% (FIG. 47B3-47B4).

The procedure's versatility allows it to introduce many other functional elements and compounds. For instance, other precious metals may be incorporated as described herein, including platinum, palladium, iridium, osmium, rhenium and non-precious metals such as iron, aluminum, titanium, tin, cobalt, manganese, molybdenum, nickel, vanadium, niobium, zirconium and/or, rare earth such as lanthanum, cerium, dysprosium, europium, gadolinium, erbium, holmium, and/or metal compounds or composites such as oxides, oxyhydroxides, salts, carbonates, aluminates, ferrites, silicates, iron phosphates, titanates, perovskites, pyroxenes, carbides, nitrides, carbonitrides.

Mechanical Characterization of Sidereal Mycotextiles

The industrial application of the described sidereal materials depends on their mechanical properties. It arises from a combination of the characteristics provided by the fungal mycelium layer, their nano-mycosynthesis skills, and the scaffold selected for its growth. Also, it arises from the combination of the methods described here because it yields at least twelve combinations of sidereal mycotextiles.

For instance, as reported before, fungal mycelium alone typically has tensile strength values below 1 MPa while, in cowhide leather, this parameter varies between 8 and 20 MPa. Moreover, synthetic leather can have values of 10-15 MPa. Other characteristics, such as elongation after a break or tear strength, must be similar to those expected in industrial applications, such as leather goods, shoe manufacturing or upholstery. The preliminary tests carried out in several of the sidereal mycelium fabrics fabricated as described herein were: i) tensile strength (TS), ii) elongation percentage before rupture (E), both according to the ASTM D2209 standard and tear strength (TeS) according to ASTM D4704-13 standard. These tests were conducted using a GESTER GT-C02-1A Universal Tensile Strength Tester (Single Column) with a 2.5 kN load cell at 254 mm/min speed. The specimens of each sample were obtained by a laser-cutting machine of the corresponding geometry requested by each standard. The rubbing color fastness test, which refers to a test in which colored samples are rubbed with dry rubbing cloth and wet rubbing cloth, respectively, was determined using a GESTER GT-D05 Crockmeter/Rubbing fastness tester. The values presented correspond to a mean value of three replicates for every experiment.

To be measured, the selected scaffold has two directions regarding the elongation and tensile strength, considering the direction of the applied force. Different from woven textiles that show a weft and warp direction, the direction of the non-woven textile is organized by the magnitude of the elongation. The results will be discussed regarding the strategy of obtention of the sidereal mycotextile. First, the control material (wild) will be compared to those resulting from AgNPs mycosynthesis (in vivo approach). Second, those obtained from the in vitro approach and the corresponding combination of AgNPs loaded mycotextile. Finally, the "in situ-Ag" mycotextile will be compared with the corresponding control (in-situ crosslinked material).

Table 3 lists the tensile strength (TS) and elongation (E) before break and tear strength (TeS) for the materials obtained by AgNPs mycosynthesis. As observed, in the direction of the higher elongation, the tensile strength does not show a difference statistically representative after the mycosynthesis of silver nanoparticles regardless of the fungal strain. However, the elongation at break increased by around 5 and 15%. Likewise, the tear strength increased in all the examples (between 28 and 38%), meaning that the reaction conditions changed the material's mechanical properties. In the direction of the lower elongation, TS, E % and TeS showed a slight increase in all the experiments. These results indicate that the process of obtaining AgNPs does not significantly affect the mechanical properties of the crude mycotextile. However, the mycotextile generated with the SCC-0006/3.6 strain used to obtain the AuNPs by chemical reduction showed a significant decrease of all the properties; for instance, TS and elongation decreased by around 30%, while TeS diminished by 44%. Therefore, the synthesis of AuNPs changes these characteristics, probably due to the immersion in the acidic solution that causes partial hydrolysis of the scaffold fibers.

Regarding the in vitro approaches comparing the materials "wild-Cu", "wild-magnetic IO", and "wild-red IO", it is possible to observe the effect of the incorporation of the nanoparticles in the mechanical properties. The results are listed in Table 4. In the direction of the highest elongation, TS increases after immersion of the mat in the dispersion of copper and magnetic IO NPs obtained by biosynthesis. The change with the "wild-red IO" was negligible. Likewise, the elongation before the break and the tear strength increased in all the experiments. Remarkably, the tear strength shows enhancements between 24 and 44% in this direction. On the other hand, analyzing the results in the direction of the lower elongation, it was observed that the elongation in this direction did not change in these experiments. The most relevant changes were observed in the TS and TeS values: TS increased between 30 and 46%, while TeS increased between 7 and 38%.

Table 4 shows the mechanical properties of the materials obtained by combining the Ag NPs-loaded mycotextile with the different oxides tested herein. In this case, the results differ significantly from those observed using the wild mycotextile as starting material, because the properties of these materials are not predictable. Therefore, the effect of the oxides in these examples will fulfill two leading roles, one related to the unique look and feel of the resulting combinations and the other regarding the functionality imparted by them. For instance, it could be observed that in the case of the incorporation of biosynthesized oxides in the AgNPs loaded mycotextile, all the parameters diminished after the process in both directions of the material. After immersion, in the formulation containing the nanopigments, the mycotextiles do not show a predictable behavior. These differences could be explained by the deficient distribution of the nanoparticles in the materials previously loaded with Ag NPs, as observed in the SEM images above. Thus, this variability in the distribution also causes variability in the mechanical properties.

The example of silver biosynthesis (in vivo) using the material crosslinked during the fermentation (e.g., in situ nano-crosslinking) showed a behavior similar to the one described before for obtaining a prototype (see Table 5). In this case, a slight increase in the tensile strength and the tear strength was obtained, while the elongation showed an increase of around 34 and 41%.

All the metrics compared herein confirm the viability of the application of these materials in the fashion industry, where they could comprise all the mechanical and esthetic requirements to become a useful material as an alternative to other materiality in the market based on animal hides or plastic-based leather.

TABLE 3

Maximum stress, Tensile strength (TS), elongation percentage (E) and tear strength (TeS) for the sidereal mycotextiles obtained by mycosynthesis of silver.

| Prototype | TS (MPa) | E (%) | TeS (N/mm) |
|---|---|---|---|
| Control 1 (wild) | 5.83 ± 1.05 | 70 ± 1 | 3.91 ± 0.56 |
| | 6.04 ± 0.93 | 41 ± 1 | 5.06 ± 0.43 |
| AgNPs (SCC-0006/3.6) | 6.34 ± 0.93 | 74 ± 4 | 6.31 ± 0.72 |
| | 6.34 ± 0.57 | 47 ± 2 | 5.07 ± 0.49 |
| AgNPs (SCC-0002) | 6.23 ± 0.79 | 82 ± 4 | 5.59 ± 0.84 |
| | 6.21 ± 0.44 | 49 ± 4 | 5.12 ± 0.74 |
| AgNPs (SCC-0013) | 6.39 ± 0.10 | 80 ± 2 | 5.41 ± 0.11 |
| | 6.15 ± 0.77 | 50 ± 2 | 5.26 ± 0.59 |
| Ag—Au NPs | 4.23 ± 0.11 | 49 ± 3 | 3.53 ± 0.84 |
| | 4.27 ± 0.56 | 34 ± 4 | 2.84 ± 0.15 |

TABLE 4

Maximum stress, Tensile strength (TS), elongation percentage (E), and tear strength (TeS) for the sidereal mycotextiles obtained by combining metal nanoparticles at the post-fermentation stage.

| Prototype | TS (MPa) | E (%) | TeS (N/mm) |
|---|---|---|---|
| Cu | 7.37 ± 0.32 | 78 ± 1 | 5.15 ± 0.10 |
| | 11.16 ± 0.55 | 47 ± 5 | 7.00 ± 0.09 |
| Magnetic IO | 7.77 ± 0.32 | 72 ± 2 | 5.41 ± 0.75 |
| | 10.77 ± 0.55 | 41 ± 6 | 6.73 ± 0.76 |
| red IO | 5.46 ± 0.55 | 85 ± 5 | 6.13 ± 0.88 |
| | 8.64 ± 0.36 | 46 ± 1 | 5.47 ± 0.69 |
| Ag—Cu | 4.50 ± 0.41 | 52 ± 4 | 3.26 ± 0.58 |
| | 5.07 ± 0.58 | 41 ± 4 | 3.34 ± 0.51 |
| Ag-magnetic IO | 4.60 ± 0.20 | 60 ± 3 | 5.02 ± 0.36 |
| | 4.57 ± 0.38 | 42 ± 1 | 3.98 ± 0.20 |
| Ag-red IO | 5.96 ± 0.31 | 73 ± 4 | 6.49 ± 0.31 |
| | 9.32 ± 0.40 | 50 ± 3 | 5.40 ± 0.98 |
| Ag-yellow IO | 6.70 ± 0.54 | 81 ± 3 | 4.25 ± 0.38 |
| | 7.45 ± 0.38 | 53 ± 3 | 5.14 ± 0.47 |

TABLE 5

Maximum stress, Tensile strength (TS), elongation percentage (E), and tear strength (TeS) for the in-situ-AgNPs mycotextile compared to the control.

| Prototype | TS (MPa) | E (%) | TeS (N/mm) |
|---|---|---|---|
| Control 2 (In-Situ nano-crosslinking) | 6.84 ± 0.46 | 39 ± 7 | 4.23 ± 0.88 |
| | 6.58 ± 1.05 | 31 ± 4 | 4.85 ± 0.53 |

TABLE 5-continued

Maximum stress, Tensile strength (TS), elongation percentage (E), and tear strength (TeS) for the in-situ-AgNPs mycotextile compared to the control.

| Prototype | TS (MPa) | E (%) | TeS (N/mm) |
|---|---|---|---|
| In situ-AgNPs | 7.66 ± 1.06 | 66 ± 7 | 5.59 ± 0.70 |
| | 7.43 ± 0.95 | 47 ± 2 | 4.60 1.06 |

In general, the method, compositions and apparatuses described herein may include nanoparticles, which may be added (e.g., functionalized NP) and/or may be formed by an in vivo formation of metallic NP (e.g., silver, gold, iron oxide) by adding metallic salts, and/or in vitro (e.g., ex vivo) formation of metallic NP using extracts (plant or fungal) that are then added as previously described. Using in vitro nanoparticles may have a final distribution of the nanoparticles within the material that is particularly distinct as compared with the distribution identified when adding nanoparticles (including ex vivo addition) during growth of the mycelium mat. In some cases, the mycotextile may include nanoparticles added to the mycelium mat, e.g., an in vitro approach, and nanoparticles formed in vivo. For example, the in vitro approach may be performed on materials previously reinforced with $SiO_2$ nanoparticles. These added nanoparticles (in vitro) may be derived from a plant and/or fungal-based source. The examples shown here were done with plant extracts. These nanoparticles, based on the in vitro source, may be deposited in the surface of the mycotextile because they were added, e.g., after the post-fermentation stage, as a type of pigment or functional coating. SEM analysis on transversal sections confirms that they may penetrate the mycelium network.

In variations in which, as described herein, the nanoparticles are synthesized, in vivo, by the fungal strain, the resulting nanoparticles do not need to be separately functionalized. In ex vivo embodiments, the added nanoparticles may be synthesized using plant extracts and one or more metabolites may act as organic capping agents to stabilize them, thus adding a barrier between the NPs and the surface of the hypha. This "layer" could be equivalent to a functionalizing agent. The ex vivo nanoparticles may not include a crosslinker (because they may be added after the crosslinking stage of the post-fermentation process), and the mechanical properties of the resulting materials may be increased in comparison to a material reinforced only with $SiO_2$.

Nanoparticles (e.g., metallic nanoparticles) synthesized in vivo in the fungal strain during fabrication of the mycotextile may be distributed through the final mycotextile in a manner that is distinct from nanoparticles (including ex vivo formed and added nanoparticles) added during fabrication. For example, all of the SEM images and elemental mapping shown in FIGS. 24 to 47 illustrate the presence of either in vivo silver or gold nanoparticles along with the nanoparticles included by in vitro approach in the corresponding cases. The resulting images shown with the SEM analysis correspond to a resulting mycotextile. The nanoparticles are distributed in regions not achieved by simple addition.

In practice the in vivo process may include the addition of a metallic salt solution to the freshly harvested mycotextile. This in vivo approach uses living fungus for the incubation in the metallic salts just before the post-fermentation. After incubating, the material is processed by immersion in the nanoemulsion, e.g., in a formulation of an oil-in-water nanoemulsions such as (but not limited to): 1% of coconut oil, 4.66% of a non-ionic surfactant (hydrogenated castor oil) and 94.34% of water. After immersion for 10 minutes all the materials are dried until losing between 80-90% of humidity.

In general, any of these methods of forming, particularly but not limited to in vivo nanoparticle formation, may include a UV treatment, e.g., breaking up the larger particles formed from the metallic salt solution. This may be done before other post-fermentation steps (e.g., addition of nanoemulsion). The application of UV radiation may help to desegregate the NPs to homogenize the nanoparticle distribution and may thereby provide a more intense color. This is the last (or one of the last) steps of the process, may be performed after the nanoemulsion and the application of a prolamine protein solution (e.g., zein:glycerol mixture).

When adding nanoparticles to a formulation, these particles may be added after the post-fermentation process. Either starting from an in vitro mycotextile or from an Ag or Au in vivo loaded mycotextile. For example, in some cases, the in vitro addition of nanoparticles in the mycotextile may be obtained by: (i) harvesting, (ii) inactivation, (iii) nanoemulsion, (iv) functionalized-$SiO_2$, (v) zein. In contrast, the in vivo Ag or Au loaded mycotextile may be obtained by: (i) harvesting, (ii) in vivo Ag or Au synthesis, (iii) nanoemulsion, (iv) zein, (v) UV-irradiation.

In general, in any of the mycotextiles described herein, the mycotextile may include both in vivo nanoparticles (metallic nanoparticles, such as silver or gold nanoparticles which may color/dye the final mycotextile) as well as ceramic nanoparticles (such as $SiO_2$ nanoparticles) added in vitro, which may provide additional structural reinforcement.

Engraving of Mycofabrics

Also described herein are methods, compositions and apparatuses that may beneficially allow the imprinting of a pattern, design and/or texture to the material in a manner that is significantly more environmentally favorable, requiring less resources, including energy, producing less waste, and resulting in a product having superior properties. These methods and compositions may include mycotextiles in which a pattern, design or texture are engraved onto the living mycelium mat prior to post-processing.

In general, the search for crafting innovative materials, it is crucial that such material may be imbued with distinctive personality and characteristics. It is particularly desirous to forge new embossing patterns that seamlessly align with the conceptual essence of sidereal mycelium fabrics. The sidereal space described herein may provide an inexhaustible wellspring of inspiration. While conventional embossing patterns for texturing leather and its alternatives often draw from the intricate patterns found in the skins of animals (e.g., live or death), such as cows, crocodiles, snakes, and ostriches, a notable sense persists in deriving textures from other elements. Thus, pioneering the integration of such organic motifs into materials akin to leather or its substitutes represents uncharted territory, brimming with potential for groundbreaking innovation.

Adding surface patterns and textures to the mycofabrics as described herein may be of particular use. Traditionally leather and similar fabrics are embossed by the application of high pressure to transfer a pattern. Described herein are methods, compositions and apparatuses for performing an engraving procedure on the living mycelium mat that may require significantly less pressure and other resources and may result in a more robust pattern transfer in the material, without weaking (or generating compressed regions of weaker/stronger domains) of the material. These methods and compositions may also be significantly easier, less expensive and require fewer additional components, including chemicals and energy. Although these materials and techniques may be referred to herein as embossing, they are more similar to an engraving technique and are otherwise distinguished from traditional embossing of fabric materials. The patterning of the sidereal mycelium fabrics described herein may be inspired in the natural world and universe to ground an awareness of environmental responsibility and raise a profound sense that we are not alone in the universe and that humanity's interconnectedness within the vast cosmos by extending our conception far beyond the limits of our body, our niche of life and the planet where we live. This expanded cosmovision serves as a catalyst for inspiring collective action and fostering a sense of expanded unity (e.g., totality) and empathy towards both our planet and the incommensurable sidereal space. For example, our muse can be born from the elements of nature and the universe, such as morphological structures of mushrooms (Basiodiomycota division), as possible alien inhabitants, geological and orographic impressions, volcanoes, craters and surface marks on planets and satellites, falling meteorites and comets, as well as constellations of stars, black holes and galaxies.

The Fungi Kingdom offers great bioinspiration, including the lower part of the mushroom cap, lamellar or porous structures that are precisely ordered. In the lamellar structures, thin sheets or plates extend from the center towards the edges of the cap where basidia are located. These specialized cells produce the spores (Basidiospores), allowing the sexual reproduction and dispersion of the fungus. These sheets can develop in tight, separate, very separated or anastomosed structures that tend to interconnect. They can also be bifurcated as they approach the edges of the cap. Bioinspired patterns on these mushroom-ordered structures refer to applying principles observed in nature to the design of artificial structures that could be imprinted or engraved either in vitro embossing or in vivo engraving.

Taking as inspiration the mushroom structures (lamellar or porous), four types of embossing have been designed to differentiate the look and feel of the sidereal mycelium fabrics from any related material existing in the global market. The patterns shown in FIGS. 48A1-48A4 correspond to embossing plates patterned with myco-inspired designs. The patterns used for the print were bioinspired by the hymnenia of some fruiting bodies that are part of a culture collection. However, hymenia structures from all Basiodiomycota fungi can be used as bioinspiration. The emulated patterns are as follows: pattern A (shown in FIGS. 48A1, 48B1, 48C1, 481, 48E1, 48F1 and 48G1) corresponds to the hymenium of laminae, which can be found in fungi of the Agaricales order, Pattern B (shown in FIGS. 48A2, 48B2, 48C2, 48D2, 48E2, 48F2 and 48G2) has a folded shape present in fungi of the Auriculariales order. Pattern C (shown in FIGS. 48A3, 48B3, 48C3, 48D3, 48E3, 48F3 and 48G3) is shaped like stingers and is present in fungi of the Cantharellales order, and finally, pattern D (shown in FIGS. 48A4, 48B4, 48C4, 48D4, 48E4 and 48F4) is shaped like tubes or channels, bioinspired by the Polyporales order.

AI-based simulations of the resulting materials applying these myco-inspired embossing are shown in FIGS. 48B1-48B4, 48C1-48C4, 48D1-48D4, 48E1-48E4, 48F1-48F4, and 48G1-48G4 for the following sidereal mycelium fabrics: "Ag"; "Ag—Au": "Ag—Cu", "Ag-magnetic IO", "Ag-yellow IO", and "Ag-red IO", respectively. These patterns could be applied to any type of mycelium-based articles since they could be adapted to the conventional embossing technique using machines with high pressures and temperatures, as applied for leather.

Figure 49A:
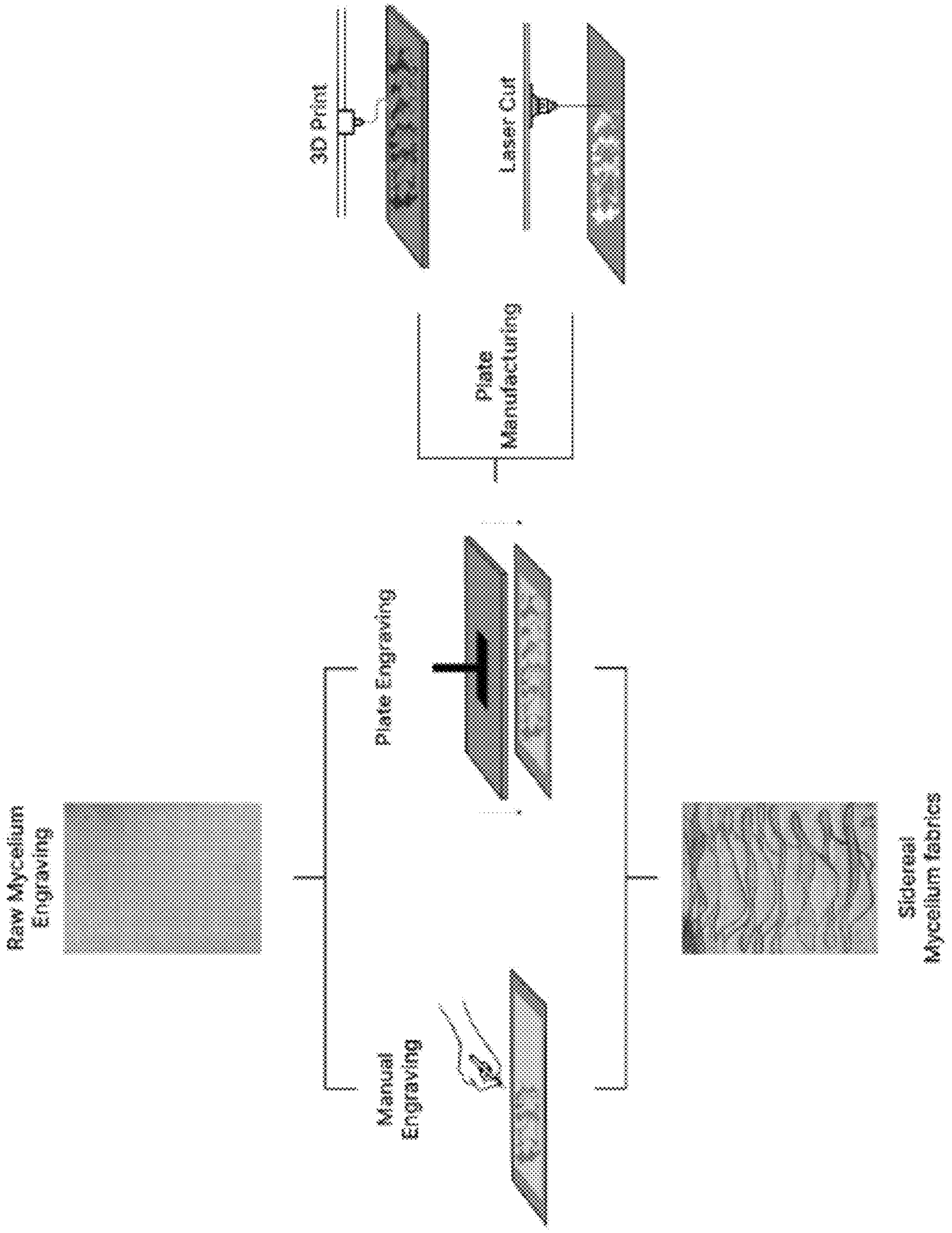
FIG. 49A schematically illustrates a method of an engraving process and the methods to obtain an engraved sidereal mycelium fabric.

The examples by in vivo engraving are most profoundly related to the nature of the fungal growth process. This technique must be applied in the process in which the fungal mycelium is still alive (this treatment may be performed before the mycosynthesis of the nanoparticles). In this case, manual engraving, 3D printed patterns, or any other artistic intervention is allowed, as the raw mycelium mat acts as a living canvas. The in vivo engraving considers a raw mycelium fabric with the living mycelium; this avoids the energetic costs associated with conventional embossing processes that require high pressures and temperatures, considerably diminishing the post-fermentation stage's carbon footprint. As outlined in FIG. 49A, this engraving process could be used to artistically intervene in the sidereal mycelium fabric, allowing consumers unique pieces of art and more meaningful pieces. As shown in FIG. 49A, the process may be manually performed or may be automatic (or semi-automatic), including forming and using plates applied to the raw mat and/or directly engraving onto the raw mat. In some cases, current 3D or laser-cut techniques driven by informatic software could allow a personal design to be transferred to plates made with soft materials such as silicon, PLA, nylon, ABS, etc. Because the mycelium is still alive and the density of this material is low (e.g., around 0.01 g/cm), it is not necessary to use high pressures or temperatures to allow the engraving. Once the raw mycelium fabric is patterned, it is used in any of the processes described above to obtain a determined combination of sidereal mycelium fabric. Two examples of manually engraved sidereal mycelium fabric are shown in FIGS. 49B1-49B2.

In general, the engraving techniques described herein, in which the mycotextile is "engraved" by applying pressure to the harvested mycotextile, may apply pressure within a range from about 1-50 kg/ft$^2$ (e.g., 2 to 30 kg/ft$^2$, 4 to 20 kg/ft$^2$, 5 to 15 kg/ft$^2$, about 10 kg/ft$^2$, etc.). The time period the pressure is applied may be, e.g., between about 1 second to about 500 seconds (e.g., 5 seconds to 400 seconds, 10 seconds to 300 seconds, 60 seconds to 180 seconds, 90 seconds to 150 seconds, about 90 seconds, about 120 seconds, about 150 seconds, etc.). The pressure may be applied immediately after the harvesting while the fungus are alive during the in vivo synthesis (which is the following step). The engraving depth will depend on the mycelium thickness. However, a fully defined pattern may have, at least, about half of the depth of the mycelium thickness (e.g., between about 30%-70% of the depth of the mycelium, about 35%-65%, about 40%-60%, etc.). For instance, with a mycelium layer of around 4-5 mm a plate with a 2 mm pattern-depth may be used for the engraving. Regarding the manual engraving, modeling tools used for ceramics and clay pottery may be used. In any of these examples, a flat press may be used to perform the engraving, taking into consideration the parameters described above.

The final structure of the engraved mycotextile may be distinct from other fabrics, including embossed fabrics. For example, the mycotextile that has been "engraved" as described herein may have compressed regions where it was engraved. The resulting look and structure is different from what is seen in conventional embossing processes in which it is mandatory to add a PU coating to avoid die-cutting of the material. This coating layer exhibits the pattern and also contains pigments and finishing resins used for different looks (Matte, Satin, Shiny, Glossy, Patent, etc.), all equivalent to the finishing strategies used in the leather industry.

Also, the patterns used to resemble different animal skins (crocodile, snake, ostrich, etc.). By using the proposed engraving, the mycelium layer receives all the pressure and therefore, the pattern is visualized as a combination of compressed areas and less compressed regions, where both the in vivo nanoparticles and the in vitro nanoparticles may be differentially deposited, increasing the "contrast" between both regions.

The differences between the technique for engraving the living mycelium mat as described herein and other embossing a cross-linked mycotextile (in which the mycelium mat has been cross-linked) is shown schematically in FIGS. 49C1-49C3. FIG. 49C1 shows a section through an example of a mycotextile including a cross-linked hyphae matrix embed over a scaffold layer 4902. The mycotextile has an upper surface 4904 and a lower surface 4906. The upper surface is separated from the scaffold layer 4902 by a distance, d, and the scaffold layer extends flat, essentially in the same plane as the mycotextile. The thickness of the upper region (above the scaffold layer) may be equal to or different from the thickness of the lower region of the hyphae matrix.

Embossing the mycotextile, e.g., after cross-linking (and in some cases, drying) the hyphae matrix may result in a sectional profile similar to that shown in FIGS. 49B1-49B2, in which the upper surface 4904 is compressed to form regions of different thicknesses (in this example, relative to the bottom surface 4906) and the scaffold layer 4902' is displaced from the horizontal by a proportion of the compression of the upper layer. In this example the scaffold layer remains relatively centered between the upper and lower layers, as shown.

In FIG. 49C3, the mycotextile is engraved by compressing (e.g., using a tool, plate, etc.) the upper region of the living mycelium mat as described above. In this example although the scaffold layer 4902" may be compressed somewhat, the relative amount of compression (as compared with embossing, FIG. 49C2) is substantially less. For example, the scaffold layer may be displaced relative to the plane of the mycotextile (in this example, parallel to the bottom surface 4906) by less than, e.g., 25%, 20%, 15%, 10%, 5%, etc. This may be true so long as the depth of the engraving remains less than the thickness of the upper region. In this example, the scaffold layer also does not remain centered between the upper and lower surfaces, so that the distance between the scaffold layer and the up surface is different along the length and width of the mycotextile underlying the engraved region, as compared to a non-engraved region. This may be the result of engraving into the living mycelium mat.

Functional Properties of the Sidereal Mycelium Fabrics:

The incorporation of the nanoparticles not only provides novel characteristics regarding the material reinforcement and the esthetic (look and feel) and avoids the use of petrochemical-based dyes, but it provides a wide option of smart functionalities. For example, specific properties include antibacterial, antifungal, magnetic, adsorptive and photocatalytic activity, among others. Nanoparticles possess unique physical and chemical properties due to their large surface area in the nanoscale range. Its optical properties are known to be size-dependent, revealing different colors due to absorption in the visible region. Its reactivity, hardness and other properties also depend on its unique size, shape and structure.

Antibacterial activity: Antibacterial textiles provide resistance to bacterial growth, improve hygiene, reduce odors, and potentially prevent the spread of infections and diseases. This property is beneficial in consumer products like clothing and shoes as they can help to maintain freshness and cleanliness. It has been observed that different nanoparticles have antibacterial activity that mainly depends on the size of the particles, and the smaller ones have the best activity. Metallic nanoparticles destabilize the outer membrane of bacteria, producing ruptures in the plasma membrane and reducing the synthase activity of the intracellular adenosine triphosphate (ATP) depletion layer, thus reducing the metabolic process. Furthermore, they destroy the ribosome subunit by binding to the tRNA and, thus, ultimately, the total collapse of the biological mechanism. Nanoparticles based on metals and metal oxides have been widely studied for their antimicrobial efficacy against various bacterial strains. For example, silver nanoparticles have received special attention due to their application as an antimicrobial device coating. Similarly, gold, copper oxide, gallium, zinc oxide, and magnesium oxide nanoparticles have shown promising antimicrobial effects. Furthermore, combining different nanoparticles to enhance their efficacy in a synergistic approach has been widely investigated.

An antibacterial assay was made using the disk diffusion technique in agar plates inoculated with a Gram-negative control bacteria (*Escherichia coli*). In this test, the size of an area around the disc where bacteria cannot grow (called the "zone of inhibition") indicates the effectiveness of the antimicrobial compounds. Initially, the bacterial inoculum of ampicillin-resistant *E. coli* was prepared in Lisogenia broth (LB medium), which was left to incubate overnight at 37° C. with constant shaking. The turbidity of the inoculum was adjusted to the bacterial suspension obtained until reaching the standard turbidity of 0.5 on the Mc scale Farland. The inoculum (70 L) was plated on Mueller Hinton agar plates. Then, discs of "wild-Ag", "Wild-Cu", "Ag—Cu", "wild-magnetic IO", and "Ag-magnetic IO" mycotextiles were carefully placed on the inoculated medium and allowed to incubate overnight at 37° C.

Figure 50A:
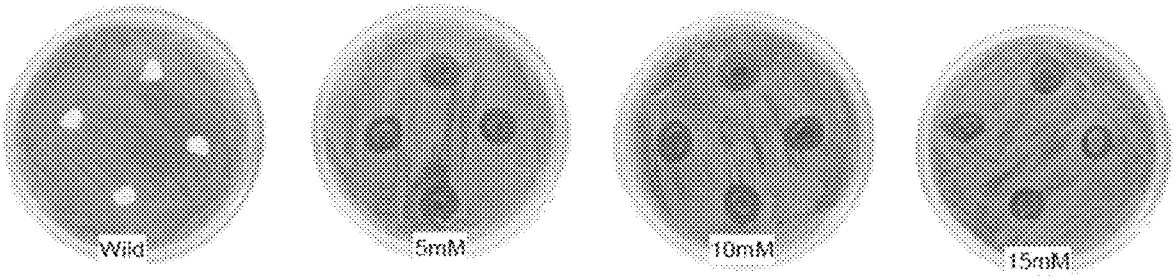
FIG. 50A show antibacterial activity tests on 1 cm discs of mycotextiles loaded with AgNPs biosynthesized at different concentrations of silver nitrate.
Figure 50B:
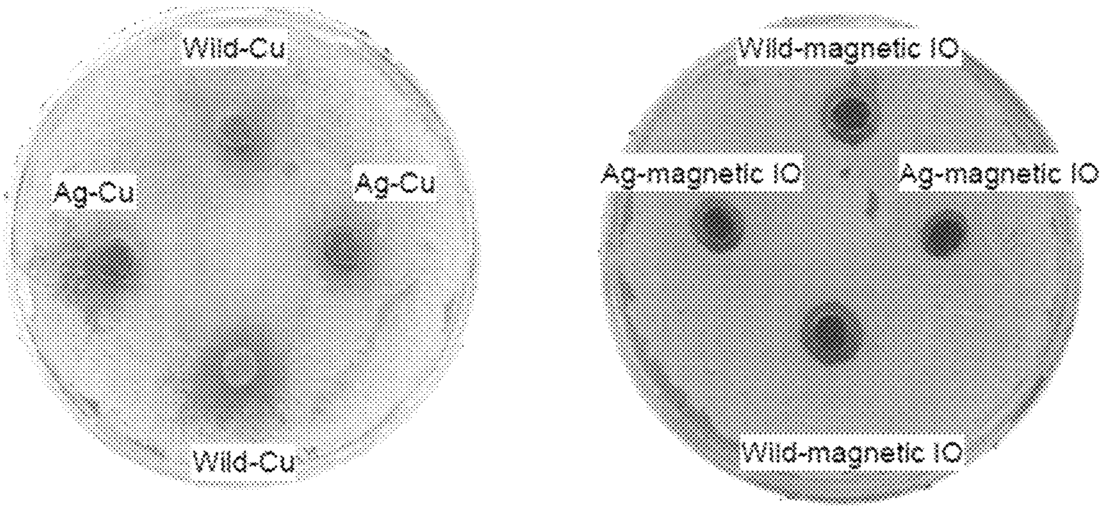
FIG. 50B shows antibacterial activity tests on prototype discs of "wild-Cu" and "Ag—Cu" (LEFT). Antibacterial activity tests on prototype discs of "wild-magnetic IO" and "Ag-magnetic IO mycotextiles" (RIGHT).

Results of the antibacterial assay by disk diffusion: FIG. 50A shows the antibacterial activity tests of discs made with the prototypes obtained by AgNPs mycosynthesis starting with different concentrations of $AgNO_3$. The control ("wild" prototype) does not show inhibition zones and does not present antibacterial activity. All mycotextiles with mycosynthesized silver nanoparticles ("wild-Ag") showed efficient antibacterial activity against *E. coli*. However, it should be highlighted that there is no difference between the different concentrations (5 to 15 mM of $AgNO_3$) showing halos around 9 mm. This similarity could be explained as these nanoparticles are immobilized in the hyphae; therefore, the bactericidal effects could be more associated with a possible release of surface silver atoms instead of a penetration of the nanoparticles in the cell membrane. In the case of "wild-Cu" and "Ag-Cud, the inhibition zones are not well defined, as shown in FIG. 50B. It is known that copper or copper oxide nanoparticles generally damage microbial cells mainly by generating reactive oxygen species (ROS). Therefore, the combination of silver and copper oxide may hinder ROS generation, limiting the bactericidal activity. The "wild-magnetic IO" and "Ag-magnetic IO" mycotextiles showed inhibition halos around 10 mm. It is known that magnetic IO NPs have higher antimicrobial actions against Gram-negative bacteria since they can concentrate between the outer and inner membranes of the cell wall of these bacteria due to the binding with the FHL complex in the inner membrane.

Magnetic properties: Magnetic nanostructures are attracting considerable interest due to their unique potential in storage, sensing, spintronics, and optoelectronics in flexible devices. Several factors, such as composition, shape, size, surface morphology, anisotropy, layer thickness, and molecular interactions, govern the magnetic properties of nanostructures. Furthermore, the bactericidal action of magnetic iron oxide nanoparticles could be enhanced by the magnetic properties producing local hyperthermia and several cell wall damages induced by vibrations such as membrane rupture, fusion of different cells with each other, and death. Magnetic nanoparticles are nanomaterials composed of elements such as iron, nickel, cobalt, chromium, manganese, gadolinium and some of their compounds. Nanostructured magnetite ($Fe_3O_4$) and metallic ferrites ($M_xFe_{3-x}O_4$) are the most explored magnetic nanoparticles due to their high magnetic response and the possibility of being biosynthesized. Likewise, magnetic mycotextiles can be used as elements of magnetic cores and as parts of meters, transmitters and textile actuators. They can be used in electronic circuits and smart clothing.

Figure 51A:
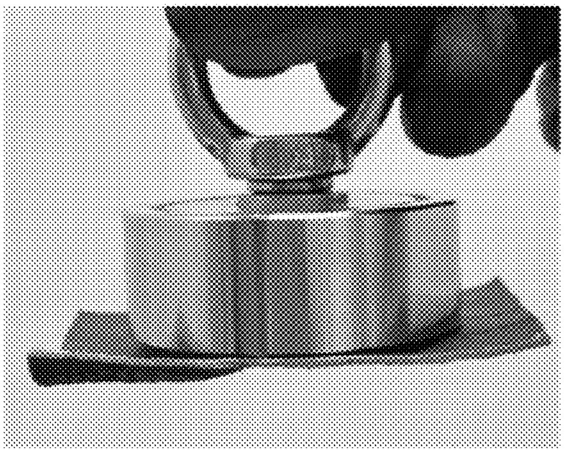
FIGS. 51A-51B show photographs demonstrating the attractive forces occurring between the prototypes containing magnetic IO NPs synthesized using an extract of *Ilex paraguariensis*. On the left is the "wild-magnetic IO", and on the right is the "Ag-magnetic IO" prototype.
Figure 51B:
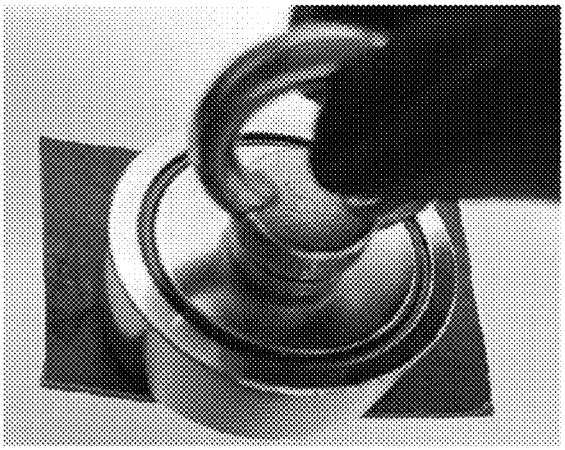

FIGS. 51A-51B show the behavior of a “Wild-magnetic” (left, FIG. 51A) and an “Ag-magnetic IO” (right, FIG. 51B) mycotextiles in the presence of a neodymium magnet. This neodymium-iron-boron (NdFeB) magnet is the strongest type of permanent magnet commercially available. The working principle of a neodymium magnet is based on the alignment of magnetic moments within the material. In a neodymium magnet, the neodymium atoms act as tiny magnets due to the alignment of their electron spins. When many of these atoms are aligned in the same direction, they create a strong magnetic field. Neodymium magnets attract ferromagnetic materials, such as those based on iron, nickel, and cobalt.

Photocatalytic properties: Textile washing requires a lot of water, and the concept of self-cleaning is very concerning for reducing the consumption of this vital substance. In addition to self-cleaning materials, they clean the surface, degrade the stain, and inhibit microbial growth. The photocatalytic activity of the nanocomposites is carried out by submerging the mycotextiles in an aqueous solution of a cationic organic dye. The experiments were carried out using an 8 W UV lamp ($\lambda_{max}$=254 nm) located in a zenithal plane along the prototype’s surface at a distance of 10 cm. For the experiment, 5×5 cm pieces of the “wild”, “Ag—Au”, and “Au mycosynthesized” prototypes were incubated in containers with 25 ml of crystal violet (“CV”), (at 10 mg/ml). Each container was exposed to ultraviolet light for 90 minutes and 5 mL aliquots were withdrawn every 30 min. The remaining solutions after 90 min of reaction were measured by UV-Vis spectroscopy. Likewise, the results were compared with the adsorption experiments (keeping all the conditions without light).

The adsorption experiments in FIG. 52A revealed the color change of the CV solution after the adsorption experiments revealed bleaching or discoloration of the solution because of the adsorption of the dye molecules. Compared to the control sample, where no color change was observed in 90 minutes, the resulting solutions in contact with the materials showed discoloration. This result indicates that the materials are capable of adsorbing the CV molecules. As observed at the first 30 minutes of incubation, the solution experienced a higher color change in the “Ag—Au” and “Au-mycosynthesized” materials. However, after 60 minutes, the adsorption in the material “Ag—Au” increased, as evidenced by a higher discoloration of the solution. After 90 min in contact with the materials, the CV solutions did not show a significant change, suggesting that the adsorption reached a plateau around 60 min of incubation at the tested conditions. The resulting coloration of the materials after the adsorption experiment is revealed in FIGS. 52B1-52B3. The “wild” prototype experienced a change in the coloration, turning from yellow to purple, accounting for the adsorption of the crystal violet. The color change in the “Ag—Au” and “Au-mycosynthesized” materials is less evident in the image because of the dark color of the original material. However, the discoloration of the solution indicates that an adsorption process occurred also with these samples.

When the same experiment was carried out in the presence of UV irradiation, the discoloration process was accelerated because of a photocatalytic effect driven by the Ag and or AuNPs. As observed in FIG. 53A, the control solution (without any sidereal mycelium fabric) also suffered a slight discoloration because of a photolysis effect, acting as a control of this test. However, the change in the color of the solution is evident in those cases where the mycelium fabric was submerged. After 90 minutes of reaction, the CV solutions experienced a great color change.

As observed in FIGS. 53B1-53B3, the resulting materials after these photocatalysis experiments are less dyed than those obtained during the adsorption experiments, suggesting that the dye molecules were bleached through a photocatalytic process during the incubation with light. Several enhancements could be further tested to increase the effectiveness of these techniques. For instance, hybrid photocatalysts can be fabricated, including combinations with semiconductors such as $TiO_2$/Au, ZnO/Au, $Fe_2O_3$/Au, or composites.

FIGS. 54A-54B shows a comparative photograph of the CV solutions after 90 minutes of adsorption (left, FIG. 54A) and photocatalysis (right, FIG. 54B), together with the comparison of the UV-vis spectrum of the remaining solutions using “Ag—Au” and “Au-mycosynthetized” materials. During the adsorption experiment, a diminution in the intensity of the color was observed, consistent with the adsorption of CV molecules in the substrates submerged during the experiment. After the photocatalysis experiments, the remaining solutions showed a change in the coloration, indicating that the molecule is chemically transformed during the process, which is consistent with the catalytic process induced by the UV irradiation. The UV-vis profile in both samples after the photocatalysis shows differences from those resulting from the adsorption, evidencing a chemical change during the photocatalytic process. FIG. 54C shows the different spectrum for absorbance between metallic nanoparticles formed in vivo.

Considering the versatility of these protocols the incorporation of chemical elements such as silver, gold, platinum, palladium, iridium, osmium, rhenium and, non-precious metals such as iron, aluminum, titanium, tin, cobalt, manganese, molybdenum, nickel, vanadium, niobium, titanium, zirconium and/or, rare earths such as lanthanum, cerium, dysprosium, europium, gadolinium, erbium, holmium, and/or metal compounds or composites such as oxides, oxyhydroxides, salts, carbonates, aluminates, ferrites, silicates, iron phosphates, titanates, perovskites, pyroxenes, carbides, nitrides, carbonitrides, these methods and compositions may provide a wide range of applications including: (i) catalysis for pharmaceuticals, petrochemicals, and environmental remediation, (ii) medical diagnostics and therapeutics, drug delivery, imaging, and photothermal therapy, (iii) as sensors for detecting gases, biomolecules, and environmental pollutants, (iv) in flexible electronics and displays for solar cells, (v) catalytic converters and fuel cells among others.

All publications and patent applications mentioned in this specification are herein incorporated by reference in their entirety to the same extent as if each individual publication or patent application was specifically and individually indicated to be incorporated by reference. Furthermore, it should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element, or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under", or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

In general, any of the apparatuses, compositions and/or methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A mycotextile comprising:

a support scaffold layer embedded within a crosslinked mycelium matrix, wherein the support scaffold layer is crosslinked to the mycelium matrix and the mycelium matrix extends in a plane above and below the support scaffold layer;

a plurality of metallic nanoparticles formed in vivo within the crosslinked mycelium matrix, characterized by a distribution of metallic nanoparticles through a dikaryotic hyphae network within the crosslinked mycelium matrix, wherein the color of the mycotextile is determined by the plurality of metallic nanoparticles.

2. The mycotextile of claim 1, wherein the plurality of metallic nanoparticles are distributed through the hyphae network both over the hyphae and within the hyphae.

3. The mycotextile of claim 1, further comprising a second plurality of ceramic nanoparticles.

4. The mycotextile of claim 3, wherein the ceramic nanoparticles have a different distribution than the metallic nanoparticles of the plurality of nanoparticles.

5. The mycotextile of claim 3, wherein the ceramic nanoparticles are only distributed over the hyphae of the hyphae network.

6. The mycotextile of claim 3, wherein the ceramic nanoparticles are functionalized by the adsorption of a prolamin on their surface.

7. The mycotextile of claim 1, wherein the metallic nanoparticles comprise silver, gold, iron oxide, and/or copper oxide nanoparticles.

8. The mycotextile of claim 1, wherein the mycotextile is coated with a prolamin.

9. The mycotextile of claim 1, wherein the color of the mycotextile is determined by the localized surface plasmon resonance (LSPR) of the metallic nanoparticles.

10. A mycotextile comprising:

a support scaffold layer embedded within a crosslinked mycelium matrix, wherein the support scaffold layer is crosslinked to the mycelium matrix and the mycelium matrix extends in a plane above and below the support scaffold layer;

a plurality metallic nanoparticles within the crosslinked mycelium matrix, distributed over a dikaryotic, aerial hyphae network, wherein the color of the mycotextile is determined by the localized surface plasmon resonance (LSPR) of the metallic nanoparticles.

11. The mycotextile of claim 1, wherein the dikaryotic hyphae network comprises generative hyphae with fibulas.

12. The mycotextile of claim 1, wherein the dikaryotic hyphae network comprises clamp connections, and/or an enrichment for molecules related to clamp connections.

13. A mycotextile comprising:

a support scaffold layer embedded within a crosslinked mycelium matrix, wherein the support scaffold layer is crosslinked to the mycelium matrix and the mycelium matrix extends in a plane above and below the support scaffold layer; and a plurality of metallic nanoparticles formed in vivo within the crosslinked mycelium matrix, characterized by a distribution of metallic nanoparticles through a dikaryotic hyphae network within the crosslinked mycelium matrix, wherein the dikaryotic hyphae network comprises clamp connections, and/or an enrichment for molecules related to clamp connections, further wherein the color of the mycotextile is determined by the plurality of metallic nanoparticles.

* * * * *